United States Patent [19]
Ewing et al.

[11] Patent Number: 5,958,918
[45] Date of Patent: *Sep. 28, 1999

[54] SUBSTITUTED (SULFINIC ACID, SULFONIC ACID, SULFONYLAMINO OR SULFINYLAMINO) N-[(AMINOMINOMETHYL)PHENYLALKYL]-AZAHETEROCYCLYLAMIDE COMPOUNDS

[75] Inventors: William R. Ewing, Downingtown; Michael R. Becker, Norristown; Henry W. Pauls; Daniel L. Cheney, both of Collegeville; Jonathan Stephen Mason, Phoenixville; Alfred P. Spada, Lansdale; Yong Mi Choi-Sledeski, Collegeville, all of Pa.

[73] Assignee: Rhone-Poulenc Rorer Pharmaceuticals Inc.

[*] Notice: This patent is subject to a terminal disclaimer.

[21] Appl. No.: 08/976,034

[22] Filed: Nov. 21, 1997

Related U.S. Application Data

[63] Continuation of application No. PCT/US96/09816, Jun. 7, 1996, which is a continuation-in-part of application No. 08/481,024, Jun. 7, 1995, Pat. No. 5,612,353.

[51] Int. Cl.[6] .......................... C07D 401/02; A61K 31/40; A61K 31/435
[52] U.S. Cl. .......................... 514/212; 514/307; 514/309; 514/329; 514/343; 514/422; 514/426; 540/606; 546/141; 546/223; 546/281; 546/139; 546/276.4; 548/527; 548/557

[58] Field of Search .............................. 540/606; 546/141, 546/223, 281, 139, 276.4; 548/527, 557; 514/212, 307, 309, 343, 320, 422, 426

[56] References Cited

U.S. PATENT DOCUMENTS

| 5,612,353 | 3/1997 | Ewing et al. . |
| 5,731,315 | 3/1998 | Ewing et al. . |

OTHER PUBLICATIONS

Valerio et al, Synthesis, vol. 10, pp. 786–789, 1988.

*Primary Examiner*—Zinna Northington Davis
*Attorney, Agent, or Firm*—Raymond S. Parker, III

[57] ABSTRACT

The compounds of formula I exhibit useful pharmacological activity and accordingly are incorporated into pharmaceutical compositions and used in the treatment of patients suffering from certain medical disorders. More especially, they are inhibitors of the activity of Factor Xa. The present invention is directed to compounds of formula I, compositions containing compounds of formula I, and their use, which are for treating a patient suffering from, or subject to, physiological condition which can be ameliorated by the administration of an inhibitor of the activity of Factor Xa.

57 Claims, No Drawings

SUBSTITUTED (SULFINIC ACID, SULFONIC ACID, SULFONYLAMINO OR SULFINYLAMINO) N-[(AMINOMINOMETHYL)PHENYLALKYL]-AZAHETEROCYCLYAMIDE COMPOUNDS

This application is a continuation of copending International Application No. PCT/US96109816, filed Jun. 7, 1996, which designates the United States, which, in turn, is a continuation-in-part application of U.S. patent application Ser. No. 08/481,024, filed Jun. 7, 1995, now U.S. Pat. No. 5,612,353.

FIELD OF THE INVENTION

The compounds of formula I exhibit useful pharmacological activity and accordingly are incorporated into pharmaceutical compositions and used in the treatment of patients suffering from certain medical disorders. More especially, they are Factor Xa inhibitors. The present invention is directed to compounds of formula I, compositions containing compounds of formula I, and their use, which are for treating a patient suffering from, or subject to, conditions which can be ameliorated by the administration of an inhibitor of Factor Xa.

Factor Xa is the penultimate enzyme in the coagulation cascade. Both free factor Xa and factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to the pharmaceutical use of a compound of formula I below for treating a patient suffering from a physiological disorder capable of being modulated by inhibiting an activity of Factor Xa, where formula I is as follows:

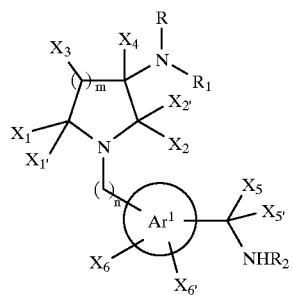

$Ar^1$ is phenyl or monocyclic heteroaryl;

R is hydrogen, optionally substituted alkyl, optionally substituted aralkyl, optionally substituted heteroaralkyl or hydroxyalkyl;

$R_1$ is hydrogen, $R_3S(O)_p$— or $R_3R_4NS(O)_p$—;

$R_2$ is hydrogen, or when $X_5$ and $X_{5'}$ taken together are $=NR_5$, then $R_2$ is hydrogen, optionally substituted lower alkyl, optionally substituted aralkyl or optionally substituted heteroaralkyl;

$R_3$ is optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or R and $R_3$ taken together form a 5 to 7 membered ring; and $R_4$ is optionally substituted alkyl, optionally substituted cycloalkyl or optionally substituted aryl, optionally substituted heteroaryl, optionally substituted aralkyl or optionally substituted heteroaralkyl, or $R_3$ and $R_4$ taken together with the nitrogen to which $R_3$ and $R_4$ are attached form an optionally substituted 4 to 7 membered heterocyclyl;

$X_1$ and $X_{1'}$ are independently selected from hydrogen, optionally substituted alkyl, optionally substituted aryl, optionally substituted aralkyl, optionally substituted heteroaryl, optionally substituted heteroaralkyl or hydroxyalkyl, or $X_1$ and $X_{1'}$ taken together form oxo;

$X_2$ and $X_{2'}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1'}$ taken together form a 4 to 7 membered ring;

$X_4$ is hydrogen, optionally substituted alkyl, optionally substituted aralkyl, or hydroxyalkyl;

$X_5$ and $X_{5'}$ are hydrogen or taken together are $=NR_5$;

$R_5$ is hydrogen, $R_6O_2C$—, $R_6O$—, cyano, $R_6CO$—, optionally substituted lower alkyl, nitro or $Y^1Y^{2'}N$—;

$Y^{1'}$ and $Y^{2'}$ are independently hydrogen, alkyl, aralkyl or heteroaralkyl;

$X_6$ and $X_{6'}$ are independently hydrogen, $R_7R_8N$—, $R_9O$—, $R_7R_8NCO$—, $R_7R_8NSO_2$—, $R_9CO$—, halo, cyano or nitro;

$R_6$ is hydrogen, optionally substituted lower alkyl or optionally substituted aralkyl or optionally substituted heteroaralkyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$— or lower acyl;

$R_9$ is hydrogen, optionally substituted lower alkyl, lower acyl or $R_{10}(O)CCH_2$—;

$R_{10}$ is hydrogen, optionally substituted lower alkyl, alkoxy or hydroxy;

m is 0, 1, 2 or 3;

n is 1, 2 or 3; or p is 1 or 2, a pharmaceutically acceptable salt thereof, an N-oxide thereof, a hydrate thereof or a solvate thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, alkoxy, amino, acylamino, aroylamino, carboxy, alkoxycarbonyl, aralkyloxycarbonyl, heteroaralkyloxycarbonyl or $Y^{1'}Y^{2'}NCO$—, where $Y^{1'}$ and $Y^{2'}$ are independently hydrogen, alkyl, aralkyl or heteroaralkyl. Exemplary alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, pyridylmethyloxycarbonylmethyl.

"Cycloalkyl" means a non-aromatic mono- or multicyclic ring system of about 3 to about 10 carbon atoms. Exemplary monocyclic cycloalkyl rings include cyclopentyl, fluorocyclopentyl, cyclohexyl and cycloheptyl. The cycloalkyl group is optionally partially unsaturated or optionally substituted by one or more halo, methylene ($H_2C=$), alkyl, fused ary or fused heteroaryl. Exemplary multicyclic cycloalkyl rings include 1-decalin, adamant-(1- or 2-)yl and norbornyl.

"Heterocyclyl" means a non-aromatic monocyclic or multicyclic ring system of about 3 to about 10 ring atoms. Preferred rings include about 5 to about 6 ring atoms wherein one of the ring atoms is oxygen, nitrogen or sulfur. The heterocyclyl is optionally partially unsaturated or optionally substituted by one or more alkyl, halo, aryl, heteroaryl, fused aryl or fused heteroaryl. Exemplary monocyclic rings include pyrrolidyl, piperidyl, tetrahydrofuranyl, tetrahydrothienyl and tetrahydrothiopyranyl. The thio or nitrogen moiety of the heterocyclyl may also be optionally oxidized to the corresponding N-oxide, S-oxide or S,S-dioxide.

"Aryl" means aromatic carbocyclic radical containing about 6 to about 10 carbon atoms. Exemplary aryl include phenyl or naphthyl, or phenyl substituted or naphthyl substituted with one or more aryl group substituents which may be the same or different, where "aryl group substituent" includes hydrogen, alkyl, aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, fused cycloalkyl, fused heterocyclyl, arylazo, heteroarylazo, $Y^1Y^2N$—, $Y^1Y^2NCO$— or $Y^1Y^2NSO_2$—, where $Y^1$ and $Y^2$ are independently hydrogen, alkyl, aryl, aralkyl or heteroaralkyl, or $Y^1$, $Y^2$ and N taken together form a heterocyclyl. The aryl group substituents are as defined herein.

Preferred aryl groups are optionally substituted phenyl or optionally substituted naphthyl. Preferred aryl group substituents include hydrogen, alkyl, hydroxy, acyl, aryl aroyl, aryloxy, halo, nitro, alkoxy, cyano, alkoxycarbonyl, acylamino, alkylthio, $Y^{1'}Y^{2'}N$—, $Y^{1'}Y^{2'}NCO$— or $Y^{1'}Y^{2'}NSO_2$—, where $Y^{1'}$ and $Y^{2'}$ are independently hydrogen, alkyl, aralkyl or heteroaralkyl; preferred phenyl group substituents are aryloxy and aryl; and preferred naphthyl group substituents are nitro, alkoxy and amino.

"Heteroaryl" means about a 5- to about a 10- membered aromatic monocyclic or multicyclic hydrocarbon ring system in which one or more of the carbon atoms in the ring system is/are element(s) other than carbon, for example nitrogen, oxygen or sulfur. The "heteroaryl" may also be substituted by one or more of the above-mentioned "aryl group substituents". Exemplary heteroaryl groups include pyrazinyl, furanyl, thienyl, pyridyl, pyrimidinyl, isoxazolyl, isothiazolyl, oxazolyl, thiazolyl, pyrazolyl, furazanyl, pyrrolyl, imidazo[2,1-b]thiazolyl, benzofurazanyl, indolyl, azaindolyl, benzimiddazolyl, benzothienyl, quinolinyl, imidazolyl and isoquinolinyl. Preferred heteroaryl groups in the R substituent include benzothienyl, thienyl, imidazolyl, pyridyl and quinolinyl all of which may be optionally substituted. Where

is monocylic heteroaryl, then preferred heteroaryls include thienyl, pyridyl and furanyl.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthalenemethyl.

"Heteroaralkyl" means a heteroaryl-alkyl- group in which the heteroaryl and alkyl are as previously described. Preferred heteroaralkyls contain a lower alkyl moiety. Exemplary heteroaralkyl groups may contain thienyl, pyridyl, imidazolyl and pyrazinyl.

"Aralkenyl" means an aryl-alkenyl- group in which the aryl and alkenyl are as previously described. Preferred aralkenyls contain a lower alkenyl moiety. An exemplary aralkenyl group is 2-phenethenyl.

"Heteroaralkenyl" means a heteroaryl-alkenyl- group in which the heteroaryl and alkenyl are as previously described. Preferred heteroaralkenyls contain a lower alkenyl moiety. Exemplary heteroaralkenyl groups may contain thienyl, pyridyl, imidazolyl and pyrazinyl.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl-CO— group in which the alkyl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthalenemethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$Y^3Y^4N-$" means a substituted or unsubstituted amino group, wherein $Y^3$ and $Y^4$ are as previously described. Exemplary groups include amino ($H_2N-$), methylamino, ethylmethylamino, dimethylamino and diethylamino.

"Alkoxycarbonyl" means an alkyl-O—CO— group. Exemplary alkoxycarbonyl groups include methoxy- and ethoxycarbonyl.

"Aryloxycarbonyl" means an aryl-O—CO— group. Exemplary aryloxycarbonyl groups include phenoxy- and naphthoxycarbonyl.

"Aralkoxycarbonyl" means an aralkyl-O—CO— group. An exemplary aralkoxycarbonyl group is benzyloxycarbonyl.

"$Y^3Y^4NCO-$" means a substituted or unsubstituted carbamoyl group, wherein $Y^3$ and $Y^4$ are as previously described. Exemplary groups are carbamoyl ($H_2NCO-$) and dimethylaminocarbamoyl ($Me_2NCO-$).

"$Y^3Y^4NSO_2-$" means a substituted or unsubstituted sulfamoyl group, wherein $Y^3$ and $Y^4$ are as previously described. Exemplary groups are aminosulfamoyl ($H_2NSO_2-$) and dimethylaminosulfamoyl ($Me_2NSO_2-$).

"Acylamino" is an acyl-NH— group wherein acyl is as defined herein.

"Aroylamino" is an aroyl-NH— group wherein aroyl is as defined herein.

"Alkylsulfonyl" means an alkyl-$SO_2-$ group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2-$ group.

"Arylsulfinyl" means an aryl-SO— group.

"Halo" means fluoro, chloro, bromo, or iodo. Preferred are fluoro, chloro or bromo, and more preferred are fluoro or chloro.

Preferred Embodiments

A preferred embodiment of the invention is a method for treating a patient suffering from a physiological disorder capable of being modulated by inhibiting an activity of Factor Xa by administering a therapeutically effective amount of a compound of formula I.

A preferred compound aspect of the invention is the compound of formula I wherein $R_3$ is optionally substituted phenyl, optionally substituted naphthyl, optionally substituted thienyl or optionally substituted benzothienyl.

Another preferred compound aspect of the invention is the compound of formula I wherein n is 1, and m is 1.

Another preferred compound aspect of the invention is the compound of formula I wherein $X_2$ and $X_{2'}$ taken together are oxo.

Another preferred compound aspect of the invention is the compound of formula I wherein $X_1$, $X_{1'}$, $X_3$ and $X_4$ are hydrogen.

Another preferred compound aspect of the invention is the compound of formula I wherein $X_5$ and $X_{5'}$ taken together are =NH.

Another preferred compound aspect of the invention is the compound of formula I wherein $X_5$ and $X_{5'}$ taken together are =$NR_5$ wherein $R_5$ is $R_6O_2C-$.

Another preferred compound aspect of the invention is the compound of formula I wherein

is phenyl and the carbon substituted with $X_5$, $X_{5'}$ and $HR_2N-$ is attached to the 3-position of the phenyl.

Another preferred compound aspect of the invention is the compound of formula I wherein

is of the formula

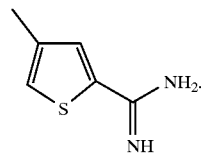

Another preferred compound aspect of the invention is the compound of formula I wherein R is hydrogen, methyl, aralkyl, heteroaralkyl, $HO_2CCH_2-$, $HOC(O)CH_2-$, $H_2NC(O)CH_2-$, (aralkyl)HNC(O)$CH_2-$ or (heteroaralkyl)HNC(O)$CH_2-$.

Another preferred compound aspect of the invention is the compound of formula I wherein $X_1$ is hydrogen and $X_{1'}$ is carboxyalkyl, alkoxycarbonylalkyl or aryl, or $X_1$ and $X_{1'}$ taken together form oxo.

Another preferred compound aspect of the invention is the compound of formula I wherein $R_1$ is $R_3SO_2-$.

Another preferred compound aspect of the invention is the compound of formula I wherein $R_1$ is $R_3R_4NSO_2-$.

Another preferred compound aspect of the invention is the compound of claim 1 wherein one of $X_6$ and $X_{6'}$ is amino in a para position relative to the

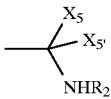

moiety.

Species according to the invention are selected from the group consisting of:

Naphthalene-2-sulfonic acid {1-[3-(aminoiminomethyl)benzyl]-2-oxopyrrolidin-3-(S)-yl}amide trifluoroacetate;

Dibenzofuran-2-sulfonic acid {1-[3-(aminoiminomethyl)benzyl]-5-oxopyrrolidin-3-yl}amide trifluoroacetate;

Toluene-4-sulfonic acid {1-[3-(aminoiminomethyl)benzyl]-2-oxopyrrolidin-3-(S)-yl}amide trifluoroacetate;

3,4-Dihydro-1H-isoquinoline-2-sulfonic acid {1-[3-(aminoiminomethyl)benzyl]-2-oxopyrrolidin-3-(S)-yl}amide trifluoroacetate;

3'-Methoxy-biphenyl-4-sulfonic acid {1-[3-(aminoiminomethyl)benzyl]-2-oxopyrrolidin-3-(S)-yl}amide trifluoroacetate;

Naphthalene-1-sulfonic acid {1-[3-(aminoiminomethyl)benzyl]-2-oxopyrrolidin-3-(S)-yl}amide trifluoroacetate;

5-Pyrid-2-ylthiophene-2-sulfonic acid {1-[3-(aminoiminomethyl)benzyl]-2-oxopyrrolidin-3-(S)-yl}amide trifluoroacetate;

Biphenyl-4-sulfonic acid {1-[3-(aminoiminomethyl)benzyl]-2-oxopyrrolidin-3-(S)-yl}amide trifluoroacetate;

7-Methoxynaphthalene-2-sulfonic acid {1-[3-(aminoiminomethyl)benzyl]-2-oxopyrrolidin-3-(S)-yl}amide trifluoroacetate;

7-Ethoxynaphthalene-2-sulfonic acid {1-[3-(aminoiminomethyl)benzyl]-2-oxopyrrolidin-3-(S)-yl}amide trifluoroacetate;

5-Chloro-6-methoxynaphthalene-2-sulfonic acid {1-[3-(aminoiminomethyl)benzyl]-2-oxopyrrolidin-3-(S)-yl}amide trifluoroacetate;

5-Chloro-6,7-dimethoxynaphthalene-2-sulfonic acid {1-[3-(aminoiminomethyl)benzyl]-2-oxopyrrolidin-3-(S)-yl}amide trifluoroacetate;

7-Aminonaphthalene-2-sulfonic acid {1-[3-(aminoiminomethyl)benzyl]-2-oxopyrrolidin-3-(S)-yl}amide bistrifluoroacetate;

Naphthalene-2-sulfonic acid {1-[4-(aminoiminomethyl)benzyl]-2-oxopyrrolidin-3-(S)-yl}amide trifluoroacetate;

7-Methoxynaphthalene-2-sulfonic acid [1-(3-aminomethylbenzyl)-2-oxopyrrolidin-3-(S)-yl]amide trifluoroacetate;

Naphthalene-2-sulfonic acid {1-[3-(aminoiminomethyl)benzyl]-2-oxopyrrolidin-3-(S)-yl}methyl amide trifluoroacetate;

Naphthalene-2-sulfonic acid {1-[3-(aminoiminomethyl)benzyl]pyrrolidin-3-(S)-yl}amide bistrifluoroacetate;

7-Methoxynaphthalene-2-sulfonic acid {1-[3-(aminoiminomethyl)benzyl]-2,5-dioxopyrrolidin-3-(S)-yl}amide trifluoroacetate;

Naphthalene-2-sulfonic acid {1-[3-(aminoiminomethyl)benzyl]-2-oxopiperidin-3-yl}amide trifluoroacetate;

7-Methoxynaphthalene-2-sulfonic acid {1-[3-(aminoiminomethyl)benzyl]-2-oxo-azepan-3-(S)-yl}amide trifluoroacetate;

7-Methoxynaphthalene-2-sulfonic acid {1-[3-(aminoiminomethyl)benzyl]-2-oxopyrrolidin-3-(S)-yl}methyl amide trifluoroacetate;

6-Methoxynaphthalene-2-sulfonic acid {1-[3-(aminoiminomethyl)benzyl]-2-oxopyrrolidin-3-(S)-yl}amide trifluoroacetate;

6-Methoxynaphthalene-2-sulfonic acid {1-[3-(aminoiminomethyl)benzyl]-2-oxopyrrolidin-3-(S)-yl}methyl amide trifluoroacetate;

2-[{1-[3-(Aminoiminomethyl)benzyl]-2-oxopyrrolidin-3-(S)-yl}-6-methoxynaphthalene-2-sulfonylamino]-N-phenethylacetamide trifluoroacetate;

9,10-Dioxo-8a,9, 10,10a-tetrahydroanthracene-2-sulfonic acid {1-[3-(aminoiminomethyl)benzyl]-2-oxopyrrolidin-3-(S)-yl}amide trifluoroacetate;

8-Chloro-7-methoxynaphthalene-2-sulfonic acid {1-[3-(aminoiminomethyl)-benzyl]-2-oxopyrrolidin-3-(S)-yl}amide trifluoroacetate;

7-Methoxynaphthalene-2-sulfonic acid {1-[4-(aminoiminomethyl)benzyl]-2-oxopyrrolidin-3-(S)-yl}amide trifluoroacetate;

6,7-Dimethoxynaphthalene-2-sulfonic acid {1-[3-(aminoiminomethyl)benzyl]-2-oxopyrrolidin-3-(S)-yl}amide trifluoroacetate;

Naphtho(2,3-d)-(1,3)dioxole-6-sulfonic acid {1-[3-(aminoiminomethyl)benzyl]-2-oxopyrrolidin-3-(S)-yl}amide trifluoroacetate;

7-Benzyloxynaphthalene-2-sulfonic acid {1-[3-(aminoiminomethyl)benzyl]-2-oxopyrrolidin-3-(S)-yl}amide trifluoroacetate;

7-Hydroxynaphthalene-2-sulfonic acid {1-[3-(aminoiminomethyl)benzyl]-2-oxopyrrolidin-3-(S)-yl}amide trifluoroacetate;

6-Hydroxynaphthalene-2-sulfonic acid {1-[3-(aminoiminomethyl)benzyl]-2-oxopyrrolidin-3-(S)-yl}amide trifluoroacetate;

5-Chloro-3-methylbenzo[b]thiophene-2-sulfonic acid {1-[3-(aminoiminomethyl)benzyl]-2-oxopyrrolidin-3-(S)-yl}amide trifluoroacetate;

5-Chloro-3-methylbenzo[b]thiophene-2-sulfonic acid {1-[3-(aminoiminomethyl)benzyl]-2-oxopyrrolidin-3-(S)-yl}methyl amide trifluoroacetate;

7-Methylnaphthalene-2-sulfonic acid {1-[3-(aminoiminomethyl)benzyl]-2-oxopyrrolidin-3-(S)-yl}amide trifluoroacetate;

7-Ethylnaphthalene-2-sulfonic acid {1-[3-(aminoiminomethyl)benzyl]-2-oxopyrrolidin-3-(S)-yl}amide trifluoroacetate;

5-Chloro-6-aminonaphthalene-2-sulfonic acid {1-[3-aminoiminomethyl)benzyl]-2-oxopyrrolidin-3-(S)-yl}amide bistrifluoroacetate;

7-Methylaminonaphthalene-2-sulfonic acid {1-[3-(aminoiminomethyl)benzyl]-2-oxopyrrolidin-3-(S)-yl}amide bistrifluoroacetate;

2-Methyl-1,2,3,4-tetrahydroisoquinolinyl-7-sulfonic acid {1-[3-(aminoiminomethyl)benzyl]-2-oxopyrrolidin-3-(S)-yl}amide bistrifluoroacetate;

1,2,3,4-Tetrahydroisoquinolinyl-7-sulfonic acid {1-[3-(aminoiminomethyl)benzyl]-2-oxopyrrolidin-3-(S)-yl}methyl amide dihydrochloride;

7-Methoxynaphthalene-2-sulfonic acid {1-[3-(aminoiminomethyl)benzyl]-2-oxopyrrolidin-3-(S)-yl]-(4-nitrobenzyl)amide trifluoroacetate;

7-Methoxynaphthalene-2-sulfonic acid {1-[3-(aminoiminomethyl)benzyl]-2-oxopyrrolidin-3-(S)-yl]-(4-aminobenzyl)amide bistrifluoroacetate;

7-Methoxynaphthalene-2-sulfonic acid {1-[3-(aminoiminomethyl)benzyl]-2-oxopyrrolidin-3-(S)-yl} (3-nitrobenzyl)amide trifluoroacetate;

7-Methoxynaphthalene-2-sulfonic acid {1-[3-(aminoiminomethyl)benzyl]-2-oxopyrrolidin-3-(S)-yl)} (3-aminobenzyl)amide bistrifluoroacetate;

7-Methoxynaphthalene-2-sulfonic acid {1-[3-(aminoiminomethyl)benzyl]-2-oxopyrrolidin-3-(S)-yl}-(2-nitrobenzyl)amide trifluoroacetate;

3-[2-Oxo-3(S)-(2-phenylethenesulfonylamino)pyrrolidin-1-ylmethyl]-benzamidine trifluoroacetate;

3-[2-Oxo-3(S)-(2-phenylethanesulfonylamino)pyrrolidin-1-ylmethyl]-benzamidine trifluoroacetate;

[Imino-(3-{3-[7-Methoxynaphthalene-2-sulfonyl)methylamino]-2-oxo-3(S)-pyrrolidin-1-ylmethyl]phenyl}methyl]carbamic acid ethyl ester;

3-[2-Oxo-3(S)-{2-(pyridin-4-ylamino)-ethanesulfonylamino}-pyrrolidin-1-ylmethyl]-benzamidine bistrifluoroacetate;

2'-Methoxybiphenyl-4-sulfonic acid {1-[3-(aminoiminomethyl)benzyl]-2-oxopyrrolidin-3(S)-yl}amide trifluoroacetate;

5,6,7,8-Tetrahydrophenanthrene-3-sulfonic acid {1-[3-(aminoiminomethyl)benzyl]-2-oxo-3(S)-pyrrolidin-3-yl}amide trifluoroacetate;

Isoquinolinyl-5-sulfonic acid {1-[3-(aminoiminomethyl)benzyl]-2-oxo-3(S)-pyrrolidin-3-yl}amide bistrifluoroacetate;

5-Chlorothiophene-2-sulfonic acid {1-[3-(aminoiminomethyl)benzyl]-2-oxo-3(S)-pyrrolidin-3-yl}amide trifluoroacetate;

2,4-Diaminoquinazoline-6-sulfonic acid {1-[3-(aminoiminomethyl)benzyl]-2-oxo-3(S)-pyrrolidin-3-yl}amide trifluoroacetate;

7-Methoxy-2-naphthalenesulfonic acid {1-[3-(aminoiminomethyl)benzyl]-2-oxo-3(S)-pyrrolidin-3-yl}ethylamide trifluoroacetate;

7-Methoxy-2-napthalenesulfonic acid {1-[3-(aminoiminomethyl)benzyl]-2-oxo-3(S)-pyrrolidin-3-yl}(3-fluorobenzyl)amide trifluoroacetate;

7-Methoxy-2-napthalenesulfonic acid {1-[3-(aminoiminomethyl)benzyl]-2-oxo-3(S)-pyrrolidin-3-yl}(4-methylbenzyl)amide trifluoroacetate;

7-Methoxy-2-napthalenesulfonic acid {1-[3-(aminoiminomethyl)benzyl]-2-oxo-3(S)-pyrrolidin-3-yl}(3-methylbenzyl)amide trifluoroacetate;

7-Methoxy-2-napthalenesulfonic acid {1-[3-(aminoiminomethyl)benzyl]-2-oxo-3(S)-pyrrolidin-3-yl}napthalene-2-ylmethylamide trifluoroacetate;

7-Methoxy-2-napthalenesulfonic acid {1-[3-(aminoiminomethyl)benzyl]-2-oxo-3(S)-pyrrolidin-3-yl}(3-phenylallyl)amide trifluoro acetate;

7-Methoxy-2-napthalenesulfonic acid {1-[3-(aminoiminomethyl)benzyl]-2-oxo-3(S)-pyrrolidin-3-yl}(3-methylbenzyl)amide trifluoroacetate;

7-Methoxy-2-napthalenesulfonic acid {1-[3-(aminoiminomethyl)benzyl]-2-oxo-3(S)-pyrrolidin-3-yl}(2-fluorobenzyl)amide trifluoroacetate;

2-Fluorobiphenyl-4-sulfonic acid {1-[3-(aminoiminomethyl)benzyl]-2-oxo-3(S)-pyrrolidin-3-yl}methylamide trifluoroacetate;

3-[{1-[3-(Aminoiminomethyl)benzyl]-2-oxopyrrolidin-3(S)-3-yl}-(7-methoxynaphthalene-2-sulfonyl)amino]propionamide trifluoroacetate;

2-[{1-[3-(Aminoiminomethyl)benzyl]-2-oxopyrrolidin-3-(S)-yl}naphthalene-2-sulfonylamino]-N-phenethylacetamide trifluoroacetate;

2-[{1-[3-(Aminoiminomethyl)benzyl]-2-oxopyrrolidin-3-(S)-yl}biphenyl-4-sulfonylamino]-N-phenethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-phenethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-ethylacetamide trifluoroacetate;

2-[{1-[3-(Aminoiminomethyl)benzyl]-2-oxopyrrolidin-3-(S)-yl}-7-methoxynaphthalene-2-sulfonylamino]-N,N-dimethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-benzylacetamide trifluoroacetate;

2-[{1-[3-(Aminoiminomethyl)benzyl]-2-oxopyrrolidin-3-(S)-yl}-7-methoxynaphthalene-2-sulfonylamino]-N-(2-p-toluylethyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-(3-phenylpropyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-(4-methylbenzyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-[2-(3-fluorophenyl)ethyl]acetamide trifluoroacetate;

2-[{1-[3-(Aminoiminomethyl)benzyl]-2-oxopyrrolidin-3-(S)-yl}-7-methoxynaphthalene-2-sulfonylamino]-N-indan-2-ylacetamide trifluoroacetate;

2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate;

4,5-Dichlorothiophene-2-sulfonic acid {1-[3-(aminoiminomethyl)benzyl]-2-oxo-3(S)-pyrrolidin-3-yl}amide trifluoroacetate 4,5-Dichlorothiophene-2-sulfonic acid {1-[3-(aminoiminomethyl)benzyl]-2-oxo-3(S)-pyrrolidin-3-yl}-methylamide trifluoroacetate;

4,5-Dichlorothiophene-2-sulfonic acid {1-[3-(aminoiminomethyl)benzyl]-2-oxo-3(S)-pyrrolidin-3-yl}benzylamide trifluoroacetate;

7-Methoxy-2-napthalenesulfonic acid {1-[3-(aminoiminomethyl)benzyl]-2-oxo-3(S)-pyrrolidin-3-yl}-2-cyclopropylphenethylamide trifluoroacetate;

3'-Methyl-biphenyl-4-sulfonic acid {1-[3-(aminoiminomethyl)benzyl]-2-oxopyrrolidin-3(S)-yl}amide trifluoroacetate;

3-[{1-[3-(Aminoiminomethyl)benzyl]-2-oxopyrrolidin-3(S)-3-yl}-(7-methoxynaphthalene-2-sulfonyl)amino]acetamide trifluoroacetate;

3-[{1-[3-(Aminoiminomethyl)benzyl]-2-oxopyrrolidin-3(S)-3-yl}-(7-methoxynaphthalene-2-sulfonyl)amino]-2-methylacetamide trifluoroacetate;

7-Methoxynaphthalene-2-sulfonic acid {1-[3-(aminoiminomethyl)benzyl]-2-oxo-azetidin-3(S)-yl}amide trifluoroacetate;

7-Methoxynaphthalene-2-sulfonic acid {1-[3-(aminoiminomethyl)benzyl]-2-oxo-azetidin-3(S)-yl}benzylamide trifluoroacetate;

5,6,7,8-Tetrahydronaphthalene-2-sulfonic acid {1-[3-(aminoiminomethyl)-benzyl]-2-oxopyrrolidin-3(S)-yl}amide trifluoroacetate;

7-Methoxy-2-napthalenesulfonic acid {1-[3-(aminoiminomethyl)benzyl]-2-oxo-3(S)-pyrrolidin-3-yl}-(2-methoxybenzyl)amide trifluoroacetate;

7-Methoxy-2-napthalenesulfonic acid {1-[3-(aminoiminomethyl)benzyl]-2-oxo-3(S)-pyrrolidin-3-yl}-(3-methoxybenzyl)amide trifluoroacetate;

7-Methoxy-2-napthalenesulfonic acid {1-[3-(aminoiminomethyl)benzyl]-2-oxo-3(S)-pyrrolidin-3-yl}-(4-methoxybenzyl)amide trifluoroacetate;

7-Methoxy-2-napthalenesulfonic acid {1-[3-(aminoiminomethyl)benzyl]-2-oxo-3(S)-pyrrolidin-3-yl}(pyridin-2-ylmethyl)amide trifluoroacetate;

7-Methoxy-2-napthalenesulfonic acid {1-[3-(aminoiminomethyl)benzyl]-2-oxo-3(S)-pyrrolidin-3-yl}(pyridin-3-ylmethyl)amide trifluoroacetate;

7-Methoxy-2-napthalenesulfonic acid {1-[3-(aminoiminomethyl)benzyl]-2-oxo-3(S)-pyrrolidin-3-yl}(pyridin-4-ylmethyl)amide trifluoroacetate;

7-Methoxy-2-napthalenesulfonic acid {1-[3-(aminoiminomethyl)benzyl]-2-oxo-3(S)-pyrrolidin-3-yl}-(1-benzyl-1H-imidazol-2-ylmethyl)amide trifluoroacetate;

(1-Methyl-1H-imidazol-2-yl)benzene-4-sulfonic acid {1-[3-(aminoiminomethyl)benzyl]-2-oxopyrrolidin-3(S)-yl}amide trifluoroacetate;

7-Methoxy-2-napthalenesulfonic acid {1-[3-(aminoiminomethyl)benzyl]-2-oxo-3(S)-pyrrolidin-3-yl}-(3-hydroxybenzyl)amide trifluoroacetate;

7-Methoxy-2-napthalenesulfonic acid {1-[3-(aminoiminomethyl)benzyl]-2-oxo-3(S)-pyrrolidin-3-yl}-(2-hydroxybenzyl)amide trifluoroacetate;

7-Methoxy-2-napthalenesulfonic acid {1-[3-(aminoiminomethyl)benzyl]-2-oxo-3(S)-pyrrolidin-3-yl}(pyrazol-3-ylmethyl)amide trifluoroacetate;

Quinoline-6-sulfonic acid {1-[3-(aminoiminomethyl)benzyl]-2-oxopyrrolidin-3-(S)-yl}amide trifluoroacetate;

4-Pyridin-4-ylbenzene sulfonic acid {1-[3-(aminoiminomethyl)benzyl]-2-oxopyrrolidin-3(S)-yl}amide bistrifluoroacetate;

7-Methoxy-2-napthalenesulfonic acid {1-[3-(aminoiminomethyl)benzyl]-2-oxo-3(S)-pyrrolidin-3-yl}(thiophene-2-ylmethyl)amide trifluoroacetate;

4-Pyridin-3-ylbenzene sulfonic acid {1-[3-(aminoiminomethyl)benzyl]-2-oxopyrrolidin-3(S)-yl}amide bistrifluoroacetate;

N-Methylpyrid-4-ylphenyl-4-sulfonic acid {1-[3-(aminoiminomethyl)benzyl]-2-oxopyrrolidin-3(S)-yl}amide trifluoroacetate;

2-Methoxyquinoline-7-sulfonic acid {1-[3-(aminoiminomethyl)benzyl]-2-oxopyrrolidin-3-(S)-yl}amide trifluoroacetate;

4-(6-Methoxypyridin-2-yl)benzene-4-sulfonic acid {1-[3-(aminoiminomethyl)benzyl]-2-oxopyrrolidin-3(S)-yl}amide bistrifluoroacetate;

4-(3-Chloropyridin-2-yloxy)benzene-4-sulfonic acid {1-[3-(aminoiminomethyl)benzyl]-2-oxopyrrolidin-3(S)-yl}amide trifluoroacetate;

4-(N-Oxidopyridin-3-yl)benzene-4-sulfonic acid {1-[3-(aminoiminomethyl)benzyl]-2-oxopyrrolidin-3(S)-yl}amide trifluoroacetate;

4-Phenoxybenzene-4-sulfonic acid {1-[3-(aminoiminomethyl)benzyl]-2-oxopyrrolidin-3(S)-yl}amide trifluoroacetate;

7-Methoxy-2-napthalenesulfonic acid {1-[3-(aminoiminomethyl)benzyl]-2-oxo-3(S)-pyrrolidin-3-yl}(thiophen-3-ylmethyl)amide trifluoroacetate;

6-Methoxynaphthalene-2-sulfonic acid {1-[3-(methoxyaminoiminomethyl)-benzyl]-2-oxopyrrolidin-3-(S)-yl}methyl amide trifluoroacetate;

6-Methoxynaphthalene-2-sulfonic acid {1-[3-(cyanoaminoiminomethyl)benzyl]-2-oxopyrrolidin-3-(S)-yl}methylamide trifluoroacetate;

6-Methoxynaphthalene-2-sulfonic acid {1-[3-(hydroxyaminoiminomethyl)-benzyl]-2-oxopyrrolidin-3-(S)-yl}-methylamide trifluoroacetate;

4-Amino-3-[3-(S)-(7-methoxynaphthalene-2-sulfonylamino)-2-oxopyrrolidin-1-yl-methyl]benzamidine dihydrochloride;

4-Amino-3-[3-(S)-(7-methoxynaphthalene-2-sulfonylmethylamino)-2-oxopyrrolidin-1-yl-methyl]benzamidine trifluoroacetate;

N-(4-Carbamimidoyl-2-{3-[(7-methoxynaphthalene-2-sulfonyl)methylamino]-2-oxopyrrolidin-1-(S)-ylmethyl}phenyl)acetamide trifluroacetate;

4-Amino-3-[3-(S)-(4-tert-butylbenzenesulfonylamino)-2-oxopyrrolidin-1-yl-methyl]benzamidine trifluoroacetate;

3-Amino-5-[3-(S)-(7-methoxynaphthalene-2-sulfonylamino)-2-oxopyrrolidin-1-yl-methyl]benzamidine bistrifluoroacetate;

{4-(Aminoiminomethyl)-2-[3-(7-methoxynaphthalene-2-sulfonylamino)-2-oxopyrrolidin-1-ylmethyl]phenoxy}acetic acid methyl ester trifluoroacetate;

{4-(Aminoiminomethyl)-2-[3-(7-methoxynaphthalene-2-sulfonylamino)-2-oxopyrrolidin-1-ylmethyl]phenoxy}acetic acid trifluoroacetate;

2-Chloro-6-nitrophenoxybenzene sulfonic acid {1-[3-(aminoiminomethyl)benzyl]-2-oxopyrrolidin-3(S)-yl}amide trifluoroacetate;

4-[3-(S)-(7-Methoxynaphthalene-2-sulfonylamino)-2-oxopyrrolidin-1-ylmethyl]-thiophene-2-carboxamidine trifluoroacetate;

4-{3-(S)-[(7-Methoxynaphthalene-2-sulfonyl)methylamino]-2-oxopyrrolidin-1-ylmethyl}thiophene-2-carboxamidine trifluoroacetate;

2-[[1-(5-Carbamimidoylthiophene-3-ylmethyl)-2-oxopyrrolidin-3-(S)-yl](7-methoxynaphthalene-2-sulfonyl)amino]acetamide trifluoroacetate;

4-{3-(S)-[(7-Methoxynaphthalene-2-sulfonyl)benzylamino]-2-oxopyrrolidin-1-ylmethyl}thiophene-2-carboxamidine trifluoroacetate;

4-[3-(S)-(5-Chloro-3-methylbenzo[b]thiophene-2-sulfonylamino)-2-oxo-pyrrolidin-1-ylmethyl]thiophene-2-carboxamidine trifluoroacetate;

5-{3-(S)-[(7-Methoxynaphthalene-2-sulfonyl)methylamino]-2-oxopyrrolidin-1-ylmethyl}thiophene-3-carboxamidine trifluoroacetate;

4-{3-(S)-[(5-Chloro-3-methylbenzo[b]thiophene-2-sulfonyl)benzylamino]-2-oxopyrrolidin-1-ylmethyl}thiophene-2-carboxamidine trifluoroacetate;

4-{3-(S)-[(Methanesulfonyl)-(3-phenylpropyl)amino]-2-oxopyrrolidin-1-ylmethyl}thiophene-2-carboxamidine trifluoroacetate;

4-{3-(S)-[(Methanesulfonyl)(naphthalene-2-yl)amino]-2-oxopyrrolidin-1-ylmethyl}thiophene-2-carboxamidine trifluoroacetate;

4-{3-(S)-[(4,5-Dichlorothiophene-2-sulfonyl)benzylamino]-2-oxopyrrolidin-1-ylmethyl}thiophene-2-carboxamidine trifluoroacetate;

4-{3-(S)-[(5-Chloro-3-methylbenzo[b]thiophene-2-sulfonyl)methylamino]-2-oxopyrrolidin-1-ylmethyl}thiophene-2-carboxamidine trifluoroacetate;

2-[[1-(5-Carbamimidoylthiophene-3-ylmethyl)-2-oxopyrrolidin-3-(S)-yl]-(7-methoxynaphthalene-2-sulfonyl)amino]-N-phenethylacetamide trifluoroacetate;

2-[[1-(5-Carbaiminidoylthiophene-3-ylmethyl)-2-oxopyrrolidin-3-(S)-yl]-(4,5-dichlorothiophene-2-sulfonyl)amino]-N-benzylacetamide trifluoroacetate;

2-[[1-(5-Carbamimidoylthiophene-3-ylmethyl)-2-oxopyrrolidin-3-(S)-yl]-(7-methoxynaphthalene-2-sulfonyl)amino]-N-benzylacetamide trifluoroacetate;

2-[[1-(4-Carbamimidoylthiophene-2-ylmethyl)-2-oxopyrrolidin-3-(S)-yl]-(7-methoxynaphthalene-2-sulfonyl)amino]acetamide trifluoroacetate;

2-[[1-(4-Carbamimidoylthiophene-2-ylmethyl)-2-oxopyrrolidin-3-(S)-yl]-(5-chloro-3-methylbenzo[b]thiophene-2-sulfonyl)amino]acetic acid methyl ester;

4-{3-(S)-[(7-Aminonaphthalene-2-sulfonyl)benzylamino]-2-oxopyrrolidin-1-ylmethyl}thiophene-2-carboxamidine bistrifluoroacetate;

4-{3-(S)-[(7-Aminonaphthalene-2-sulfonyl)methylamino]-2-oxopyrrolidin-1-ylmethyl}thiophene-2-carboxamidine bistrifluoroacetate;
2-[[1-(5-Carbamimidoylthiophene-3-ylmethyl)-2-oxopyrrolidin-3-(S)-yl]-(7-aminonaphthalene-2-sulfonyl)amino]acetamide bistrifluoroacetate;
4-[3-(S)-(6-Amino-5-chloro-2-sulfonylamino)-2-oxopyrrolidin-1-ylmethyl]-thiophene-2-carboxamidine trifluoroacetate;
4-{3-(S)-[(6-Amino-5-chloro-naphthalene-2-sulfonyl)methylamino]-2-oxopyrrolidin-1-ylmethyl}thiophene-2-carboxamidine trifluoroacetate;
2-[[1-(5-Carbamimidoylthiophene-3-ylmethyl)-2-oxopyrrolidin-3-(S)-yl]-(6-amino-5-chloronaphthalene-2-sulfonyl)amino]acetamide trifluoroacetate;
4-[3-(S)-(6-Aminonaphthalene-2-sulfonylamino)-2-oxopyrrolidin-1-ylmethyl]-thiophene-2-carboxamidine dihydrochloride;
5-[3-(S)-(7-Methoxynaphthalene-2-sulfonylamino)-2-oxopyrrolidin-1-ylmethyl]-thiophene-2-carboxamidine trifluoroacetate;
5-{3-(S)-[(7-Methoxynaphthalene-2-sulfonyl)methylamino]-2-oxopyrrolidin-1-ylmethyl}thiophene-2-carboxamidine trifluoroacetate;
5-{3-(S)-[(7-Methoxynaphthalene-2-sulfonyl)benzylamino]-2-oxopyrrolidin-1-ylmethyl}thiophene-2-carboxamidine trifluoroacetate;
[Amino-(4-{3-(S)-(7-methoxynaphthalene-2-sulfonyl)methylamino]-2-oxopyrrolidin-1-ylmethyl}thiophene-2-yl)methylene]carbamic acid methyl ester trifluoroacetate;
4-{3-(S)-[(7-Methoxynaphthalene-2-sulfonyl)methylamino]-2-oxopyrrolidin-1-ylmethyl}thiophene-2-N-hydroxycarboxamidine trifluoroacetate;
4-[3-(S)-(7-Methoxynaphthalene-2-sulfonylamino)-2-oxopyrrolidin-1-ylmethyl]-pyridine-2-carboxamidine trifluoroacetate;
4-{3-(S)-[(7-Methoxynaphthalene-2-sulfonyl)benzylamino]-2-oxopyrrolidin-1-ylmethyl}pyridine-2-carboxamidine trifluoroacetate;
4-{3-(S)-[(7-Methoxynaphthalene-2-sulfonyl)methylamino]-2-oxopyrrolidin-1-ylmethyl}pyridine-2-carboxamidine trifluoroacetate;
4-[3-(S)-(5-Chloro-3-methylbenzo[b]thiophene-2-sulfonylamino)-2-oxopyrrolidin-1-ylmethyl]pyridine-2-carboxamidine trifluoroacetate;
4-{3-(S)-[(5-Chloro-3-methylbenzo[b]thiophene-2-sulfonyl)methylamino]-2-oxopyrrolidin-1-ylmethyl}pyridine-2-carboxamidine trifluoroacetate;
2-{[1-(2-Carbamimidoylpyridine-4-ylmethyl)-2-oxopyrrolidin-3-(S)-yl]-(7-methoxynaphthalene-2-sulfonyl)amino}acetamide trifluoroacetate;
2-{[1-(2-Carbamimidoyl-pyridine-4-ylmethyl)-2-oxopyrrolidin-3-(S)-yl]-(7-methoxynaphthalene-2-sulfonyl)amino}-N-phenethylacetamide trifluoroacetate;
4-{3-(S)-[(7-Methoxynaphthalene-2-sulfonyl)-thiophen-3-ylmethylamino]-2-oxopyrrolidin-1-ylmethyl}pyridine-2-carboxamidine trifluoroacetate;
4-{3-(S)-[(7-Methoxynaphthalene-2-sulfonyl)thiophen-3-ylmethylamino]-2-oxopyrrolidin-1-ylmethyl}thiophene-2-carboxamidine trifluoroacetate;
4-{3-(S)-[(4-(6-Nitro-2-chlorophenoxy)benzenesulfonyl)amino]-2-oxopyrrolidin-1-ylmethyl}thiophene-2-carboxamidine trifluoroacetate;
5-{3-(S)-[(7-Methoxynaphthalene-2-sulfonylamino]-2-oxopyrrolidin-1-ylmethyl}-furan-2-carboxamidine trifluoroacetate; and
4-[3-(S)-(5-Chloro-3-methylbenzo[b]thiophene-2-sulfonylamino)-2-oxopyrrolidin-1-ylmethyl]furan-2-carboxamidine trifluoroacetate.

Preferred compounds the group consisting essentially of include:
7-Methoxynaphthalene-2-sulfonic acid {1-[3-(aminoiminomethyl)benzyl]-2-oxopyrrolidin-3-(S)-yl}methyl amide trifluoroacetate;
3'-Methoxy-biphenyl-4-sulfonic acid {1-[3-(aminoiminomethyl)benzyl]-2-oxopyrrolidin-3-(S)-yl}amide trifluoroacetate;
5-Pyrid-2-ylthiophene-2-sulfonic acid {1-[3-(aminoiminomethyl)benzyl]-2-oxopyrrolidin-3-(S)-yl}amide trifluoroacetate;
7-Methoxynaphthalene-2-sulfonic acid {1-[3-(aminoiminomethyl)benzyl]-2-oxopyrrolidin-3-(S)-yl}amide trifluoroacetate;
7-Aminonaphthalene-2-sulfonic acid {1-[3-(aminoiminomethyl)benzyl]-2-oxopyrrolidin-3-(S)-yl}amide bistrifluoroacetate;
5-Chloro-3-methylbenzo[b]thiophene-2-sulfonic acid {1-[3-(aminoiminomethyl)benzyl]-2-oxopyrrolidin-3-(S)-yl}amide trifluoroacetate;
2-[{1-[3-(Aminoiminomethyl)benzyl]-2-oxopyrrolidin-3-(S)-yl}-7-methoxynaphthalene-2-sulfonylamino]-N-phenethylacetamide trifluoroacetate;
2-[{1-[3-(Aminoiminomethyl)benzyl]-2-oxopyrrolidin-3-(S)-yl}-7-methoxynaphthalene-2-sulfonylamino]-N-benzylacetamide trifluoroacetate;
2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate;
4,5-Dichlorothiophene-2-sulfonic acid {1-[3-(aminoiminomethyl)benzyl]-2-oxo-3(S)-pyrrolidin-3-yl}amide trifluoroacetate;
3'-Methyl-biphenyl-4-sulfonic acid {1-[3-(aminoiminomethyl)benzyl]-2-oxopyrrolidin-3(S)-yl}amide trifluoroacetate;
3-[{1-[3-(Aminoiminomethyl)benzyl]-2-oxopyrrolidin-3(S)-3-yl}-(7-methoxynaphthalene-2-sulfonyl)amino]acetamide trifluoroacetate;
7-Methoxy-2-napthalenesulfonic acid {1-[3-(aminoiminomethyl)benzyl]-2-oxo-3(S)-pyrrolidin-3-yl}(pyridin-2-ylmethyl)amide trifluoroacetate;
Quinoline-6-sulfonic acid {1-[3-(aminoiminomethyl)benzyl]-2-oxopyrrolidin-3-(S)-yl}amide trifluoroacetate;
4-Amino-3-[3-(S)-(7-methoxynaphthalene-2-sulfonylamino)-2-oxopyrrolidin-1-yl-methyl]benzamidine dihydrochloride;
4-Amino-3-[3-(S)-(7-methoxynaphthalene-2-sulfonyl-methylamino)-2-oxopyrrolidin-1-yl-methyl]benzamidine trifluoroacetate;
4-Amino-3-[3-(S)-(4-tert-butylbenzenesulfonylamino)-2-oxopyrrolidin-1-yl-methyl]benzamidine trifluoroacetate;
{4-(Aminoiminomethyl)-2-[3-(7-methoxynaphthalene-2-sulfonylamino)-2-oxopyrrolidin-1-ylmethyl]phenoxy}acetic acid methyl ester trifluoroacetate;
4-[3-(S)-(7-Methoxynaphthalene-2-sulfonylamino)-2-oxopyrrolidin-1-ylmethyl]-thiophene-2-carboxamidine trifluoroacetate;
4-{3-(S)-[(7-Methoxynaphthalene-2-sulfonyl)methylamino]-2-oxopyrrolidin-1-ylmethyl}thiophene-2-carboxamidine trifluoroacetate;
2-[[1 -(5-Carbaiminidoylthiophene-3-ylmethyl)-2-oxopyrrolidin-3-(S)-yl](7-methoxynaphthalene-2-sulfonyl)amino]acetamide trifluoroacetate;
4-[3-(S)-(5-Chloro-3-methylbenzo[b]thiophene-2-sulfonylamino)-2-oxo-pyrrolidin-1-ylmethyl]thiophene-2-carboxamidine trifluoroacetate;
4-{3-(S)-[(5-Chloro-3-methylbenzo[b]thiophene-2-sulfonyl)methylamino]-2-oxopyrrolidin-1-ylmethyl}thiophene-2-carboxamidine trifluoroacetate;

2-[[1-(5-Carbamimidoylthiophene-3-ylmethyl)-2-oxopyrrolidin-3-(S)-yl]-(7-methoxynaphthalene-2-sulfonyl)amino]-N-phenethylacetamide trifluoroacetate;

[Amino-(4-{3-(S)-(7-methoxynaphthalene-2-sulfonyl)methylamino]-2-oxopyrrolidin-1-ylmethyl}thiophene-2-yl)methylene]carbamic acid methyl ester trifluoroacetate;

4-{3-(S)-[(6-Amino-5-chloro-naphthalene-2-sulfonyl)methylamino]-2-oxopyrrolidin-1-ylmethyl}thiophene-2-carboxamidine trifluoroacetate;

4-[3-(S)-(6-Amino-5-chloro-2-sulfonylamino)-2-oxopyrrolidin-1-ylmethyl]-thiophene-2-carboxamidine trifluoroacetate;

4-{3-(S)-[(7-Aminonaphthalene-2-sulfonyl)benzylamino]-2-oxopyrrolidin-1-ylmethyl}thiophene-2-carboxamidine bistrifluoroacetate;

4-[3-(S)-(7-Methoxynaphthalene-2-sulfonylamino)-2-oxopyrrolidin-1-ylmethyl]-pyridine-2-carboxamidine trifluoroacetate;

4-{3-(S)-[(7-Methoxynaphthalene-2-sulfonyl)benzylamino]-2-oxopyrrolidin-1-ylmethyl}pyridine-2-carboxamidine trifluoroacetate;

2-{[1-(2-Carbamimidoyl-pyridine-4-ylmethyl)-2-oxopyrrolidin-3-(S)-yl]-(7-methoxynaphthalene-2-sulfonyl)amino}-N-phenethylacetamide trifluoroacetate;

4-{3-(S)-[(7-Methoxynaphthalene-2-sulfonyl)thiophen-3-ylmethylamino]-2-oxopyrrolidin-1-ylmethyl}thiophene-2-carboxamidine trifluoroacetate; and 4-{3-(S)-[(4-(6-Nitro-2-chlorophenoxy)benzenesulfonyl)amino]-2-oxopyrrolidin-1-ylmethyl}thiophene-2-carboxamidine trifluoroacetate.

Compounds of formula I may be prepared by the application or adaptation of known methods, by which is meant methods used heretofore or described in the literature.

A preparative embodiment according to the invention for preparing a compound of formula I

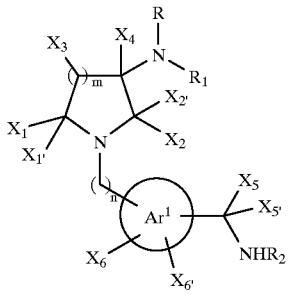

(I)

wherein $Ar^1$, R, $R_1$, $R_2$, $X_3$, $X_4$, $X_5$, $X_{5'}$, $X_6$, $X_{6'}$, m and n are as defined above, and $X_1$ and $X_{1'}$ are hydrogen and $X_2$ and $X_{2'}$, taken together are oxo, may be prepared by reacting a compound of formula II

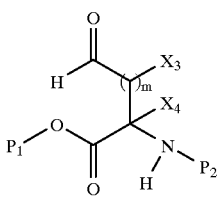

(II)

wherein $X_3$, $X_4$ and m are as defined above, and $P_1$ is alkyl, aralkyl, or aryl, and $P_2$ is (alkyl, aralkyl, or aryl)carbamate, by reductive amination using a cyano(phenyl or heteroaryl)alkylamine of formula III

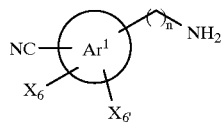

(III)

wherein $Ar^1$, $X_6$, $X_{6'}$ and n are as defined above, in an alcoholic solvent such as methanol and an imine reducing reagent such as sodium cyanoborohydride, sodium triacetoxyborohydride or catalytic hydrogenation using for example palladium at a temperature from about 0° C. to about 100° C. to give the cyclic structure represented by formula IV.

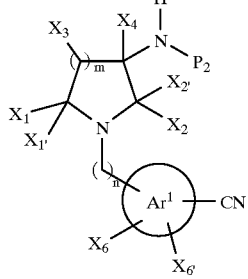

(IV)

wherein $Ar^1$, $X_3$, $X_4$, $X_6$, $X_{6'}$, m and n are as defined above, and $X_1$ and $X_{1'}$ are hydrogen, $X_2$ and $X_{2'}$, taken together are oxo, and $P_2$ is (alkyl, aralkyl, or aryl)carbamate. The $P_2$ group is then removed by the appropriate deblocking procedures known for carbamates such as strong acid, strong base or catalytic hydrogenation to give compounds of formula V.

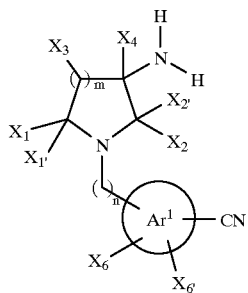

(V)

wherein $Ar^1$, $X_3$, $X_4$, $X_6$, $X_{6'}$, m and n are as defined above, and $X_1$ and $X_{1'}$ are hydrogen, and $X_2$ and $X_{2'}$, taken together are oxo. The amine of the compound of formula V is then coupled to any of the groups represented by formulae VIa or VIb $R_3S(O)_p$Halo (VIa)

or $R_3R_4NS(O)_p$Halo; (VIb)

where $R_3$, $R_4$, and p are as defined above, and Halo is a halogen atom such as chloro, using a base such as a trialkylamine in an inert solvent such as dichloromethane, tetrahydrofuran, ether or acetonitrile at temperatures from about 0° C. to about 100° C. in the presence or absence of an activating agent such as dimethyl aminopyridine (DMAP) to give compounds of formulae VIIa or VIIb.

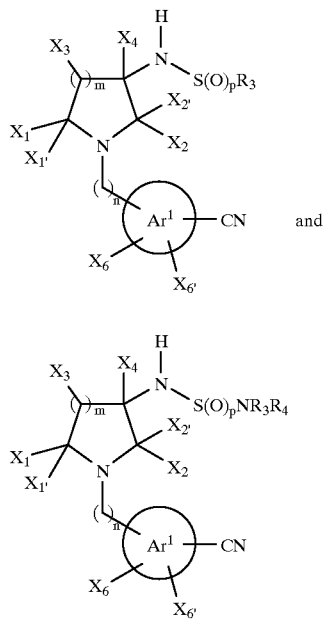

(VIIa)

(VIIb)

wherein $Ar^1$, $R_3$, $R_4$, $X_3$, $X_4$, $X_6$, $X_{6'}$, m, n and p are as defined above, and $X_1$ and $X_{1'}$ are hydrogen, $X_2$ and $X_{2'}$, taken together are oxo. Compounds represented by formulae VIIa or VIIb may be converted to the corresponding imidate ester by the use of an alcoholic solvent such as ethanol saturated with hydrogen chloride (gas). The resulting product is then dissolved in an alcoholic solvent such as methanol saturated with ammonia to give compounds of formula I, wherein $X_5$ and $X_{5'}$ taken together are =NH. Alternatively, compounds of formula VII can be dissolved in a solution of pyridine containing a tertiary amine base such as triethyl amine saturated with hydrogen sulfide at a temperature from about 0° C. to about 60° C. The resulting product is then dissolved in an organic solvent such as acetone and reacted with an alkyl halide such as methyl iodide at a temperature 0° C. to about 80° C. The resulting product is then dissolved in an alcoholic solvent such as methanol and reacted with ammonium acetate to give compounds of formula I, wherein $X_5$ and $X_{5'}$ taken together are =NH.

When $X_1$ and $X_{1'}$ are O, and $X_2$ and $X_{2'}$, are independently selected from hydrogen, optionally substituted alkyl, optionally substituted aryl, optionally substituted aralkyl, optionally substituted heteroaryl, optionally substituted heteroaralkyl or hydroxyalkyl, compounds of formula I may be prepared starting with may be prepared by reacting a compound of formula VIII

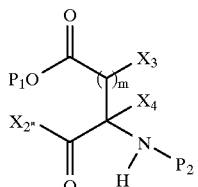

(VIII)

wherein $X_3$, $X_4$ and m are as defined above, $X_{2''}$ is hydrogen, optionally substituted alkyl, optionally substituted aryl, optionally substituted aralkyl, optionally substituted heteroaryl, optionally substituted heteroaralkyl, carboxyalkyl, alkoxycarbonylalkyl or hydroxyalkyl, and $P_1$ is alkyl, aralkyl, or aryl, and $P_2$ is (alkyl, aralkyl, or aryl)carbamate, with a compound of formula III as defined above in an analogous fashion to the reaction of the compound of formula II with a compound of formula III. The product of the reaction of compounds of formulae VIII and III yields a compound of formula IV wherein $Ar^1$, $X_3$, $X_4$, $X_6$, $X_{6'}$, m and n are as defined above, and $X_1$ and $X_{1'}$ taken together are oxo, one $X_2$ and $X_{2'}$, is hydrogen and the other of $X_2$ and $X_{2'}$ is hydrogen, optionally substituted alkyl, optionally substituted aryl, optionally substituted aralkyl, optionally substituted heteroaryl, optionally substituted heteroaralkyl or hydroxyalkyl, and $P_2$ is an (alkyl, aralkyl or aryl)carbamate. That compound of formula IV may then be converted to a compound of formula V and then on to compounds of formulae VIIa and VIIb wherein $Ar^1$, $R_3$, $R_4$, $X_3$, $X_4$, $X_6$, $X_{6'}$, m, n and p are as defined above, and $X_1$ and $X_{1'}$ are oxo, and one $X_2$ and $X_{2'}$, is hydrogen and the other of $X_2$ and $X_{2'}$ is hydrogen, optionally substituted alkyl, optionally substituted aryl, optionally substituted aralkyl, optionally substituted heteroaryl, optionally substituted heteroaralkyl, or hydroxyalkyl in an analogous procedure to that given for the conversion of a compound of formula IV to a compound of formula V which is then converted to compounds of formulae VIIa or VIIIb.

Alternatively, compounds of formula V and formula IV may be converted to a compounds of formula I as follows. Compounds of formulae IV or V are treated with an alcoholic solvent such as ethanol saturated with HCl. The resulting product is then treated with an alcoholic solvent such as methanol saturated with ammonia to give respectively a compound of formula IX or X

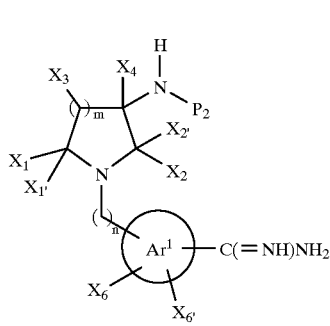

(IX)

-continued

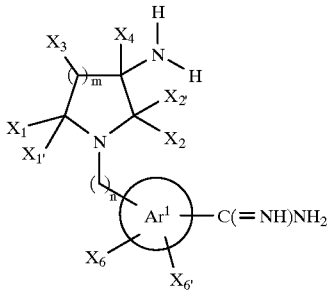
(X)

wherein $Ar^1$, $X_1$, $X_{1'}$, $X_2$, $X_{2'}$, $X_3$, $X_4$, $X_6$, $X_{6'}$, $P_2$, m and n are as defined above. A compound of formula IX may then be converted to a compound of formula X by an appropriate deblocking procedure described above. A compound of formula X may then be dissolved in an organic solvent such as ethanol or dimethylformamide and compounds of formulae VIa or VIb are added at a temperature from about 0° C. to about 100° C. in the presence or absence of an activating reagent such as DMAP with a sulfonylchloride to give compounds represented by formula I.

Alternatively a compound of formula I may be prepared starting with a compound of formula XI.

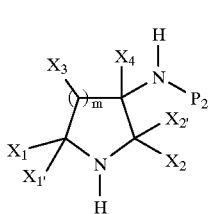
(XI)

wherein $X_1$, $X_{1'}$, X, $X_{2'}$, $X_3$, $X_4$, $X_6$, $X_{6'}$, m and $P_2$ are as defined above. A compound of formula XI is dissolved in an inert organic solvent such as tetrahydrofuran at a temperature from about −78° C. to about 25° C. To that solution is added a strong base such as sodium hydride, lithium hexamethyldisilylazide, or lithium diisopropyl amine, followed by the addition of a compound of formula XII

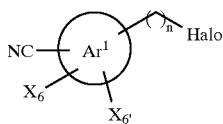
(XII)

wherein $X_6$, $X_{6'}$ and n are as defined above, and halo is a halogen atom such as chloro bromo or iodo to give a compound of formula IV which is then converted to a compound of formula I as described above.

A compound of formula I in which R is other than hydrogen may be prepared starting with compounds of formulae VIIa or VIIb. Compounds of formulae VIIa or VIIb may be dissolved in an inert organic solvent such as tetrahydrofuran, dioxane, or dimethyl formamide at a temperature of about 0° C. to about 100° C. To the resulting solution is added a base such as sodium hydride or potassium carbonate and a compound of formula XIII.

R—Halo
XIII wherein R is as defined above except for hydrogen and halo is a halogen such as chloro or bromo. The product of this preparation is a compound of formula XIV.

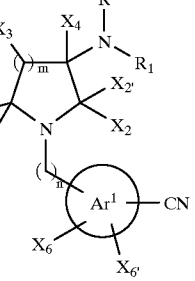
(XIV)

wherein $R_1$, $X_1$, $X_{1'}$, X, $X_{2'}$, $X_3$, $X_4$, $X_6$, $X_{6'}$, m and n are as defined above, and R is optionally substituted alkyl, optionally substituted aralkyl, optionally substituted heteroaralkyl or hydroxyalkyl. A compounds of formula XIV is then converted to a compound of formula I as described above, that contains a —C(═NH)NH$_2$ moiety.

Alternatively, a compound of formula XIV may be treated with an alcoholic solvent such as ethanol saturated with HCl. The resulting product is then treated with an alcoholic solvent such as methanol saturated with an alkylamine, hydrazine or alkoxyamine to give a compound of formula I wherein R, $R_1$, $X_2$, $X_{2'}$, $X_3$, $X_4$, $X_6$, $X_{6'}$, m and n are as defined above, $X_5$ and $X_{5'}$ taken together are ═NR$_5$; $R_2$ and $R_5$ are independently hydrogen or alkyl, or when one of $R_2$ or $R_5$ is hydrogen, then the of $R_2$ or $R_5$ may be alkoxy or amino. A compound of the formula I wherein $X_5$ and $X_{5'}$ taken together are ═NR$_5$ and $R_5$ is nitro may be prepared by standard nitrating reactions on a compound of formula I wherein $X_5$ and $X_{5'}$ taken together are ═NR$_5$ and $R_5$ is hydrogen.

A compounds of formula I wherein $X_5$ and $X_{5'}$ taken together are ═NR$_5$ and $R_5$ is $R_6O_2C$, $R_6CO$ or cyano may be prepared from compounds of formula I wherein $X_5$ and $X_{5'}$ taken together are ═NR$_5$ wherein $R_5$ is hydrogen. For example, the amidine species is treated with an alkyl chloroformate in an appropriate solvent such as methylene chloride or dimethyl formamide in the presence of a base such as a trialkylamine to give a compound of formula I wherein $R_5$ is $R_6O_2C$. Similarly, the amidine may be treated with an acylating species such as an acyl chloride in the presence of a base such as trialkylamine to give compounds of formula I wherein $R_5$ is $R_6OC$. Alternatively, compounds wherein $R_5$ is cyano may be prepared by treatment of the amidine with cyanogen bromide and a trialkyl amine in an appropriate an alcoholic solvent.

A compound of formula I wherein $X_5$ and $X_{5'}$ are hydrogen may be prepared by reduction of compounds of formulae VIIa, VIIb or XIV using hydrogenation in an appropriate solvent such as methanol in the presence of a catalyst such as rhodium on alumina. This transformation may also be achieved using a hydride reagent such as diisobutyl aluminum hydride to give a compound of formula I wherein $X_5$ and $X_{5'}$ are hydrogen.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on the activity of Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be regenerated from the acid addition salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on the activity of Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Salt forms according to invention also include compounds having a quarternarized nitrogen. The quarternarized salts are formed by methods such as by alkylation of a $Sp^3$ or $sp^2$ hybridized nitrogen in the compounds.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

Compounds of the present invention may contain asymmetric centers. These asymmetric centers may independently be in either the R or S configuration. It will also be apparent to those skilled in the art that certain compounds of formula I may exhibit geometrical isomerism. Geometrical isomers include the cis and trans forms of compounds of the invention having alkenyl or diazenyl (azo) moieties. The present invention comprises the individual geometrical isomers and stereoisomers and mixtures thereof.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

The present invention is further exemplified but not limited by the following examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad, bs=broad singlet, q=quartet, AB=AB pattern.

EXAMPLE 1

Naphthalene-2-sulfonic acid {1-[3-(aminoiminomethyl)benzyl]-2-oxopyrrolidin-3-(S)-yl}amide trifluoroacetate.

A. Boc-L-Asp(H)-OBn.

Boc-L-Asp-OBn (15 g, 46.4 mmol) is dissolved in 50 mL of THF and cooled to −10° C. The solution is treated with N-methylmorpholine (4.9 g, 48.7 mmol) and stirred for 5 minutes. To the solution is added dropwise isobutyl chloroformate (6.3 g, 46.4 mmol). After the addition is completed, the solution is stirred for 1 minute, then filtered through a pad of Celite. The collected solution is cooled to −10° C. To the solution is added sodium borohydride (2.63 g, 70 mmol) predissolved in 50 mL of water. The solution is stirred for 2 minutes. The solution is poured into a separatory funnel and diluted with 800 mL of EtOAc. The organic layer is washed with water and saturated NaCl. The organic layer is dried over $MgSO_4$, filtered and concentrated. The resulting residue is added to a solution of oxalyl chloride (30 mL of a 2 M solution in $CH_2Cl_2$, 60 mmol), and methyl sulfoxide (7.25 g, 92.8 mmol) in 250 mL of $CH_2Cl_2$ at −78° C. The reaction mixture is stirred at −78° C. for 40 minutes, then triethylamine (14 g, 140 mmol) is added. The reaction mixture is stirred at −78° C. for 1 hour and then is stirred at room temperature for 30 minutes. The solution is poured into 200 mL of a 20% citric acid/water solution. The resulting mixture is poured into a separatory funnel and the layers are separated. The organic layer is washed with water and saturated NaCl. The organic layer is dried over $MgSO_4$, filtered and concentrated. The residue is purified by column chromatography eluting with a gradient of 10% EtOAc/hexanes to 30% EtOAc/hexanes. The product aldehyde (12 g, 39 mmol) is obtained as an oil.

$^1$H NMR ($CDCl_3$, 300 MHz) δ9.68 (s, 1 H), 7.32 (m, 4 H), 5.42 (bs, 1 H), 5.16 (s, 2 H), 4.62 (m, 3 H), 3.05 (ddd, 2 H), 1.40 (s, 9 H).

B. [1-(3-Cyanobenzyl)-2-oxopyrrolidin-3-(S)-yl]carbamic acid tert-butyl ester.

To a solution of Boc-L-Asp(H)-OBn (13.5 g, 44 mmol) dissolved in 75 mL of methanol is added m-cyanobenzylamine hydrochloride (7.4 g, 44 mmol) and triethylamine (4.7 g, 46 mmol). The solution is stirred for 30 minutes. After this time, a solution of sodium cyanoborohydride (3 g, 48.4 mmol) and zinc chloride (3.3 g, 24.2 mmol) in 30 mL of MeOH is added. The mixture is stirred for an additional 2 hours. After this time, 20 mL of 1 N NaOH and 100 mL of water is added, and the resulting mixture is concentrated. The residue is treated with 100 mL of water and 800 mL of EtOAc. The solution is filtered through a pad of Celite, poured into a separatory funnel and the layers are separated. The organic layer is washed with 1 N HCl, 10% $Na_2CO_3$ and saturated NaCl. The organic layer is dried over $MgSO_4$, filtered and concentrated. The residue is purified by column chromatography eluting with a gradient of 20% EtOAc/$CH_2Cl_2$ to 40% EtOAc/$CH_2Cl_2$ to give the title compound (9.1 g, 29 mmol) as a white solid.

$^1$H NMR ($CDCl_3$, 300 MHz) δ7.55 (m, 4 H), 5.18 (bs, 1 H), 4.47 (AB, 2 H), 4.18 (dd, 1 H), 3.21 (m, 2 H), 2.60 (m, 1 H), 1.88 (m, 1 H), 1.42 (s, 9 H).

C. 3-(3-(S)-Amino-2-oxopyrrolidin-1-ylmethyl)benzonitrile hydrochloride.

To a solution of [1-(3-cyanobenzyl)-2-oxopyrrolidin-3-(S)-yl]carbamic acid tert-butyl ester (9.1 g, 29 mmol) in 150 mL of EtOAc at 0° C. is bubbled HCl gas for 10 minutes. After this time, the solution is stirred for 4 hours. The solution is then concentrated to give the title compound (7.3 g, 29 mmol) as a white solid.

$^1$H NMR (DMSO-$d_6$, 300 MHz) δ8.71 (bs, 3 H), 7.85 (m, 2 H), 7.70 (m, 2 H), 4.58 (AB, 2 H), 4.13 (m, 1 H), 3.32 (m, 2 H), 2.44 (m, 1 H), 2.18 (m, 1 H).

D. Naphthalene-2-sulfonic acid [1-(3-cyanobenzyl)-2-oxopyrrolidin-3-(S)-yl]amide.

3-(3-(S)-Amino-2-oxopyrrolidin-1-ylmethyl)benzonitrile hydrochloride (0.4 g, 1.6 mmol) is suspended in 10 mL of $CH_2Cl_2$. To the solution is added triethylamine (0.49 g, 4.8 mmol) followed by 2-naphthalene sulfonyl chloride (0.4 g, 1.8 mmol). After stirring for 2 hours, the solution is diluted with $CH_2Cl_2$. The solution is washed with 1 N HCl, 10% $Na_2CO_3$ and saturated NaCl. The organic layer is dried over $MgSO_4$, filtered and concentrated. The residue is triturated with ether to give the title compound (0.46 g, 1.13 mmol) as a solid.

$^1$H NMR (DMSO-$d_6$, 300 MHz) δ8.56 (d, 1 H), 8.32 (d, 1 H), 8.20 (m, 3 H), 8.09 (m, 1 H), 7.93 (d, 1 H), 7.74 (m, 3 H), 7.48 (d, 2 H), 4.38 (AB, 2 H), 4.17 (m, 1 H), 3.05 (m, 2 H), 2.02 (m, 1 H), 1.57 (m, 1 H).

E. Naphthalene-2-sulfonic acid {1-[3-(aminoiminomethyl)benzyl]-2-oxopyrrolidin-3-(S)-yl}amide trifluoroacetate.

Naphthalene-2-sulfonic acid [1-(3-cyanobenzyl)-2-oxopyrrolidin-3-(S)-yl]amide (0.46 g, 1.13 mmol) is dissolved in 50 mL of ethanol. The solution is cooled to 0° C. and HCl gas is bubbled through the solution for 10 minutes. The ice bath is removed and the reaction mixture is stirred at room temperature for 6 hours. After this time, the solution is concentrated. The residue is dissolved in 50 mL of methanol. The solution is cooled to 0° C. and ammonia gas is bubbled through the solution for 10 minutes. The reaction mixture is stirred for 24 hours. After this time, the solution is concentrated. The residue is purified by RP-HPLC eluting with a gradient of 10% $CH_3CN/H_2O$ (0.1% TFA) to 60% $CH_3CN/H_2O$ (0.1% TFA). The appropriate fractions are lyophilized to give the title compound (0.33 g, 0.61 mmol) as a solid.

$^1$H NMR (DMSO-$d_6$, 300 MHz) δ9.30 (bs, 2 H), 9.14 (bs, 2 H), 8.50 (s, 1 H), 8.28 (d, 1 H), 8.13 (m, 3 H), 8.04 (d, 1 H), 7.91 (d, 1 H), 7.80 (m, 3 H), 7.62 (d, 2 H), 4.42 (AB, 2 H), 4.18 (m, 1 H), 3.10 (m, 2 H), 2.00 (m, 1 H), 1.57 (m, 1 H). FAB MS, [M+H]$^+$=423. Elemental analysis calculated with 1.5 mole of $H_2O$: C=51.15%, H=4.65%, N=9.94%, found C=51.16%, H=4.19%, N=9.61%.

EXAMPLE 2

Dibenzofuran-2-sulfonic acid {1-[3-(aminoiminomethyl)benzyl]-5-oxopyrrolidin-3-yl}amide trifluoroacetate.

A. Boc-Asp(OBn)-H.

The title compound is prepared as in EXAMPLE 1, Part A, using Boc-Asp(OBn)-OH in place of Boc-L-Asp-OBn.

$^1$H NMR ($CDCl_3$, 300 MHz) δ9.67 (s, 1 H), 7.32 (m, 5 H), 5.60 (bs, 1 H), 5.12 (AB, 2 H), 4.40 (m, 1 H), 3.94 (AB, 1 H), 3.72 (AB, 1 H), 1.41 (s, 9 H).

B. [1-(3-Cyanobenzyl)-5-oxopyrrolidin-3-yl]carbamic acid tert-butyl ester.

The title compound is prepared as in EXAMPLE 1, Part B using Boc-Asp(OBn)-H in place of Boc-Asp(H)-OBn.

$^1$H NMR (CDCl$_3$, 300 MHz) δ7.65 (d, 1 H), 7.61 (s, 1 H), 7.52 (m, 2 H), 4.82 (bs, 1 H), 4.51 (s, 2 H), 4.22 (m, 1 H), 3.53 (q, 1 H), 3.16 (dd, 1 H), 2.83 (AB, 1 H), 2.33 (AB, 1 H), 1.40 (s, 9 H).

C. 3-(3-Amino-5-oxopyrrolidin-1-ylmethyl)benzonitrile hydrochloride.

The title compound is prepared as in EXAMPLE 1, Part C using [1-(3-cyanobenzyl)-5-oxopyrrolidin-3-yl]carbamic acid tert-butyl ester in place of [1-(3-cyanobenzyl)-2-oxopyrrolidin-3-(S)-yl]carbamic acid tert-butyl ester.

$^1$H NMR (DMSO-d$_6$, 300 MHz) δ8.5 (bs, 3 H), 7.72 (m, 2 H), 7.61 (m, 1 H), 7.55 (m, 1 H), 4.46 (AB, 2 H), 3.89 (m, 1 H), 3.57 (q, 1 H), 3.30 (dd, 1 H), 2.78 (AB, 1 H), 2.42 (AB, 1 H).

D. Dibenzofuran-2-sulfonic acid [1-(3-cyanobenzyl)-5-oxopyrrolidin-3-yl]amide.

The title compound is prepared from 3-(3-amino-5-oxopyrrolidin-1-ylmethyl)benzonitrile hydrochloride as in EXAMPLE 1, Part D using 2-dibenzofuransulfonyl chloride in place of 2-naphthalene sulfonyl chloride. The crude product is purified by column chromatography in a gradient of CH$_2$Cl$_2$ to 5% MeOH/CH$_2$Cl$_2$.

$^1$H NMR (CDCl$_3$, 300 MHz) δ8.45 (d, 1 H), 7.91 (m, 2 H), 7.61 (m, 2 H), 7.58 (d, 1 H), 7.44 (m, 5 H), 5.55 (m, 1 H), 4.42 (AB, 2 H), 4.09 (m, 1 H), 3.50 (dd, 1 H), 3.21 (dd, 1 H), 2.62 (dd, 1 H), 2.29 (dd, 1 H).

E. Dibenzofuran-2-sulfonic acid {1-[3-(aminoiminomethyl)benzyl]-5-oxopyrrolidin-3-yl}amide trifluoroacetate.

Hydrogen sulfide gas is bubbled through a solution of dibenzofuran-2-sulfonic acid [1-(3-cyanobenzyl)-5-oxopyrrolidin-3-yl]amide (0.44 g, 0.99 mmol) in 10 mL of 10:1 pyridine/triethylamine. After stirring the pale green solution for a period of 18 hours, the reaction mixture is concentrated in vacuo. The residue is diluted in EtOAc and 0.5 N HCl solution. The layers are separated and the organic phase is washed with saturated NaCl. The organic layer is dried over anhydrous MgSO$_4$, filtered and concentrated to give crude thioamide. To a solution of thioamide in 20 mL of acetone is added methyl iodide (2 mL, 32 mmol). The resulting mixture is heated at reflux for 1 hour, allowed to cool to room temperature and concentrated in vacuo to provide the crude thioimidate hydroiodide. To a solution of thioimidate hydroiodide in 20 mL of MeOH is added ammonium acetate (0.3 g, 3.89 mmol). The resulting mixture is heated at reflux for 3.5 hours, allowed to cool to room temperature and concentrated in vacuo to provide the crude amidine salt. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound (0.21 g, 0.36 mmol) as a white solid.

$^1$H NMR (DMSO-d$_6$, 300 MHz) δ9.29 (s, 4 H), 8.64 (s, 1 H), 8.24 (d, 1 H), 8.13 (d, 1 H), 7.91 (m, 2 H), 7.84 (d, 1 H), 7.60 (m, 6 H), 4.39 (AB, 2 H), 3.91 (m, 1 H), 3.41 (dd, 1 H), 3.08 (dd, 1 H), 2.46 (dd, 1 H), 2.13 (dd, 1 H). FAB MS, [M+H]$^+$=463. Elemental analysis calculated with 2.3 mole of H$_2$O: C=50.50%, H=4.51 %, N=9.06%; found C=50.49%, H=3.66%, N=8.61%.

EXAMPLE 3

Toluene-4-sulfonic acid {1-[3-(aminoiminomethyl)benzyl]-2-oxopyrrolidin-3-(S)-yl}amide trifluoroacetate.

A. Toluene-4-sulfonic acid [1-(3-cyanobenzyl)-2-oxopyrrolidin-3-(S)-yl]amide.

The title compound is prepared as in EXAMPLE 1, Part D using toluene sulfonyl chloride in place of 2-naphthalene sulfonyl chloride.

$^1$H NMR (DMSO-d$_6$, 300 MHz) d 8.08 (d, 1 H), 7.78 (m, 3 H), 7.62 (s, 1 H), 7.51 (d, 2 H), 7.33 (d, 2 H), 4.40 (AB, 2 H), 4.05 (m, 1 H), 3.05 (m, 2 H), 2.36 (s, 3 H), 1.97 (m, 1 H), 1.57 (m, 1 H).

B. Toluene-4-sulfonic acid {1-[3-(aminoiminomethyl)benzyl]-2-oxopyrrolidin-3-(S)-yl}amide trifluoroacetate.

The title compound is prepared as in EXAMPLE 1, Part E using toluene-4-sulfonic acid [1-[3-(cyanobenzyl)-2-oxopyrrolidin-3-(S)-yl]amide as the starting material.

$^1$H NMR (DMSO-d$_6$, 300 MHz) d 9.27 (bs, 2 H), 9.10 (bs, 2 H), 8.03 (d, 1 H), 7.79 (d, 2 H), 7.68 (m, 1 H), 7.59 (m, 4 H), 7.40 (d, 2 H), 4.44 (AB, 2 H), 4.12 (m, 1 H), 3.08 (m, 1 H), 2.38 (s, 3 H), 2.04 (m, 1 H), 1.58, (m, 1 H). FAB MS, [M+H]$^+$=355. Elemental analysis calculated with 1.25 mole of H$_2$O: C=48.23%, H=4.59%, N=10.39%, found C=48.15%, H=4.59%, N=10.39%.

EXAMPLE 4

3,4-Dihydro-1H-isoquinoline-2-sulfonic acid {1-[3-(aminoiminomethyl)benzyl]-2-oxopyrrolidin-3-(S)-yl}amide trifluoroacetate.

A. 3,4-Dihydro-1H-isoquinoline-2-sulfonic acid [1-(3-cyanobenzyl)-2-oxopyrrolidin-3-(S)-yl]amide.

A 1 M solution of sulfuryl chloride (14.1 mL, 14.1 mmol) in CH$_2$Cl$_2$ is cooled to 0° C. To the solution is added triethylamine (0.71 g, 7.1 mmol) dropwise. 1,2,3,4-Tetrahydroisoquinoline (0.94 g, 7.1 mmol) is then added dropwise. The ice bath is removed and the solution is stirred for 2 hours. The solution is diluted with CH$_2$Cl$_2$ and poured into an ice bath. The layers are separated. The organic layer is washed with 1 N HCl and saturated NaCl. The organic layer is dried over MgSO$_4$, filtered and concentrated. To the crude residue dissolved in 10 mL of CH$_2$Cl$_2$ is added 3-(3-(S)-amino-2-oxopyrrolidin-1-ylmethyl)benzonitrile hydrochloride (0.5 g, 2 mmol). Triethylamine (0.4 g, 4 mmol) is added and the mixture is stirred for 16 hours. The reaction mixture is diluted with EtOAc and washed with 1 N HCl, 10% Na$_2$CO$_3$ and saturated NaCl. The residue is purified by column chromatography eluting with a gradient of 10% EtOAc/CH$_2$Cl$_2$ to 15% EtOAc/CH$_2$Cl$_2$ to give the title compound (0.15 g, 0.36 mmol) as a solid.

$^1$H NMR (CDCl$_3$, 300 MHz) d 7.62 (m, 1 H), 7.58 (d, 2 H), 7.18 (m, 4 H), 7.09 (m, 2 H), 5.10 (bs, 1 H), 4.46 (AB, 2 H), 4.08 (m, 1 H), 3.65 (m, 2 H), 3.22 (m, 2 H), 3.02 (m, 2 H), 2.61 (m, 1 H), 2.05 (m, 1 H). FAB MS, [M+H]$^+$=411.

B. 3,4-Dihydro-1H-isoquinoline-2-sulfonic acid {1-[3-(aminoiminomethyl)benzyl]-2-oxopyrrolidin-3-(S)-yl}amide trifluoroacetate.

The title compound is prepared as described in EXAMPLE 1, Part E using 3,4-dihydro-1H-isoquinoline-2-sulfonic acid [1-(3-cyanobenzyl)-2-oxopyrrolidin-3-(S)-yl]amide as the starting material.

$^1$H NMR (DMSO-d$_6$, 300 MHz) d 9.29 (bs, 2 H), 9.13 (bs, 2 H), 7.86 (d, 1 H), 7.66 (m, 2 H), 7.52 (m, 2 H), 7.14 (m, 4 H), 4.47 (AB, 2 H), 4.33 (AB, 2 H), 4.12 (m, 1 H), 3.43 (m, 2 H), 3.18 (m, 2 H), 2.88 (m, 2 H), 2.30 (m, 1 H), 1.77 (m, 1 H). FAB MS, [M+H]$^+$=428. Elemental analysis calculated with 2 mole of $H_2O$: C=47.83%, H=5.24%, N=12.13%, found C=47.43%, H=4.88%, N=11.63%.

EXAMPLE 5

3'-Methoxy-biphenyl-4-sulfonic acid {1-[3-(aminoiminomethyl)benzyl]-2-oxopyrrolidin-3-(S)-yl}amide trifluoroacetate.

A. 3'-Methoxy-biphenyl-4-bromide.

3-Bromoanisole (3.5 g, 18.7 mmol) is dissolved in 40 mL of THF and cooled to −78° C. To the solution is added dropwise a 2.5 M solution of n-butyllithium in hexanes (7.5 mL, 18.7 mmol). After 10 minutes, a solution of zinc chloride (20 mL, 19.6 mmol) in ether is added and the cooling bath is removed. The reaction mixture is stirred at room temperature for 2 hours. After this time, a solution of 4-iodobromobenzene (5.6 g, 19.6 mmol) and $Pd(Ph_3P)_4$ (1.1 g, 1 mmol) in 10 mL of THF is added to the reaction flask. The solution is stirred 2 hours, poured into 100 mL of water and extracted with EtOAc. The organic layer is washed with water and saturated NaCl. The organic layer is dried over $MgSO_4$, filtered and concentrated. The crude residue is purified by column chromatography eluting with 10% $CH_2Cl_2$/hexanes to 20% $CH_2Cl_2$/hexanes to give the title compound (1.5 g, 5.7 mmol) as a solid.

$^1$H NMR ($CDCl_3$, 300 MHz) d 7.55 (d, 2 H), 7.43 (m, 2 H), 7.32 (m, 1 H), 7.12 (m, 1 H), 7.07 (m, 1 H), 6.87 (dd, 1 H), 3.79 (s, 3 H). FAB MS, [M+H]$^+$=262.

B. 3'-Methoxy-biphenyl-4-sulfonyl chloride.

3'-Methoxy-biphenyl-4-bromide (1.5 g, 5.7 mmol) is dissolved in 20 mL of THF and cooled to −78° C. To the solution is added a 2.5 M solution of n-butyllithium in THF (2.3 mL, 5.7 mmol). The reaction mixture is stirred for 15 minutes and then is transferred via cannula to a solution of condensed sulfur dioxide gas (10 mL) in 40 mL of ether at −78° C. The solution is stirred for 30 minutes, allowed to warm to room temperature and then concentrated in vacuo. The resulting residue is triturated with ether to give 1 g of the lithium biarylsulfinate as a solid. The solid is suspended in 15 mL of hexanes and cooled to 0° C. To the suspension is added a 1 M solution of sulfuryl chloride (4.2 mL, 4.2 mmol) in $CH_2Cl_2$. After 1 hour at 0° C., the resulting solution is concentrated.

The residue is triturated with hexanes to give the title compound (0.6 g, 2.25 mmol) as a solid. FAB MS, [M+H]$^+$= 267.

C. 3'-Methoxybiphenyl-4-sulfonic acid [1-3-(cyanobenzyl)-2-oxopyrrolidin-3-(S)-yl]amide.

The title compound is prepared as described in EXAMPLE 1, Part D using 3'-methoxybiphenyl-4-sulfonyl chloride in place of 2-naphthalene sulfonyl chloride.

$^1$H NMR ($CDCl_3$, 300 MHz) δ7.95 (d, 1 H), 7.72 (m, 2 H), 7.52 (m, 1 H), 7.40 (m, 5 H), 7.16 (d, 1 H), 7.10 (d, 1 H), 6.95 (d, 1 H), 5.33 (bs, 1 H), 4.43 (AB, 2 H), 3.88 (s, 3 H), 3.81 (m, 1 H), 3.24 (m, 2 H), 2.64 (m, 1 H) 2.07 (m, 1 H).

D. 3'-Methoxybiphenyl-4-sulfonic acid {1-[3-(aminoiminomethyl)benzyl]-2-oxopyrrolidin-3-(S)-yl}amide trifluoroacetate.

The title compound is prepared as described in EXAMPLE 1, Part E using 3'-methoxybiphenyl-4-sulfonic acid [1-3-(cyanobenzyl)-2-oxopyrrolidin-3-(S)-yl]amide as the starting material.

$^1$H NMR (DMSO-$d_6$, 300 MHz) δ9.30 (bs, 2 H), 9.05 (bs, 2 H), 8.20 (d, 1 H), 7.90 (m, 4 H), 7.71 (m, 2 H), 7.55 (m, 2 H), 7.40 (m, 2 H), 7.28 (m, 2 H), 6.99 (d, 1 H), 4.43 (AB, 2 H), 4.18 (m, 1 H), 3.82 (s, 3 H), 3.12 (m, 1 H), 2.05 (m, 1 H), 1.62 (m, 1 H). FAB MS, [M+H]$^+$=479. Elemental analysis calculated with 1 mole of $H_2O$: C=53.11%, H=4.79%, N=9.18%, found C=53.31%, H=4.51%, N=9.15%.

EXAMPLE 6

Naphthalene-1-sulfonic acid {1-[3-(aminoiminomethyl)benzyl]-2-oxopyrrolidin-3-(S)-yl}amide trifluoroacetate.

A. Naphthalene-1-sulfonic acid [1-(3-cyanobenzyl)-2-oxopyrrolidin-3-(S)-yl]amide.

The title compound is prepared as described in EXAMPLE 1, Part D using 1-naphthalene sulfonyl chloride in place of 2-naphthalene sulfonyl chloride.

$^1$H NMR ($CDCl_3$, 300 MHz) δ8.67 (d, 1 H), 8.28 (d, 1 H), 8.06 (d, 1 H), 7.96 (d, 1 H), 7.67 (m, 2 H), 7.55 (m, 2 H), 7.38 (m, 2 H), 7.19 (s, 1 H), 5.52 (bs, 1 H), 4.37 (AB, 2 H), 3.75 (m, 1 H), 3.14 (m, 2 H), 2.40 (m, 1 H), 1.97 (m, 1 H).

B. Naphthalene-1-sulfonic acid {1-[3-(aminoiminomethyl)benzyl]-2-oxopyrrolidin-3-(S)-yl}amide trifluoroacetate.

The title compound is prepared as described in EXAMPLE 1, Part E using naphthalene-1-sulfonic acid [1-(3-cyanobenzyl)-2-oxopyrrolidin-3-(S)-yl]amide as the starting material.

$^1$H NMR (DMSO-$d_6$, 300 MHz) δ9.30 (bs, 2 H), 9.13 (bs, 2 H), 8.65 (d, 1 H), 8.51 (d, 1 H), 8.32 (d, 1 H), 8.22 (d, 1 H), 8.09 (d, 1 H), 7.64 (m, 5 H), 7.50 (m, 3 H), 4.40 (AB, 2 H), 4.17 (m, 1 H), 3.07 (m, 1 H), 1.89 (m, 1 H), 1.53 (m, 1 H). FAB MS, [M+H]$^+$=423. Elemental analysis calculated with 1 mole of $H_2O$: C=51.98%, H=4.54%, N=10.10%, found C=52.20%, H=4.17%, N=9.73%.

EXAMPLE 7

5-Pyrid-2-ylthiophene-2-sulfonic acid {1-[3-(aminoiminomethyl)benzyl]-2-oxopyrrolidin-3-(S)-yl}amide trifluoroacetate.

A. 5-Pyrid-2-ylthiophene-2-sulfonic acid [1-(3-cyanobenzyl)-2-oxopyrrolidin-3-(S)-yl]amide.

The title compound is prepared as described in EXAMPLE 1, Part D using 5-pyrid-2-ylthiophene-2-sulfonyl chloride in place of 2-naphthalene sulfonyl chloride.

$^1$H NMR ($CDCl_3$, 300 MHz) δ8.62 (m, 1 H), 7.78 (m, 1 H), 7.69 (m, 1 H), 7.58 (m, 2 H), 7.50 (d, 1 H), 7.46 (m, 2 H), 7.20 (m, 2 H), 5.43 (bs, 1 H), 4.42 (AB, 2 H), 3.98 (m, 1 H), 3.26 (m, 2 H), 2.68 (m, 1 H), 2.15 (m, 1 H).

B. 5-Pyrid-2-ylthiophene-2-sulfonic acid {1-[3-(aminoiminomethyl)benzyl]-2-oxopyrrolidin-3-(S)-yl}amide trifluoroacetate.

The title compound is prepared as described in EXAMPLE 1, Part E using 5-pyrid-2-ylthiophene-2-sulfonic acid [1-(3-cyanobenzyl)-2-oxopyrrolidin-3-(S)-yl]amide as the starting material.

$^1$H NMR (DMSO-$d_6$, 300 MHz) δ9.32 (bs, 2 H), 9.13 (bs, 2 H), 8.56 (d, 1 H), 8.49 (d, 1 H), 8.04 (d, 1 H), 7.89 (m, 3 H), 7.58 (m, 4 H), 7.38 (m, 1 H), 4.46 (AB, 2 H), 4.23 (m, 1 H), 3.16 (m, 2 H), 2.16 (m, 1 H), 1.70 (m, 1 H). FAB MS, [M+H]$^+$=456. Elemental analysis calculated: C=43.93%, H=3.39%, N=10.24%, found C=44.04%, H=3.43%, N=10.26%.

EXAMPLE 8

Biphenyl-4-sulfonic acid {1-[3-(aminoiminomethyl)benzyl]-2-oxopyrrolidin-3-(S)-yl}amide trifluoroacetate.

A. Biphenyl-4-sulfonic acid [1-(3-cyanobenzyl)-2-oxopyrrolidin-3-(S)-yl]amide

The title compound is prepared as described in EXAMPLE 1, Part D using biphenyl-4-sulfonyl chloride in place of 2-naphthalene sulfonyl chloride.

$^1$H NMR (CDCl$_3$, 300 MHz) δ8.14 (s, 1 H), 7.95 (d, 1 H), 7.82 (d, 1 H), 7.64 (m, 5 H), 7.47 (m, 6 H), 5.42 (bs, 1 H), 4.42 (AB, 2 H), 3.82 (m, 1 H), 3.22 (m, 1 H), 2.62 (m, 1 H), 2.13 (m, 1 H).

B. Biphenyl-4-sulfonic acid {1-[3-(aminoiminomethyl)benzyl]-2-oxopyrrolidin-3-(S)-yl}amide trifluoroacetate.

The title compound is prepared as described in EXAMPLE 1, Part E using biphenyl-4-sulfonic acid [1-(3-cyanobenzyl)-2-oxopyrrolidin-3-(S)-yl]amide as the starting material.

$^1$H NMR (DMSO-d$_6$, 300 MHz) δ9.31 (bs, 2 H), 9.14 (bs, 2 H), 8.22 (d, 1 H), 7.91 (m, 6 H), 7.60 (m, 8 H), 4.45 (AB, 2 H), 4.16 (m, 1 H), 3.12 (m, 1 H), 2.07 (m, 1 H), 1.65 (m, 1 H). FAB MS, [M+H]$^+$=449. Elemental analysis calculated with 0.25 mole of H$_2$O: C=55.07%, H=4.53%, N=9.88%, found C=55.12%, H=4.41%, N=10.05%.

EXAMPLE 9

7-Methoxynaphthalene-2-sulfonic acid {1-[3-(aminoiminomethyl)benzyl]-2-oxopyrrolidin-3-(S)-yl}amide trifluoroacetate.

A. 7-Methoxynaphthalene-2-sulfonyl chloride.

To a suspension of 7-hydroxynaphthalene-2-sulfonic acid, sodium salt (15 g, 60.9 mmol) in 150 mL of 2:1 H$_2$O/ethanol is added solid NaOH (2.68 g, 67 mmol) at room temperature. The mixture is stirred until a homogenous solution forms, and dimethyl sulfate (6.34 mL, 67 mmol) is then added. A precipitate eventually forms and the mixture is stirred over a period of 16 hours. The crude mixture is concentrated in vacuo and the residue is stirred in 100 mL of absolute EtOH as a slurry for 2 hours. The precipitate is filtered and dried. The solid is heated at reflux in 100 mL of 95% EtOH for 2 hours, allowed to cool to room temperature, filtered and dried to give 12.6 g of crude 7-methoxynaphthalene-2-sulfonic acid, sodium salt. A mixture of the sulfonic acid, sodium salt (12.6 g, 48.6 mmol) in 20 mL of phosphorous oxychloride and phosphorous pentachloride (13.2 g, 63.2 mmol) is heated slowly to 60° C. until a homogenous solution forms and then is heated at 120° C. for 4 hours. The resulting mixture is cooled in an ice bath and a mixture of ice/ice water is added slowly with stirring. The mixture is diluted with water and extracted with CHCl$_3$ (2×100 mL). The combined organic layers are washed successively with water, saturated NaHCO$_3$ solution and saturated NaCl. The organic phase is dried over anhydrous MgSO$_4$, filtered and concentrated to give 10 g of a crude oil. The crude product is purified by column chromatography in a gradient of 5% EtOAc/hexanes to 30% EtOAc/hexanes to afford the title compound (3.8 g, 14.8 mmol) as a white crystalline solid.

$^1$H NMR (CDCl$_3$, 300 MHz) δ8.49 (d, 1 H), 7.96 (d, 1 H), 7.85 (d, 2 H), 7.39 (dd, 1 H), 7.29 (d, 1 H), 3.99 (s, 3 H). EI MS, [M]$^+$=256. The 8-chloro-7-methoxynaphthalene-2-sulfonyl chloride (1.49 g, 5.12 mmol) is also isolated as a minor by-product from the above procedure.

$^1$H NMR (CDCl$_3$, 300 MHz) δ8.95 (d, 1 H), 8.01 (d, 1 H), 7.90 (d, 2 H), 7.55 (d, 1 H), 4.09 (s, 3 H). EI MS, [M]$^+$=290.

B. 7-Methoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using 7-methoxynaphthalene-2-sulfonyl chloride. The crude product is triturated from 50% EtOAc/hexanes solution to give the title compound as a beige solid.

$^1$H NMR (CDCl$_3$, 300 MHz) δ8.38 (d, 1 H), 7.91 (d, 1 H), 7.81 (d, 1 H), 7.73 (dd, 1 H), 7.59 (m, 1 H), 7.42 (m, 3 H), 7.30 (dd, 1 H), 7.25 (m, 1 H), 5.39 (d, 1 H), 4.45 (AB, 2 H), 3.92 (s, 3 H), 3.75 (m, 1 H), 3.20 (m, 2 H), 2.60 (m, 1 H), 2.10 (m, 1 H).

C. 7-Methoxynaphthalene-2-sulfonic acid {1-[3-(aminoiminomethyl)benzyl]-2-oxopyrrolidin-3-(S)-yl}amide trifluoroacetate.

7-Methoxynaphthalene-2-sulfonic acid [1-(3-cyanobenzyl)-2-oxopyrrolidin-3-(S)-yl]amide is dissolved in 10 mL of a 2:1 mixture of EtOH/CH$_2$Cl$_2$ and converted to the title compound as in EXAMPLE 1, Part E. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.41 (bs, 2 H), 9.29 (bs, 2 H), 8.33 (d, 1 H), 8.19 (d, 1 H), 7.96 (d, 1 H), 7.87 (d, 1 H), 7.68 (dd, 1 H), 7.64 (m, 1 H), 7.50 (m, 4 H), 7.27 (dd, 1 H), 4.36 (AB, 2 H), 4.16 (dd, 1 H), 3.48 (s, 3 H), 3.04 (m, 2 H), 1.93 (m, 1 H), 1.59 (m, 1 H). FAB MS, [M+H]$^+$=453. Elemental analysis calculated with 1.7 mole of H$_2$O: C=50.28%, H=4.79%, N=9.38%; found C=50.27%, H=4.14%, N=9.07%. 7-Methoxynaphthalene-2-sulfonic acid {1-[3-(aminoiminomethyl)benzyl]-2-oxopyrrolidin-3-(R)-yl}amide trifluoroacetate is prepared from 7-methoxynaphthalene-2-sulfonic acid [1-(3-cyanobenzyl)-2-oxopyrrolidin-(3R)-yl]amide as above.

EXAMPLE 10

7-Ethoxynaphthalene-2-sulfonic acid {1-[3-(aminoiminomethyl)benzyl]-2-oxopyrrolidin-3-(S)-yl}amide trifluoroacetate.

A. 7-Ethoxynaphthalene-2-sulfonyl chloride.

A 60% dispersion of sodium hydride (0.74 g, 18.45 mmol) in mineral oil is washed with hexanes twice and suspended in 35 mL of DMF. To this mixture is added slowly via an addition funnel 7-hydroxynaphthalene-2-sulfonic acid, sodium salt (2.5 g, 10.1 mmol) in 50 mL of DMF at room temperature. The reaction mixture is stirred for 75 min during which time mild bubbling is observed (H$_2$ evolution). The mixture is treated with bromoethane (2.42 mL, 32.5 mmol) and stirred for 16 hours at room temperature. A little ice is added to decompose the excess NaH and the resultant mixture is concentrated in vacuo. The residue is suspended in acetone and concentrated in vacuo two times and then is dried under high vacuum. The solid is suspended in acetone, filtered and dried to yield the crude 7-ethoxynaphthalene-2-sulfonic acid, sodium salt as a beige solid. A mixture of the sulfonic acid, sodium salt (3.77 g) in 10 mL of thionyl chloride is heated at 80° C. for 2 hours. The mixture is allowed to cool to room temperature and concentrated in vacuo. The residue is diluted in EtOAc and washed successively with water (2×), saturated NaHCO$_3$ solution and saturated NaCl. The organic layer is dried over anhydrous MgSO$_4$, filtered and concentrated to yield 2.65 g of a crude brown oil. The crude product is purified by column chromatography in a gradient of 10% EtOAc/hexanes to 20% EtOAc/hexanes to afford the title compound (1.67 g, 6.17 mmol) as a pale yellow solid.

$^1$H NMR (CDCl$_3$, 300 MHz) δ8.46 (s, 1 H), 7.97 (d, 1 H), 7.85 (d, 1 H), 7.84 (d, 1 H), 7.38 (dd, 1 H), 7.28 (s, 1 H), 4.19 (q, 2 H), 1.50 (t, 3 H).

B. 7-Ethoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using 7-ethoxynaphthalene-2-sulfonyl chloride. The crude product is triturated from 50% EtOAc/hexanes solution to give the title compound as a beige solid.

$^1$H NMR (CDCl$_3$+DMSO-d$_6$, 300 MHz) δ8.27 (d, 1 H), 7.80 (d, 1 H), 7.67 (m, 2 H), 7.47 (m, 1 H), 7.41 (bs, 1 H), 7.34 (d, 2 H), 7.17 (m, 3 H), 4.34 (AB, 2 H), 4.06 (q, 2 H), 3.87 (m, 1 H), 3.04 (m, 2 H), 2.25 (m, 1 H), 1.81 (m, 1H), 1.39 (t, 3 H).

C. 7-Ethoxynaphthalene-2-sulfonic acid {1-[3-(aminoiminomethyl)benzyl]-2-oxopyrrolidin-3-(S)-yl}amide trifluoroacetate.

7-Ethoxynaphthalene-2-sulfonic acid [1-(3-cyanobenzyl)-2-oxopyrrolidin-3-(S)-yl]amide is dissolved in 10 mL of a 2:1 mixture of EtOH/CH$_2$Cl$_2$ and converted to the title compound as in EXAMPLE 1, Part E. The imidate intermediate is formed over a period of 18 hours at room temperature. The amidine formation occurred over a period of 48 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.41 (bs, 2 H), 9.33 (bs, 2 H), 8.37 (d, 1 H), 8.24 (d, 1 H), 8.02 (d, 1 H), 7.94 (d, 1 H), 7.73 (dd, 1 H), 7.70 (d, 1 H), 7.56 (m, 4 H), 7.32 (dd, 1 H), 4.43 (AB, 2 H), 4.17 (q, 2 H), 4.15 (m, 1 H), 3.10 (m, 2 H), 2.00 (m, 1 H), 1.59 (m, 1 H), 1.40 (t, 3 H). FAB MS, [M+H]$^+$=467. Elemental analysis calculated with 1.9 mole of H$_2$O: C=50.91%, H=5.04%, N=9.13%; found C=50.92%, H=4.44%, N=8.57%.

EXAMPLE 11

5-Chloro-6-methoxynaphthalene-2-sulfonic acid {1-[3-(aminoiminomethyl)benzyl]-2-oxopyrrolidin-3-(S)-yl}amide trifluoroacetate.

A. 5-Chloro-6-methoxynaphthalene-2-sulfonyl chloride.

The title compound is prepared from 6-hydroxynaphthalene-2-sulfonic acid, sodium salt as in EXAMPLE 9, Part A. The crude product mixture is purified by column chromatography in a gradient of 5% EtOAc/hexanes to 10% EtOAc/hexanes to provide the title compound as a minor by-product.

$^1$H NMR (CDCl$_3$, 300 MHz) δ8.57 (d, 1 H), 8.42 (d, 1 H), 8.05 (dd, 1 H), 8.00 (d, 1 H), 7.50 (d, 1 H), 4.10 (s, 3 H).

B. 5-Chloro-6-methoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using 5-chloro-6-methoxynaphthalene-2-sulfonyl chloride. The crude product is triturated from EtOAc to give the title compound as a beige solid.

$^1$H NMR (CDCl$_3$, 300 MHz) δ8.44 (d, 1 H), 8.38 (d, 1 H), 7.98 (dd, 1 H), 7.91 (d, 1 H), 7.60 (m, 1 H), 7.42 (m, 4 H), 5.51 (d, 1 H), 4.45 (AB, 2 H), 4.09 (s, 3 H), 3.80 (m, 1 H), 3.20 (m, 2 H), 2.60 (m, 1 H), 2.10 (m, 1 H).

C. 5-Chloro-6-methoxynaphthalene-2-sulfonic acid {1-[3-(aminoiminomethyl)benzyl]-2-oxopyrrolidin-3-(S)-yl}amide trifluoroacetate.

5-Chloro-6-methoxynaphthalene-2-sulfonic acid [1-(3-cyanobenzyl)-2-oxopyrrolidin-3-(S)-yl]amide is dissolved in 10 mL of a 2:1 mixture of EtOH/CH$_2$Cl$_2$ and converted to the title compound as in EXAMPLE 1, Part E. The imidate intermediate is formed over a period of 16 hours at room temperature. The amidine formation occurred over a period of 24 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.29 (bs, 2 H), 9.10 (bs, 2 H), 8.52 (d, 1 H), 8.29 (d, 1 H), 8.23 (d, 1 H), 8.21 (d, 1 H), 7.98 (dd, 1 H), 7.71 (d, 1 H), 7.67 (d, 1 H), 7.58 (d, 1 H), 7.54 (bs, 1 H), 7.52 (d, 1 H), 4.41 (AB, 2 H), 4.16 (m, 1 H), 4.04 (s, 3 H), 3.09 (m, 2 H), 2.01 (m, 1 H), 1.59 (m, 1 H). FAB MS, [M+H]$^+$=487. Elemental analysis calculated with 1.5 mole of H$_2$O: C=47.88%, H=4.32%, N=8.93%; found C=47.88%, H=3.88%, N=8.48%.

EXAMPLE 12

5-Chloro-6,7-dimethoxynaphthalene-2-sulfonic acid {1-[3-(aminoiminomethyl)benzyl]-2-oxopyrrolidin-3-(S)-yl}amide trifluoroacetate.

A. 5-Chloro-6,7-dimethoxynaphthalene-2-sulfonyl chloride.

The title compound is prepared from 6,7-dihydroxynaphthalene-2-sulfonic acid, sodium salt hemihydrate as in EXAMPLE 9, Part A. The crude product mixture is purified by column chromatography in a gradient of 5% EtOAc/hexanes to 30% EtOAc/hexanes to give the title compound as a minor by-product.

$^1$H NMR (CDCl$_3$, 300 MHz) δ8.48 (d, 1 H), 8.38 (d, 1 H), 7.45 (dd, 1 H), 7.30 (s, 1 H), 4.05 (s, 3 H), 4.00 (s, 3 H).

B. 5-Chloro-6,7-dimethoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using 5-chloro-6,7-dimethoxynaphthalene-2-sulfonyl chloride. The crude product is triturated from EtOAc to give the title compound as a beige solid.

$^1$H NMR (CDCl$_3$, 300 MHz) δ8.49 (d, 1 H), 8.25 (d, 1 H), 7.86 (dd, 1 H), 7.55 (m, 1 H), 7.40 (m, 3 H), 7.20 (s, 1 H), 5.89 (m, 1 H), 4.44 (AB, 2 H), 4.03 (s, 3 H), 4.00 (s, 3 H), 3.86 (m, 1 H), 3.20 (m, 2 H), 2.59 (m, 1 H), 2.07 (m, 1 H).

C. 5-Chloro-6,7-dimethoxynaphthalene-2-sulfonic acid {1-[3-(aminoiminomethyl)benzyl]-2-oxopyrrolidin-3-(S)-yl}amide trifluoroacetate.

5-Chloro-6,7-dimethoxynaphthalene-2-sulfonic acid [1-(3-cyanobenzyl)-2-oxopyrrolidin-3-(S)-yl]amide is dissolved in 10 mL of a 2:1 mixture of EtOH/CH$_2$Cl$_2$ and converted to the title compound as in EXAMPLE 1, Part E. The imidate intermediate is formed over a period of 24 hours at room temperature. The amidine formation occurred over a period of 24 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.29 (bs, 2 H), 9.12 (bs, 2 H), 8.43 (d, 1 H), 8.30 (d, I H), 8.19 (d, 1 H), 7.87 (dd, 1 H), 7.73 (s, 1 H), 7.67 (m, 1 H), 7.55 (m, 3 H), 4.41 (AB, 2 H), 4.14 (m, 1 H), 3.97 (s, 3 H), 3.89 (s, 3 H), 3.08 (m, 2 H), 1.99 (m, 1 H), 1.60 (m, 1 H). ISP MS, [M+H]$^+$=517.

Elemental analysis calculated with 1.5 mole of H₂O: C=47.38%, H=3.91%, N=8.14%; found C=47.40%, H=4.05%, N=8.22%.

EXAMPLE 13

Dibenzofuran-2-sulfonic acid {1-[3-(aminoiminomethyl)benzyl]-2-oxopyrrolidin-3-(S)-yl}amide trifluoroacetate.

A. Dibenzofuran-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using 2-dibenzofuransulfonyl chloride. The crude product is triturated from EtOAc to give the title compound as a beige solid.

$^1$H NMR (CDCl₃, 300 MHz) δ8.59 (d, 1 H), 8.04 (dd, 1 H), 7.95 (d, 1 H), 7.64 (d, 1 H), 7.60 (m, 1 H), 7.52 (m, 2 H), 7.40 (m, 5 H), 4.42 (AB, 2 H), 3.89 (m, 1 H), 3.19 (m, 2 H), 2.57 (m, 1 H), 2.08 (m, 1 H).

B. Dibenzofuran-2-sulfonic acid {1-[3-(aminoiminomethyl)benzyl]-2-oxopyrrolidin-3-(S)-yl}amide trifluoroacetate.

Dibenzofuran-2-sulfonic acid [1-(3-cyanobenzyl)-2-oxopyrrolidin-3-(S)-yl]amide is dissolved in 10 mL of a 2:1 mixture of EtOH/CH₂Cl₂ and converted to the title compound as in EXAMPLE 1, Part E. The imidate intermediate is formed over a period of 24 hours at room temperature. The amidine formation occurred over a period of 40 hours at room temperature. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a white solid.

$^1$H NMR (DMSO-d₆, 300 MHz) δ9.30 (bs, 2 H), 9.12 (bs, 2 H), 8.72 (d, 1 H), 8.30 (d, 1 H), 8.22 (d, 1 H), 8.04 (dd, 1 H), 7.92 (d, 1 H), 7.79 (d, 1 H), 7.67 (m, 1 H), 7.61 (m, 2 H), 7.56 (m, 1 H), 7.55 (bs, 1 H), 7.48 (m, 1 H), 4.42 (AB, 2 H), 4.19 (m, 1 H), 3.10 (m, 2 H), 2.04 (m, 1 H), 1.61 (m, 1 H). FAB MS, [M+H]⁺=463. Elemental analysis calculated with 1.3 mole of H₂O: C=51.97%, H=4.31%, N=9.32%; found C=51.99%, H=3.76%, N=9.00%.

EXAMPLE 14

7-Aminonaphthalene-2-sulfonic acid {1-[3-(aminoiminomethyl)benzyl]-2-oxopyrrolidin-3-(S)-yl}amide bistrifluoroacetate.

A. N-Cbz-7-aminonaphthalene-2-sulfonyl chloride.

To a suspension of 7-aminonaphthalene-2-sulfonic acid, sodium salt (3 g, 12.2 mmol) in 70 mL of water is added solid NaOH (0.98 g, 24 mmol) at room temperature. The mixture is stirred for 30 minutes, and benzyl chloroformate (3.43 mL, 24 mmol) is then added. The resulting mixture is stirred over a period of 16 hours. The crude product is treated as in EXAMPLE 9, Part A, to give 4.18 g of crude N-CBz-7-aminonaphthalene-2-sulfonic acid, sodium salt. A mixture of the sulfonic acid, sodium salt (4.18 g, 11 mmol) in 12 mL of thionyl chloride is heated at 80° C. for 3 hours. The mixture is allowed to cool to room temperature and concentrated in vacuo. The residue is diluted with EtOAc and washed successively with water (2×), saturated NaHCO₃ solution and saturated NaCl. The organic layer is dried over anhydrous MgSO₄, filtered and concentrated to give a brown oil. The crude product is purified by column chromatography in a gradient of 10% EtOAc/hexanes to 30% EtOAc/hexanes to afford the title compound (1.76 g, 4.68 mmol) as a beige solid.

$^1$H NMR (CDCl₃, 300 MHz) δ8.38 (s, 1 H), 8.12 (s, 1 H), 7.88 (d, 1 H), 7.80 (d, 2 H), 7.60 (dd, 1 H), 7.34 (m, 5 H), 7.27 (s, 1 H), 5.21 (s, 2 H).

B. N-Cbz-7-aminonaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 1, Part D using N-Cbz-7-aminonaphthalene-2-sulfonyl chloride in place of 7-methoxynaphthalene-2-sulfonyl chloride. The crude product is purified by column chromatography using a gradient of 10% EtOAc/CH₂Cl₂ to 25% EtOAc/CH₂Cl₂ to give the title compound as a solid.

$^1$H NMR (CDCl₃, 300 MHz) δ8.31 (s, 1 H), 8.03 (s, 1 H), 7.71 (m, 3 H), 7.55 (m, 2 H), 7.40 (m, 9 H), 5.78 (s, 1 H), 5.25 (d, 1 H), 5.21 (d, 1 H), 4.41 (AB, 2 H), 3.85 (m, 1 H), 3.15 (m, 2 H), 2.53 (m, 1 H), 2.02 (m, 1 H).

C. 7-Aminonaphthalene-2-sulfonic acid {1-[3-(aminoiminomethyl)benzyl]-2-oxopyrrolidin-3-(S)-yl}amide bistrifluoroacetate.

N-Cbz-7-aminonaphthalene-2-sulfonic acid [1-(3-cyanobenzyl)-2-oxopyrrolidin-3-(S)-yl]amide is dissolved in 10 mL of a 2:1 mixture of EtOH/CH₂Cl₂ and converted to the title compound as in EXAMPLE 1, Part E. The imidate intermediate is formed over a period of 18 hours at room temperature. The amidine formation occurred over a period of 18 hours at room temperature. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a white solid.

$^1$H NMR (DMSO-d₆, 300 MHz) δ9.29 (bs, 2 H), 9.20 (bs, 2 H), 8.11 (d, 1 H), 8.08 (s, 1 H), 7.82 (d, 1 H), 7.72 (d, 1 H), 7.67 (m, 1 H), 7.55 (m, 3 H), 7.48 (dd, 1 H), 7.13 (dd, 1 H), 7.00 (d, 1 H), 5.11 (bs, 3 H), 4.42 (AB, 2 H), 4.12 (m, 1 H), 3.06 (m, 2 H), 1.94 (m, 1 H), 1.56 (m, 1 H). FAB MS, [M+H]⁺=438. Elemental analysis calculated with 0.8 mole of H₂O: C=45.96%, H=3.94%, N=10.31%; found C=45.97%, H=4.02%, N=10.41%.

EXAMPLE 15

Naphthalene-2-sulfonic acid {1-[4-(aminoiminomethyl)benzyl]-2-oxopyrrolidin-3-(S)-yl}amide trifluoroacetate.

A. [1-(4-Cyanobenzyl)-2-oxopyrrolidin-3-(S)-yl]carbamic acid tert-butyl ester.

The title compound is prepared from Boc-L-Asp(H)-OBn as in EXAMPLE 1, Part B, using p-cyanobenzylamine hydrochloride in place of m-cyanobenzylamine hydrochloride. The crude residue is purified by column chromatography eluting with a gradient of 20% EtOAc/CH₂Cl₂ to 40% EtOAc/CH₂Cl₂ to give the title compound as a white solid.

$^1$H NMR (CDCl₃, 300 MHz) δ7.62 (d, 2 H), 7.31 (d, 2 H), 5.15 (bs, 1 H), 4.53 (AB, 2 H), 4.21 (m, 1 H), 3.24 (m, 2 H), 2.61 (m, 1 H), 1.90 (m, 1 H), 1.46 (s, 9 H).

B. 4-(3-(S)-Amino-2-oxopyrrolidin-1-ylmethyl)benzonitrile hydrochloride.

The title compound is prepared as a white solid from [1-(4-cyanobenzyl)-2-oxopyrrolidin-3-(S)-yl]carbamic acid tert-butyl ester as described in EXAMPLE 1, Part C.

$^1$H NMR (DMSO-d₆, 300 MHz) δ8.65 (bs, 3 H), 7.81 (d, 2 H), 7.49 (d, 2 H), 4.54 (AB, 2 H), 4.08 (m, 1 H), 3.30 (m, 2 H), 2.40 (m, 1 H), 2.01 (m, 1 H).

C. Naphthalene-2-sulfonic acid [1-(4-cyanobenzyl)-2-oxopyrrolidin-3-(S)-yl]amide.

The title compound is prepared from 4-(3-(S)-amino-2-oxopyrrolidin-1-ylmethyl)benzonitrile hydrochloride as in EXAMPLE 1, Part D. The crude product is triturated from EtOAc to give the title compound as a white solid. $^1$H NMR (DMSO-d₆, 300 MHz) δ8.50 (s, 1 H), 8.00 (m, 2 H), 7.93 (m, 3 H), 7.65 (m, 5 H), 7.28 (m, 1 H), 4.45 (AB, 2 H), 3.80 (m, 1 H), 3.20 (m, 2 H), 2.55 (m, 1 H), 2.11 (m, 1 H).

D. Naphthalene-2-sulfonic acid {1-[4-(aminoiminomethyl) benzyl]-2-oxopyrrolidin-3-(S)-yl}amide trifluoroacetate.

Naphthalene-2-sulfonic acid [1-(4-cyanobenzyl)-2-oxopyrrolidin-3-(S)-yl]amide is dissolved in 10 mL of a 2:1 mixture of EtOH/CH$_2$Cl$_2$ and converted to the title compound as in EXAMPLE 1, Part E. The imidate intermediate is formed over a period of 18 hours at room temperature. The amidine formation occurred over a period of 48 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.26 (bs, 2 H), 9.10 (bs, 2 H), 8.49 (d, 1 H), 8.30 (d, 1 H), 8.12 (d, 1 H), 8.11 (d, 1 H), 8.03 (d, 1 H), 7.88 (dd, 1 H), 7.74 (d, 2 H), 7.68 (m, 2 H), 7.40 (d, 2 H), 4.44 (AB, 2 H), 4.17 (m, 1 H), 3.07 (m, 2 H), 2.01 (m, 1 H), 1.58 (m, 1 H). FAB MS, [M+H]$^+$=423. Elemental analysis calculated with 1.4 mole of H$_2$O: C=51.32%, H=4.63%, N=9.97%, found C=51.32%, H=4.36%, N=9.78%.

EXAMPLE 16

7-Methoxynaphthalene-2-sulfonic acid [1-(3-aminomethylbenzyl)-2-oxopyrrolidin-3-(S)-yl]amide trifluoroacetate.

To a solution of 7-methoxynaphthalene-2-sulfonic acid [1-(3-cyanobenzyl)-2-oxopyrrolidin-3-(S)-yl]amide (0.12 g, 0.27 mmol) in 10 mL of 7 N NH$_3$/MeOH is added a catalytic amount of 5% rhodium on alumina powder. The resulting mixture is hydrogenated at room temperature on a Paar apparatus at 50 p.s.i. for 3 hours. The crude mixture is filtered through a pad of Celite, washed with MeOH (2×10 mL) and concentrated in vacuo. The crude product is purified by RP-HPLC eluting in a gradient of 10% CH$_3$CN/H$_2$O (0.1% TFA) to 60% CH$_3$CN/H$_2$O (0.1 % TFA) and the appropriate product fractions are lyophilized to provide the title compound as a white solid.

$^1$H NMR (DMSO-d$_6$, 300 MHz) δ8.39 (d, 1 H), 8.21 (d, 1 H), 8.13 (bs, 3 H), 8.01 (d, 1 H), 7.93 (d, 1), 7.71 (dd, 1 H), 7.55 (d, 1 H), 7.32 (m, 3 H), 7.20 (m, 2 H), 4.30 (AB, 2 H), 4.10 (m, 1 H), 4.00 (m, 2 H), 3.90 (s, 3 H), 3.03 (m, 2 H), 1.96 (m, 1 H), 1.55 (m, 1 H). FAB MS, [M+H]$^+$=440.

EXAMPLE 17

Naphthalene-2-sulfonic acid {1-[3-(aminoiminomethyl)benzyl]-2-oxopyrrolidin-3-(S)-yl}methyl amide trifluoroacetate.

A. Naphthalene-2-sulfonic acid [1-(3-cyanobenzyl)-2-oxopyrrolidin-3-(S)-yl]methyl amide.

Naphthalene-2-sulfonic acid [1-(3-cyanobenzyl)-2-oxopyrrolidin-3-(S)-yl]amide (0.3 g, 0.74 mmol) is dissolved in 9 mL of an 8:1 mixture of THF/DMF and cooled to 0° C. Sodium hydride (30 mg of a 60% dispersion in mineral oil, 0.75 mmol) is added and the solution is stirred for 15 minutes. To the mixture is added methyl iodide (0.33 g, 2.34 mmol). The cooling bath is removed and the solution is stirred at room temperature for 2 hours. The solution is poured into a separatory funnel and diluted with 100 mL of EtOAc. The organic layer is washed with 1 N HCl, dried over MgSO$_4$ and concentrated. The residue is purified by column chromatography eluting with 10% EtOAc/CH$_2$Cl$_2$ to give the title compound (0.23 g, 0.52 mmol) as a solid.

$^1$H NMR (CDCl$_3$, 300 MHz) δ8.52 (s, 1 H), 8.00 (m, 4 H), 7.62 (m, 4 H), 7.48 (m, 3 H), 4.95 (m, 1 H), 4.45 (AB, 2 H), 3.20 (m, 1 H), 2.80 (s, 3 H), 2.37 (m, 1 H), 2.05 (m, 1 H). FAB MS, [M+H]$^+$=420.

B. Naphthalene-2-sulfonic acid {1-[3-(aminoiminomethyl) benzyl]-2-oxopyrrolidin-3-(S)-yl}methyl amide trifluoroacetate.

The title compound is prepared as described in EXAMPLE 1, Part E using naphthalene-2-sulfonic acid [1-(3-cyanobenzyl)-2-oxopyrrolidin-3-(S)-yl]methyl amide as the starting material.

$^1$H NMR (DMSO-d$_6$, 300 MHz) δ9.30 (bs, 2 H), 9.10 (bs, 2 H), 8.52 (s, 1 H), 8.15 (m, 3 H), 7.85 (d, 1 H), 7.68 (m, 3 H), 7.55 (m, 3 H), 4.98 (m, 1 H), 4.42 (AB, 2 H), 3.15 (m, 2 H), 2.69 (s, 3 H), 2.02 (m, 1 H), 1.82 (m, 1 H). FAB MS, [M+H]$^+$=437. Elemental analysis calculated with 2 mole of H$_2$O: C=51.19%, H=4.985%, N=9.55%, found C=51.01%, H=4.35%, N=9.10%.

EXAMPLE 18

Naphthalene-2-sulfonic acid {1-[3-(aminoiminomethyl)benzyl]-pyrrolidin-3-(S)-yl] amide bistrifluoroacetate.

A. Naphthalene-2-sulfonic acid-N-Boc-3-(S)-aminopyrrolidine.

N-Boc-3-aminopyrrolidine (1.09 g, 5.83 mmol) is dissolved in 30 mL of CH$_2$Cl$_2$. To the solution is added triethylamine (0.61 g, 6.02 mmol) followed by 2-naphthalene sulfonyl chloride (1.32 g, 5.83 mmol). The reaction mixture is stirred for 4 hours. The crude mixture is diluted with 150 mL of EtOAc and washed with 1 N HCl, 10% Na$_2$CO$_3$ and saturated NaCl. The organic layer is dried over MgSO$_4$, filtered and concentrated to give the title compound (2.19 g, 5.8 mmol) as an oil.

$^1$H NMR (CDCl$_3$, 300 MHz) δ8.42 (s, 1 H), 7.95 (m, 4 H), 7.66 (m, 3 H), 5.03 (bs, 1 H), 3.88 (m, 1 H), 3.30 (m, 2 H), 3.10 (m, 1 H), 1.95 (m, 2 H), 1.45 (s, 9 H).

B. Naphthalene-2-sulfonic acid-pyrrolidin-3-(S)-ylamide trifluoroacetate.

Naphthalene-2-sulfonic acid-N-Boc-3-(S)-aminopyrrolidine (1.8 g, 4.78 mmol) is dissolved in 50 mL of CH$_2$Cl$_2$. Trifluoroacetic acid (8 mL) is added dropwise. The reaction mixture is stirred for 16 hours. The solution is concentrated in vacuo and then reconcentrated from toluene to give the title compound (1.8 g, 4.64 mmol).

$^1$H NMR (CDCl$_3$, 300 MHz) δ9.10 (bs, 1 H), 8.82 (bs, 1 H), 8.39 (s, 1 H), 7.90 (m, 3 H), 7.78 (d, 1 H), 7.61 (m, 3 H), 4.00 (bs, 1 H), 3.51 (m, 2 H), 3.38 (m, 2 H), 2.05 (m, 2 H).

C. Naphthalene-2-sulfonic acid [1-(3-cyanobenzyl)-pyrrolidin-3-(S)-yl]amide.

Naphthalene-2-sulfonic acid-pyrrolidin-3-(S)-ylamide trifluoroacetate (0.52 g, 1.34 mmol) is dissolved in 7 mL of DMF. Triethylamine (0.16 g, 1.6 mmol) is added and the reaction mixture is cooled to 0° C. a-Bromo-m-toluyl nitrile (0.25 g, 1.27 mmol) is added and the mixture is warmed to room temperature and stirred for 2 hours. The reaction mixture is diluted with 150 mL of EtOAc and the solution is washed with 1 N HCl, 10% Na$_2$CO$_3$ and saturated NaCl. The organic layer is dried over MgSO$_4$, filtered and concentrated. The residue is purified by column chromatography eluting with 50% EtOAc/CH$_2$Cl$_2$ to give the title compound (0.2 g, 0.51 mmol) as an oil.

$^1$H NMR (CDCl$_3$, 300 MHz) δ8.40 (s, 1 H), 7.95 (m, 3 H), 7.80 (d, 1 H), 7.64 (m, 2 H), 7.50 (m, 3 H), 7.31 (m, 1 H), 5.04 (d, 1 H), 3.92 (m, 1 H), 3.05 (q, 2 H), 2.70 (m, 1 H), 2.40 (m, 2 H), 2.18 (m, 2 H), 1.59 (m, 1 H).

D. Naphthalene-2-sulfonic acid {1-[3-(aminoiminomethyl) benzyl]-pyrrolidin-3-(S)-yl}amide bistrifluoroacetate.

The title compound is prepared as in EXAMPLE 1, Part E using naphthalene-2-sulfonic acid [1-(3-cyanobenzyl)-pyrrolidin-3-(S)-yl]amide as the starting material.

¹H NMR (CDCl₃, 300 MHz) δ10.6 (bs, 1 H), 9.32 (bs, 3 H), 8.45 (s, 1 H), 8.14 (m, 2 H), 8.05 (d, 1 H), 7.72 (m, 9 H), 3.85 (m, 1 H), 3.65 (AB, 2 H), 3.25 (m, 4 H), 1.95 (m, 2 H). FAB MS, [M+H]⁺=409. Elemental analysis calculated with 1.25 mole of H₂O: C=47.39%, H=4.36%, N=8.50%, found C=47.12%, H=3.97%, N=8.50%.

EXAMPLE 19

7-Methoxynaphthalene-2-sulfonic acid {1-[3-(aminoiminomethyl)benzyl]-2,5-dioxopyrrolidin-3-(S)-yl}amide trifluoroacetate.

A. N-Boc-Asp-(m-cyanobenzylamine)-OBn.

Boc-Asp-OBn (3.23 g, 10 mmol) is dissolved in 100 mL of THF. Triethylamine (2.53 g, 25 mmol) is added followed by m-cyanobenzylamine hydrochloride (1.75 g, 10.4 mmol). The reaction mixture is cooled to −10° C., and the BOP reagent (4.42 g, 10 mmol) is added. The mixture is stirred for 16 hours. The crude mixture is diluted with 200 mL of EtOAc and washed with 1 N HCl, 10% Na₂CO₃ and saturated NaCl. The organic layer is dried over MgSO₄, filtered and concentrated. The residue is purified by column chromatography eluting with 20% EtOAc/CH₂Cl₂ to give the title compound (3.4 g, 7.8 mmol) as a solid.

¹H NMR (CDCl₃, 300 MHz) δ7.48 (m, 9 H), 7.00 (bs, 1 H), 5.68 (bs, 1 H), 5.15 (AD, 2 H), 4.60 (m, 2 H), 4.35 (dd, 1 H), 3.12 (dd, 1 H), 2.75 (dd, 1 H), 1.45 (s, 9 H).

B. [1-(3-Cyanobenzyl)-2,5-dioxopyrrolidin-3-(S)-yl] carbamic acid tert-butyl ester.

N-Doc-Asp-(m-cyanobenzylamine)-OBn (1 g, 2.08 mmol) is dissolved in 20 mL of THF and cooled to −78° C. A 1 M solution of lithium hexamethyldisilylazide (4.8 mL, 4.8 mmol) in THF is added dropwise. The mixture is stirred for 20 minutes and 20 mL of saturated NH₄Cl is added. The solution is extracted with EtOAc and then washed with 1 N HCl, 10% Na₂CO₃ and saturated NaCl. The organic layer is dried over MgSO₄, filtered and concentrated. The residue is purified by column chromatography eluting with 20% EtOAc/CH₂Cl₂ to give the title compound (0.65 g, 1.8 mmol) as a solid.

¹H NMR (CDCl₃, 300 MHz) δ7.71 (s, 1 H), 7.58 (m, 2 H), 7.41 (m, 1 H), 5.12 (bs, 1 H), 4.75 (AB, 2 H), 4.20 (m, 1 H), 3.10 (dd, 1 H), 2.89 (dd, 1 H), 1.45 (s, 9 H).

C. 3-(3-(S)-amino-2,5-dioxopyrrolidin-1-ylmethyl) benzonitrile hydrochloride.

The title compound is prepared as in EXAMPLE 1, Part C using 1-(3-cyanobenzyl)-2,5-dioxopyrrolidin-3-(S)-yl}carbamic acid tert-butyl ester as the starting material.

¹H NMR (DMSO-d₆, 300 MHz) δ8.85 (bs, 2 H), 7.60 (m, 4 H), 4.68 (AB, 2 H), 4.45 (m, 1 H), 3.12 (dd, 1 H), 2.80 (dd, 1 H).

D. 7-Methoxynaphthalene-2-sulfonic acid [1-(3-cyanobenzyl)-2,5-dioxopyrrolidin-3-(S)-yl]amide.

The title compound is prepared as in EXAMPLE 1, Part D using 3-(3-(S)-amino-2,5-dioxopyrrolidin-1-ylmethyl) benzonitrile hydrochloride and 7-methoxynaphthalene-2-sulfonyl chloride.

¹H NMR (CDCl₃, 300 MHz) δ8.31 (s, 1 H), 7.91 (d, 1 H), 7.81 (d, 1 H), 7.70 (d, 1 H), 7.56 (m, 2 H), 7.35 (m, 2 H), 7.21 (m, 2 H), 5.39 (bs, 1 H), 4.62 (AB, 2 H), 4.12 (m, 1 H), 3.92 (s, 3 H), 3.15 (dd, 1 H), 2.90 (dd, 1 H).

E. 7-Methoxynaphthalene-2-sulfonic acid {1-[3-(aminoiminomethyl)benzyl]-2,5-dioxopyrrolidin-3-(S)-yl}amide trifluoroacetate.

The title compound is prepared as in EXAMPLE 1, Part E using 7-methoxynaphthalene-2-sulfonic acid [1-(3-cyanobenzyl)-2,5-dioxopyrrolidin-3-(S)-yl]amide as the starting material.

¹H NMR (DMSO-d₆, 300 MHz) δ9.29 (bs, 2 H), 9.18 (bs, 2 H), 8.42 (d, 1 H), 8.39 (s, 1 H), 8.05 (d, 1 H), 7.95 (d, 1 H), 7.70 (m, 3 H), 7.48 (m, 3 H), 7.37 (d, 1 H), 4.68 (m, 3 H), 3.89 (s, 3 H), 2.80 (dd, 1 H), 2.32 (dd, 1 H) FAB MS, [M+H]⁺=467. Elemental analysis calculated with 1.75 mole of H₂O: C=49.06%, H=4.36%, N=9.15%, found C=48.99%, H=4.17%, N=8.98%.

EXAMPLE 20

Naphthalene-2-sulfonic acid {1-[3-(aminoiminomethyl)benzyl]-2-oxopiperidin-3-yl}amide trifluoroacetate.

A. 3-[(N-Boc)-3-amino-2-oxopiperidin-1-ylmethyl]-benzonitrile.

A mixture of N-a-Boc-L-ornithine (1.5 g, 6.45 mmol) and 3-cyanobenzaldehyde (0.42 g, 3.23 mmol) are suspended in 20 mL of MeOH. A solution of anhydrous zinc chloride (0.24 g, 1.79 mmol) and sodium cyanoborohydride (0.22 g, 3.5 mmol) in 5 mL of MeOH is added. The mixture is stirred for 16 hours at room temperature. After this time, 20 mL of 1 N NaOH is added. The solution is concentrated and the residue is partitioned between EtOAc and water. The organic layer is washed with saturated NaCl. The organic layer is dried over MgSO₄, filtered and concentrated to give N-a-Boc-N-d-(3-cyanobenzyl)-L-ornithine. A portion of the crude residue (0.75 g, 2.16 mmol), BOP reagent (1.05 g, 2.38 mmol) and potassium hydrogen carbonate (1.08 g, 10.8 mmol) are dissolved in 20 mL of DMF. The reaction mixture is stirred for 16 hours and then diluted with 300 mL of EtOAc. The organic layer is washed with 1 N HCl, 10% Na₂CO₃ and saturated NaCl. The organic layer is dried over MgSO₄, filtered and concentrated. The residue is purified by column chromatography eluting with a gradient of 15% EtOAc/CH₂Cl₂ to 35% EtOAc/CH₂Cl₂ to give the title compound (0.26 g, 0.76 mmol) as a solid.

¹H NMR (CDCl₃, 300 MHz) δ7.49 (m, 4 H), 5.50 (bs, 1 H), 4.59 (s, 2 H), 4.08 (m, 1 H), 3.21 (m, 2 H), 2.48 (m, 1 H), 1.89 (m, 2 H), 1.62 (m, 1 H), 1.45 (s, 9 H).

B. Naphthalene-2-sulfonic acid [1-(3-cyanobenzyl)-2-oxopiperidin-3-yl]amide.

3-[(N-Boc)-3-amino-2-oxopiperidin-1-ylmethyl]-benzonitrile (0.25 g, 0.76 mmol) is dissolved in 5 mL of CH₂Cl₂. To the solution is added 1 mL of trifluoroacetic acid. The mixture is stirred for 3 hours at room temperature and then concentrated. The residue is reconcentrated from toluene to give 3-(3-amino-2-oxopiperidin-1-ylmethyl) benzonitrile trifluoroacetate (0.23 g, 0.76 mmol) as a solid. The crude product is then treated as in EXAMPLE 1, Part D to give the title compound.

¹H NMR (CDCl₃, 300 MHz) δ8.49 (s, 1 H), 7.94 (m, 4 H), 7.51 (m, 6 H), 6.10 (s, 1 H), 4.47 (AB, 2 H), 3.56 (m, 1 H), 3.20 (m, 2 H), 2.52 (m, 1 H), 1.83 (m, 3 H).

C. Naphthalene-2-sulfonic acid {1-[3-(aminoiminomethyl) benzyl]-2-oxopiperidin-3-yl}amide trifluoroacetate.

The title compound is prepared as in EXAMPLE 1, Part E using naphthalene-2-sulfonic acid [1-(3-cyanobenzyl)-2-oxopiperidin-3-yl]amide as the starting material.

¹H NMR (DMSO-d₆, 300 MHz) δ9.29 (bs, 2 H), 9.19 (bs, 2 H), 8.48 (s, 1 H), 8.04 (m, 4 H), 7.90 (d, 1 H), 7.60 (m, 6 H), 4.48 (s, 2 H), 3.95 (m, 1 H), 3.18 (s, 2 H), 1.86 (m, 1 H), 1.69 (m, 3 H). FAB MS, [M+H]⁺=437. Elemental analysis calculated with 1 mole of H₂O: C=52.81%, H=4.79%, N=9.84%, found C=52.85%, H=4.77%, N=9.15%.

EXAMPLE 21

7-Methoxynaphthalene-2-sulfonic acid {1-[3-(aminoiminomethyl)benzyl]-2-oxo-azepan-3-(S)-yl}amide trifluoroacetate.

A. L-(-)-a-Boc-amino-e-caprolactam.

L-(-)-a-Amino-e-caprolactam (5 g, 39 mmol) and triethylamine (4.9 g, 49 mmol) are dissolved in 100 mL of $CH_2Cl_2$. To the solution is added Boc anhydride (8.5 g, 39 mmol) and dimethylaminopyridine (0.1 g). The reaction mixture is stirred for 16 hours at room temperature. After this time, the solution is washed with 1 N HCl, 10% $Na_2CO_3$ and saturated NaCl. The organic layer is dried over $MgSO_4$, filtered and concentrated to give the title compound (6.23 g, 27 mmol) as a solid.

$^1$H NMR (CDCl$_3$, 300 MHz) δ6.15 (bs, 1 H), 5.90 (bs, 1 H), 4.24 (m, 1 H), 3.21 (m, 2 H), 2.05 (m, 2 H), 1.79 ( m, 2 H), 1.45 (m, 11 H).

B. [1-(3-Cyanobenzyl)-2-oxoazepan-3-(S)-yl]carbamic acid tert-butyl ester.

L-(-)-a-Boc-amino-e-caprolactam (1.07 g, 4.7 mmol) is dissolved in 45 mL of THF and cooled to 0° C. To the solution is added a 1M solution of lithium hexamethyldisilylazide (4.7 mL, 4.7 mmol) in THF. The mixture is stirred for 30 minutes at 0° C. To the resulting solution is added a-bromo-m-toluyl nitrile (0.9 g, 4.7 mmol). The reaction mixture is stirred for 4 hours. The solution is diluted with 100 mL of EtOAc and is washed with 1 N HCl, 10% $Na_2CO_3$ and saturated NaCl. The organic layer is dried over $MgSO_4$, filtered and concentrated. The residue is purified by column chromatography eluting with 20% EtOAc/$CH_2Cl_2$ to give the title compound (1.05 g, 3.1 mmol) as a solid.

$^1$H NMR (CDCl$_3$, 300 MHz) δ7.45 (m, 4 H), 5.95 (d, 1 H), 4.85 (AB, 1 H), 4.35 (AB, 1 H), 4.40 (m, 1 H), 3.48 (m, 1 H), 3.15 (dd, 1 H), 2.05 (m, 1 H), 1.90 (m, 1 H), 1.70 (m, 2 H), 1.49 (m, 1 H), 1.45 (s, 9 H), 1.20 (m, 1 H).

C. 3-(3-(S)-Amino-2-oxoazepan-1-ylmethyl)benzonitrile hydrochloride.

The title compound is prepared as in EXAMPLE 1, Part C using [1-(3-cyanobenzyl)-2-oxoazepan-3-(S)-yl]carbamic acid tert-butyl ester as the starting material. EI MS, [M]+= 243.

D. 7-Methoxynaphthalene-2-sulfonic acid [1-(3-cyanobenzyl)-2-oxoazepan-3-(S)-yl]amide.

The title compound is prepared as in EXAMPLE 1, Part D using 3-(3-(S)-amino-2-oxoazepan-1-ylmethyl) benzonitrile hydrochloride and 7-methoxynaphthalene sulfonyl chloride as the starting materials.

$^1$H NMR (CDCl$_3$, 300 MHz) δ8.32 (s, 1 H), 7.88 (m, 2 H), 7.68 (d, 1 H), 7.29 (m, 3 H), 7.08 (m, 1 H), 6.96 (m, 1 H), 6.35 (d, 1 H), 4.80 (AB, 1 H), 4.10 (AB, 1 H), 4.00 (m, 1 H), 3.92 (s, 3 H), 3.19 (m, 1 H), 3.05 (m, 2 H), 2.18 (m, 1 H), 1.95 (m, 1 H), 1.65 (m, 2 H), 1.18 (m, 3 H).

E. 7-Methoxynaphthalene-2-sulfonic acid {1-[3-(aminoiminomethyl)benzyl]-2-oxoazepan-3-(S)-yl}amide trifluoroacetate.

The title compound is prepared as in EXAMPLE 1, Part E using 7-methoxy naphthalene-2-sulfonic acid [1-(3-cyanobenzyl)-2-oxoazepan-3-(S)-yl]amide as the starting material.

$^1$H NMR (DMSO-d$_6$, 300 MHz) δ9.28 (bs, 2 H), 9.08 (bs, 2 H), 8.32 (s, 1 H), 7.95 (m, 2 H), 7.79 (d, 1 H), 7.62 (m, 3 H), 7.60 (d, 1 H), 7.32 (m, 2 H), 7.10 (d, 1 H), 4.13 (AB, 2 H), 3.89 (s, 3 H), 3.40 (m, 1 H), 3.15 (m, 1 H), 1.79 (m, 3 H), 1.51 (m, 3 H), 1.12 (m, 1 H). FAB MS, [M+H]$^+$=481. Elemental analysis calculated with 0.5 mole of $H_2O$: C=53.73%, H=5.01%, N=9.28%, found C=53.77%, H=4.86%, N=9.26%.

EXAMPLE 22

7-Methoxynaphthalene-2-sulfonic acid {1-[3-(aminoiminomethyl)benzyl]-2-oxo-pyrrolidin-3-(S)-yl}methyl amide trifluoroacetate.

A. 7-Methoxynaphthalene-2-sulfonic acid [1-(3-cyanobenzyl)-2-oxopyrrolidin-3-(S)-yl]methyl amide.

The title compound is prepared as in EXAMPLE 17, Part A using 7-methoxynaphthalene-2-sulfonic acid [1-(3-cyanobenzyl)-2-oxopyrrolidin-3-(S)-yl]amide as the starting material.

$^1$H NMR (CDCl$_3$, 300 MHz) δ8.44 (d, 1 H), 7.92 (d, 1 H), 7.82 (m, 2 H), 7.61 (m, 1 H), 7.47 (m, 3 H), 7.28 (m, 2 H), 4.97 (m, 1 H), 4.53 (AB, 1 H), 4.39 (AB, 1 H), 3.96 (s, 3 H), 3.13 (m, 2 H), 2.83 (s, 3 H), 2.36 (m, 1 H), 2.37 (m, 1 H), 2.06 (m, 1 H).

B. 7-Methoxynaphthalene-2-sulfonic acid {1-[3-(aminoiminomethyl)benzyl]-2-oxopyrrolidin-3-(S)-yl}methyl amide trifluoroacetate.

The title compound is prepared as described in EXAMPLE 1, Part E using 7-methoxynaphthalene-2-sulfonic acid [1-(3-cyanobenzyl)-2-oxopyrrolidin-3-(S)-yl] methyl amide as the starting material.

$^1$H NMR (DMSO-d$_6$, 300 MHz) δ9.28 (bs, 2 H), 9.07 (bs, 2 H), 8.38 (s, 1 H), 8.01 (d, 1 H), 7.93 (s, 1 H), 7.68 (m, 2 H), 7.54 (m, 4 H), 7.33 (d, 1 H), 4.90 (m, 1 H), 4.40 (AB, 2 H), 3.88 (s, 3 H), 3.12 (m, 2 H), 2.66 (s, 3 H), 1.98 (m, 1 H), 1.75 (m, 1 H). FAB MS, [M+H]$^+$=467. Elemental analysis calculated with 2.5 mole of $H_2O$: C=49.92%, H=5.16%, N=8.96%, found C=50.03%, H=4.56%, N=8.70%.

EXAMPLE 23

3-(3-(S)-Amino-2-oxopyrrolidin-1-ylmethyl) benzonitrile hydrochloride.

A. (2-Oxopyrrolidin-3-(S)-yl)-carbamic acid tert-butyl ester.

To a solution of (S)-Boc-diaminobutyric acid (25 g, 115 mmol), triethylamine (35 g, 344 mmol), and hydroxybenzotriazole (19.3 g, 143 mmol) in 0.5 L of THF is added 1-(3-dimethylaminopropyl)-3-ethylcarbodiimide hydrochloride (27.4 g, 143 mmol). The solution is heated to 60° C. over 15 minutes. A white precipitate forms and the solution is kept at 60° C. for 4 hours. After this time, the solution is filtered and the collected liquid is concentrated. The crude product is purified by column chromatography in a gradient of 1% MeOH/$CH_2Cl_2$ to 3% MeOH/$CH_2Cl_2$ to afford the title compound (19.6 g, 98 mmol) as a white solid.

$^1$H NMR (CDCl$_3$, 300 MHz) δ6.17 (bs, 1 H), 5.08 (bs, 1 H), 4.12 (m, 1 H), 3.33 (m, 2 H), 2.65 (m, 1 H), 2.00 (m, 1 H), 1.42 (s, 9 H).

B. [1-(3-Cyanobenzyl)-2-oxopyrrolidin-3-(S)-yl]carbamic acid tert-butyl ester.

To a solution of (2-oxopyrrolidin-3-(S)-yl)-carbamic acid tert-butyl ester (9 g, 45 mmol) and α-bromo-m-toluyl nitrile (9.3 g, 47 mmol) in 225 mL of THF/DMF (10:1) at 0° C. is added a 60% mineral oil dispersion of sodium hydride (1.8 g, 46 mmol). The reaction mixture is stirred at 0° C. for 0.5 hours and then is allowed to warm to ambient temperatures. After 3 hours, the reaction mixture is quenched by the addition of saturated $NH_4Cl$ and diluted with EtOAc. The layers are separated. The organic layer is washed with 1 N HCl, $H_2O$ and saturated NaCl. The organic layer is dried over $MgSO_4$, filtered, and concentrated. The crude product is purified by column chromatography eluting with gradient of 20% EtOAc/hexanes to 40% EtOAc/hexanes to afford the title compound (12.7 g, 40 mmol) as a white solid.

$^1$H NMR (CDCl$_3$, 300 MHz) δ7.55 (m, 4 H), 5.18 (bs, 1 H), 4.47 (AB, 2 H), 4.18 (dd, 1 H), 3.21 (m, 2 H), 2.60 (m, 1 H), 1.42 (s, 9 H).

C. 3-(3-(S)-Amino-2-oxopyrrolidin-1-ylmethyl)benzonitrile hydrochloride.

To a solution of [1-(3-cyanobenzyl)-2-oxopyrrolidin-3-(S)-yl]carbamic acid tert-butyl ester (9.1 g, 29 mmol) in 150 mL of EtOAc at 0° C. is bubbled HCl gas for 10 minutes. After this time, the solution is stirred for 4 hours. The solution is then concentrated to give the title compound (7.3 g, 29 mmol) as a white solid.

$^1$H NMR (DMSO-d$_6$, 300 MHz) δ8.71 (bs, 3 H), 7.85 (m, 2 H), 7.70 (m, 2 H), 4.58 (AB, 2 H), 4.13 (m, 1 H), 3.32 (m, 2 H), 2.44 (m, 1 H), 2.18 (m, 1 H).

EXAMPLE 24

6-Methoxynaphthalene-2-sulfonic acid {1-[3-(aminoiminomethyl)benzyl]-2-oxopyrrolidin-3-(S)-yl}amide trifluoroacetate.

A. 6-Methoxynaphthalene-2-sulfonyl chloride.

To a suspension of 6-hydroxynaphthalene-2-sulfonic acid, sodium salt (5 g, 20.3 mmol) in 40 mL of 2:1 H$_2$O/ethanol is added solid NaOH (0.89 g, 22.3 mmol) at room temperature. The resulting black mixture is stirred until a homogenous solution forms, and dimethyl sulfate (2.11 mL, 22.3 mmol) is then added. The mixture is stirred over a period of 16 hours as a precipitate eventually forms. The crude mixture is concentrated in vacuo and the residue is stirred in 70 mL of absolute EtOH as a slurry. The precipitate is filtered and dried. The solid is heated at reflux in 100 mL of 95% EtOH for 2.5 hours allowed to cool to room temperature, filtered and dried to give 3.31 g of crude 6-methoxynaphthalene-2-sulfonic acid, sodium salt. A mixture of the sulfonic acid, sodium salt (3.31 g, 12.7 mmol) in 5.3 mL of phosphorous oxychloride and phosphorous pentachloride (3.44 g, 16.5 mmol) is heated slowly to 60° C. until a homogenous solution forms and then is heated at 120° C. for 4 hours. The resulting mixture is allowed to stir at room temperature overnight, then is added slowly to a mixture of ice/ice water. The mixture is diluted with water and extracted with CHCl$_3$. The combined organic layers are washed successively with water and saturated NaHCO$_3$ solution. The organic phase is dried over anhydrous MgSO$_4$, filtered and concentrated to give 4 g of a crude product. The crude product is purified by column chromatography in a gradient of 10% EtOAc/hexanes to 20% EtOAc/hexanes to afford the title compound (1.51 g, 5.88 mmol) as a crystalline solid.

$^1$H NMR (CDCl$_3$, 300 MHz) δ8.50 (d, 1 H), 7.91 (m, 3 H), 7.31 (d, 1 H), 7.21 (d, 1 H), 3.99 (s, 3 H). EI MS, [M]$^+$=256.

B. 6-Methoxynaphthalene-2-sulfonic acid [1-(3-cyanobenzyl)-2-oxopyrrolidin-3-(S)-yl]amide.

3-(3-(S)-Amino-2-oxopyrrolidin-1-ylmethyl)benzonitrile hydrochloride (0.20 g, 0.79 mmol) is suspended in 10 mL of CH$_2$Cl$_2$. To the solution is added triethylamine (0.24 g, 2.37 mmol) followed by 6-methoxynaphthalene-2-sulfonyl chloride (0.25 g, 0.99 mmol). After stirring for 1.5 hours the solution is diluted with EtOAc and washed with 1 N aqueous HCl, water, saturated NaHCO$_3$ solution and saturated NaCl solution. The organic layer is dried over MgSO$_4$, filtered and concentrated to provide crude material which is purified by column chromatography in a gradient of 20% EtOAc/CH$_2$Cl to 50% EtOAc/CH$_2$Cl$_2$ to afford the title compound (0.18 g, 0.41 mmol) as a solid.

$^1$H NMR (CDCl$_3$, 300 MHz) δ8.40 (s, 1 H), 7.90 (m, 3 H), 7.59 (m, 1 H), 7.46 (m, 3 H), 7.29 (m, 1 H), 7.20 (d, 1 H), 5.40 (d, 1 H), 4.40 (s, 2 H), 3.99 (s, 3 H), 3.75 (m, 1 H), 3.20 (m, 2 H), 2.60 (m, 1 H), 2.13 (m, 1 H).

C. 6-Methoxynaphthalene-2-sulfonic acid {1-[3-(aminoiminomethyl)benzyl]-2-oxopyrrolidin-3-(S)-yl}amide trifluoroacetate.

6-Methoxynaphthalene-2-sulfonic acid [1-(3-cyanobenzyl)-2-oxopyrrolidin-3-(S)-yl]amide (0.18 g, 0.41 mmol) is dissolved in 10 mL of a 2:1 mixture of EtOH/CH$_2$Cl$_2$. The solution is cooled to 0° C. and HCl gas is bubbled through the solution for 10 minutes. The ice bath is removed and the reaction mixture is stirred at room temperature for 18 hours. After this time, the solution is concentrated and pumped under high vacuum until dry. The residue is dissolved in 10 mL of methanol, cooled to 0° C. and ammonia gas is bubbled through the solution for 10 minutes. The reaction mixture is stirred at room temperature for 42 hours. After this time, the solution is concentrated and the residue is purified by RP-HPLC eluting with a gradient of 10% CH$_3$CN/H$_2$O (0.1% TFA) to 60% CH$_3$CN/H$_2$O (0.1 % TFA) over a 30 min period. The appropriate fractions are lyophilized to give the title compound (0.11 g, 0.19 mmol) as an amorphous white solid.

$^1$H NMR (DMSO-d$_6$, 300 MHz) δ9.30 (bs, 2 H), 9.10 (bs, 2 H), 8.40 (s, 1 H), 8.19 (d, 1 H), 8.04 (d, 1 H), 8.00 (d, 1 H), 7.82 (dd, 1 H), 7.68 (m, 1 H), 7.55 (m, 3 H), 7.45 (d, 1 H), 7.30 (dd, 1 H), 4.42 (AB, 2 H), 4.15 (m, 1 H), 3.91 (s, 3 H), 3.09 (m, 2 H), 1.99 (m, 1 H), 1.58 (m, 1 H). FAB MS, [M+H]$^+$=453. Elemental analysis calculated with 2.5 mole of H$_2$O: C=50.60%, H=5.13%, N=9.45%; found C=50.66%, H=4.28%, N=9.13%.

EXAMPLE 25

6-Methoxynaphthalene-2-sulfonic acid {1-[3-(aminoiminomethyl)benzyl]-2-oxopyrrolidin-3-(S)-yl}methyl amide trifluoroacetate.

A. 6-Methoxynaphthalene-2-sulfonic acid {1-(3-cyanobenzyl)-2-oxopyrrolidin-3-(S)-yl}methyl amide.

6-Methoxynaphthalene-2-sulfonic acid [1-(3-cyanobenzyl)-2-oxopyrrolidin-3-(S)-yl]amide (0.24 g, 0.55 mmol) is dissolved in 5 mL of an 8:1 mixture of THF/DMF and cooled to 0° C. Sodium hydride (24 mg of a 60% dispersion in mineral oil, 0.61 mmol) is added and the solution is stirred for 15 minutes. To the mixture is added methyl iodide (0.15 g, 1.10 mmol). The cooling bath is removed and the solution is stirred at room temperature for 2 hours. The solution is poured into a separatory funnel and diluted with 100 mL of EtOAc. The organic layer is washed with 1 N HCl, saturated NaHCO$_3$ and saturated NaCl, then dried over MgSO$_4$, filtered and concentrated. The crude residue is purified by column chromatography eluting with 25% EtOAc/CH$_2$Cl$_2$ to give the title compound (0.23 g, 0.51 mmol) as a solid.

$^1$H NMR (CDCl$_3$, 300 MHz) δ8.45 (s, 1 H), 7.87 (m, 3 H), 7.59 (m, 4 H), 7.20 (m, 2 H), 4.95 (m, 1 H), 4.44 (AB, 2 H), 3.95 (s, 3 H), 3.21 (m, 2 H), 2.80 (s, 3 H), 2.40 (m, 1 H), 2.09 (m, 1 H).

B. 6-Methoxynaphthalene-2-sulfonic acid {1-[3-(aminoiminomethyl)benzyl]-2-oxopyrrolidin-3-(S)-yl}methyl amide trifluoroacetate.

The title compound is prepared as described in EXAMPLE 24, Part C using 6-methoxynaphthalene-2-sulfonic acid [1-(3-cyanobenzyl)-2-oxopyrrolidin-3-(S)-yl] methyl amide as the starting material. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

¹H NMR (DMSO-d₆, 300 MHz) δ9.30 (bs, 2 H), 9.17 (bs, 2 H), 8.43 (d, 1 H), 8.06 (d, 1 H), 7.99 (d, 1 H), 7.81 (dd, 1 H), 7.70 (m, 1 H), 7.58 (m, 3 H), 7.46 (d, 1 H), 7.30 (dd, 1 H), 4.92 (m, 1 H), 4.43 (AB, 2 H), 3.90 (s, 3 H), 3.17 (m, 2 H), 2.67 (s, 3 H), 2.00 (m, 1 H), 1.79 (m, 1 H). FAB MS, [M+H]⁺=467. Elemental analysis calculated with 1.8 mole of H₂O: C=50.91%, H=5.04%, N=9.13%, found C=50.92%, H=4.55%, N=8.83%.

EXAMPLE 26

2-[{1-[3-(Aminoiminomethyl)benzyl]-2-oxopyrrolidin-3-(S)-yl}-6-methoxynaphthalene-2-sulfonylamino]-N-phenethylacetamide trifluoroacetate.

A. 2-[{1-(3-Cyanobenzyl)-2-oxopyrrolidin-3-(S)-yl}-6-methoxynaphthalene-2-sulfonylamino]-N-acetic acid t-butyl ester.

To a solution of 6-methoxynaphthalene-2-sulfonic acid [1-(3-cyanobenzyl)-2-oxopyrrolidin-3-(S)-yl]amide, prepared as described in EXAMPLE 24 part B, (0.33 g, 0.76 mmol) and t-butyl bromoacetate (0.15 g, 0.77 mmol) in DMF (6 mL) is added K₂CO₃ (0.21 g, 1.5 mmol). The reaction mixture is stirred for 3 hours. After this time, the reaction mixture is diluted with EtOAc and H₂O. The layers are separated. The organic layer is washed with H₂O and saturated NaCl. The crude product is purified by column chromatography in a gradient of 10% EtOAc/CH₂Cl₂ to 20% EtOAc/CH₂Cl₂ to afford the title compound (0.42 g, 0.76 mmol) as a white foam.

B. 2-[{1-(3-Cyanobenzyl)-2-oxopyrrolidin-3-(S)-yl}-6-methoxynaphthalene-2-sulfonylamino]-N-acetic acid.

2-[{1-(3-Cyanobenzyl)-2-oxopyrrolidin-3-(S)-yl}-6-methoxynaphthalene-2-sulfonylamino]-N-acetic acid t-butyl ester is dissolved in 25 mL CH₂Cl₂/trifluoroacetic acid (5:1). After 3 hours, the solution is concentrated to give the title compound as a white foam.

¹H NMR (CDC₃, 300 MHz) δ8.39 (s, 1 H), 7.85 (m, 3 H), 7.60 (d, 1 H), 7.49 (m, 3 H), 7.19 (m, 2 H), 4.77 (t, 1 H), 4.51 (AB, 2 H), 4.02 (m, 1 H), 3.92 (s, 3 H), 3.82 (m, 1 H), 3.28 (m, 2 H), 2.39 (m, 1 H), 2.11 (m, 1 H).

C. 2-[{1-(3-Cyanobenzyl)-2-oxopyrrolidin-3-(S)-yl}-6-methoxynaphthalene-2-sulfonylamino]-N-phenethylacetamide.

To a solution of 2-[{1-(3-cyanobenzyl)-2-oxopyrrolidin-3-(S)-yl}-6-methoxynaphthalene-2-sulfonylamino]-N-acetic acid (0.41 g, 0.83 mmol), triethylamine (0.28 g, 2.8 mmol) and phenethylamine (0.28 g, 2.8 mmol) in 8 mL of DMF is added benzotriazol-1-yloxy-tris(dimethylamino)phosphonium hexafluorophosphate (0.37 g, 0.83 mmol). The solution is stirred for 16 hours. After this time, the solution is diluted with EtOAc. The organic layer is washed with 1 N HCl, 10% Na₂CO₃ and saturated NaCl. The organic layer is dried over MgSO₄, filtered, and concentrated. The crude product is purified by column chromatography eluting with gradient of 10% EtOAc/CH₂Cl₂ to 20% EtOAc/CH₂Cl₂ to afford the title compound (0.40 g, 0.70 mmol) as a white solid.

¹H NMR (CDCl₃, 300 MHz) δ8.38 (s, 1 H), 7.86 (m, 4 H), 7.51 (m, 4 H), 7.19 (m, 6 H), 4.58 (AB, 1 H), 4.38 (m, 3 H), 3.91 (m, 3 H), 3.78 (AB, 2 H), 3.29 (m, 4 H), 2.62 (m, 2 H), 2.21 (m, 2 H).

D. 2-[{1-[3-(Aminoiminomethyl)benzyl]-2-oxopyrrolidin-3-(S)-yl}-6-methoxynaphthalene-2-sulfonylamino]-N-phenethylacetamide trifluoroacetate.

The title compound is prepared as described in EXAMPLE 24, Part C using 2-[{1-(3-cyanobenzyl)-2-oxopyrrolidin-3-(S)-yl}-6-methoxynaphthalene-2-sulfonylamino]-N-phenethylacetamide as the starting material. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 4 H), 8.48 (s, 1 H), 8.19 (m, 1 H), 8.00 (m, 2 H), 7.88 (m, 1 H), 7.69 (m, 1 H), 7.54 (m, 3 H), 7.42 (m, 1 H), 7.18 (m, 5 H), 4.80 (t, 1 H), 4.41 (m, 2 H), 3.89 (m, 4 H), 3.56 (m, 1 H), 3.18 (m, 4 H), 2.62 (m, 2 H), 2.01 (m, 2 H). FAB MS, [M+H]⁺=614. Elemental analysis calculated with 2.25 mole of H₂O cal. C=54.90%, H=4.79%, N=9.01%, found C=54.72%, H=5.31%, N=9.12%.

EXAMPLE 27

9,10-Dioxo-8a,9,10,10a-tetrahydroanthracene-2-sulfonic acid {1-[3-(aminoiminomethyl)benzyl]-2-oxopyrrolidin-3-(S)-yl}amide trifluoroacetate.

A. Anthraquinone-2-sulfonyl chloride.

A mixture of anthraquinone-2-sulfonic acid, sodium salt (5 g, 15.2 mmol) in 6.4 mL of phosphorous oxychloride and phosphorous pentachloride (4.12 g, 19.8 mmol) is heated slowly to 60° C. until a homogenous solution forms and then is heated at 120° C. for 4 hours. The resulting mixture is cooled in an ice bath and a mixture of ice/ice water is added slowly with stirring. The mixture is diluted with water and extracted twice with CHCl₃. The combined organic layers are washed successively with saturated NaHCO₃ solution and saturated NaCl solution. The organic phase is dried over anhydrous MgSO₄, filtered and concentrated to give 4.50 g of crude product sulfonyl chloride which is of sufficient purity to be used in subsequent reactions.

¹H NMR (CDCl₃, 300 MHz) δ8.99 (d, 1 H), 8.58 (d, 1 H), 8.39 (m, 3 H), 7.90 (m, 2 H). EI MS, [M]⁺=306.

B. 9,10-Dioxo-8a,9,10,10a-tetrahydroanthracene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using anthraquinone-2-sulfonyl chloride in place of 6-methoxynaphthalene-2-sulfonyl chloride. The crude product is purified by column chromatography in a gradient of 20% EtOAc/CH₂Cl₂ to 40% EtOAc/CH₂Cl₂ to give the title compound as a solid.

¹H NMR (CDCl₃, 300 MHz) δ8.82 (d, 1 H), 8.41 (d, 1 H), 8.30 (m, 3 H), 7.85 (m, 2 H), 7.58 (d, 1 H), 7.47 (m, 3 H), 6.20 (bs, 1 H), 4.50 (AB, 2 H), 4.03 (m, 1 H), 3.29 (m, 2 H), 2.69 (m, 1 H), 2.15 (m, 1 H).

C. 9,10-Dioxo-8a,9,10,10a-tetrahydroanthracene-2-sulfonic acid {1-[3-(aminoiminomethyl)benzyl]-2-oxopyrrolidin-3-(S)-yl}amide trifluoroacetate.

9,10-Dioxo-8a,9, 10,10a-tetrahydroanthracene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.28 (bs, 2 H), 9.05 (bs, 2 H), 8.63 (d, 1 H), 8.59 (d, 1 H), 8.32 (m, 2 H), 8.20 (m, 2 H), 7.94 (m, 2 H), 7.61 (m, 1 H), 7.50 (m, 3 H), 4.36 (AB, 2 H), 4.21 (m, 1 H), 3.08 (m, 2 H), 2.09 (m, 1 H), 1.60 (m, 1 H). FAB MS, [M+H]⁺=503. Elemental analysis calculated with 1.8 mole of H₂O: C=51.78%, H=4.14%, N=8.63%, found C=51.79%, H=3.82%, N=8.28%.

EXAMPLE 28

8-Chloro-7-methoxynaphthalene-2-sulfonic acid {1-[3-(aminoiminomethyl)benzyl]-2-oxopyrrolidin-3-(S)-yl}amide trifluoroacetate.

A. 8-Chloro-7-methoxynaphthalene-2-sulfonyl chloride.

The title compound is prepared as described in EXAMPLE 24, Part A using 7-hydroxynaphthalene-2-sulfonic acid, sodium salt (15 g, 60.9 mmol) in place of 6-hydroxynaphthalene-2-sulfonic acid, sodium salt. The crude 7-methoxynaphthalene-2-sulfonic acid, sodium salt (12.6 g) obtained is likewise chlorinated in the presence of excess phosphorous oxychloride and phosphorous pentachloride. The crude product (10 g) is purified by column chromatography in a gradient of 5% EtOAc/hexanes to 30% EtOAc/hexanes to afford the title compound (1.49 g, 5.12 mmol) as the minor component as a solid.

$^1$H NMR (CDCl$_3$, 300 MHz) δ 8.95 (d, 1 H), 8.01 (d, 1 H), 7.90 (d, 2 H), 7.55 (d, 1 H), 4.09 (s, 3 H). EI MS, [M]$^+$=290.

The 7-methoxynaphthalene-2-sulfonyl chloride (3.80 g, 14.8 mmol) is also isolated as the major component from the above procedure as a white crystalline solid.

$^1$H NMR (CDCl$_3$, 300 MHz) δ 8.49 (d, 1 H), 7.96 (d, 1 H), 7.85 (d, 2 H), 7.39 (dd, 1 H), 7.29 (d, 1 H), 3.99 (s, 3 H). EI MS, [M]$^+$=256.

B. 8-Chloro-7-methoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 8-chloro-7-methoxynaphthalene-2-sulfonyl chloride in place of 6-methoxynaphthalene-2-sulfonyl chloride. The crude product is triturated from 50% EtOAc/hexanes solution to give the title compound as a beige solid.

$^1$H NMR (CDCl$_3$, 300 MHz) δ 8.81 (s, 1 H), 8.00 (d, 1 H), 7.86 (m, 2 H), 7.59 (m, 1 H), 7.45 (m, 4 H), 5.49 (s, 1 H), 4.47 (s, 2 H), 4.10 (s, 3 H), 3.81 (m, 1 H), 3.22 (m, 2 H), 2.65 (m, 1 H), 2.10 (m, 1 H).

C. 8-Chloro-7-methoxynaphthalene-2-sulfonic acid {1-[3-(aminoiminomethyl)benzyl]-2-oxopyrrolidin-3-(S)-yl}amide trifluoroacetate.

8-Chloro-7-methoxynaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1 % TFA) to 60% CH$_3$CN/H$_2$O (0.1 % TFA) and the appropriate product fractions are lyophilized to provide the title compound as a white solid.

$^1$H NMR (DMSO-d$_6$, 300 MHz) δ 9.35 (bs, 2 H), 9.30 (bs, 2 H), 8.60 (s, 1 H), 8.41 (d, 1 H), 8.15 (d, 1 H), 8.10 (d, 1 H), 7.81 (dd, 1 H), 7.76 (d, 1 H), 7.68 (m, 1 H), 7.55 (m, 3 H), 4.41 (AB, 2 H), 4.21 (m, 1 H), 4.08 (s, 3 H), 3.10 (m, 2 H), 2.00 (m, 1 H), 1.60 (m, 1 H). FAB MS, [M+H]$^+$=487. Elemental analysis calculated with 1 mole of H$_2$O: C=48.54%, H=4.23%, N=9.06%; found C=48.53%, H=4.08%, N=8.72%.

EXAMPLE 29

7-Methoxynaphthalene-2-sulfonic acid {1-[4-(aminoiminomethyl)benzyl]-2-oxopyrrolidin-3-(S)-yl}amide trifluoroacetate.

A. Boc-L-Asp(H)-OBn.

Boc-L-Asp-OBn (15 g, 46.4 mmol) is dissolved in 50 mL of THF and cooled to −10° C. The solution is treated with N-methylmorpholine (4.9 g, 48.7 mmol) and stirred for 5 minutes. To the solution is added dropwise isobutyl chloroformate (6.3 g, 46.4 mmol). After the addition is completed, the solution is stirred for 1 minute, then filtered through a pad of Celite. The collected solution is cooled to −10° C. To the solution is added sodium borohydride (2.63 g, 70 mmol) predissolved in 50 mL of water. The solution is stirred for 2 minutes. The solution is poured into a separatory funnel and diluted with 800 mL of EtOAc. The organic layer is washed with water and saturated NaCl. The organic layer is dried over MgSO$_4$, filtered and concentrated. The resulting residue is added to a solution of oxalyl chloride (30 mL of a 2 M solution in CH$_2$Cl$_2$, 60 mmol), and methyl sulfoxide (7.25 g, 92.8 mmol) in 250 mL of CH$_2$Cl$_2$ at −78° C. The reaction mixture is stirred at −78° C. for 40 minutes, then triethylamine (14 g, 140 mmol) is added. The reaction mixture is stirred at −78° C. for 1 hour and then is stirred at room temperature for 30 minutes. The solution is poured into 200 mL of a 20% citric acid/water solution. The resulting mixture is poured into a separatory funnel and the layers are separated. The organic layer is washed with water and saturated NaCl. The organic layer is dried over MgSO$_4$, filtered and concentrated. The residue is purified by column chromatography eluting with a gradient of 10% EtOAc/hexanes to 30% EtOAc/hexanes. The product aldehyde (12 g, 39 mmol) is obtained as an oil.

$^1$H NMR (CDCl$_3$, 300 MHz) δ 9.68 (s, 1 H), 7.32 (m, 4 H), 5.42 (bs, 1 H), 5.16 (s, 2 H), 4.62 (m, 2 H), 3.05 (ddd, 2 H), 1.40 (s, 9 H).

B. [1-(4-Cyanobenzyl)-2-oxopyrrolidin-3-(S)-yl]carbamic acid tert-butyl ester.

To a solution of Boc-L-Asp(H)-OBn (1.82 g, 5.93 mmol) dissolved in 30 mL of methanol is added p-cyanobenzylamine hydrochloride (1 g, 5.93 mmol) and triethylamine (0.66 g, 6.52 mmol). The solution is stirred for 45 minutes. After this time, a solution of sodium cyanoborohydride (0.41 g, 6.52 mmol) and zinc chloride (0.41 g, 3 mmol) in 6 mL of MeOH is added. The mixture is stirred for an additional 1.5 hours. After this time, 5 mL of 0.5 N NaOH and 10 mL of water is added, and the resulting mixture is concentrated. The residue is treated with 40 mL of water and 300 mL of EtOAc. The solution is filtered through a pad of Celite, poured into a separatory funnel and the layers are separated. The organic layer is washed with 1 N HCl, 10% Na$_2$CO$_3$ and saturated NaCl. The organic layer is dried over MgSO$_4$, filtered and concentrated. The residue is purified by column chromatography eluting with a gradient of 10% EtOAc/CH$_2$Cl$_2$ to 35% EtOAc/CH$_2$Cl$_2$ to give the title compound (0.67 g, 2.12 mmol) as a solid.

$^1$H NMR (CDCl$_3$, 300 MHz) δ 7.62 (d, 2 H), 7.31 (d, 2 H), 5.15 (bs, 1 H), 4.53 (AB, 2 H), 4.21 (m, 1 H), 3.24 (m, 2 H), 2.61 (m, 1 H), 1.90 (m, 1 H), 1.46 (s, 9 H).

C. 4-(3-(S)-Amino-2-oxopyrrolidin-1-ylmethyl)benzonitrile hydrochloride.

The title compound is prepared as a white solid from [1-(4-cyanobenzyl)-2-oxopyrrolidin-3-(S)-yl]carbamic acid tert-butyl ester as described in EXAMPLE 23, Part C.

$^1$H NMR (DMSO-d$_6$, 300 MHz) δ 8.65 (bs, 3 H), 7.81 (d, 2 H), 7.49 (d, 2 H), 4.54 (AB, 2 H), 4.08 (m, 1 H), 3.30 (m, 2 H), 2.40 (m, 1 H), 2.01 (m, 1 H).

D. 7-Methoxynaphthalene-2-sulfonic acid [1-(4-cyanobenzyl)-2-oxopyrrolidin-3-(S)-yl]amide.

The title compound is prepared from 4-(3-(S)-amino-2-oxopyrrolidin-1-ylmethyl)benzonitrile hydrochloride as in EXAMPLE 24, Part B using 7-methoxynaphthalene-2-sulfonyl chloride in place of 6-methoxynaphthalene-2-sulfonyl chloride. The crude product is triturated from EtOAc to give the title compound as a white solid.

$^1$H NMR (CDCl$_3$, 300 MHz) δ8.36 (s, 1 H), 7.93 (d, 1 H), 7.81 (d, 1 H), 7.75 (dd, 1 H), 7.60 (d, 2 H), 7.31 (dd, 1 H), 7.25 (m, 3 H), 5.38 (s, 1 H), 4.45 (AB, 2 H), 3.93 (s, 3 H), 3.74 (m, 1 H), 3.20 (m, 2 H), 2.61 (m, 1 H), 2.10 (m, 1 H).

E. 7-Methoxynaphthalene-2-sulfonic acid {1-[4-(aminoiminomethyl)benzyl]-2-oxopyrrolidin-3-(S)-yl}amide trifluoroacetate.

7-Methoxynaphthalene-2-sulfonic acid [1-(4-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-$_6$, 300 MHz) δ9.22 (bs, 2 H), 9.18 (bs, 2 H), 8.31 (s, I H), 8.20 (d, 1 H), 7.96 (d, 1 H), 7.86 (d, 1 H), 7.70 (d, 2 H), 7.66 (dd, 1 H), 7.49 (d, 1 H), 7.34 (d, 2 H), 7.28 (dd, 1 H), 4.38 (AB, 2 H), 4.10 (m, 1 H), 3.82 (s, 3 H), 3.03 (m, 2 H), 1.96 (m, 1 H), 1.52 (m, 1 H). ISP MS, [M+H]$^+$=453. Elemental analysis calculated with 1.2 mole of H$_2$O: C=51.09%, H=4.69%, N=9.53%, found C=51.09%, H=4.35%, N=9.31%.

EXAMPLE 30

6,7-Dimethoxynaphthalene-2-sulfonic acid {1-[3-(aminoiminomethyl)benzyl]-2-oxopyrrolidin-3-(S)-yl}amide trifluoroacetate.

A. 6,7-Dimethoxynaphthalene-2-sulfonyl chloride.

The title compound is prepared as in EXAMPLE 24, Part A using 6,7-dihydroxynaphthalene-2-sulfonic acid, sodium salt hemihydrate in place of 6-hydroxynaphthalene-2-sulfonic acid, sodium salt. The crude product mixture is purified by column chromatography in a gradient of 10% EtOAc/hexanes to 30% EtOAc/hexanes to give the title compound as the major component.

$^1$H NMR (CDCl$_3$, 300 MHz) δ8.45 (d, 1 H), 7.89 (s, 2 H), 7.29 (d, 1 H), 7.20 (s, 1 H), 4.09 (s, 3 H), 4.07 (s, 3 H). EI MS, [M]$^+$=286.

B. 6,7-Dimethoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 6,7-dimethoxynaphthalene-2-sulfonyl chloride in place of 6-methoxynaphthalene-2-sulfonyl chloride. The crude product is purified by column chromatography in 50% EtOAc/CH$_2$Cl$_2$ to afford the title compound as a beige solid.

$^1$H NMR (CDCl$_3$, 300 MHz) δ8.31 (d, 1 H), 7.81 (m, 2 H), 7.59 (m, 1 H), 7.45 (m, 3 H), 7.20 (d, 2 H), 5.39 (d, 1 H), 4.48 (AB, 2 H), 4.07 (s, 3 H), 4.06 (s, 3 H), 3.75 (m, 1 H), 3.20 (m, 2 H), 2.60 (m, 1 H), 2.10 (m, 1 H).

C. 6,7-Dimethoxynaphthalene-2-sulfonic acid {1-[3-(aminoiminomethyl)benzyl]-2-oxopyrrolidin-3-(S)-yl}amide trifluoroacetate.

6,7-Dimethoxynaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.29 (bs, 2 H), 9.12 (bs, 2 H), 8.28 (d, 1 H), 8.09 (d, 1 H), 7.90 (d, 1 H), 7.67 (m, 2 H), 7.52 (m, 4 H), 7.40 (s, 1 H), 4.40 (AB, 2 H), 4.10 (m, 1 H), 3.90 (s, 3 H), 3.91 (s, 3 H), 3.05 (m, 2 H), 1.92 (m, 1 H), 1.53 (m, 1 H). ISP MS, [M+H]$^+$=483.

Elemental analysis calculated with 1.75 mole of H$_2$O: C=49.72%, H=4.89%, N=8.92%; found C=49.72%, H=4.41%, N=8.68%.

EXAMPLE 31

Naphtho(2,3-d)-(1,3)dioxole-6-sulfonic acid {1-[3-(aminoiminomethyl)benzyl]-2-oxopyrrolidin-3-(S)-yl}amide trifluoroacetate.

A. Naphtho(2,3-d)-(1,3)dioxole-6-sulfonyl chloride.

To a solution of 6,7-dihydroxynaphthalene-2-sulfonic acid, sodium salt (5 g, 18.4 mmol) in 40 mL of DMF is added cesium fluoride (14 g, 92.1 mmol) at room temperature.

Dibromomethane (2.29 mL, 20.3 mmol) is added and the resulting mixture is heated at 120° C. for 3 hours, and then allowed to cool to room temperature. A precipitate is formed after stirring overnight. A mixture of ice and water is added and the resulting mixture is diluted with acetone (100 mL). The crude mixture is concentrated in vacuo and the azeotrope with acetone is repeated twice to remove all the DMF. The crude residue is stirred in acetone to form a slurry and the solid is filtered and dried. The crude solid is dissolved in 40 mL of 1 N NaOH solution and 95% EtOH (~100 mL) is added until a precipitate is formed and the solid is filtered and dried to give 1.49 g of the crude naphtho(2,3-d)-(1,3) dioxole-6-sulfonic acid, sodium salt. The crude sulfonic acid, sodium salt (1.49 g, 5.27 mmol) is chlorinated in the presence of excess phosphorous oxychloride and phosphorous pentachloride as described in EXAMPLE 24, Part A to give the crude title compound. This product is of sufficient purity to be used in subsequent reactions.

$^1$H NMR (CDCl$_3$, 300 MHz) δ8.37 (s, 1 H), 7.82 (m, 2 11), 7.26 (s, 1 H), 7.19 (s, 1 H), 6.16 (s, 2 H).

B. Naphtho(2,3-d)-(1,3)dioxole-6-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using naphtho(2,3-d)-(1,3)dioxole-6-sulfonyl chloride in place of 6-methoxynaphthalene-2-sulfonyl chloride. The crude product is triturated from CH$_2$Cl$_2$ to give the title compound as a beige solid.

$^1$H NMR (CDCl$_3$, 300 MHz) δ8.30 (s, 1 H), 8.14 (d, 1 H), 7.89 (d, 1 H), 7.72 (m, 1 H), 7.62 (m, 2 H), 7.52 (m, 3 H), 7.45 (s, 1 H), 6.20 (s, 2 H), 4.40 (AB, 2 H), 4.15 (m, 1 H), 3.07 (m, 2 H), 1.98 (m, 1 H), 1.57 (m, 1 H).

C. Naphtho(2,3-d)-(1,3)dioxole-6-sulfonic acid {1-[3-(aminoiminomethyl)benzyl]-2-oxopyrrolidin-3-(S)-yl}amide trifluoroacetate.

Naphtho(2,3-d)-(1,3)dioxole-6-sulfonic acid [1-(3-cyanobenzyl)-2-oxopyrrolidin-3-(S)-yl)amide is converted to the title compound as described in EXAMPLE 24, Part C. The imidate intermediate is formed over a period of 18 hours at room temperature. The amidine formation occurs over a period of 18 hours at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2 H), 9.10 (bs, 2 H), 8.30 (s, 1 H), 8.15 (d, 1 H), 7.90 (d, 1 H), 7.70 (m, 2 H), 7.58 (m, 4 H), 7.45 (s, 1 H), 6.20 (s, 2 H), 4.41 (AB, 2 H), 4.12 (m, 1 H), 3.10 (m, 2 H), 1.99 (m, 1 H), 1.56 (m, 1

H). ISP MS, [M+H]+=467. Elemental analysis calculated with 1.8 mole of $H_2O$: C=49.02%, H=4.37%, N=9.15%; found C=49.04%, H=3.98%, N=8.85%.

EXAMPLE 32

7-Benzyloxynaphthalene-2-sulfonic acid {1-[3-(aminoiminomethyl)benzyl]-2-oxopyrrolidin-3-(S)-yl}amide trifluoroacetate.

A. 7-Benzyloxynaphthalene-2-sulfonyl chloride.

A 60% dispersion of sodium hydride (0.37 g, 9.22 mmol) in mineral oil is washed with hexanes twice and suspended in 40 mL of DMF. To this mixture is added slowly via an addition funnel 7-hydroxynaphthalene-2-sulfonic acid, sodium salt (1.25 g, 5.08 mmol) in 25 mL of DMF at room temperature. The reaction mixture is stirred for 2 hours during which time mild bubbling is observed ($H_2$ evolution). The mixture is treated with benzyl bromide (1.5 mL, 12.6 mmol) and stirred for 18 hours at room temperature. Ice is added to decompose the excess NaH and the resultant mixture is concentrated in vacuo. The residue is suspended in acetone and concentrated in vacuo two times and then is dried under high vacuum. The solid is suspended in acetone, filtered and dried to yield the crude 7-benzyloxynaphthalene-2-sulfonic acid, sodium salt as a beige solid. A mixture of the sulfonic acid, sodium salt (2.47 g) in 8 mL of thionyl chloride is heated at 80° C. for 4 hours. A drop of DMF is added with vigorous bubbling resulting and the mixture is heated for an additional 30 minutes. The mixture is allowed to cool to room temperature and concentrated in vacuo. The residue is diluted in EtOAc and washed successively with water (2×), saturated $NaHCO_3$ solution and saturated NaCl. The organic layer is dried over anhydrous $MgSO_4$, filtered and concentrated to yield the title compound as a beige solid (1.26 g, 3.78 mmol). The crude product is of sufficient purity to be used in subsequent reactions.

$^1$H NMR ($CDCl_3$, 300 MHz) δ8.46 (s, 1 H), 7.97 (d, 1 H), 7.83 (m, 2 H), 7.45 (m, 6 H), 7.33 (d, 1 H), 5.28 (s, 2 H).

B. 7-Benzyloxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 7-benzyloxynaphthalene-2-sulfonyl chloride in place of 6-methoxynaphthalene-2-sulfonyl chloride. The crude product is purified by column chromatography in a gradient of 10% $EtOAc/CH_2Cl_2$ to 20% $EtOAc/CH_2Cl_2$ to afford the title compound as a white solid.

$^1$H NMR ($CDCl_3$, 300 MHz) δ8.39 (s, 1 H), 7.86 (d, 1 H), 7.77 (m, 2 H), 7.52 (m, 1 H), 7.40 (m, 9 H), 7.30 (d, 1 H), 5.72 (s, 1 H), 5.16 (s, 2 H), 4.40 (s, 2 H), 3.80 (m, 1 H), 3.15 (m, 2 H), 2.51 (m, 1 H), 2.02 (m, 1 H).

C. 7-Benzyloxynaphthalene-2-sulfonic acid {1-[3-(aminoiminomethyl)benzyl]-2-oxopyrrolidin-3-(S)-yl}amide trifluoroacetate.

Hydrogen sulfide gas is bubbled for 5 minutes through a solution of 7-benzyloxynaphthalene-2-sulfonic acid [1-(3-cyanobenzyl)-2-oxopyrrolidin-3-(S)-yl]amide (0.32 g, 0.63 mmol) in 10 mL of a 10:1 mixture of pyridine/triethylamine. After stirring the pale green solution for a period of 18 hours, the reaction mixture is concentrated in vacuo. The residue is diluted in acetone and concentrated to give the crude thioamide. To a solution of thioamide in 20 mL of acetone is added methyl iodide (2 mL, 32 mmol). The resulting mixture is heated at reflux for 2 hours, allowed to cool to room temperature and concentrated in vacuo to provide the crude thioimidate hydroiodide. To a solution of thioimidate hydroiodide in 20 mL of MeOH is added ammonium acetate (0.24 g, 3.17 mmol). The resulting mixture is heated at reflux for 3 hours, allowed to cool to room temperature and stirred overnight. The resulting mixture is concentrated in vacuo to provide the crude amidine salt. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound (0.05 g, 0.08 mmol) as a white solid.

$^1$H NMR (DMSO-$d_6$, 300 MHz) δ9.30 (bs, 2 H), 9.03 (bs, 2 H), 8.35 (s, 1 H), 8.21 (d, 1 H), 8.01 (d, 1 H), 7.95 (d, 1 H), 7.71 (dd, 1 H), 7.65 (m, 2 H), 7.51 (m, 5 H), 7.40 (m, 4 H), 5.24 (s, 2 H), 4.41 (AB, 2 H), 4.18 (m, 1 H), 3.08 (m, 2 H), 1.98 (m, 1 H), 1.59 (m, 1 H). ISP MS, [M+H]+=529.

EXAMPLE 33

7-Hydroxynaphthalene-2-sulfonic acid {1-[3-(aminoiminomethyl)benzyl]-2-oxopyrrolidin-3-(S)-yl}amide trifluoroacetate.

7-Benzyloxynaphthalene-2-sulfonic acid (1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 42 hours at room temperature. The crude product is purified by RP-HPLC eluting in a gradient of 10% $CH_3CN/H_2O$ (0.1% TFA) to 60% $CH_3CN/H_2O$ (0.1 % TFA) and the appropriate product fractions are lyophilized to provide the title compound as a white solid.

$^1$H NMR (DMSO-$d_6$, 300 MHz) δ9.30 (bs, 2 H), 9.08 (bs, 2 H), 8.26 (s, 1 H), 8.19 (d, 1 H), 7.95 (d, 1 H), 7.89 (d, 1 H), 7.65 (m, 2 H), 7.54 (m, 3 H), 7.30 (d, 1 H), 7.25 (dd, 1 H), 4.44 (AB, 2 H), 4.15 (m, 1 H), 3.10 (m, 2 H), 2.00 (m, 1 H), 1.59 (m, 1 H). FAB MS, [M+H]+=439. Elemental analysis calculated with 2.6 mole of $H_2O$: C=48.13%, H=4.74%, N=9.35%; found C=48.14%, H=4.08%, N=9.32%.

EXAMPLE 34

6-Hydroxynaphthalene-2-sulfonic acid {1-[3-(aminoiminomethyl)benzyl]-2-oxopyrrolidin-3-(S)-yl}amide trifluoroacetate.

A. 6-Benzyloxynaphthalene-2-sulfonyl chloride.

The title compound is prepared as described in EXAMPLE 32, Part A using 6-hydroxynaphthalene-2-sulfonic acid, sodium salt in place of 7-hydroxynaphthalene-2-sulfonic acid, sodium salt. The crude 6-benzyloxynaphthalene-2-sulfonic acid, sodium salt obtained is likewise chlorinated with excess thionyl chloride and 3 drops of DMF. The crude product is triturated from 50% EtOAc/hexanes to give the title compound which is of sufficient purity to be used in subsequent reactions.

$^1$H NMR ($CDCl_3$, 300 MHz) δ8.50 (d, 1 H), 7.91 (m, 3 H), 7.46 (m, 2 H), 7.40 (m, 4 H), 7.30 (d, 1 H), 5.22 (s, 2).

B. 6-Benzyloxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 6-benzyloxynaphthalene-2-sulfonyl chloride in place of 6-methoxynaphthalene-2-sulfonyl chloride. The crude product is purified by column chromatography in a gradient of 10% $EtOAc/CH_2Cl_2$ to 25% $EtOAc/CH_2Cl_2$ to afford the title compound as a white solid.

$^1$H NMR ($CDCl_3$, 300 MHz) δ8.39 (s, 1 H), 7.88 (d, 1 H), 7.84 (m, 2 H), 7.58 (m, 1 H), 7.42 (m, 8 H), 7.35 (dd, 1 H), 7.25 (d, 1 H), 5.52 (s, 1 H), 5.21 (s, 2 H), 4.43 (s, 2 H), 3.75 (m, 1 H), 3.20 (m, 2 H), 2.60 (m, 1 H), 2.08 (m, 1 H).

C. 6-Hydroxynaphthalene-2-sulfonic acid {1-[3-(aminoiminomethyl)benzyl]-2-oxopyrrolidin-3-(S)-yl}amide trifluoroacetate.

6-Benzyloxynaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.33 (bs, 2 H), 9.29 (bs, 2 H), 8.33 (d, 1 H), 8.11 (d, 1 H), 7.96 (d, 1 H), 7.85 (d, 1 H), 7.74 (dd, 1 H), 7.69 (m, 1 H), 7.54 (m, 3 H), 7.20 (m, 2 H), 4.41 (AB, 2 H), 4.12 (m, 1 H), 3.07 (m, 2 H), 1.96 (m, 1 H), 1.57 (m, 1 H). FAB MS, $[M+H]^+$=439.

Elemental analysis calculated with 2.2 mole of $H_2O$: C=48.64%, H=4.67%, N=9.45%; found C=48.63%, H=4.14%, N=9.52%.

EXAMPLE 35

5-Chloro-3-methylbenzo[b]thiophene-2-sulfonic acid {1-[3-(aminoiminomethyl)benzyl]-2-oxopyrrolidin-3-(S)-yl}amide trifluoroacetate.

A. 5-Chloro-3-methylbenzo[b]thiophene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 5-chloro-3-methylbenzo[b]thiophene-2-sulfonyl chloride in place of 6-methoxynaphthalene-2-sulfonyl chloride. The crude product is triturated from EtOAc to afford the title compound as a white solid.

$^1$H NMR (CDCl$_3$, 300 MHz) δ7.82 (d, 1 H), 7.78 (d, 1 H), 7.60 (m, 1 H), 7.45 (m, 4 H), 5.59 (bs, 1 H), 4.50 (s, 2 H), 3.91 (m, 1 H), 3.25 (m, 2 H), 2.75 (s, 3 H), 2.65 (m, 1 H), 2.11 (m, 1 H).

B. 5-Chloro-3-methylbenzo[b]thiophene-2-sulfonic acid {1-[3-(aminoiminomethyl)benzyl]-2-oxopyrrolidin-3-(S)-yl}amide trifluoroacetate.

5-Chloro-3-methylbenzo[b]thiophene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 20 hours at room temperature. The amidine formation occurred over a period of 22 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$_6$, 300 MHz) δ9.32 (bs, 2 H), 9.21 (bs, 2 H), 8.76 (d, 1 H), 8.09 (d, 1 H), 8.04 (d, 1 H), 7.68 (m, 1 H), 7.53 (m, 4 H), 4.41 (AB, 2 H), 4.20 (m, 1 H), 3.11 (m, 2 H), 2.63 (s, 3 H), 2.09 (m, 1 H), 1.67 (m, 1 H). FAB MS, $[M+H]^+$=477. Elemental analysis calculated with 1.7 mole of $H_2O$: C=44.37%, H=4.13%, N=9.00%; found C=44.37%, H=4.03%, N=8.66%.

EXAMPLE 36

5-Chloro-3-methylbenzo[b]thiophene-2-sulfonic acid {1-[3-(aminoiminomethyl)benzyl]-2-oxopyrrolidin-3-(S)-yl}methyl amide trifluoroacetate.

A. 5-Chloro-3-methylbenzo[b]thiophene-2-sulfonic acid [1-(3-cyanobenzyl)-2-oxopyrrolidin-3-(S)-yl]methyl amide.

The title compound is prepared as described in EXAMPLE 25, Part A using 5-chloro-3-methylbenzo[b]thiophene-2-sulfonic acid [1-(3-cyanobenzyl)-2-oxopyrrolidin-3-(S)-yl]amide as the starting material. The crude product is purified by column chromatography in a gradient of 2% EtOAc/CH$_2$Cl$_2$ to 10% EtOAc/CH$_2$Cl$_2$ to afford the title compound as a white solid.

$^1$H NMR (CDCl$_3$, 300 MHz) δ7.81 (s, 1 H), 7.76 (d, 1 H), 7.60 (m, 1 H), 7.45 (m, 4 H), 4.92 (m, 1 H), 4.43 (AB, 2 H), 3.23 (m, 2 H), 2.90 (s, 3 H), 2.72 (s, 3 H), 2.41 (m, 1 H), 2.09 (m, 1 H).

B. 5-Chloro-3-methylbenzo[b]thiophene-2-sulfonic acid {1-[3-(aminoiminomethyl)benzyl]-2-oxopyrrolidin-3-(S)-yl}methyl amide trifluoroacetate. 5-Chloro-3-methylbenzo[b]thiophene-2-sulfonic acid [1-(3-cyanobenzyl)-2-oxopyrrolidin-3-(S)-yl]methyl amide is converted to the title compound as described in EXAMPLE 24, Part C. The imidate intermediate is formed over a period of 24 hours at room temperature. The amidine formation occurred over a period of 3 days at room temperature. The crude product is purified by RP-HPLC eluting in a gradient of 10% $CH_3CN/H_2O$ (0.1 % TFA) to 60% $CH_3CN/H_2O$ (0.1 % TFA) and the appropriate product fractions are lyophilized to provide the title compound as a white solid.

$^1$H NMR (DMSO-$d_6$, 300 MHz) δ9.31 (bs, 2 H), 9.19 (bs, 2 H), 8.11 (d, 1 H), 8.08 (d, 1 H), 7.68 (m, 1 H), 7.56 (m, 4 H), 4.94 (m, 1 H), 4.42 (AB, 2 H), 3.19 (m, 2 H), 2.78 (s, 3 H), 2.66 (s, 3 H), 2.10 (m, 1 H), 1.97 (m, 1 H). FAB MS, $[M+H]^+$=491. Elemental analysis calculated with 0.9 mole of $H_2O$: C=46.43%, H=4.18%, N=9.02%; found C=46.42%, H=4.06%, N=8.90%.

EXAMPLE 37

7-Methylnaphthalene-2-sulfonic acid {1-[3-(aminoiminomethyl)benzyl]-2-oxopyrrolidin-3-(S)-yl}amide trifluoroacetate.

A. 2-Methoxy-7-trifluoromethanesulfonylnaphthalene.

To a solution of 7-methoxy-2-naphthol (5 g, 28.7 mmol) in 150 mL $CH_2CL_2$ at 0° C. is added triethylamine (5.95 g, 58.8 mmol), trifluoromethsulfonic anhydride (10.1 g, 35.6 mmol) and 4-dimethylaminopyridine (0.36 g, 2.94 mmol). The brown solution is stirred for 1 hour at 0° C., then concentrated in vacuo to remove most of the $CH_2Cl_2$. The residue is diluted with EtOAc and washed with 1 N aqueous HCl, water, 10% $Na_2CO_3$ solution and saturated NaCl solution. The organic layer is dried over MgSO$_4$, filtered and concentrated to provide crude material which is purified by column chromatography in a gradient of 2% EtOAc/hexanes to 10% EtOAc/hexanes to afford the title compound (8.44 g, 27.5 mmol) as an oil.

$^1$H NMR (CDCl$_3$, 300 MHz) δ7.90 (d, 1 H), 7.78 (d, 1 H), 7.65 (d, 1 H), 7.22 (m, 2 H), 7.15 (d, 1 H), 3.95 (s, 3 H).

B. 2-Methoxy-7-methylnaphthalene.

2-Methoxy-7-trifluoromethanesulfonylnaphthalene (10 g, 32.6 mmol) is dissolved in 300 mL of DMF and treated with lithium chloride (7.20 g, 170 mmol) and tetramethyltin (12.4 g, 69.3 mmol). Bis-(triphenylphosphine)palladium(II) chloride (1.44 g, 2 mmol) is added and the resulting heterogeneous mixture is heated at 80° C. for 18 hours. The reaction mixture is cooled to room temperature, filtered through a Celite pad and washed with EtOAc. The filtrate is washed with water and the layers separated. The aqueous layer is extracted twice with EtOAc and the combined organic layers are washed with water and saturated NaCl solution. The organic layer is dried over $MgSO_4$, filtered and concentrated to give crude material which is purified by column chromatography in a gradient of 2% EtOAc/hexanes to 5% EtOAc/hexanes to yield the title compound (5.34 g, 31 mmol) as a solid.

$^1$H NMR ($CDCl_3$, 300 MHz) δ7.69 (m, 2 H), 7.52 (s, 1 H), 7.19 (d, 1 H), 7.10 (m, 2 H), 3.93 (s, 3 H), 2.50 (s, 3 H).

C. 7-Methyl-2-naphthol.

A suspension of 2-methoxy-7-methylnaphthalene (5.30 g, 30.8 mmol) in 90 mL of 48% aqueous HBr is heated at reflux for a period of 2 hours. The resulting mixture is allowed to cool to room temperature, diluted with water and partially neutralized with saturated $NaHCO_3$ solution. The aqueous mixture is extracted with EtOAc twice and the combined organic layers are washed with water, saturated $NaHCO_3$ solution and saturated NaCl solution. The organic phase is dried over $MgSO_4$, filtered and concentrated to provide crude material which is purified by column chromatography in a gradient of 5% EtOAc/hexanes to 20% EtOAc/hexanes to afford the title compound (3.05 g, 19.3 mmol) as a solid.

$^1$H NMR ($CDCl_3$, 300 MHz) δ7.69 (m, 2 H), 7.47 (s, 1 H), 7.18 (m, 1 H), 7.03 (m, 2 H), 5.01 (m, 1 H), 2.50 (s, 3 H).

D. 7-Methyl-2-trifluoromethanesulfonylnaphthalene.

7-Methyl-2-naphthol (3.05 g, 19.3 mmol) is converted to the title compound as described in EXAMPLE 37, Part A. The crude product is purified by column chromatography in a gradient of 2% EtOAc/hexanes to 10% EtOAc/hexanes to give the title compound (4.74 g, 16.3 mmol) as an oil.

$^1$H NMR ($CDCl_3$, 300 MHz) δ7.89 (d, 1 H), 7.80 (d, 1 H), 7.69 (m, 2 H), 7.40 (m, 1 H), 7.30 (m, 1 H), 2.59 (s, 3 H).

E. 7-Methyl-2-trimethylstannylnaphthalene.

7-Methyl-2-trifluoromethanesulfonylnaphthalene (1.50 g, 5.17 mmol) is dissolved in 30 mL of p-dioxane and treated with lithium chloride (0.66 g, 15.5 mmol) and hexamethylditin (1.86 g, 5.68 mmol). Bis-(triphenylphosphine) palladium(II) chloride (0.30 g, 0.26 mmol) is added and the resulting heterogeneous mixture is heated at reflux for 1 hour. The reaction mixture is cooled to room temperature, diluted with 10% $NH_4OH$ solution and $CH_2Cl_2$ and stirred for 45 minutes. The layers are separated and the aqueous layer is extracted twice with $CH_2Cl_2$. The combined organic layers are washed with saturated NaCl solution. The organic layer is dried over $MgSO_4$, filtered and concentrated to give crude material which is purified by column chromatography in a gradient of 2% EtOAc/hexanes to 5% EtOAc/hexanes to yield the title compound (0.60 g, 1.97 mmol) as an oil.

$^1$H NMR ($CDCl_3$, 300 MHz) δ7.90 (s, 1 H), 7.75 (d, 1 H), 7.70 (d, 1 H), 7.60 (s, 1 H), 7.51 (d, 1 H), 7.30 (d, 1 H), 2.54 (s, 3 H), 0.34 (m, 9 H).

F. 7-Methylnaphthalene-2-sulfonyl chloride.

To a solution of 7-methyl-2-trimethylstannylnaphthalene (0.60 g, 1.97 mmol) in 13 mL of THF at −78° C. is added n-butyllithium (1.40 mL of a 1.6 M solution in hexanes, 2.24 mmol). The reaction mixture is stirred for 5 min at −78° C. then warmed to 0° C. over a 30 min period. The mixture is cooled to −78° C. again and the solution is transferred via cannula to a flask containing 10 mL of condensed $SO_2$ (g) in 20 mL of THF at −78° C. The solution is stirred at −78° C. for 10 minutes, and then at ambient temperature for 2 hours. At this time, the reaction mixture is concentrated in vacuo, triturated with EtO and filtered. The solid is suspended in 8 mL of hexanes, cooled to 0° C. and treated with sulfuryl chloride (1.70 mL of a 1 M solution in $CH_2Cl_2$, 1.70 mmol). The resulting solution is stirred for 15 minutes, and then concentrated. The crude residue is purified by column chromatography in a gradient of 10% EtOAc/hexanes to 20% EtOAc/hexanes to afford the title compound (0.23 g, 0.96 mmol) as a solid.

$^1$H NMR ($CDCl_3$, 300 MHz) δ8.51 (s, 1 H), 8.01 (d, 1 H), 7.92 dd, 1 H), 7.89 (d, 1 H), 7.80 (s, 1 H), 7.58 (d, 1 H), 2.58 (s, 3 H).

G. 7-Methylnaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 7-methylnaphthalene-2-sulfonyl chloride in place of 6-methoxynaphthalene-2-sulfonyl chloride. The crude product is triturated from 50% EtOAc/ hexanes to give the title compound as a white solid.

$^1$H NMR ($CDCl_3$, 300 MHz) δ8.41 (s, 1 H), 7.96 (s, 1 H), 7.81 (m, 2 H), 7.76 (s, 1 H), 7.58 (m, 1 H), 7.46 (m, 4 H), 5.50 (bs, 1 H), 4.47 (s, 2 H), 3.79 (m, 1 H), 3.20 (m, 2 H), 2.59 (m, 1 H), 2.55 (s, 3 H), 2.10 (m, 1 H).

H. 7-Methylnaphthalene-2-sulfonic acid {1-[3-(aminoiminomethyl)benzyl]-2-oxopyrrolidin-3-(S)-yl}amide trifluoroacetate.

7-Methylnaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.32 (bs, 2 H), 9.28 (bs, 2 H), 8.38 (s, 1 H), 8.26 (d, 1 H), 8.05 (d, 1 H), 7.93 (d, 1 H), 7.88 (s, 1 H), 7.79 (dd, 1 H), 7.65 (m, 1 H), 7.52 (m, 4 H), 4.41 (AB, 2 H), 4.16 (m, 1 H), 3.08 (m, 2 H), 2.49 (s, 3 H), 1.97 (m, 1 H), 1.56 (m, 1 H). FAB MS, [M+H]$^+$=437. Elemental analysis calculated with 1.7 mole of $H_2O$: C=51.71%, H=4.92%, N=9.65%; found C=51.70%, H=4.66%, N=9.41%.

EXAMPLE 38

7-Ethylnaphthalene-2-sulfonic acid {1-[3-(aminoiminomethyl)benzyl]-2-oxopyrrolidin-3-(S)-yl}amide trifluoroacetate.

A. 2-Methoxy-7-trimethylstannylnaphthalene.

The title compound is prepared as described in EXAMPLE 37, Part E using 2-methoxy-7-trifluoromethanesulfonylnaphthalene in place of 7-methyl-2-trifluoromethanesulfonylnaphthalene. The crude product is purified by column chromatography in a gradient of 2% EtOAc/hexanes to 5% EtOAc/hexanes to afford the title compound as an oil.

$^1$H NMR ($CDCl_3$, 300 MHz) δ7.89 (s, 1 H), 7.70 (m, 2 H), 7.43 (d, 1 H), 7.35 (s, 1 H), 7.12 (m, 1 H), 3.91 (s, 3 H), 0.39 (m, 9 H).

B. 2-Methoxy-7-ethylnaphthalene.

To a solution of 2-methoxy-7-trimethylstannylnaphthalene (1.61 g, 3.60 mmol) in 24 mL of THF at −78° C. is added n-butyllithium (2.80 mL of a 1.6 M solution in hexanes, 4.48 mmol). The reaction mixture is stirred for 5 min at −78° C. then warmed to 0° C. over a 30 min period. The mixture is cooled to −78° C. again and bromoethane (1.46 g, 13.4 mmol) is added. The solution is stirred at −78° C. for 10 minutes, and then at ambient temperature for 4 hours. At this time, the reaction mixture is quenched with saturated $NH_4Cl$ solution, diluted with EtOAc and the layers are separated. The organic layer is washed with 1 N aqueous HCl, water, saturated $NaHCO_3$ solution and saturated NaCl solution. The organic layer is dried over $MgSO_4$, filtered and concentrated to provide crude product which is purified by column chromatography in a gradient of 2% EtOAc/hexanes to 5% EtOAc/hexanes to give a 3.5:1 mixture (0.56 g, 3.01 mmol) of the title compound as the major component and 2-methoxynaphthalene as the minor component.

$^1$H NMR ($CDCl_3$, 300 MHz) δ7.72 (m, 2 H), 7.54 (s, 1 H), 7.32 (s, 1 H), 7.11 (d, 1 H), 7.08 (s, 1 H), 3.90 (s, 3 H), 2.80 (q, 2 H), 1.31 (t, 3 H).

C. 7-Ethylnaphthalene-2-sulfonyl chloride.

A mixture of 7-ethyl-2-naphthol and naphthol is prepared as described in EXAMPLE 37, Part C using the 3.5:1 mixture of 2-methoxy-7-ethylnaphthalene and 2-methoxynaphthalene in place of 2-methoxy-7-methylnaphthalene. The crude demethylated product is partially purified by column chromatography in a gradient of 5% EtOAc/hexanes to 20% EtOAc/hexanes. The 7-ethyl-2-naphthol mixture is converted to 7-ethyl-2-trifluoromethanesulfonylnaphthalene as described in EXAMPLE 37, Part A. The crude triflated material is partially purified by column chromatography in a gradient of 2% EtOAc/hexanes to 5% EtOAc/hexanes. The crude 7-ethyl-2-trifluoromethanesulfonylnaphthalene is then converted to 7-ethyl-2-trimethylstannylnaphthalene as described in EXAMPLE 37, Part E. The stannylated product is partially purified by column chromatography in a gradient of 2% EtOAc/hexanes to 5% EtOAc/hexanes. The 7-ethyl-2-trimethylstannylnaphthalene is converted to the title compound as described in EXAMPLE 37, Part F using 7-ethyl-2-trimethylstannylnaphthalene in place of 7-methyl-2-trimethylstannylnaphthalene and $Et_2O$ in place of THF. The crude mixture is purified by column chromatography in a gradient of 5% EtOAc/hexanes to 10% EtOAc/hexanes to afford the title compound as an oil.

$^1$H NMR ($CDCl_3$, 300 MHz) δ8.54 (s, 1 H), 8.01 (d, 1 H), 7.90 (m, 1 H), 7.87 (s, 1 H), 7.81 (s, 1 H), 7.61 (d, 1 H), 2.88 (q, 2 H), 1.35 (t, 3 H).

D. 7-Ethylnaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 7-ethylnaphthalene-2-sulfonyl chloride in place of 6-methoxynaphthalene-2-sulfonyl chloride. The crude product is triturated from 50% EtOAc/hexanes to give the title compound as a white solid.

$^1$H NMR ($CDCl_3$, 300 MHz) δ8.41 (s, 1 H), 7.96 (d, 1 H), 7.85 (m, 2 H), 7.75 (s, 1 H), 7.55 (m, 2 H), 7.45 (m, 3 H), 5.42 (s, 1 H), 4.46 (AB, 2 H), 3.76 (m, 1 H), 3.20 (m, 2 H), 2.85 (q, 2 H), 2.60 (m, 1 H), 2.10 (m, 1 H), 1.39 (t, 3 H).

E. 7-Ethylnaphthalene-2-sulfonic acid {1-[3-(aminoiminomethyl)benzyl]-2-oxopyrrolidin-3-(S)-yl}amide trifluoroacetate.

7-Ethylnaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 18 hours at room temperature. The amidine formation occurred over a period of 3 days at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.30 (bs, 2 H), 9.20 (bs, 2 H), 8.40 (s, 1 H), 8.25 (d, 1 H), 8.07 (d, 1 H), 7.97 (d, 1 H), 7.90 (s, 1 H), 7.80 (dd, 1 H), 7.68 (m, 1 H), 7.55 (m, 4 H), 4.43 (AB, 2 H), 4.16 (m, 1 H), 3.10 (m, 2 H), 2.80 (q, 2 H), 1.97 (m, 1 H), 1.59 (m, 1 H), 1.30 (t, 3 H). FAB MS, [M+H]$^+$=451. Elemental analysis calculated with 1.6 mole of $H_2O$: C=52.67%, H=5.13%, N=9.45%; found C=52.65%, H=4.60%, N=9.17%.

EXAMPLE 39

5-Chloro-6-aminonaphthalene-2-sulfonic acid {1-[3-(aminoiminomethyl)benzyl]-2-oxopyrrolidin-3-(S)-yl}amide bistrifluoroacetate.

A. N-Cbz-5-Chloro-6-aminonaphthalene-2-sulfonyl chloride.

To a suspension of 6-aminonaphthalene-2-sulfonic acid, sodium salt (3 g, 12.2 mmol) in 70 mL of water is added solid NaOH (1.01 g, 25 mmol) at room temperature. The mixture is stirred for 1 hour, and benzyl chloroformate (3.43 mL, 24 mmol) is then added. The resulting mixture is stirred over a period of 16 hours. The crude product is treated as in EXAMPLE 24, Part A to give 4.70 g of crude N-CBz-6-aminonaphthalene-2-sulfonic acid, sodium salt. A mixture of the sulfonic acid, sodium salt (2.3 g, 6.10 mmol) in 15 mL of thionyl chloride is heated at 80° C. for 5 hours. The mixture is allowed to cool to room temperature and concentrated in vacuo. The residue is diluted with EtOAc and washed successively with water (2×), saturated $NaHCO_3$ solution and saturated NaCl. The organic layer is dried over anhydrous $MgSO_4$, filtered and concentrated to give a solid. The crude product is triturated from 50% EtOAc/hexanes to afford the title compound (0.50 g, 1.33 mmol) as a beige solid.

$^1$H NMR ($CDCl_3$, 300 MHz) δ8.75 (d, 1 H), 8.60 (d, 1 H), 8.39 (d, 1 H), 8.09 (dd, 1 H), 8.00 (d, 1 H), 7.68 (d, 1 H), 7.46 (m, 5 H), 5.30 (s, 2 H).

B. N-Cbz-5-Chloro-6-aminonaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using N-Cbz-5-chloro-6-aminonaphthalene-2-sulfonyl chloride in place of 6-methoxynaphthalene-2-sulfonyl chloride. The crude product is purified by column chromatography using a gradient of 10% EtOAc/$CH_2Cl_2$ to 25% EtOAc/$CH_2Cl_2$ to give the title compound as a solid.

$^1$H NMR ($CDCl_3$, 300 MHz) δ8.49 (d, 1 H), 8.41 (s, 1 H), 8.15 (d, 1 H), 7.99 (d, 1 H), 7.80 (d, 1 H), 7.60 (s, 1 H), 7.45 (m, 9 H), 6.30 (d, 1 H), 5.29 (s, 2 H), 4.45 (s, 2 H), 3.97 (m, 1 H), 3.20 (m, 2 H), 2.55 (m, 1 H), 2.06 (m, 1 H).

C. 5-Chloro-6-aminonaphthalene-2-sulfonic acid {1-[3-(aminoiminomethyl)benzyl]-2-oxopyrrolidin-3-(S)-yl}amide bistrifluoroacetate.

N-Cbz-5-Chloro-6-aminonaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 3 days at room temperature. The amidine formation occurred over a period of 18 hours at room temperature. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.28 (bs, 2 H), 9.10 (bs, 2 H), 8.25 (d, 1 H), 8.09 (d, 1 H), 7.95 (d, 1 H), 7.81 (m, 2 H), 7.65 (m, 1 H), 7.50 (m, 3 H), 7.20 (d, 1 H), 4.40 (AB, 2 H), 4.10 (m, 1 H), 3.06 (m, 2 H), 1.95 (m, 1 H), 1.52 (m, 1 H). FAB MS, [M+H]$^+$=472.

EXAMPLE 40

7-Methylaminonaphthalene-2-sulfonic acid {1-[3-(aminoiminomethyl)benzyl]-2-oxopyrrolidin-3-(S)-yl}amide bistrifluoroacetate.

A. N-Cbz-7-Methylaminonaphthalene-2-sulfonyl chloride.

N-Cbz-7-Aminonaphthalene-2-sulfonic acid, sodium salt is prepared as described in EXAMPLE 39, Part A using 7-aminonaphthalene-2-sulfonic acid, sodium salt (3 g, 12.2 mmol) in place of 6-aminonaphthalene-2-sulfonic acid, sodium salt. A 60% dispersion of sodium hydride (0.21 g, 5.27 mmol) in mineral oil is washed with hexanes twice, suspended in 20 mL of DMF and the resulting suspension is cooled to 0° C. To this mixture is added the crude N-Cbz-7-aminonaphthalene-2-sulfonic acid, sodium salt (1 g, 2.64 mmol) in 15 mL of DMF. The reaction mixture is stirred for 10 min at 0° C. and then treated with methyl iodide (0.49 mL, 7.92 mmol). The resulting mixture is allowed to warm to room temperature with stirring overnight. The reaction mixture is worked up according to the similar procedure used in EXAMPLE 32, Part A to yield the crude N-Cbz-7-methylaminonaphthalene-2-sulfonic acid, sodium salt (0.88 g) as a beige solid. A mixture of the sulfonic acid, sodium salt (0.88 g, 2.23 mmol) is chlorinated as described in EXAMPLE 32, Part A. The crude product is purified by column chromatography in a gradient of 10% EtOAc/hexanes to 30% EtOAc/hexanes to afford the title compound (0.38 g, 0.97 mmol) as a beige solid.

$^1$H NMR (CDCl$_3$, 300 MHz) δ8.55 (d, 1 H), 7.98 (m, 3 H), 7.84 (s, 1 H), 7.75 (d, 1 H), 7.38 (m, 5 H), 5.25 (s, 2 H), 3.50 (s, 3 H).

B. N-Cbz-7-Methylaminonaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using N-Cbz-7-methylaminonaphthalene-2-sulfonyl chloride in place of 6-methoxynaphthalene-2-sulfonyl chloride. The crude product is purified by column chromatography using a gradient of 10% EtOAc/CH$_2$Cl$_2$ to 25% EtOAc/CH$_2$Cl$_2$ to give the title compound as a solid.

$^1$H NMR (CDCl$_3$, 300 MHz) δ8.41 (s, 1 H), 7.97 (d, 1 H), 7.87 (m, 2 H), 7.80 (s, 1 H), 7.60 (m, 2 H), 7.45 (m, 3 H), 7.38 (m, 5 H), 5.53 (bs, 1 H), 5.21 (s, 2 H), 4.43 (s, 2 H), 3.79 (m, 1 H), 3.45 (s, 3 H), 3.20 (m, 2 H), 2.60 (m, 1 H), 2.10 (m, 1 H).

C. 7-Methylaminonaphthalene-2-sulfonic acid {1-[3-(aminoiminomethyl)benzyl]-2-oxopyrrolidin-3-(S)-yl}amide bistrifluoroacetate.

N-Cbz-7-Methylaminonaphthalene-2-sulfonic acid [1-(3-cyanobenzyl)-2-oxopyrrolidin-3-(S)-yl]amide is converted to the title compound as described in EXAMPLE 24, Part C. The imidate intermediate is formed over a period of 48 hours at room temperature. The amidine formation occurred over a period of 3 days at room temperature. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.28 (bs, 2 H), 9.08 (bs, 2 H), 8.11 (s, 1 H), 8.08 (d, 1 H), 7.80 (d, 1 H), 7.70 (d, 1 H), 7.68 (m, 1 H), 7.54 (m, 3 H), 7.45 (dd, 1 H), 7.08 (dd, 1 H), 6.80 (d, 1 H), 4.42 (AB, 2 H), 4.10 (m, 1 H), 3.05 (m, 2 H), 2.77 (s, 3 H), 1.93 (m, 1 H), 1.51 (m, 1 H). FAB MS, [M+H]$^+$=452. Elemental analysis calculated with 0.9 mole of H$_2$O: C=46.64%, H=4.17%, N=10.07%; found C=46.63%, H=4.10%, N=10.13%.

EXAMPLE 41

2-Methyl-1,2,3,4-Tetrahydroisoquinoline-7-sulfonic acid {1-[3-(aminoiminomethyl)benzyl]-2-oxopyrrolidin-3-(S)-yl}amide bistrifluoroacetate.

A. 2-Trifluoromethylacetamide-1,2,3,4-tetrahydro-isoquinoline-7-sulfonyl chloride.

The title compound is prepared according to the procedure described in J. Med. Chem., 23, 837 (1980), which is incorporated herein by reference. The crude residue obtained is triturated with Et$_2$O to yield product which is of sufficient purity to be used in subsequent reactions.

$^1$H NMR (CDCl$_3$, 300 MHz) δ7.90 (m, 2 H), 7.49 (m, 1 H), 4.90 (s, 2 H), 3.95 (m, 2 H), 3.10 (m, 2 H).

B. 2-Trifluoromethylacetamide-1,2,3,4-tetrahydro-isoquinoline-7-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 2-trifluoromethylacetamide-1,2,3,4-tetrahydro-isoquinoline-7-sulfonyl chloride in place of 6-methoxynaphthalene-2-sulfonyl chloride. The crude product is purified by column chromatography using a gradient of 10% EtOAc/CH$_2$Cl$_2$ to 25% EtOAc/CH$_2$Cl$_2$ to give the title compound as a solid.

$^1$H NMR (CDCl$_3$, 300 MHz) δ7.79 (m, 2 H), 7.63 (m, 1 H), 7.50 (m, 3 H), 7.39 (m, 1 H), 5.50 (bs, 1 H), 4.90 (AB, 2 H), 4.49 (AB, 2 H), 3.91 (m, 2 H), 3.79 (m, 1 H), 3.25 (dd, 2 H), 3.05 (m, 2 H), 2.60 (m, 1 H), 2.10 (m, 1 H).

C. 1,2,3,4-Tetrahydro-isoquinoline-7-sulfonic acid [1-(3-cyanobenzyl)-2-oxopyrrolidin-3-(S)-yl]amide.

To a solution of 2-trifluoromethylacetamide-1,2,3,4-tetrahydro-isoquinoline-7-sulfonic acid [1-(3-cyanobenzyl)-2-oxopyrrolidin-3-(S)-yl]amide (0.50 g, 0.99 mmol) in 6 mL of EtOH is added a solution of sodium carbonate (0.56 g, 5.27 mmol) in 6 mL of H$_2$O. The solution is stirred at room temperature for 5 hours. After this time, the solution is concentrated in vacuo, diluted with CH$_2$Cl$_2$ and washed with H$_2$O and saturated NaCl solution. The organic phase is dried over anhydrous MgSO$_4$, filtered and concentrated to yield the title compound (0.29 g, 0.71 mmol) as a beige solid.

$^1$H NMR (CDCl$_3$, 300 MHz) δ7.68 (d, 1 H), 7.60 (m, 2 H), 7.49 (m, 3 H), 7.28 (m, 1 H), 4.50 (s, 2 H), 4.10 (s, 2 H), 3.75 (m, 1 H), 3.20 (m, 4 H), 2.90 (m, 2 H), 2.60 (m, 1 H), 2.10 (m, 1 H).

D. 2-Methyl-1,2,3,4-tetrahydro-isoquinoline-7-sulfonic acid {1-[3-(aminoiminomethyl)benzyl]-2-oxopyrrolidin-3-(S)-yl}amide bistrifluoroacetate.

To a solution of 1,2,3,4-tetrahydro-isoquinoline-7-sulfonic acid [1-(3-cyanobenzyl)-2-oxopyrrolidin-3-(S)-yl]amide (0.29 g, 0.71 mmol) in 10 mL of CH$_2$Cl$_2$ is added 0.27 mL of 37% aqueous formaldehyde. The solution is stirred at room temperature for 1 hour. After this time, sodium triacetoxyborohydride (0.05 g, 0.22 mmol) is added and the resulting mixture is stirred for 18 hours. The reaction mixture is diluted with CH$_2$Cl$_2$ and washed with saturated NaHCO$_3$ solution. The organic phase is dried over anhydrous MgSO$_4$, filtered and concentrated to give 2-methyl-1,2,3,4-tetrahydro-isoquinoline-7-sulfonic acid [1-(3-cyanobenzyl)-2-oxopyrrolidin-3-(S)-yl]amide (0.16 g, 0.71 mmol) as a solid. The crude methylated material is then converted to the title compound as described in EXAMPLE 24, Part C. The imidate intermediate is formed over a period of 18 hours at room temperature. The amidine formation occurred upon heating at reflux for 2 hours. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.34 (bs, 2 H), 9.31 (bs, 2 H), 8.26 (d, 1 H), 7.75 (m, 3 H), 7.57 (m, 3 H), 7.49 (d, 1 H), 4.60 (s, 1 H), 4.45 (s, 2 H), 4.40 (m, 1 H), 4.15 (m, 1 H), 3.40 (m, 2 H), 3.15 (m, 4 H), 2.95 (s, 3 H), 2.10 (m, 1 H), 1.62 (m, 1 H). FAB MS, [M+H]$^+$=442.

Elemental analysis calculated with 2.2 mole of $H_2O$: C=44.03%, H=4.75%, N=9.87%; found C=44.03%, H=4.28%, N=9.96%.

EXAMPLE 42

1,2,3,4-Tetrahydroisoquinoline-7-sulfonic acid {1-[3-(aminoiminomethyl)benzyl]-2-oxopyrrolidin-3-(S)-yl}methyl amide dihydrochloride.

A. 1,2,3,4-Tetrahydroisoquinoline-7-sulfonic acid {1-(3-cyanobenzyl)-2-oxopyrrolidin-3-(S)-yl}methyl amide.

2-Trifluoromethylacetamide-1,2,3,4-tetrahydroisoquinoline-7-sulfonic acid [1-(3-cyanobenzyl)-2-oxopyrrolidin-3-(S)-yl]methyl amide is prepared as described in EXAMPLE 25, Part A using 2-trifluoromethylacetamide-1,2,3,4-tetrahydroisoquinoline-7-sulfonic acid [1-(3-cyanobenzyl)-2-oxopyrrolidin-3-(S)-yl]amide as the starting material. The crude material is purified by column chromatography in 25% EtOAc/$CH_2Cl_2$ to afford the methylated product as a solid. The title compound is prepared as described in EXAMPLE 41, Part C using 2-trifluoromethylacetamide-1,2,3,4-tetrahydro-isoquinoline-7-sulfonic acid [1-(3-cyanobenzyl)-2-oxopyrrolidin-3-(S)-yl]methyl amide as the starting material. The crude product is triturated from 50% EtOAc/$CH_2Cl_2$ to afford the title compound as a solid.

$^1$H NMR (CDCl$_3$, 300 MHz) δ7.71 (dd, 1 H), 7.62 (m, 2 H), 7.50 (m, 3 H), 7.25 (s, 1 H), 4.90 (m, 1 H), 4.47 (AB, 2 H), 4.10 (s, 2 H), 3.20 (m, 4 H), 2.90 (m, 1 H), 2.79 (s, 3 H), 2.36 (m, 1 H), 2.05 (m, 1 H).

B. 1,2,3,4-Tetrahydroisoquinoline-7-sulfonic acid {1-[3-(aminoiminomethyl)benzyl]-2-oxopyrrolidin-3-(S)-yl}methyl amide dihydrochloride.

1,2,3,4-Tetrahydro-isoquinoline-7-sulfonic acid [1-(3-cyanobenzyl)-2-oxopyrrolidin-3-(S)-yl]methyl amide is converted to the title compound as described in EXAMPLE 24, Part C. The imidate intermediate is formed over a period of 18 hours at room temperature. The amidine formation occurred upon heating at reflux for 1.5 hours. The crude product is purified by RP-HPLC eluting in a gradient of 10% $CH_3CN/H_2O$ to 60% $CH_3CN/H_2O$ and the appropriate product fractions are lyophilized to provide the title compound as a white solid.

$^1$H NMR (DMSO-$d_6$, 300 MHz) δ9.69 (bs, 2 H), 9.46 (bs, 2 H), 9.20 (bs, 2 H), 7.78 (s, 1 H), 7.73 (m, 2 H), 7.60 (m, 3 H), 7.44 (d, 1 H), 4.89 (m, 1 H), 4.44 (AB, 2 H), 4.32 (s, 2 H), 3.32 (m, 2 H), 3.18 (m, 2 H), 3.09 (m, 2 H), 2.64 (s, 3 H), 2.03 (m, 1 H), 1.80 (m, 1 H). FAB MS, [M+H]$^+$=442.

EXAMPLE 43

7-Methoxynaphthalene-2-sulfonic acid {1-[3-(aminoiminomethyl)benzyl]-2-oxopyrrolidin-3-(S)-yl}-(4-nitrobenzyl)amide trifluoroacetate.

A. 7-Methoxynaphthalene-2-sulfonic acid [1-(3-cyanobenzyl)-2-oxopyrrolidin-3-(S)-yl]amide.

The title compound is prepared from 3-(3-(S)-amino-2-oxopyrrolidin-1-ylmethyl)benzonitrile hydrochloride as in EXAMPLE 24, Part B using 7-methoxynaphthalene-2-sulfonyl chloride in place of 6-methoxynaphthalene-2-sulfonyl chloride. The crude product is triturated from EtOAc to give the title compound as a white solid.

$^1$H NMR (CDCl$_3$, 300 MHz) δ8.38 (d, 1 H), 7.91 (d, 1 H), 7.81 (d, 1 H), 7.73 (dd, 1 H), 7.59 (m, 1 H), 7.42 (m, 3 H), 7.30 (dd, 1 H), 7.25 (m, 1 H), 5.39 (d, 1 H), 4.45 (AB, 2 H), 3.92 (s, 3 H), 3.75 (m, 3 H), 3.20 (m, 2 H), 2.60 (m, 1 H), 2.10 (m, 1 H).

B. 7-Methoxynaphthalene-2-sulfonic acid [1-(3-cyanobenzyl)-2-oxopyrrolidin-3-(S)-yl]-(4-nitrobenzyl)amide.

The title compound is prepared as described in EXAMPLE 25, Part A using 7-methoxynaphthalene-2-sulfonic acid [1-(3-cyanobenzyl)-2-oxopyrrolidin-3-(S)-yl]amide as the starting material and p-nitrobenzyl bromide in place of methyl iodide. The crude product is purified by column chromatography in 50% EtOAc/hexanes to afford the title compound as a solid.

$^1$H NMR (CDCl$_3$, 300 MHz) δ8.31 (s, 1 H), 8.10 (m, 2 H), 7.91 (d, 1 H), 7.84 (d, 1 H), 7.81 (d, 1 H), 7.60 (m, 3 H), 7.50 (s, 1 H), 7.45 (d, 2 H), 7.31 (m, 1 H), 7.19 (d, 1 H), 4.65 (AB, 2 H), 4.50 (m, 1 H), 4.38 (AB, 2 H), 3.97 (s, 3 H), 3.17 (m, 2 H), 2.41 (m, 1 H), 1.99 (m, 1 H).

C. 7-Methoxynaphthalene-2-sulfonic acid {1-[3-(aminoiminomethyl)benzyl]-2-oxopyrrolidin-3-(S)-yl}-(4-nitrobenzyl)amide trifluoroacetate.

7-Methoxynaphthalene-2-sulfonic acid [1-(3-cyanobenzyl)-2-oxopyrrolidin-3-(S)-yl]-(4-nitrobenzyl)amide is converted to the title compound as described in EXAMPLE 24, Part C. The imidate intermediate is formed over a period of 18 hours at room temperature. The amidine formation occurred upon heating at reflux for 1 hour. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as an amorphous white solid.

$^1$H NMR (DMSO-$d_6$, 300 MHz) δ9.30 (bs, 2 H), 9.25 (bs, 2 H), 8.38 (s, 1 H), 8.13 (d, 2 H), 8.04 (d, 1 H), 7.96 (d, 1 H), 7.80 (dd, 1 H), 7.70 (m, 3 H), 7.55 (m, 4 H), 7.34 (dd, 1 H), 4.94 (m, 1 H), 4.50 (AB, 2 H), 4.36 (AB, 2 H), 3.89 (s, 3 H), 3.16 (m, 1 H), 3.07 (m, 1 H), 2.15 (m, 1 H), 1.74 (m, 1 H). FAB MS, [M+H]$^+$=588. Elemental analysis calculated with 1.2 mole of $H_2O$: C=53.14%, H=4.52%, N=9.68%; found C=53.14%, H=4.24%, N=9.42%.

EXAMPLE 44

7-Methoxynaphthalene-2-sulfonic acid {1-[3-(aminoiminomethyl)benzyl]-2-oxopyrrolidin-3-(S)-yl}(4-aminobenzyl)amide bistrifluoroacetate.

To a solution of 7-methoxynaphthalene-2-sulfonic acid {1-[3-(aminoiminomethyl)benzyl]-2-oxopyrrolidin-3-(S)-yl}(4-nitrobenzyl)amide (0.23 g, 0.33 mmol) in 10 mL of MeOH is added a catalytic amount of 10% palladium on activated carbon. The heterogeneous mixture is hydrogenated at room temperature under a balloon of $H_2$ for 18 hours. The crude mixture is diluted with MeOH, filtered through a pad of Celite, washed with MeOH (2×10 mL) and concentrated in vacuo. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound (0.11 g, 0.14 mmol) as a white solid.

$^1$H NMR (DMSO-$d_6$, 300 MHz) δ9.29 (bs, 2 H), 9.06 (bs, 2 H), 8.44 (s, 1 H), 8.03 (d, 1 H), 7.96 (d, 1 H), 7.82 (dd, 1

H), 7.68 (d, 1 H), 7.56 (m, 3 H), 7.51 (d, 1 H), 7.35 (dd, 1 H), 7.12 (d, 2 H), 6.72 (d, 2 H), 4.71 (m, 1 H), 4.39 (AB, 2 H), 4.26 (AB, 2 H), 3.90 (s, 3 H), 3.10 (m, 1 H), 2.95 (m, 1 H), 2.10 (m, 1 H), 1.70 (m, 1 H). FAB MS, $[M+H]^+$=558. Elemental analysis calculated with 1.2 mole of $H_2O$: C=50.61%, H=4.42%, N=8.68%; found C=50.61%, H=4.25%, N=8.64%.

EXAMPLE 45

7-Methoxynaphthalene-2-sulfonic acid {1-[3-(aminoiminomethyl)benzyl]-2-oxopyrrolidin-3-(S)-yl}(3-nitrobenzyl)amide trifluoroacetate.

A. 7-Methoxynaphthalene-2-sulfonic acid [1-(3-cyanobenzyl)-2-oxopyrrolidin-3-(S)-yl](3-nitrobenzyl) amide.

The title compound is prepared as described in EXAMPLE 25, Part A using 7-methoxynaphthalene-2-sulfonic acid [1-(3-cyanobenzyl)-2-oxopyrrolidin-3-(S)-yl] amide as the starting material and m-nitrobenzyl bromide in place of methyl iodide. The crude product is purified by column chromatography in 10% $EtOAc/CH_2Cl_2$ to afford the title compound as a solid.

$^1$H NMR ($CDCl_3$, 300 MHz) δ8.34 (s, 1 H), 8.17 (s, 1 H), 8.02 (d, 1 H), 7.90 (d, 1 H), 7.72 (m, 3 H), 7.60 (m, 1 H), 7.45 (m, 4 H), 7.29 (m, 1 H), 7.19 (d, 1 H), 4.70 (m, 1 H), 4.52 (AB, 2 H), 4.46 (AB, 2 H), 3.94 (s, 3 H), 3.17 (m, 2 H), 2.41 (m, 1 H), 2.00 (m, 1 H).

B. 7-Methoxynaphthalene-2-sulfonic acid {1-[3-(aminoiminomethyl)benzyl]-2-oxopyrrolidin-3-(S)-yl}-(3-nitrobenzyl)amide trifluoroacetate.

7-Methoxynaphthalene-2-sulfonic acid [1-(3-cyanobenzyl)-2-oxopyrrolidin-3-(S)-yl]-(3-nitrobenzyl) amide is converted to the title compound as described in EXAMPLE 24, Part C. The imidate intermediate is formed over a period of 3 days at room temperature. The amidine formation occurred upon heating at reflux for 2 hours. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.29 (bs, 2 H), 9.18 (bs, 2 H), 8.39 (s, 1 H), 8.33 (s, 1 H), 8.03 (m, 2 H), 7.97 (d, 1 H), 7.86 (d, 1 H), 7.79 (d, 1 H), 7.67 (d, 1 H), 7.55 (m, 5 H), 7.36 (dd, 1 H), 4.92 (m, 1 H), 4.50 (AB, 2 H), 4.37 (AB, 2 H), 3.89 (s, 3 H), 3.15 (m, 2 H), 2.15 (m, 1 H), 1.80 (m, 1H). FAB MS, $[M+H]^+$=588. Elemental analysis calculated with 0.8 mole of $H_2O$: C=53.74%, H=4.44%, N=9.79%; found C=53.73%, H=4.12%, N=9.54%.

EXAMPLE 46

7-Methoxynaphthalene-2-sulfonic acid {1-[3-(aminoiminomethyl)benzyl]-2-oxopyrrolidin-3-(S)-yl}(3-aminobenzyl)amide bistrifluoroacetate 7-Methoxynaphthalene-2-sulfonic acid {1-[3-(aminoiminomethyl)benzyl]-2-oxopyrrolidin-3-(S)-yl}(3-nitrobenzyl)amide is converted to the title compound as described in EXAMPLE 44, Part A. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.30 (bs, 2H), 9.19 (bs, 2H), 8.46 (s, 1H), 8.04 (d, 1H), 7.97 (d, 1H), 7.82 (d, 1H), 7.68 (d, 1H), 7.57 (m, 3H), 7.50 (d, 1H), 7.36 (dd, 1H), 7.12 (m, 1H), 7.04 (bs, 1H), 6.82 (m, 2H), 4.80 (m, 1H), 4.35 (AB, 2H), 4.34 (AB, 2H), 3.90 (s, 3H), 3.11 (m, 1H), 2.95 (m, 1H), 2.15 (m, 1H), 1.70 (m, 1H). FAB MS, $[M+H]^+$= 558.

EXAMPLE 47

7-Methoxynaphthalene-2-sulfonic acid {1-[3-(aminoiminomethyl)benzyl]-2-oxopyrrolidin-3-(S)-yl}-(2-nitrobenzyl)amide trifluoroacetate A. 7-Methoxynaphthalene-2-sulfonic acid [1-(3-cyanobenzyl)-2-oxopyrrolidin-3-(S)-yl]-(2-nitrobenzyl) amide The title compound is prepared as described in EXAMPLE 25, Part A using 7-methoxynaphthalene-2-sulfonic acid [1-(3-cyanobenzyl)-2-oxopyrrolidin-3-(S)-yl] amide as the starting material and o-nitrobenzyl bromide in place of methyl iodide. The crude product is triturated from 50% EtOAc/hexanes to afford the title compound as a solid.

$^1$H NMR ($CDCl_3$, 300 MHz) δ8.38 (s, 1H), 8.12 (d, 1H), 7.94 (d, 1H), 7.89 (m, 2H), 7.79 (d, 1H), 7.58 (m, 2H), 7.44 (m, 3H), 7.35 (m, 1H), 7.29 (dd, 1H), 7.23 (d, 1H), 4.81 (AB, 2H), 4.65 (m, 1H), 4.42 (AB, 2H), 3.94 (s, 3H), 3.17 (m, 2H), 2.39 (m, 1H), 2.05 (m, 1H).

B. 7-Methoxynaphthalene-2-sulfonic acid {1-[3-(aminoiminomethyl)benzyl]-2-oxopyrrolidin-3-(S)-yl}-(2-nitrobenzyl)amide trifluoroacetate 7-Methoxynaphthalene-2-sulfonic acid [1-(3-cyanobenzyl)-2-oxopyrrolidin-3-(S)-yl]-(2-nitrobenzyl) amide is converted to the title compound as described in EXAMPLE 24, Part C. The imidate intermediate is formed over a period of 5 hours at room temperature. The amidine formation occurred upon heating at reflux for 2 hours. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.27 (bs, 2H), 9.19 (bs, 2H), 8.43 (s, 1H), 8.05 (m, 3H), 7.96 (d, 1H), 7.82 (d, 1H), 7.71 (m, 1H), 7.65 (m, 1H), 7.52 (m, 5H), 7.34 (dd, 1H), 4.91 (m, 1H), 4.73 (AB, 2H), 4.36 (AB, 2H), 3.89 (s, 3H), 3.18 (m, 1H), 3.09 (m, 1H), 2.25 (m, 1H), 1.82 (m, 1H). FAB MS, $[M+H]^+$=588. Elemental analysis calculated with 1.7 mole of $H_2O$: C=52.52%, H=4.59%, N=9.57%; found C=52.53%, H=4.21%, N=9.24%.

EXAMPLE 48

7-Methoxynaphthalene-2-sulfonic acid {1-[3-(aminoiminomethyl)benzyl]-2-oxopyrrolidin-3-(S)-yl}-(2-aminobenzyl)amide bistrifluoroacetate 7-Methoxynaphthalene-2-sulfonic acid {1-[3-(aminoiminomethyl)benzyl]-2-oxopyrrolidin-3-(S)-yl}-(2-nitrobenzyl)amide is converted to the title compound as described in EXAMPLE 44, Part A. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.28 (bs, 2H), 9.12 (bs, 2H), 8.45 (s, 1H), 8.04 (d, 1H), 7.96 (d, 1H), 7.83 (d, 1H), 7.68 (d, 1H), 7.55 (m, 4H), 7.36 (d, 1H), 6.98 (m, 2H), 6.65 (d, 1H), 6.47 (m, 1H), 4.79 (m, 1H), 4.33 (AB, 2H), 4.32 (AB, 2H), 3.89 (s, 3H), 3.10 (m, 1H), 2.85 (m, 1H), 2.15 (m, 1H), 1.69 (m, 1H). FAB MS, $[M+H]^+$=558.

EXAMPLE 49

3-[2-Oxo-3(S)-(2-phenylethenesulfonylamino)
pyrrolidin-1-ylmethyl]-benzamidine trifluoroacetate A. 2-Phenylethenesulfonic acid [1-(3-cyanobenzyl)-2-oxopyrrolidin-3(S)-yl]amide The title compound is prepared from 3-(3-(S)-amino-2-oxopyrrolidin-1-ylmethyl)benzonitrile hydrochloride as in EXAMPLE 24, Part B using trans-b-styrenesulfonyl chloride in place of 6-methoxynaphthalene-2-sulfonyl chloride. The crude product is triturated from 50% EtOAc/hexanes to give the title compound as a solid.

$^1$H NMR (CDCl$_3$, 300 MHz) δ7.60 (m, 1H), 7.48 (m, 9H), 6.93 (d, 1H), 5.35 (d, 1H), 4.51 (AB, 2H), 4.04 (m, 1H), 3.27 (m, 2H), 2.65 (m, 1H), 2.12 (m, 1H).

B. 3-[2-Oxo-3(S)-(2-phenylethenesulfonylamino) pyrrolidin-1-ylmethyl]-benzamidine trifluoroacetate 2-Phenylethenesulfonic acid [1-(3-cyanobenzyl)-2-oxopyrrolidin-3(S)-yl]amide is converted to the title compound as described in EXAMPLE 24, Part C. The imidate intermediate is formed over a period of 18 hours at room temperature. The amidine formation occurred over a period of 18 hours at room temperature. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.35 (bs, 2H), 9.20 (bs, 2H), 7.90 (d, 1H), 7.70 (m, 3H), 7.60 (m, 3H), 7.48 (m, 3H), 7.35 (m, 2H), 4.50 (s, 2H), 4.18 (m, 1H), 3.20 (m, 2H), 2.39 (m, 1H), 1.88 (m, 1H). FAB MS, [M+H]$^+$=399. Elemental analysis calculated with 1.3 mole of H$_2$O: C=49.35%, H=4.81%, N=10.46%, found C=49.35%, H=4.35%, N=10.28%.

EXAMPLE 50

3-[2-Oxo-3(S)-(2-phenylethanesulfonylamino) pyrrolidin-1-ylmethyl]-benzamidine trifluoroacetate A. 2-Phenylethanesulfonic acid [1-(3-cyanobenzyl)-2-oxopyrrolidin-3(S)-yl]amide 2-Phenylethenesulfonic acid [1-(3-cyanobenzyl)-2-oxopyrrolidin-3(S)-yl]amide is converted to the title compound as described in EXAMPLE 44, Part A. The crude product is purified by column chromatography in a gradient of 10% EtOAc/CH$_2$Cl$_2$ to 25% EtOAc/CH$_2$Cl$_2$ to afford the title compound as a solid.

$^1$H NMR (CDCl$_3$, 300 MHz) δ7.59 (d, 1H), 7.52 (s, 1H), 7.46 (m, 2H), 7.28 (m, 5H), 5.54 (d, 1H), 4.45 (AB, 2H), 4.25 (m, 1H), 3.50 (m, 2H), 3.25 (m, 4H), 2.59 (m, 1H), 2.00 (m, 1H).

B. 3-[2-Oxo-3(S)-(2-phenylethanesulfonylamino) pyrrolidin-1-ylmethyl]-benzamidine trifluoroacetate 2-Phenylethanesulfonic acid [1-(3-cyanobenzyl)-2-oxopyrrolidin-3(S)-yl]amide is converted to the title compound as described in EXAMPLE 24, Part C. The imidate intermediate is formed over a period of 18 hours at room temperature. The amidine formation occurred over a period of 3 days at room temperature. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.32 (bs, 2H), 9.22 (bs, 2H), 7.85 (d, 1H), 7.70 (m, 1H), 7.60 (m, 3H), 7.30 (m, 4H), 7.23 (m, 1H), 4.49 (AB, 2H), 4.25 (m, 1H), 3.45 (m, 2H), 3.21 (m, 3H), 2.98 (m, 2H), 2.40 (m, 1H), 1.89 (m, 1H). FAB MS, [M+H]$^+$=401.

EXAMPLE 51

[Imino-(3-{3-[7-Methoxynaphthalene-2-sulfonyl) methylamino]-2-oxo-3(S)-pyrrolidin-1-ylmethyl] phenyl)methyl]carbamic acid ethyl ester To a solution of 7-methoxy-2-napthalenesulfonic acid {1-[3-(aminoiminomethyl)benzyl]-2-oxo-3(S)-pyrrolidin-3-yl}methylamide trifluoroacetate (4.85 g, 8.5 mmol) in 80 mL of CH$_2$Cl$_2$ and 5 mL of DMF is added N-methylpiperidine (2.93 g, 29.5 mmol) followed by ethyl chloroformate (0.93 g, 8.5 mmol). After 1.5 hours, the solution is diluted with EtOAc. The solution is washed with H$_2$O, saturated NaHCO$_3$ and saturated NaCl. The organic layer is dried over MgSO$_4$, filtered and concentrated. The crude product is purified by column chromatography eluting with gradient of 20% CH$_2$Cl$_2$/EtOAc to 30% CH$_2$Cl$_2$/EtOAc to afford the title compound (3 g, 5.6 mmol) as a white solid.

$^1$H NMR (DMSO-d$_6$, 300 MHz) δ9.02 (bs, 2H), 8.79 (s, 1H), 8.02 (d, 1H), 7.93 (d, 1H), 7.81 (d, 1H), 7.76 (s, 1H), 7.70 (d, 1H), 7.56 (s, 1H), 7.37 (m, 3H), 4.90 (t, 1H), 4.36 (AB, 2H), 4.00 (m, 3H), 3.87 (s, 3H), 3.11 (m, 2H), 2.66 (s, 3H), 1.94 (m, 1H), 1.70 (m, 1H). FAB MS, [M+H]$^+$=539. Elemental analysis calculated with 0.5 mole of H$_2$O: C=59.22%, H=5.71%, N=10.23%, found C=59.24%, H=5.90%, N=9.78%.

EXAMPLE 52

3-[2-Oxo-3(S)-{2-(pyridin-4-ylamino)-ethanesulfonylamino}-pyrrolidin-1-ylmethyl]-benzamidine bistrifluoroacetate A. Ethenesulfonic acid [1-(3-cyanobenzyl)-2-oxopyrrolidin-3(S)-yl]amide The title compound is prepared from 3-(3-(S)-amino-2-oxopyrrolidin-1-ylmethyl)benzonitrile hydrochloride as in EXAMPLE 24, Part B using 2-chloroethanesulfonyl chloride in place of 6-methoxynaphthalene-2-sulfonyl chloride. The crude product is purified by column chromatography in a gradient of 10% EtOAc/CH$_2$Cl$_2$ to 40% EtOAc/CH$_2$Cl$_2$ to afford the title compound as a solid.

$^1$H NMR (CDCl$_3$, 300 MHz) δ7.62 (d, 1H), 7.51 (m, 3H), 6.70 (m, 1H), 6.42 (d, 1H), 6.03 (d, 1H), 5.20 (bs, 1H), 4.52 (AB, 2H), 3.99 (m, 1H), 3.25 (m, 2H), 2.62 (m, 1H), 2.08 (m, 1H).

B. 3-[2-Oxo-3(S)-{2-(pyridin-4-ylamino) ethanesulfonylamino}-pyrrolidin-1-ylmethyl]-benzamidine bistrifluoroacetate To a solution of ethenesulfonic acid [1-(3-cyanobenzyl)-2-oxopyrrolidin-3(S)-yl]amide (0.20 g, 0.64 mmol) in 20 mL of a 1:1 mixture of THF/CH$_2$Cl$_2$ is added 4-aminopyridine (0.20 g, 0.64 mmol). The mixture is stirred at room temperature for 18 hours, and then heated at reflux for 3 hours. The reaction mixture is allowed to cool and concentrated in vacuo. The crude 2-(pyridin-4-ylamino)-ethanesulfonic acid [1-(3-cyanobenzyl)-2-oxopyrrolidin-3 (S)-yl]amide is converted to the title compound as described in EXAMPLE 24, Part C. The imidate intermediate is formed over a period of 18 hours at room temperature. The amidine formation occurred upon heating at reflux for 4 hours. The crude product is purified by RP-HPLC eluting in a gradient of 2% CH$_3$CN/H$_2$O (0.1% TFA) to 50% CH$_3$CN/H$_2$O (0.1% TFA) and the appropriate product fractions are lyophilized to provide the title compound as a white solid.

$^1$H NMR (DMSO-d$_6$, 300 MHz) δ9.47 (bs, 2H), 9.36 (bs, 2H), 8.20 (m, 3H), 8.14 (m, 1H), 8.10 (s, 1H), 7.71 (m, 1H), 7.63 (s, 1H), 7.59 (d, 2H), 6.80 (m, 1H), 4.61 (m, 2H), 4.50

(AB, 2H), 4.27 (m, 1H), 3.80 (m, 2H), 3.23 (m, 2H), 2.40 (m, 1H), 1.80 (m, 1H). FAB MS, [M+H]$^+$=417. Elemental analysis calculated with 2.5 mole of $H_2O$: C=40.06%, H=4.53%, N=12.19%, found C=40.06%, H=3.68%, N=11.73%.

EXAMPLE 53

2'-Methoxybiphenyl-4-sulfonic acid {1-[3-(aminoiminomethyl)benzyl]-2-oxopyrrolidin-3(S)-yl}amide trifluoroacetate A. 4-(2-Methoxyphenyl)-bromobenzene To a solution of 2-bromoanisole (3.5 g, 18.7 mmol) in 40 mL of THF at −7° C. is added n-butyl lithium (11.7 mL of a 1.6 M solution in THF, 18.7 mmol). The solution is stirred for 15 minutes. After this time, $ZnCl_2$ (20 mL of a 1 M solution in $Et_2O$, 20 mmol) is added. The solution is allowed to warm to ambient temperature, and stirred for 3 hours. After this time, a solution of 4-iodobromobenzene (5.6 g, 19.8 mmol) and tetrakis(triphenylphosphine)-palladium(0) (1.1 g, 1 mmol) in 30 mL of THF is added. The reaction mixture is stirred for 16 hours. After this time, the solution is poured into 100 mL of $H_2O$. The solution is diluted with EtOAc. The organic layer is washed with 2 N $NH_4OH$, $H_2O$ and saturated NaCl. The organic layer is dried over $MgSO_4$, filtered, and concentrated. The crude product is purified by column chromatography eluting with gradient of 10% $CH_2Cl_2$/hexanes to 20% $CH_2Cl_2$/hexanes to afford the title compound (2.61 g, 10 mmol) as a crystalline solid.

$^1$H NMR ($CDCl_3$, 300 MHz) δ7.62 (d, 2H), 7.51 (d, 2H), 7.38 (m, 2H), 7.08 (m, 2H), 3.85 (s, 3H).

B. 2'-Methoxybiphenyl-4-sulfonyl chloride

To a solution of 4-(2-methoxyphenyl)bromobenzene (0.82 g, 3.2 mmol) in 15 mL of THF at −78° C. is added n-butyl lithium (2 mL of a 1.6 M solution in hexanes, 3.2 mmol). After 30 minutes, the solution is transferred to a flask containing 10 mL of $SO_2$ in 40 mL of $Et_2O$ at −78° C. The solution is stirred at −78° C. for 30 minutes, and then at ambient temperature for 2 hours. After this time, the solution is concentrated. The residue is dissolved in 20 mL of hexanes. The solution is cooled to 0° C. and sulfuryl chloride (3.2 mL of a 1 M solution in $CH_2Cl_2$) is added. The solution is stirred for 1 hour. After this time, the solution is concentrated. The crude product is purified by column chromatography eluting with 2% EtOAc/hexanes to afford the title compound (0.34 g, 2.6 mmol) as an oil.

$^1$H NMR ($CDCl_3$, 300 MHz) δ8.07 (d, 2H), 7.81 (d, 2H), 7.44 (m, 2H), 7.02 (m, 2H), 3.88 (s, 3H).

C. 2'-Methoxybiphenyl-4-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B using 2'-methoxybiphenyl-4-sulfonyl chloride in place of 6-methoxynaphthalene-2-sulfonyl chloride. The crude product is purified by column chromatography eluting with a gradient of 10% EtOAc/$CH_2Cl_2$ to 20% EtOAc/$CH_2Cl_2$ to give the title compound as a white foam.

$^1$H NMR ($CDCl_3$, 300 MHz) δ7.95 (m, 2H), 7.48 (d, 7H), 7.08 (m, 2H), 5.51 (bs, 1H), 4.50 (AB, 2H), 3.88 (s, 3H), 3.26 (m, 2H), 2.62 (m, 1H), 2.19 (m, 1H).

D. 2'-Methoxybiphenyl-4-sulfonic acid {1-[3-(aminoiminomethyl)benzyl]-2-oxopyrrolidin-3(S)-yl}amide trifluoroacetate 2'-Methoxybiphenyl-4-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.31 (bs, 4H), 8.21 (d, 1H), 7.90 (m, 2H), 7.61 (m, 3H), 7.41 (m, 2H), 7.35 (m, 2H), 7.12 (m, 3H), 4.45 (AB, 2H), 4.18 (m, 1H), 3.76 (s, 3H), 3.15 (m, 2H), 2.15 (m, 1H), 1.68 (m, 1H). FAB MS, [M+H]$^+$=479.

EXAMPLE 54

5,6,7,8-Tetrahydrophenanthrene-3-sulfonic acid {1-[3-(aminoiminomethyl)benzyl]-2-oxo-3(S)-pyrrolidin-3-yl}amide trifluoroacetate A. 5,6,7,8-Tetrahydrophenanthrene-3-sulfonyl chloride 5,6,7,8-Tetrahydrophenanthrene-3-sulfonic acid sodium salt (1 g, 3.68 mmol) is suspended in 5 mL of thionyl chloride. DMF (2 drops) is added and the solution is heated to 60° C. for 30 minutes. After this time, the reaction mixture is concentrated. The residue is triturated with $CH_2Cl_2$ and the resulting solid is filtered off. The collected organic solution is concentrated. The crude product is purified by column chromatography eluting with 10% EtOAc/hexanes to give the title compound (0.60 g, 2.3 mmol) as a white solid.

$^1$H NMR ($CDCl_3$, 300 MHz) δ8.51 (s, 1H), 8.12 (d, 1H), 8.00 (d, 1H), 7.78 (d, 1H), 7.37 (d, 1H), 3.12 (m, 2H), 2.98 (m, 2H), 1.98 (m, 4H).

B. 5,6,7,8-Tetrahydrophenanthrene-3-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting 5,6,7,8-tetrahydrophenanthrene-3-sulfonyl chloride for 6-methoxynaphthalene-2-sulfonyl chloride. The crude product is purified by column chromatography eluting with a gradient of 20% EtOAc/$CH_2Cl_2$ to 30% EtOAc/$CH_2Cl_2$ to give the title compound as a white foam.

$^1$H NMR ($CDCl_3$, 300 MHz) δ8.38 (s, 1H), 8.19 (d, 1H), 7.89 (m, 1H), 7.70 (m, 1H), 7.56 (m, 1H), 7.39 (m, 4H), 5.45 (bs, 1H), 4.42 (AB, 2H), 3.76 (t, 1H), 3.19 (m, 4H), 2.99 (m, 2H), 2.58 (m, 1H), 1.94 (m, 5H).

C. 5,6,7,8-Tetrahydrophenanthrene-3-sulfonic acid {1-[3-(aminoiminomethyl)benzyl]-2-oxo-3(S)-pyrrolidin-3-yl}amide trifluoroacetate 5,6,7,8-Tetrahydrophenanthrene-3-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.31 (bs, 2H), 9.03 (bs, 2H), 8.41 (s, 1H), 8.22 (dd, 2H), 7.89 m, 1H), 7.63 (m, 4H), 7.39 (d, 1H), 4.44 (AB, 2H), 4.19 (m, 1H), 3.12 (m, 4H), 2.91 (m, 2H), 1.88 (m, 5H), 1.58 (m, 1H). FAB MS, [M+H]$^+$=477. Elemental analysis calculated with 2.50 mole of $H_2O$ cal. C=52.91%, H=5.39%, N=8.81% found C=52.67%, H=4.77%, N=8.41%.

EXAMPLE 55

Isoquinoline-5-sulfonic acid {1-[3-(aminoiminomethyl)benzyl]-2-oxo-3(S)-pyrrolidin-3-yl}amide bistrifluoroacetate A. Isoquinoline-5-sulfonyl chloride The title compound is prepared as described in EXAMPLE 54, Part A using isoquinoline-5-sulfonic acid in place of 5,6,7,8-tetrahydrophenanthrene-3-sulfonic acid, sodium salt. The crude product is purified by triturating with Et$_2$O to give the product as a white solid.

EI MS, [M]$^+$=227.

B. Isoquinoline-5-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting isoquinoline-5-sulfonyl chloride for 6-methoxynaphthalene-2-sulfonyl chloride. The crude product is purified by column chromatography eluting with a gradient of 2% MeOH/CH$_2$Cl$_2$ to 4% MeOH/CH$_2$Cl$_2$ to give the title compound as a white foam.

$^1$H NMR (CDCl$_3$, 300 MHz) δ9.38 (s, 1H), 8.81 (d, 1H), 8.49 (m, 2H), 8.22 (d, 1H), 7.70 (m, 1H), 7.56 (m, 1H), 7.41 (m, 3H), 5.77 (bs, 1H), 4.41 (AB, 2H), 3.84 (t, 1H), 3.17 (dd, 2H), 2.50 (m, 1H), 1.95 (m, 1H).

C. Isoquinoline-5-sulfonic acid {1-[3-(aminoiminomethyl)benzyl]-2-oxo-3(S)-pyrrolidin-3-yl}amide bistrifluoroacetate Isoquinoline-5-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (D$_2$O, 300 MHz) δ9.74 (s, 1H), 8.92 (d, 1H), 8.77 (d, 1H), 8.63 (m, 2H), 8.00 (t, 1H), 7.57 (m, 1H), 7.42 (m, 3H), 4.28 (m, 3H), 3.15, (m, 2H), 2.13 (m, 1), 1.66 (m, 1H). FAB MS, [M+H]$^+$=424. Elemental analysis calculated with 2 mole of H$_2$O cal. C=43.67%, H=3.96%, N=10.19%, found C=43.59%, H=3.34%, N=9.95%.

EXAMPLE 56

5-Chlorothiophene-2-sulfonic acid {1-[3-(aminoiminomethyl)benzyl]-2-oxo-3(S)-pyrrolidin-3-yl}amide trifluoroacetate A. 5-Chlorothiophene-2-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting 5-chlorothiophene-2-sulfonyl chloride for 6-methoxynaphthalene-2-sulfonyl chloride. The crude product is used without further purification.

$^1$H NMR (CDCl$_3$, 300 MHz) δ7.61 (m, 1H), 7.47 (m, 4H), 7.00 (m, 1H), 5.41 (bs, 1H), 4.50 (AB, 2H), 3.89 (m, 1H), 3.24 (m, 2H), 2.62 (m, 1H), 2.11 (m, 1H).

B. 5-Chlorothiophene-2-sulfonic acid {1-[3-(aminoiminomethyl)benzyl]-2-oxo-3(S)-pyrrolidin-3-yl}amide trifluoroacetate 5-Chlorothiophene-2-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.31 (bs, 2H), 9.12 (bs, 2H), 8.60 (d, 1H), 7.68 (m, 1H), 7.56 (m, 3H), 7.21 (m, 1H), 4.43 (AB, 2H), 4.20 (AB, 2H), 3.18 (m, 2H), 2.19 (m, 1H), 1.69 (m, 1H). FAB MS, [M+H]$^+$=413. Elemental analysis calculated with 0.75 mole of H$_2$O cal. C=40.0%, H=3.64%, N=10.37%, found C=40.04%, H=3.64%, N=10.05%.

EXAMPLE 57

2,4-Diaminoquinazoline-6-sulfonic acid {1-[3-(aminoiminomethyl)benzyl]-2-oxo-3(S)-pyrrolidin-3-yl}amide trifluoroacetate A. 2,4-Diaminoquinazoline-6-sulfonyl chloride sulfate salt To a hot solution of 2,4-diaminoquinazoline (2.3 g, 14.1 mmol) in 150 mL of H$_2$O is added 2 mL of conc. H$_2$SO$_4$. The solution is further heated until all the solid dissolves. The solution is then cooled to ambient temperatures and a solid forms. The solid is filtered off. The solid is then cooled to 0° C. and a suspension of 0.1 g of NaCl in 3 mL of chlorosulfuric acid is added dropwise. The resulting solution is heated to 150° C. for 3 hours. After this time, the solution is poured into 50 mL of ice water. the resulting solid is collected by filtration and dried under vacuum. The title compound (3.2 g, 9 mmol) is obtained as a white solid.

$^1$H NMR (DMSO-d$_6$, 300 MHz) δ12.50 (bs, 2H), 9.15 (bs, 1H), 8.78 (bs, 1H), 8.52 (s, 1H), 7.98 (d, 1H), 7.41 (d, 1H).

B. 2,4-Diaminoquinazoline-6-sulfonic acid [1-(3-cyanobenzyl)-2-oxopyrrolidin-3-(S)-yl]amide To a solution of 3-(3-(S)-amino-2-oxopyrrolidin-1-ylmethyl)benzonitrile hydrochloride (0.50 g, 2 mmol) in 8 mL of H$_2$O is added triethyl amine (0.7 g, 7 mmol). After stirring for 10 minutes, 2,4-diamino-quinazoline-6-sulfonyl chloride sulfate salt (0.71 g, 2 mmol) is added. The solution is refluxed for 1 hour. After this time, the solution is cooled to ambient temperatures. The solution is filtered. The collected solid is dried under vacuum to give the title compound (0.22 g, 0.5 mmol) as a white solid.

$^1$H NMR (DMSO-d$_6$, 300 MHz) δ8.48 (s, 1H), 7.92 (m, 1H), 7.80 (m, 1H), 7.60 (m, 1H), 7.51 (m, 2H), 7.18 (d, 1H), 6.37 (bs, 1H), 4.35 (AB, 2H), 4.08 (m, 1H), 3.05 (m, 2H), 1.98 (m, 1H), 1.52 (m, 1H).

C. 2,4-Diamino-quinazoline-6-sulfonic acid {1-[3-(aminoiminomethyl)benzyl]-2-oxo-3(S)-pyrrolidin-3-yl}amide trifluoroacetate 2,4-Diamino-quinazoline-6-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (D$_2$O, 300 MHz) δ8.41 (s, 1H), 8.08 (d, 1H), 7.55 (m, 1H), 7.43 (m, 4H), 4.32 (AB, 2H), 4.15 (m, 1H), 3.13 (m, 2H), 2.12 (m, 1H), 1.63 (m, 1H). FAB MS, [M+H]$^+$=455. Elemental analysis calculated with 0.50 mole of H$_2$O cal. C=38.77%, H=3.25%, N=13.91%, found C=38.78%, H=3.23%, N=13.92%.

EXAMPLE 58

7-Methoxy-2-napthalenesulfonic acid {1-[3-(aminoiminomethyl)benzyl]-2-oxo-3(S)-pyrrolidin-3-yl}ethylamide trifluoroacetate A. 7-Methoxy-2-napthalenesulfonic acid [1-(3-cyanobenzyl)-2-oxopyrrolidin-3-(S)-yl]ethylamide The title compound is prepared as described in EXAMPLE 25, Part A using 7-methoxynaphthalene-2-sulfonic acid [1-(3-cyanobenzyl)-2-oxopyrrolidin-3-(S)-yl]amide, prepared as described in EXAMPLE 43, Part A, and ethyl iodide. The crude product is purified by column chromatography eluting with gradient of 15% EtOAc/CH$_2$Cl$_2$ to 25% EtOAc/CH$_2$Cl$_2$ to afford the title compound as a white foam.

$^1$H NMR (CDCl$_3$, 300 MHz) δ8.46 (s, 1H), 7.92 (m, 2H), 7.81 (s, 1H), 7.50 (m, 4H), 7.28 (m, 1H), 4.59 (m, 2H), 4.39

(m, 1H), 3.92 (s, 3H), 3.26 (m, 3H), 2.49 (m, 1H), 2.23 (m, 1H), 1.22 (m, 3H).

B. 7-Methoxy-2-napthalenesulfonic acid {1-[3-(aminoiminomethyl)benzyl]-2-oxo-3(S)-pyrrolidin-3-yl}ethylamide trifluoroacetate 7-Methoxy-2-napthalenesulfonic acid [1-(3-cyanobenzyl)-2-oxopyrrolidin-3-(S)-yl]ethylamide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (CDCl$_3$, 300 MHz) δ10.24 (bs, 2H), 8.48 (s, 1H), 7.99 (m, 1H), 7.90 (m, 1H), 7.79 (m, 1H), 7.53 (m, 4H), 7.26 (m, 1H), 5.08 (d, 1H), 4.29 (m, 1H), 4.08 (m, 1H), 3.92 (s, 3H), 3.38 (m, 2H), 3.20 (m, 1H), 2.51 (m, 2H), 1.15 (m, 3H). FAB MS, [M+H]$^+$=481. Elemental analysis calculated with 1.75 mole of H$_2$O cal. C=50.39%, H=4.72%, N=8.40%, found C=49.99%, H=4.69%, N=8.12%.

EXAMPLE 59

7-Methoxy-2-napthalenesulfonic acid {1-[3-(aminoiminomethyl)benzyl]-2-oxo-3(S)-pyrrolidin-3-yl}(3-fluorobenzyl)amide trifluoroacetate A. 7-Methoxy-2-napthalenesulfonic acid [1-(3-cyanobenzyl)-2-oxopyrrolidin-3-(S)-yl]-(3-fluorobenzyl)amide The title compound is prepared as described in EXAMPLE 25, Part A using 7-methoxynaphthalene-2-sulfonic acid [1-(3-cyanobenzyl)-2-oxopyrrolidin-3-(S)-yl] amide, prepared as described in EXAMPLE 43, part A, and 3-fluorobenzyl bromide. The crude product is purified by column chromatography eluting with gradient of 40% EtOAc/hexanes to 50% EtOAc/hexanes to afford the title compound as a white foam.

$^1$H NMR (CDCl$_3$, 300 MHz) δ8.45 (s, 1H), 7.92 (m, 2H), 7.80 (d, 1H), 7.60 (m, 1H), 7.49 (m, 3H), 7.25 (m, 3H), 7.17 (m, 2H), 6.92 (m, 1H), 4.62 (m, 3H), 4.31 (m, 2H), 3.96 (s, 3H), 3.05 (m, 2H), 2.30 (m, 1H), 1.97 (m, 1H).

B. 7-Methoxy-2-napthalenesulfonic acid {1-[3-(aminoiminomethyl)benzyl]-2-oxo-3(S)-pyrrolidin-3-yl}-(3-fluorobenzyl)amide trifluoroacetate 7-Methoxy-2-napthalenesulfonic acid [1-(3-cyanobenzyl)-2-oxopyrrolidin-3-(S)-yl]-(3-fluorobenzyl) amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-d$_6$, 300 MHz) δ9.25 (bs, 4H), 8.41 (s, 1H), 7.99 (m, 2H), 7.79 (m, 1H), 7.69 (m, 1H), 7.51 (m, 4H), 7.24 (m, 1H), 7.04 (m, 1H), 4.80 (m, 1H), 4.38 (m, 4H), 3.88 (s, 3H), 3.08 (m 2H), 2.12 (m, 1H0,) 1.71 (m, 1H). FAB MS, [M+H]$^+$=561. Elemental analysis calculated with 0.25 mole of H$_2$O cal. C=56.60%, H=4.53%, N=8.25%, found C=56.54%, H=4.48%, N=8.18%.

EXAMPLE 60

7-Methoxy-2-napthalenesulfonic acid {1-[3-(aminoiminomethyl)benzyl]-2-oxo-3(S)-pyrrolidin-3-yl}(4-methylbenzyl)amide trifluoroacetate A. 7-Methoxy-2-napthalenesulfonic acid [1-(3-cyanobenzyl)-2-oxopyrrolidin-3-(S)-yl]-(4-methylbenzyl)amide The title compound is prepared as described in EXAMPLE 25, Part A using 7-methoxynaphthalene-2-sulfonic acid [1-(3-cyanobenzyl)-2-oxopyrrolidin-3-(S)-yl] amide, prepared as described in EXAMPLE 43, part A, and 4-methylbenzyl bromide. The crude product is purified by column chromatography eluting with gradient of 40% EtOAc/hexanes to 50% EtOAc/hexanes to afford the title compound as a white foam.

$^1$H NMR (CDCl$_3$, 300 MHz) δ8.43 (s, 1H), 7.92 (m, 2H), 7.78 (d, 1H), 7.57 (m, 1H), 7.43 (m, 3H), 7.22 (m, 5H), 7.04 (m, 2H), 4.56 (m, 3H), 4.28 (m, 2H), 3.92 (s, 3H), 2.99 (m, 2H), 2.27 (m, 4H), 1.99 (m, 1H).

B. 7-Methoxy-2-napthalenesulfonic acid {1-[3-(aminoiminomethyl)benzyl]-2-oxo-3(S)-pyrrolidin-3-yl}(4-methylbenzyl)amide trifluoroacetate 7-Methoxy-2-napthalenesulfonic acid [1-(3-cyanobenzyl)-2-oxopyrrolidin-3-(S)-yl](4-methylbenzyl) amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-d$_6$, 300 MHz) δ9.29 (bs, 2H), 9.11 (bs, 2H), 8.40 (s, 1H), 7.98 (m, 2H), 7.81 (d, 1H), 7.65 (m, 1H), 7.51 (m, 4H), 7.32 (m, 1H), 7.19 (m, 3H), 7.05 (d, 2H), 4.75 (t, 1H), 4.45 (m, 2H), 4.25 (m, 2H), 3.89 (s, 3H), 3.06 (m, 1H), 2.95 (m, 1H), 2.11 (s, 3H), 2.10 (m, 1H), 1.64 (m, 1H). FAB MS, [M+H]$^+$=557. Elemental analysis calculated with 2 mole of H$_2$O cal. C=56.08%, H=5.28%, N=7.93%, found C=56.00%, H=4.69%, N=7.73%.

EXAMPLE 61

7-Methoxy-2-napthalenesulfonic acid {1-[3-(aminoiminomethyl)benzyl]-2-oxo-3(S)-pyrrolidin-3-yl}(3-methylbenzyl)amide trifluoroacetate A. 7-Methoxy-2-napthalenesulfonic acid [1-(3-cyanobenzyl)-2-oxopyrrolidin-3-(S)-yl](3-methylbenzyl)amide The title compound is prepared as described in EXAMPLE 25, Part A using 7-methoxynaphthalene-2-sulfonic acid [1-(3-cyanobenzyl)-2-oxopyrrolidin-3-(S)-yl] amide, prepared as described in EXAMPLE 43, Part A, and 3-methylbenzyl bromide. The crude product is purified by column chromatography eluting with gradient of 40% EtOAc/hexanes to 50% EtOAc/hexanes to afford the title compound as a white foam.

$^1$H NMR (CDCl$_3$, 300 MHz) δ8.44 (s, 1H), 7.92 (m, 2H), 7.78 (d, 1H), 7.58 (m, 1H), 7.42 (m, 3H), 7.23 (m, 2H), 7.09 (m, 5H), 4.55 (m, 3H), 4.28 (m, 2H), 3.92 (s, 3H), 3.02 (m, 2H), 2.25 (m, 4H), 1.95 (m, 1H).

B. 7-Methoxy-2-napthalenesulfonic acid {1-[3-(aminoiminomethyl)benzyl]-2-oxo-3(S)-pyrrolidin-3-yl}(3-methylbenzyl)amide trifluoroacetate 7-Methoxy-2-napthalenesulfonic acid [1-(3-cyanobenzyl)-2-oxopyrrolidin-3-(S)-yl]-(3-methylbenzyl) amide is converted to the title compound as described in EXAMPLE 24, Part C. The crude product is purified by RP-HPLC eluting with a gradient of 10% $CH_3CN/H_2O$ (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 2H), 9.19 (bs, 2H), 8.42 (s, 1H), 7.98 (m, 2H), 7.82 (d, 1H), 7.66 (m, 1H), 7.51 (m, 4H), 7.32 (m, 1H), 7.06 (m, 4H), 4.76 (t, 1H), 4.34 (m, 4H), 3.89 (s, 3H), 3.14 (m, 1H), 2.95 (m, 1H), 2.14 (s, 3H), 2.10 (m, 1H), 1.68 (m, 1H). FAB MS, [M+H]⁺=557. Elemental analysis calculated with 1.25 mole of H₂O cal. C=57.18%, H=5.16%, N=8.08%, found C=57.35%, H=4.78%, N=7.98%.

EXAMPLE 62

7-Methoxy-2-napthalenesulfonic acid {1-[3-(aminoiminomethyl)benzyl]-2-oxo-3(S)-pyrrolidin-3-yl}napthalene-2-ylmethylamide trifluoroacetate A. 7-Methoxy-2-napthalenesulfonic acid [1-(3-cyanobenzyl)-2-oxopyrrolidin-3-(S)-yl]napthalene-2-ylmethylamide The title compound is prepared as described in EXAMPLE 25, Part A using 7-methoxynaphthalene-2-sulfonic acid [1-(3-cyanobenzyl)-2-oxopyrrolidin-3-(S)-yl] amide, prepared as described in EXAMPLE 43, part A, and 2-bromo-methylnaphthalene. The crude product is purified by column chromatography eluting with gradient of 40% EtOAc/hexanes to 50% EtOAc/hexanes to afford the title compound as a white foam.

¹H NMR (CDCl₃, 300 MHz) δ8.41 (s, 1H), 7.92 (m, 2H), 7.73 (m, 5H), 7.38 (m, 9H), 4.81 (AB, 1H), 4.64 (t, 1H), 4.51 (m, 2H), 4.31 (AB, 1H), 3.91 (s, 3H), 2.95 (m, 2H), 2.24 (m, 1H), 1.99 (m, 1H).

B. 7-Methoxy-2-napthalenesulfonic acid {1-[3-(aminoiminomethyl)benzyl]-2-oxo-3(S)-pyrrolidin-3-yl}napthalene-2-ylmethylamide trifluoroacetate 7-Methoxy-2-napthalenesulfonic acid [1-(3-cyanobenzyl)-2-oxopyrrolidin-3-(S)-yl]napthalene-2-ylmethylamide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.31 (bs, 2H), 9.20 (bs, 2H), 8.40 (s, 1H), 7.97 (m, 2H), 7.79 (m, 3H), 7.65 (m, 1H), 7.48 (m, 10H), 4.88 (t, 1H), 4.69 (m, 1H), 4.40 (m, 3H), 3.89 (s, 3H), 3.09 (m, 1H), 2.91 (m, 1H), 2.13 (m, 1H), 1.71 (m, 1H). FAB MS, [M+H]⁺=593. Elemental analysis calculated with 0.75 mole of H₂O cal. C=60.17%, H=4.63%, N=7.63%, found C=60.03%, H=4.83%, N=7.78%.

EXAMPLE 63

7-Methoxy-2-napthalenesulfonic acid {1-[3-(aminoiminomethyl)benzyl]-2-oxo-3(S)-pyrrolidin-3-yl}(3-phenylallyl)amide trifluoroacetate A. 7-Methoxy-2-napthalenesulfonic acid [1-(3-cyanobenzyl)-2-oxopyrrolidin-3-(S)-yl]-(3-phenylallyl)amide The title compound is prepared as described in EXAMPLE 25, Part A using 7-methoxynaphthalene-2-sulfonic acid [1-(3-cyanobenzyl)-2-oxopyrrolidin-3-(S)-yl] amide, prepared as described in EXAMPLE 43, part A, and cinnamyl bromide. The crude product is purified by column chromatography eluting with gradient of 20% EtOAc/hexanes to 30% EtOAc/hexanes to afford the title compound as a white foam.

¹H NMR (CDCl₃, 300 MHz) δ8.44 (s, 1H), 7.90 (m, 2H), 7.79 (d, 1H), 7.50 (m, 5H), 7.28 (m, 6H), 6.43 (d, 1H), 6.20 (m, 1H), 4.71 (t, 1H), 4.40 (AB, 2H), 4.01 (m, 2H), 3.91 (s, 3H), 3.17 (m, 2H), 2.48 (m, 1H), 2.31 (m, 1H).

B. 7-Methoxy-2-napthalenesulfonic acid {1-[3-(aminoiminomethyl)benzyl]-2-oxo-3(S)-pyrrolidin-3-yl}(3-phenylallyl)amide trifluoroacetate 7-Methoxy-2-napthalenesulfonic acid [1-(3-cyanobenzyl)-2-oxopyrrolidin-3-(S)-yl](3-phenylallyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.28 (bs, 2H), 9.06 (bs, 2H), 8.41 (s, 1H), 7.95 (m, 2H), 7.79 (m, 1H), 7.61 (m, 2H), 7.45 (m, 3H), 7.29 (m, 6H), 6.50 (d, 1H), 6.18 (m, 1H), 4.85 (t, 1H), 4.36 (AB, 2H), 4.01 (m, 1H), 3.88 (m, 1H), 3.84 (s, 3H), 3.14 (m, 2H), 2.91 (m, 1H), 2.15 (m, 1H), 1.98 (m, 1H). FAB MS, [M+H]⁺=569. Elemental analysis calculated with 1.75 mole of H₂O cal. C=57.18%, H=5.15%, N=7.84%, found C=57.10%, H=5.15%, N=7.58%.

EXAMPLE 64

7-Methoxy-2-napthalenesulfonic acid {1-[3-(aminoiminomethyl)benzyl]-2-oxo-3(S)-pyrrolidin-3-yl}(3-methylbenzyl)amide trifluoroacetate A. 7-Methoxy-2-napthalenesulfonic acid [1-(3-cyanobenzyl)-2-oxopyrrolidin-3-(S)-yl]](3-methylbenzyl)amide The title compound is prepared as described in EXAMPLE 26, Part A using 7-methoxynaphthalene-2-sulfonic acid [1-(3-cyanobenzyl)-2-oxopyrrolidin-3-(S)-yl] amide, prepared as described in EXAMPLE 43, part A, and 2-bromomethylnaphthalene. The crude product is purified by column chromatography eluting with gradient of 5% EtOAc/CH₂Cl₂ to 10% EtOAc/CH₂Cl₂ to afford the title compound as a white foam.

¹H NMR (CDCl₃, 300 MHz) δ8.45 (s, 1H), 7.92 (m, 2H), 7.80 (d, 1H), 7.58 (m, 1H), 7.45 (m, 2H), 7.31 (m, 4H), 7.12 (m, 3H), 4.71 (m, 1H), 4.49 (m, 2H), 4.31 (AB, 2H), 3.95 (s, 3H), 2.98 (m, 2H), 2.29 (s, 3H), 2.28 (m, 1H), 1.95 (m, 1H).

B. 7-Methoxy-2-napthalenesulfonic acid {1-[3-(aminoiminomethyl)benzyl]-2-oxo-3(S)-pyrrolidin-3-yl}} (3-methylbenzyl)amide trifluoroacetate 7-Methoxy-2-napthalenesulfonic acid [1-(3-cyanobenzyl)-2-oxopyrrolidin-3-(S)-yl]](3-methylbenzyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.25 (bs, 2H), 9.14 (bs, 2H), 8.41 (s, 1H), 8.00 (m, 1H), 7.92 (m, 1H), 7.81 (m, 1H), 7.65 (m, 1H), 7.51 (m, 4H), 7.32 (m, 2H), 7.08 (m, 3H), 4.72 (t, 1H), 4.55 (m, 1H), 4.28 (AB, 2H), 3.90 (s, 3H), 3.09 (m, 1H), 2.90 (m, 1H), 2.21 (s, 3H), 2.15 (m, 1H), 1.64 (m, 1H). FAB MS, [M+H]⁺=557. Elemental analysis calculated with 1.75 mole of H₂O cal. C=56.44%, H=5.24%, N=7.98%, found C=56.39%, H=4.69%, N=7.69%.

EXAMPLE 65

7-Methoxy-2-napthalenesulfonic acid {1-[3-(aminoiminomethyl)benzyl]-2-oxo-3(S)-pyrrolidin-3-yl}(2-fluorobenzyl)amide trifluoroacetate A. 7-Methoxy-2-napthalenesulfonic acid [1-(3-cyanobenzyl)-2-oxopyrrolidin-3-(S)-yl]}(2-fluorobenzyl)amide The title compound is prepared as described in EXAMPLE 26, Part A using 7-methoxynaphthalene-2-sulfonic acid [1-(3-cyanobenzyl)-2-oxopyrrolidin-3-(S)-yl] amide, prepared as described in EXAMPLE 43, part A, and 2-fluorobenzyl bromide. The crude product is purified by column chromatography eluting with gradient of 5% EtOAc/$CH_2Cl_2$ to 10% EtOAc/$CH_2Cl_2$ to afford the title compound as a white foam.

$^1$H NMR (CDCl$_3$, 300 MHz) δ8.50 (s, 1H), 7.93 (m, 2H), 7.80 (m, 1H), 7.61 (m, 2H), 7.48 (m, 2H), 7.32 (m, 5H), 7.12 (m, 1H), 6.98 (m, 1H), 4.58 (m, 4H), 4.28 (m, 1H), 3.92 (s, 3H), 3.09 (m, 2H), 2.31 (s, 1H), 2.04 (m, 1H).

B. 7-Methoxy-2-napthalenesulfonic acid {1-[3-(aminoiminomethyl)benzyl]-2-oxo-3(S)-pyrrolidin-3-yl}}(2-fluorobenzyl)amide trifluoroacetate 7-Methoxy-2-napthalenesulfonic acid [1-(3-cyanobenzyl)-2-oxopyrrolidin-3-(S)-yl]](2-fluorobenzyl)amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-d$_6$, 300 MHz) δ9.28 (bs, 4H), 8.42 (s, 1H), 7.95 (m, 2H), 7.79 (m, 1H), 7.55 (m, 6H), 7.31 (m, 2H), 7.11 (m, 2H), 4.85 (t, 1H), 4.48 (m, 4H), 3.89 (s, 3H), 3.08 (m, 2H), 2.15 (m, 1H), 1.72 (m, 1H). FAB MS, [M+H]$^+$= 561. Elemental analysis calculated with 2.50 mole of $H_2O$ cal. C=53.40%, H=4.92%, N=7.78%, found C=53.55%, H=4.28%, N=7.42%.

EXAMPLE 66

2-Fluorobiphenyl-4-sulfonic acid {1-[3-(aminoiminomethyl)benzyl]-2-oxo-3(S)-pyrrolidin-3-yl}methyl amide trifluoro acetate A. 2-Fluorobiphenyl-4-sulfonyl chloride To a solution of 4-bromo-2-fluorobiphenyl (2.54 g, 10.1 mmol) in 50 mL of THF at −78° C. is added n-butyl lithium (16.3 mL of a 1.6 M solution in hexanes, 10.1 mmol). After 0.5 hour, the solution is added to a solution of 10 mL of $SO_2$ in 10 mL of Et$_2$O at −78° C. The solution is allowed to warm to ambient temperature and stirred for another 1 hour. The solution is concentrated. The resulting solid is suspended in 40 mL of hexanes and cooled to 0° C. To the suspension is added sulfuryl chloride (10 mL of a 1 M solution in $CH_2Cl_2$, 10 mmol). The solution is warmed to ambient temperatures. After 1 hour, the solution is concentrated. The resulting residue is triturated with hexanes. The solution is filtered and the collected solvent is concentrated. The resulting solid is recrystallized from hexanes to give the title compound (0.6 g, 2.2 mmol) as a white solid.

$^1$H NMR (CDCl$_3$, 300 MHz) δ7.88 (m, 2H), 7.68 (m, 1H), 7.52 (m, 5H).

B. 2-Fluorobiphenyl-4-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting 2-fluorobiphenyl-4-sulfonyl chloride for 6-methoxynaphthalene-2-sulfonyl chloride. The crude product is purified by column chromatography eluting with gradient of 15% EtOAc/$CH_2Cl_2$ to 30% EtOAc/$CH_2Cl_2$ to afford the title compound as a white foam.

$^1$H NMR (CDCl$_3$, 300 MHz) δ7.70 (m, 2H), 7.49 (m, 10H), 5.57 (bs, 1H), 4.48 (m, 3H), 3.88 (m, 1H), 3.21 (m, 2H), 2.60 (m, 1H), 2.07 (m, 1H).

C. 2-Fluorobiphenyl-4-sulfonic acid [1-(3-cyanobenzyl)-2-oxopyrrolidin-3-(S)-yl]-methylamide The title compound is prepared as described in EXAMPLE 26, Part A using 2-fluorobiphenyl-4-sulfonic acid [1-(3-cyanobenzyl)-2-oxopyrrolidin-3-(S)-yl]amide and methyl iodide. The crude product is purified by column chromatography eluting with gradient of 10% EtOAc/$CH_2Cl_2$ to 20% EtOAc/$CH_2Cl_2$ to afford the title compound as a white foam.

$^1$H NMR (CDCl$_3$, 300 MHz) δ7.70 (m, 2H), 7.51 (m, 10H), 4.93 (t, 1H), 4.55 (AB, 2H), 3.28 (m, 2H), 2.81 (s, 3H), 2.42 (m, 1H), 2.08 (m, 1H).

D. 2-Fluorobiphenyl-4-sulfonic acid {1-[3-(aminoiminomethyl)benzyl]-2-oxo-3(S)-pyrrolidin-3-yl}}methyamide trifluoroacetate 2-Fluorobiphenyl-4-sulfonic acid [1-(3-cyanobenzyl)-2-oxopyrrolidin-3-(S)-yl]methylamide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-d$_6$, 300 MHz) δ9.39 (bs, 2H), 9.14 (bs, 2H), 7.79 (m, 3H), 7.55 (m, 9H), 4.95 (t, 1H), 4.43 (AB, 2H), 3.20 (m, 2H), 2.72 (s, 3H), 2.10 (m, 1H), 1.93 (m, 1H). FAB MS, [M+H]$^+$=481.

EXAMPLE 67

3-[{1-[3-(Aminoiminomethyl)benzyl]-2-oxopyrrolidin-3(S)-3-yl}-(7-methoxynaphthalene-2-sulfonyl)amino]propionamide trifluoroacetate A. 3-[{1-(3-Cyanobenzyl)-2-oxopyrrolidin-3-(S)-yl}-7-methoxynaphthalene-2-sulfonylamino]-N-propionic acid t-butyl ester To a solution of 7-methoxynaphthalene-2-sulfonic acid [1-(3-cyanobenzyl)-2-oxopyrrolidin-3-(S)-yl]amide, prepared as described in EXAMPLE 43, part A, (0.82 g, 1.9 mmol) in 10 mL of DMF is added $K_2CO_3$ (0.52 g, 3.8 mmol) and t-butyl acrylate (0.48 g, 3.8 mmol). The solution is heated to 60° C. and stirred for 24 hours. After this time, the solution is cooled to ambient temperatures and diluted with EtOAc. The solution is washed with 1 N HCl and saturated NaCl. The organic layer is dried over MgSO$_4$, filtered, and concentrated. The title compound (0.64 g, 11 mmol) is obtained as a white foam.

$^1$H NMR (CDCl$_3$, 300 MHz) δ8.41 (s, 1H), 7.89 (m, 2H), 7.80 (m, 1H), 7.56 (m, 4H), 7.23 (m, 2H), 4.71 (t, 1H), 4.50 (AB, 2H), 3.92 (s, 3H), 3.63 (m, 4H), 3.37 (m, 1H), 3.36 (m, 4H), 2.78 (m, 2H), 2.41 (m, 1H), 2.20 (m, 1H) 1.42 (s, 9H).

B. 3-[{1-(3-Cyanobenzyl)-2-oxopyrrolidin-3-(S)-yl}-7-methoxynaphthalene-2-sulfonylamino]-N-propionic acid 3-[{1-(3-Cyanobenzyl)-2-oxopyrrolidin-3-(S)-yl}-7-methoxynaphthalene-2-sulfonylamino]-N-propionic acid t-butyl ester is converted to the title compound as described in EXAMPLE 26, Part B. The title compound is obtained as a white foam.

$^1$H NMR (CDCl$_3$, 300 MHz) δ8.41 (s, 1H), 7.89 (d, 1H), 7.80 (m, 2H), 7.56 (m, 4H), 7.22 (m, 2H), 4.74 (t, 1H), 4.50 (AB, 2H), 3.92 (s, 3H), 3.56 (m, 1H), 3.37 (m, 1H), 3.22 (m, 2H), 2.89 (m, 2H), 2.39 (m, 2H), 2.10 (m, 1H).

C. 3-[{1-(3-Cyanobenzyl)-2-oxopyrrolidin-3-(S)-yl}-7-methoxynaphthalene-2-sulfonylamino]propionamide To a solution of 3-[{1-(3-cyanobenzyl)-2-oxopyrrolidin-3-(S)-yl}-7-methoxynaphthalene-2-sulfonylamino]-N-propionic acid (0.51 g, 1 mmol) and triethyl amine (0.12 g, 1.2 mmol) in 10 mL of THF at −20° C. is added ethyl chloroformate (0.11 g, 1 mmol). The solution is stirred for 15 minutes. After this time, 14.8 N ammonium hydroxide (0.1 mL, 1.5 mmol) is added. The solution is allowed to warm to ambient temperatures. The reaction is stirred for 16 hours. After this time, the solution is diluted with EtOAc. The organic layer is washed with 1 N HCl, 10% $Na_2CO_3$ and saturated NaCl. The organic layer is dried over $MgSO_4$, filtered, and concentrated. The title compound (0.39 g, 0.77 mmol) is obtained as a white foam.

$^1$H NMR ($CDCl_3$, 300 MHz) δ8.41 (s, 1H), 7.85 (m, 2H), 7.50 (m, 4H), 7.26 (m, 3H), 5.94 (bs, 1H), 5.34 (bs, 1H), 4.75 (t, 1H), 4.45 (AB, 2H), 3.92 (s, 3H), 3.51 (m, 1H), 3.40 (m, 1H), 3.19 (m, 2H), 2.78 (m, 2H), 2.32 (m, 1H), 2.09 (m, 1H).

D. 3-[{1-[3-(Aminoiminomethyl)benzyl]-2-oxopyrrolidin-3(S)-3-yl}-(7-methoxynaphthalene-2-sulfonyl)amino]propionamide trifluoroacetate 3-[{1-(3-Cyanobenzyl)-2-oxopyrrolidin-3-(S)-yl}-7-methoxynaphthalene-2-sulfonylamino]propionamide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.28 (bs, 2H), 8.98 (bs, 2H), 8.42 (s, 1H), 8.00 (m, 2H), 7.73 (m, 2H), 7.58 (m, 4H), 7.38 (m, 2H), 6.82 (m, 1H), 4.80 (t, 1H), 4.42 (AB, 4H), 3.88 (s, 3H), 3.22 (m, 4H), 2.52 (m, 2H), 2.12 (m, 1H), 1.81 (m, 1H). FAB MS, [M+H]$^+$=678. Elemental analysis calculated with 2.25 mole of $H_2O$ cal. C=49.59%, H=5.13%, N=10.33%, found C=49.59%, H=4.71%, N=10.01%.

EXAMPLE 68

2-[{1-[3-(Aminoiminomethyl)benzyl]-2-oxopyrrolidin-3-(S)-yl}naphthalene-2-sulfonylamino]-N-phenethylacetamide trifluoroacetate A. Naphthalene-2-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting naphthalene-2-sulfonyl chloride for 6-methoxynaphthalene-2-sulfonyl chloride. The title compound is obtained as a white solid.

$^1$H NMR ($CDCl_3$, 300 MHz) δ8.47 (s, 1H), 7.92 (m, 4H), 7.61 (m, 3H), 7.42 (m, 3H), 5.45 (bs, 1H), 4.42 (AB, 2H), 3.78 (m, 1H), 3.18 (m, 2H), 2.57 (m, 1H), 2.08 (m, 1H).

B. 2-[{1-(3-Cyanobenzyl)-2-oxopyrrolidin-3-(S)-yl}naphthalene-2-sulfonylamino]-N-acetic acid t-butyl ester The title compound is prepared as in EXAMPLE 26, Part A substituting naphthalene-2-sulfonic acid [1-(3-cyanobenzyl)-2-oxopyrrolidin-3-(S)-yl]amide for 6-methoxynaphthalene-2-sulfonic acid [1-(3-cyanobenzyl)-2-oxopyrrolidin-3-(S)-yl]amide. The title compound is obtained as a white solid.

$^1$H NMR ($CDCl_3$, 300 MHz) δ8.52 (s, 1H), 7.92 (m, 3H), 7.81 (d, 1H), 7.61 (m, 3H), 7.42 (m, 3H), 4.61 (t, 1H), 4.42 (AB, 2H), 4.12 (m, 1H), 3.78 (m, 1H), 3.21 (m, 2H), 2.60 (m, 1H), 2.41 (m, 1H), 1.42 (s, 9H).

C. 2-[{1-(3 Cyanobenzyl)-2-oxopyrrolidin-3-(S)-yl}naphthalene-2-sulfonylamino]-N-acetic acid The title compound is prepared as in EXAMPLE 26, Part B using 2-[{1-(3-cyanobenzyl)-2-oxopyrrolidin-3-(S)-yl}naphthalene-2-sulfonylamino]-N-acetic acid tert-butyl ester as the starting material. The title compound is obtained as a white foam.

$^1$H NMR ($CDCl_3$, 300 MHz) δ8.49 (s, 1H), 7.96 (m, 2H), 7.62 (m, 3H), 7.49 (m, 3H), 7.20 (m, 2H), 5.61 (bs, 1H), 4.78 (t, 1H), 4.50 (AB, 2H), 3.90 (AB, 2H), 3.29 (m, 2H), 2.41 (m, 1H), 2.11 (m, 1H).

D. 2-[{1-(3-Cyanobenzyl)-2-oxopyrrolidin-3-(S)-yl}naphthalene-2-sulfonylamino]-N-phenethylacetamide The title compound is prepared as described in EXAMPLE 26, Part C substituting 2-[{1-(3-Cyanobenzyl)-2-oxopyrrolidin-3-(S)-yl}naphthalene-2-sulfonylamino]-N-acetic acid for 2-[{1-(3-cyanobenzyl)-2-oxopyrrolidin-3-(S)-yl}-6-methoxynaphthalene-2-sulfonylamino]-N-acetic acid. The title compound is obtained as a white foam.

$^1$H NMR ($CDCl_3$, 300 MHz) δ8.48 (s, 1H), 7.93 (m, 4H), 7.58 (m, 6H), 7.16 (m, 5H), 5.61 (bs, 1H), 4.58 (m, 1H), 4.40 (m, 2H), 3.80 (AB, 2H), 3.27 (m, 4H), 2.63 (m, 2H), 2.21 (m, 2H).

E. 2-[{1-[3-(Aminoiminomethyl)benzyl]-2-oxopyrrolidin-3-(S)-yl}naphthalene-2-sulfonylamino]-N-phenethylacetamide trifluoroacetate The title compound is prepared as described in EXAMPLE 24, Part C using 2-[{1-(3-cyanobenzyl)-2-oxopyrrolidin-3-(S)-yl}naphthalene-2-sulfonylamino]-N-phenethylacetamide as the starting material. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.31 (bs, 2H), 9.23 (bs, 2H), 8.52 (s, 1H), 8.05 (m, 5H), 7.59 (m, 6H), 7.20 (m, 4H), 7.38 (m, 2H), 4.85 (t, 1H), 4.42 (AB, 4H), 3.70 (m, 3H), 3.18 (m, 4H), 2.59 (m, 2H), 2.05 (m, 2H). FAB MS, [M+H]$^+$= 584. Elemental analysis calculated with 1.75 mole of $H_2O$ cal. C=56.00%, H=5.18%, N=9.60%, found C=56.15%, H=4.84%, N=9.27%.

EXAMPLE 69

2-[{1-[3-(Aminoiminomethyl)benzyl]-2-oxopyrrolidin-3-(S)-yl}biphenyl-4-sulfonylamino]-N-phenethylacetamide trifluoroacetate A. Biphenyl-2-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting biphenyl-4-sulfonyl chloride for 6-methoxynaphthalene-2-sulfonyl chloride. The title compound is obtained as a white foam.

$^1$H NMR ($CDCl_3$, 300 MHz) δ7.96 (m, 2H), 7.76 (m, 3H), 7.61 (m, 4H), 7.49 (m, 5H), 5.35 (bs, 1H), 4.45 (AB, 2H), 3.79 (m, 1H), 3.22 (m, 2H), 2.60 (m, 1H), 2.10 (m, 1H).

B. 2-[{1-(3-Cyanobenzyl)-2-oxopyrrolidin-3-(S)-yl}biphenyl-4-sulfonylamino]-N-acetic acid t-butyl ester The title compound is prepared as in EXAMPLE 26, Part A substituting biphenyl-4-sulfonic acid [1-(3-cyanobenzyl)-2-oxopyrrolidin-3-(S)-yl]amide for 6-methoxynaphthalene-2-sulfonic acid [1-(3-cyanobenzyl)-2-oxopyrrolidin-3-(S)-yl]amide. The title compound is obtained as a white foam.

$^1$H NMR ($CDCl_3$, 300 MHz) δ8.06 (m, 2H), 7.66 (m, 2H), 7.52 (m, 4H), 7.31 (m, 5H), 4.45 (m, 3H), 4.08 (AB, 1H), 3.79 (AB, 1H), 3.18 (m, 2H), 2.52 (m, 1H), 2.31 (m, 1H), 1.41 (s, 9H).

C. 2-[{1-(3-Cyanobenzyl)-2-oxopyrrolidin-3-(S)-yl}biphenyl-4-sulfonylamino]-N-acetic acid The title compound is prepared as in EXAMPLE 26, Part B using 2-[{1-(3-cyanobenzyl)-2-oxopyrrolidin-3-(S)-yl}biphenyl-4-sulfonylamino]-N-acetic acid t-butyl ester as the starting material. The title compound is obtained as a white foam.

$^1$H NMR (CDCl$_3$, 300 MHz) δ7.92 (m, 2H), 7.74 (m, 3H), 7.52 (m, 8H), 7.21 (m, 1H), 4.61 (t, 1H), 4.52 (AB, 2H), 3.91 (AB, 2H), 3.30 (m, 2H), 2.48 (m, 1H), 2.09 (m, 1H).

D. 2-[{1-(3-Cyanobenzyl)-2-oxopyrrolidin-3-(S)-yl}biphenyl-4-sulfonylamino]-N-phenethylacetamide The title compound is prepared as described in EXAMPLE 26, Part C substituting 2-[{1-(3-Cyanobenzyl)-2-oxopyrrolidin-3-(S)-yl}-biphenyl-4-sulfonylamino]-N-acetic acid for 2-[{1-(3-cyanobenzyl)-2-oxopyrrolidin-3-(S)-yl}-6-methoxynaphthalene-2-sulfonylamino]-N-acetic acid. The title compound is obtained as a white foam.

$^1$H NMR (CDCl$_3$, 300 MHz) δ7.94 (m, 3H), 7.71 (m, 3H), 7.50 (m, 7H), 7.20 (m, 5H), 4.61 (m, 1H), 4.44 (m, 3H), 3.78 (AB, 2H), 3.30 (m, 3H), 2.71 (m, 3H), 2.24 (m, 2H).

E. 2-[{1-[3-(Aminoiminomethyl)benzyl]-2-oxopyrrolidin-3-(S)-yl}biphenyl-4-sulfonylamino]-N-phenethylacetamide trifluoroacetate The title compound is prepared as described in EXAMPLE 24, Part C using 2-[{1-(3-cyanobenzyl)-2-oxopyrrolidin-3-(S)-yl}biphenyl-4-sulfonylamino]-N-phenethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (CD$_3$OD, 300 MHz) δ8.51 (m, 1H), 8.00 (m, 2H), 7.82 (m, 2H), 7.68 (m, 5H), 7.45 (m, 3H), 7.19 (m, 5H), 4.68 (m, 2H), 4.39 (m, 1H), 3.82 (AB, 2H), 2.70 (m, 3H), 2.32 (m, 1H), 2.15 (m, 1H). FAB MS, [M+H]$^+$=610.

EXAMPLE 70

2-[{1-[3-(Aminoiminomethyl)benzyl]-2-oxopyrrolidin-3-(S)-yl}-7-methoxynaphthalene-2-sulfonylamino]-N-phenethylacetamide trifluoroacetate A. 2-[{1-(3-Cyanobenzyl)-2-oxopyrrolidin-3-(S)-yl}-7-methoxynaphthalene-2-sulfonylamino]-N-acetic acid t-butyl ester The title compound is prepared as described in EXAMPLE 26, Part A substituting 7-methoxynaphthalene-2-sulfonic acid [1-(3-cyanobenzyl)-2-oxopyrrolidin-3-(S)-yl]amide, prepared as described in EXAMPLE 43, part A, for 6-methoxynaphthalene-2-sulfonic acid [1-(3-cyanobenzyl)-2-oxopyrrolidin-3-(S)-yl]amide. The title compound is obtained as a white foam.

$^1$H NMR (CDCl$_3$, 300 MHz) δ8.41 (s, 2H), 7.81 (m, 3H), 7.50 (m, 1H), 7.44 (m, 3H), 7.22 (m, 2H), 4.61 (t, 1H), 4.42 (AB, 2H), 3.90 (s, 3H), 3.74 (AB, 3H), 3.20 (m, 2H), 2.58 (m, 1H), 2.41 (m, 1H), 1.42 (s, 9H).

B. 2-[{1-(3-Cyanobenzyl)-2-oxopyrrolidin-3-(S)-yl}-7-methoxynaphthalene-2-sulfonylamino]-N-acetic acid The title compound is prepared as described in EXAMPLE 26, Part B using 2-[{1-(3-cyanobenzyl)-2-oxopyrrolidin-3-(S)-yl}-7-methoxynaphthalene-2-sulfonylamino]-N-acetic acid t-butyl ester as the starting material. The title compound is obtained as a white foam.

$^1$H NMR (CDCl$_3$, 300 MHz) δ9.45 (bs, 1H), 8.41 (s, 2H), 7.91 (d, 1H), 7.80 (d, 1H), 7.71 (m, 1H), 7.62 (m, 1H), 7.59 (m, 3H), 7.20 (m, 1H), 4.81 (t, 1H), 4.50 (AB, 2H), 3.90 (s, 3H), 3.89 (AB, 2H), 3.28 (m, 2H), 2.41 (m, 2H), 2.16 (m, 1H).

C. 2-[{1-(3-Cyanobenzyl)-2-oxopyrrolidin-3-(S)-yl}-7-methoxynaphthalene-2-sulfonylamino]-N-phenethylacetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid for 2-[{1-(3-cyanobenzyl)-2-oxopyrrolidin-3-(S)-yl}-6-methoxynaphthalene-2-sulfonylamino]-N-acetic acid. The title compound is obtained as a white foam.

$^1$H NMR (CDCl$_3$, 300 MHz) δ8.35 (m, 1H), 8.14 (m, 2H), 7.82 (m, 4H), 7.53 (m, 5H), 7.21 (m, 4H), 5.71 (bs, 1H), 4.58 (AB, 1H), 4.42 (m, 2H), 3.91 (s, 3H), 3.80 (AB, 2H), 3.31 (m, 4H), 2.69 (m, 2H), 2.29 (m, 1H), 2.14 (m, 1H).

D. 2-[{1-[3-(Aminoiminomethyl)benzyl]-2-oxopyrrolidin-3-(S)-yl}-6-methoxynaphthalene-2-sulfonylamino]-N-phenethylacetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-phenethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.31 (bs, 2H), 9.10 (bs, 2H), 8.43 (s, 1H), 8.22 (m, 1H), 8.02 (m, 2H), 7.74 (m, 2H), 7.58 (m, 2H), 7.21 (m, 5H), 4.80 (t, 1H), 4.44 (AB, 2H), 3.85 (s, 3H), 3.84 (m, 1H), 3.58 (m, 1H), 3.21 (m, 2H), 2.64 (m, 2H), 2.15 (m, 1H), 1.99 (m, 1H). FAB MS, [M+H]$^+$=614. Elemental analysis calculated with 2.50 mole of H$_2$O cal. C=54.40%, H=5.35%, N=9.06%, found C=56.26%, H=4.87%, N=8.69%.

EXAMPLE 71

2-[{1-[3-(Aminoiminomethyl)benzyl]-2-oxopyrrolidin-3-(S)-yl}-7-methoxynaphthalene-2-sulfonylamino]-N-ethylacetamide trifluoroacetate A. 2-[{1-(3-Cyanobenzyl)-2-oxopyrrolidin-3-(S)-yl}-7-methoxynaphthalene-2-sulfonylamino]-N-ethylacetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-6-methoxynaphthalene-2-sulfonylamino]-N-acetic acid and ethyl amine hydrochloride for phenethyl amine. The title compound is obtained as a white foam.

$^1$H NMR (CDCl$_3$, 300 MHz) δ8.39 (s, 1H), 7.91 (m, 1H), 7.81 (m, 2H), 7.55 (m, 3H), 7.29 (m, 4H), 5.71 (bs, 1H), 4.50 (m, 3H), 3.93 (s, 3H), 3.80 (AB, 2H), 3.21 (m, 4H), 2.31 (m, 2H), 0.90 (m, 3H).

B. 2-[{1-[3-(Aminoiminomethyl)benzyl]-2-oxopyrrolidin-3-(S)-yl}-7-methoxynaphthalene-2-sulfonylamino]-N-ethylacetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-ethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.26 (bs, 2H), 9.00 (bs, 2H), 8.42 (s, 1H), 8.11 (m, 1H), 8.01 (m, 2H), 7.78 (m, 1H), 7.68 (m, 1H), 7.52 (m, 3H), 7.33 (m, 1H), 4.80 (t, 1H), 4.44 (AB, 2H), 3.89 (s, 3H), 3.71 (AB, 2H), 3.19 (m, 2H), 3.02

(m, 2H), 2.09 (m, 2H), 0.90 (m, 3H). FAB MS, [M+H]$^+$=538. Elemental analysis calculated with 2.25 mole of H$_2$O cal. C=50.32%, H=5.31%, N=10.12%, found C=50.21%, H=4.59%, N=9.60%.

EXAMPLE 72

2-[{1-[3-(Aminoiminomethyl)benzyl]-2-oxopyrrolidin-3-(S)-yl}-7-methoxynaphthalene-2-sulfonylamino]-N,N-dimethylacetamide trifluoroacetate A. 2-[{1-(3-Cyanobenzyl)-2-oxopyrrolidin-3-(S)-yl}-7-methoxynaphthalene-2-sulfonylamino]-N,N-dimethylacetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and dimethyl amine hydrochloride for phenethyl amine. The title compound is obtained as a white foam.

$^1$H NMR (CDCl$_3$, 300 MHz) δ8.49 (s, 1H), 7.88 (m, 1H), 7.78 (m, 1H), 7.45 (m, 5H), 7.30 (m, 3H), 4.60 (m, 2H), 4.32 (m, 1H), 4.20 (m, 2H), 3.92 (s, 3H), 3.15 (m, 2H), 3.00 (s, 3H), 2.91 (s, 3H), 2.28 (m, 2H).

B. 2-[{1-[3-(Aminoiminomethyl)benzyl]-2-oxopyrrolidin-3-(S)-yl}-7-methoxynaphthalene-2-sulfonylamino]-N,N-dimethylacetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N,N-dimethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.22 (bs, 2H), 9.02 (bs, 2H), 8.43 (s, 1H), 7.92 (m, 2H), 7.78 (d, 1H), 7.65 (m, 1H), 7.51 (m, 4H), 7.32 (m, 1H), 7.33 (m, 1H), 4.71 (t, 1H), 4.38 (m, 3H), 3.91 (m, 1H), 3.90 (s, 3H), 3.12 (m, 2H), 2.98 (s, 3H), 2.78 (s, 3H), 2.18 (m, 2H). FAB MS, [M+H]$^+$=538. Elemental analysis calculated with 2.25 mole of H$_2$O cal. C=50.32%, H=5.2%, N=10.12%, found C=50.38%, H=4.66%, N=9.65%.

EXAMPLE 73

2-[{1-[3-(Aminoiminomethyl)benzyl]-2-oxopyrrolidin-3-(S)-yl}-7-methoxynaphthalene-2-sulfonylamino]-N-benzylacetamide trifluoroacetate A. 2-[{1-(3-Cyanobenzyl)-2-oxopyrrolidin-3-(S)-yl}-7-methoxynaphthalene-2-sulfonylamino]N-benzylacetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and benzyl amine for phenethyl amine. The title compound is obtained as a white foam.

$^1$H NMR (CDCl$_3$, 300 MHz) δ8.42 (m, 2H), 7.79 (m, 4H), 7.60 (m, 4H), 7.21 (m, 5H), 5.53 (bs, 1H), 4.53 (m, 2H), 4.32 (m, 2H), 3.91 (s, 3H), 3.87 (m, 2H), 3.26 (m, 2H), 2.32 (m, 1H), 2.16 (m, 1H).

B. 2-[{1-[3-(Aminoiminomethyl)benzyl]-2-oxopyrrolidin-3-(S)-yl}-7-methoxynaphthalene-2-sulfonylamino]-N-benzylacetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-benzylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.27 (bs, 2H), 9.10 (bs, 2H), 8.63 (m, 1H), 8.43 (s, 1H), 7.96 (m, 2H), 7.73 (m, 2H), 7.58 (m, 4H), 7.32 (m, 1H), 7.24 (m, 4H), 4.83 (t, 1H), 4.52 (AB, 2H), 4.30 (m, 2H), 3.89 (s, 3H), 3.85 (AB, 2H), 3.17 (m, 2H), 2.10 (m, 2H). FAB MS, [M+H]$^+$=600. Elemental analysis calculated with 2.25 mole of H$_2$O cal. C=54.14%, H=5.15%, N=9.29%, found C=54.29%, H=4.73%, N=9.01%.

EXAMPLE 74

2-[{1-[3-(Aminoiminomethyl)benzyl]-2-oxopyrrolidin-3-(S)-yl}-7-methoxynaphthalene-2-sulfonylamino]-N-(2-p-toluylethyl)acetamide trifluoroacetate A. 2-[{1-(3-Cyanobenzyl)-2-oxopyrrolidin-3-(S)-yl}-7-methoxynaphthalene-2-sulfonylamino]N-(2-p-toluylethyl)acetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 2-p-toluylethyl amine for phenethyl amine. The title compound is obtained as a white foam.

$^1$H NMR (CDCl$_3$, 300 MHz) δ8.40 (s, 1H), 7.81 (m, 3H), 7.56 (m, 4H), 7.28 (m, 2H), 7.01 (m, 5H), 4.50 (AB, 1H), 4.41 (m, 3H), 3.91 (s, 3H), 3.76 (AB, 2H), 3.28 (m, 4H), 2.60 (m, 2H), 2.30 (m, 1H), 2.29 (s, 3H), 2.18 (m, 1H).

B. 2-[{1-[3-(Aminoiminomethyl)benzyl]-2-oxopyrrolidin-3-(S)-yl}-7-methoxynaphthalene-2-sulfonylamino]-(2-p-toluylethyl)acetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-2-p-toluylethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.34 (bs, 2H), 9.28 (bs, 2H), 8.42 (m, 1H), 8.21 (m, 1H), 8.05 (m, 1H), 7.95 (m, 1H), 7.77 (m, 1H), 7.68 (m, 1H), 7.57 (m, 1H), 7.31 (m, 1H), 7.05 (m, 4H), 4.79 (t, 1H), 4.50 (AB, 2H), 3.89 (s, 3H), 3.73 (AB, 2H), 3.14 (m, 4H), 2.55 (m, 2H), 2.21 (s, 3H), 2.03 (m, 2H). FAB MS, [M+H]$^+$=628.

EXAMPLE 75

2-[{1-[3-(Aminoiminomethyl)benzyl]-2-oxopyrrolidin-3-(S)-yl}-7-methoxynaphthalene-2-sulfonylamino]-N-(3-phenylpropyl)acetamide trifluoroacetate A. 2-[{1-(3-Cyanobenzyl)-2-oxopyrrolidin-3-(S)-yl}-7-methoxynaphthalene-2-sulfonylamino]N-(3-phenyl-propyl)acetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 3-phenyl-propyl amine for phenethyl amine. The title compound is obtained as a white foam.

$^1$H NMR (CDCl$_3$, 300 MHz) δ8.36 (s, 1H), 7.93 (m, 1H), 7.80 (m, 3H), 7.50 (m, 3H), 7.21 (m, 5H), 7.08 (m, 2H), 4.55 (AB, 2H), 4.41 (m, 2H), 3.92 (s, 3H), 3.82 (AB, 2H), 3.33 (m, 1H), 3.25 (m, 1H), 3.09 (m, 2H), 2.48 (m, 2H), 2.39 (m, 1H), 2.29 (m, 1H), 1.56 (m, 2H).

B. 2-[{1-[3-(Aminoiminomethyl)benzyl]-2-oxopyrrolidin-3-(S)-yl}-7-methoxynaphthalene-2-sulfonylamino]-(3-phenyl-propyl)acetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-3-phenylpropylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.28 (bs, 2H), 9.05 (bs, 2H), 8.42 (s, 1H), 8.18 (m, 1H), 8.01 (d, 1H), 7.92 (d, 1H), 7.75 (d, 1H), 7.68 (m, 1H), 7.58 (m, 4H), 7.33 (dd, 1H), 7.23 (m, 2H), 7.15 (m, 2H), 4.85 (t, 1H), 4.43 (AB, 2H), 3.85 (s, 3H), 3.73 (AB, 2H), 3.13 (m, 2H), 3.00 (m, 2H), 2.53 (m, 2H), 2.10 (m, 2H), 1.60 (m, 2H). FAB MS, [M+H]$^+$=628. Elemental analysis calculated with 2.25 mole of H$_2$O cal. C=55.27%, H=5.48%, N=8.98%, found C=55.27%, H=4.87%, N=8.64%.

EXAMPLE 76

2-[{1-[3-(Aminoiminomethyl)benzyl]-2-oxopyrrolidin-3-(S)-yl}-7-methoxynaphthalene-2-sulfonylamino]-N-(4-methylbenzyl)acetamide trifluoroacetate A. 2-[{1-(3-Cyanobenzyl)-2-oxopyrrolidin-3-(S)-yl}-7-methoxynaphthalene-2-sulfonylamino]-N-(4-methylbenzyl)acetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 4-methylbenzyl amine for phenethyl amine. The title compound is obtained as a white foam.

$^1$H NMR (CDCl$_3$, 300 MHz) δ8.35 (s, 1H), 8.15 (m, 1H), 7.76 (m, 2H), 7.51 (m, 5H), 7.29 (m, 3H), 6.98 (m, 2H), 4.52 (m, 3H), 4.26 (m, 2H), 3.92 (s, 3H), 3.82 (AB, 2H), 3.21 (m, 2H), 2.28 (m, 2H), 2.27 (s, 3H).

B. 2-[{1-[3-(Aminoiminomethyl)benzyl]-2-oxopyrrolidin-3-(S)-yl}-7-methoxynaphthalene-2-sulfonylamino]-(4-methylbenzyl)acetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-4-methylbenzylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.24 (bs, 2H), 9.10 (bs, 2H), 8.58 (m, 1H), 8.42 (s, 1H), 7.95 (m, 2H), 7.72 (m, 2H), 7.51 (m, 3H), 7.33 (dd, 1H), 7.05 (m, 4H), 4.73 (t, 1H), 4.40 (AB, 2H), 4.19 (m, 2H), 3.88 (s, 3H), 3.81 (AB, 2H), 3.14 (m, 2H), 2.24 (s, 3H), 2.06 (m, 2H). FAB MS, [M+H]$^+$=614.

EXAMPLE 77

2-[{1-[3-(Aminoiminomethyl)benzyl]-2-oxopyrrolidin-3-(S)-yl}-7-methoxynaphthalene-2-sulfonylamino]-N-[2-(3-fluorophenyl)ethyl]acetamide trifluoroacetate A. 2-[{1-(3-Cyanobenzyl)-2-oxopyrrolidin-3-(S)-yl}-7-methoxynaphthalene-2-sulfonylamino]N-[2-(3-fluorophenyl)ethyl]acetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 2-(3-fluorophenyl)ethylamine for phenethylamine. The title compound is obtained as a white foam.

$^1$H NMR (CDCl$_3$, 300 MHz) δ8.38 (s, 1H), 7.98 (m, 1H), 7.89 (m, 1H), 7.78 (m, 1H), 7.54 (m, 3H), 7.25 (m, 4H), 6.87 (m, 3H), 4.62 (AB, 1H), 4.38 (m, 3H), 3.94 (s, 3H), 3.75 (AB, 2H), 3.31 (m, 4H), 2.68 (m, 2H), 2.31 (m, 1H), 2.17 (m, 1H).

B. 2-[{1-[3-(Aminoiminomethyl)benzyl]-2-oxopyrrolidin-3-(S)-yl}-7-methoxynaphthalene-2-sulfonylamino]-N-[2-(3-fluorophenyl)ethyl]acetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-2-(3-fluorophenyl)ethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 9.10 (bs, 2H), 8.42 (s, 1H), 8.21 (m, 1H), 7.99 (m, 2H), 7.72 (m, 2H), 7.56 (m, 3H), 7.30 (m, 2H), 7.02 (m, 3H), 4.81 (t, 1H), 4.44 (AB, 2H), 3.99 (m, 1H), 3.95 (s, 3H), 3.60 (AB, 1H), 3.28 (m, 2H), 3.13 (m, 2H), 2.72 (m, 2H), 2.04 (m, 2H). FAB MS, [M+H]$^+$=632. Elemental analysis cal. C=51.69%, H=4.22%, N=8.13%, found C=52.19%, H=4.52%, N=8.36%.

EXAMPLE 78

2-[{1-[3-(Aminoiminomethyl)benzyl]-2-oxopyrrolidin-3-(S)-yl}-7-methoxynaphthalene-2-sulfonylamino]-N-indan-2-ylacetamide trifluoroacetate A. 2-[{1-(3-Cyanobenzyl)-2-oxopyrrolidin-3-(S)-yl}-7-methoxynaphthalene-2-sulfonylamino-N-indan-2-ylacetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 2-aminoindane for phenethylamine. The title compound is obtained as a white foam.

$^1$H NMR (CDCl$_3$, 300 MHz) δ8.35 (s, 1H), 8.14 (m, 1H), 7.75 (m, 3H), 7.54 (m, 4H), 7.21 (m, 5H), 4.66 (AB, 1H), 4.42 (m, 3H), 3.92 (s, 3H), 3.83 (AB, 2H), 3.35 (m, 1H), 3.18 (m, 1H), 2.94 (m, 1H), 2.75 (m, 1H), 2.37 (m, 3H).

B. 2-[{1-[3-(Aminoiminomethyl)benzyl]-2-oxopyrrolidin-3-(S)-yl}-7-methoxynaphthalene-2-sulfonylamino]-N-indan-2-ylacetamide trifluoroacetate The title compound is prepared as described in EXAMPLE 24, Part C using 2-[{1-(3-cyanobenzyl)-2-oxopyrrolidin-3-(S)-yl}-7-methoxynaphthalene-2-sulfonylamino]-N-indan-2-ylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.28 (bs, 2H), 9.190 (bs, 2H), 8.40 (m, 2H), 7.95 (m, 2H), 7.70 (m, 2H), 7.54 (m, 3H), 7.33 (dd, 1H), 7.11 (m, 4H), 5.08 (t, 1H), 4.44 (AB, 2H), 4.36 (m, 1H), 3.91 (m, 2H), 3.87 (s, 3H), 3.19 (m, 2H), 3.08 (m, 2H), 2.62 (m, 2H), 2.10 (m, 2H). FAB MS, [M+H]$^+$=626. Elemental analysis calculated with 1 mole of H$_2$O cal. C=52.35%, H=4.51%, N=8.03%, found C=52.40%, H=4.81%, N=8.19%.

EXAMPLE 79

2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate A. 2-[{1-(3-Cyanobenzyl)-2-oxopyrrolidin-3-(S)-yl}-7-methoxynaphthalene-2-sulfonylamino]-N-(2-pyridin-3-yl-ethyl)acetamide The title compound is prepared as described in EXAMPLE 26, Part C substituting 2-[{1-(3-cyanobenzyl)-2-oxopyrrolidin-3-(S)-yl}-7-methoxynaphthalene-2-sulfonylamino]-N-acetic acid, prepared as in EXAMPLE 70, Part B, for 2-[{1-(3-cyanobenzyl)-2-oxopyrrolidin-3-(S)-yl}-7-methoxynaphthalene-2-sulfonylamino]-N-acetic acid and 3-(2-ethylamino)pyridine for phenethyl amine. The title compound is obtained as a white foam.

$^1$H NMR (CDCl$_3$, 300 MHz) δ8.40 (m, 3H), 7.90 (m, 1H), 7.76 (m, 2H), 7.52 (m, 3H), 7.25 (m, 4H), 4.59 (AB, 1H), 4.41 (m, 2H), 3.95 (s, 3H), 3.75 (AB, 2H), 3.30 (m, 4H), 2.68 (m, 2H), 2.21 (m, 2H).

B. 2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate The title compound is prepared as described in EXAMPLE 24, Part C using 2[{1-(3-cyanobenzyl)-2-oxopyrrolidin-3-(S)-yl}-7-methoxynaphthalene-2-sulfonylamino]-N-2-pyridin-3-ylethylacetamide as the starting material. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.40 (bs, 2H), 9.30 (bs, 2H), 9.13 (bs, 1H), 8.39 (s, 1H), 8.27 (m, 2H), 7.95 (m, 2H), 7.69 (m, 2H), 7.54 (m, 5H), 7.30 (dd, 1H), 4.80 (t, 1H), 4.40 (AB, 2H), 3.87 (s, 4H), 3.73 (AB, 2H), 3.40 (m, 2H), 3.12 (m, 2H), 2.88 (m, 2H), 2.46 (m, 2H), 1.99 (m, 2H). FAB MS, [M+H]$^+$=615. Elemental analysis calculated with 3 mole of H$_2$O cal. C=48.21%, H=4.72%, N=9.37%, found C=48.28%, H=4.23%, N=8.82%.

EXAMPLE 80

4,5-Dichlorothiophene-2-sulfonic acid {1-[3-(aminoiminomethyl)benzyl]-2-oxo-3(S)-pyrrolidin-3-yl}amide trifluoroacetate A. 4,5-Dichlorothiophene-2-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting 4,5-dichlorothiophene-2-sulfonyl chloride for 6-methoxynaphthalene-2-sulfonyl chloride. The crude product is purified by column chromatography eluting with gradient of 10% EtOAc/CH$_2$Cl$_2$ to 20% EtOAc/CH$_2$Cl$_2$ to afford the title compound as a white foam.

$^1$H NMR (CDCl$_3$, 300 MHz) δ7.52 (m, 1H), 7.42 (m, 4H), 5.78 (bs, 1H), 4.50 (AB, 2H), 3.91 (dd, 1H), 3.24 (dd, 2H), 2.61 (m, 1H), 2.10 (m, 1H).

B. 4,5-Dichlorothiophene-2-sulfonic acid {1-[3-(aminoiminomethyl)benzyl]-2-oxo-3(S)-pyrrolidin-3-yl}amide trifluoroacetate 4,5-Dichlorothiophene-2-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.26 (bs, 2H), 9.05 (bs, 2H), 8.78 (s, 1H), 8.72 (s, 1H), 7.62 (m, 1H), 7.51 (m, 3H), 4.38 (AB, 2H), 4.19 (dd, 1H), 3.08 (m, 2H), 2.20 (m, 1H), 1.71 (m, 2H). FAB MS, [M+H]$^+$=447. Elemental analysis calculated with 0.50 mole of H$_2$O cal. C=37.90%, H=3.18%, N=9.82%, found C=37.84%, H=3.20%, N=9.69%.

EXAMPLE 81

4,5-Dichlorothiophene-2-sulfonic acid {1-[3-(aminoiminomethyl)benzyl]-2-oxo-3(S)-pyrrolidin-3-yl}methylamide trifluoroacetate A. 4,5-Dichlorothiophene-2-sulfonic acid [1-(3-cyanobenzyl)-2-oxopyrrolidin-3-(S)-yl]methylamide The title compound is prepared as described in EXAMPLE 25, Part A using 4,5-dichlorothiophene-2-sulfonic acid [1-(3-cyanobenzyl)-2-oxopyrrolidin-3-(S)-yl] amide, prepared as described in EXAMPLE 80, part A, and methyl iodide. The crude product is purified by column chromatography eluting with gradient of 15% EtOAc/CH$_2$Cl$_2$ to 25% EtOAc/CH$_2$Cl$_2$ to afford the title compound as a white foam.

$^1$H NMR (CDCl$_3$, 300 MHz) δ7.58 (m, 2H), 7.40 (m, 3H), 4.82 (t, 1H), 4.41 (AB, 2H), 3.21 (m, 2H), 2.82 (s, 3H), 2.38 (m, 1H), 2.04 (m, 1H).

B. 4,5-Dichlorothiophene-2-sulfonic acid {1-[3-(aminoiminomethyl)benzyl]-2-oxo-3(S)-pyrrolidin-3-yl}methylamide trifluoroacetate 4,5-Dichlorothiophene-2-sulfonic acid [1-(3-cyanobenzyl)-2-oxopyrrolidin-3-(S)-yl]methylamide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.28 (bs, 2H), 9.15 (bs, 2H), 7.90 (s, 1H), 7.62 (m, 1H), 7.51 (m, 3H), 4.85 (t, 1H), 4.41 (AB, 1H), 3.18 (m, 2H), 2.77 (s, 3H), 2.15 (m, 1H), 1.96 (m, 1H). FAB MS, [M+H]$^+$=461. Elemental analysis calculated with 1.25 mole of $H_2O$ cal. C=38.17%, H=3.62%, N=9.37%, found C=38.18%, H=3.19%, N=9.06%.

EXAMPLE 82

4,5-Dichlorothiophene-2-sulfonic acid {1-[3-(aminoiminomethyl)benzyl]-2-oxo-3(S)-pyrrolidin-3-yl}benzylamide trifluoroacetate A. 4,5-Dichlorothiophene-2-sulfonic acid [1-(3-cyanobenzyl)-2-oxopyrrolidin-3-(S)-yl]benzylamide The title compound is prepared as described in EXAMPLE 25, Part A using 4,5-dichlorothiophene-2-sulfonic acid [1-(3-cyanobenzyl)-2-oxopyrrolidin-3-(S)-yl]amide, prepared as described in EXAMPLE 80, part A, and benzyl iodide. The crude product is purified by column chromatography eluting with gradient of 20% EtOAc/hexanes to 40% EtOAc/hexanes to afford the title compound as a white foam.

$^1$H NMR (CDCl$_3$, 300 MHz) δ7.61 (m, 2H), 7.49 (m, 3H), 7.35 (m, 5H), 4.54 (m, 3H), 4.32 (AB, 2H), 3.03 (m, 2H), 2.18 (m, 1H), 1.88 (m, 1H).

B. 4,5-Dichlorothiophene-2-sulfonic acid {1-[3-(aminoiminomethyl)benzyl]-2-oxo-3(S)-pyrrolidin-3-yl}benzylamide trifluoroacetate 4,5-Dichlorothiophene-2-sulfonic acid [1-(3-cyanobenzyl)-2-oxopyrrolidin-3-(S)-yl]benzylamide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.29 (bs, 2H), 9.03 (bs, 2H), 7.94 (s, 1H), 7.63 (m, 4H), 7.30 (m, 5H), 4.81 (t, 1H), 4.40 (AB, 1H), 4.20 (AB, 2H), 3.10 (m, 2H), 2.99 (m, 1H), 2.12 (m, 1H), 1.69 (m, 1H). FAB MS, [M+H]$^+$=539. Elemental analysis calculated with 1.75 mole of $H_2O$ cal. C=43.96%, H=3.91%, N=8.20%, found C=44.11%, H=3.49%, N=7.96%.

EXAMPLE 83

7-Methoxy-2-napthalenesulfonic acid {1-[3-(aminoiminomethyl)benzyl]-2-oxo-3(S)-pyrrolidin-3-yl}-2-cyclopropylphenethylamide trifluoroacetate A. 2-cyclopropylphenethyl bromide To a solution of 1-phenyl-1-cyclopropane methanol (1 g, 6.8 mmol) in 35 mL of THF is added triphenylphosphine (1.7 g, 7.1 mmol) and carbon tetrabromide (2.34 g, 7.1 mmol). The solution is stirred at ambient temperatures for 5 hours. After this time, the solution is diluted with 100 mL of $Et_2O$. The reaction mixture is filtered and the collected solution is concentrated. The crude product is purified by column chromatography eluting with hexane to afford the title compound (1 g, 4.4 mmol) as an oil.

$^1$H NMR (CDCl$_3$, 300 MHz) δ7.36 (m, 3H), 7.25 (m, 1H), 3.62 (s, 2H), 1.12 (m, 2H), 1.00 (m, 2H).

B. 7-Methoxy-2-napthalenesulfonic acid [1-(3-cyanobenzyl)-2-oxopyrrolidin-3-(S)-yl]}-2-cyclopropylphenethylamide The title compound is prepared as described in EXAMPLE 26, Part A using 7-methoxynaphthalene-2-sulfonic acid [1-(3-cyanobenzyl)-2-oxopyrrolidin-3-(S)-yl] amide, prepared as described in EXAMPLE 43, part A, and 2-cyclopropylphenethyl bromide. The crude product is purified by column chromatography eluting with gradient of 20% EtOAc/hexanes to 40% EtOAc/hexanes to afford the title compound as a white foam.

$^1$H NMR (CDCl$_3$, 300 MHz) δ8.29 (s, 1H), 7.72 (m, 3H), 7.52 (m, 3H), 7.46 (m, 1H), 7.28 (m, 1H), 7.17 (m, 1H), 7.05 (m, 1H), 4.55 (AB, 1H), 4.32 (m, 2H), 3.95 (s, 3H), 3.50 (AB, 2H), 3.14 (m, 1H), 3.05 (m, 1H), 2.08 (m, 2H), 0.78 (m, 4H).

C. 7-Methoxy-2-naphthalenesulfonic acid{1-[3-(aminoiminomethyl)benzyl]-2-oxo-3(S)-pyrrolidin-3-yl}(2-cyclopropylphenethyl)amide trifluoroacetate 7-Methoxy-2-naphthalenesulfonic acid [1-(3-cyanobenzl)-2-oxopyrrolidin-3-(S)-yl]}(2-cyclopropylphenenethyl)amide is converted to the title compound as described in EXAMPLE 24, Part C. The crude product is purified by RP-HPLC eluting with a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.28 (bs, 2H), 9.08 (bs, 2H), 8.26 (s, 1H), 7.78 (m, 2H), 7.62 (m, 1H), 7.53 (m, 4H), 7.44 (m, 1H), 7.30 (dd, 1H), 7.17 (m, 2H), 7.05 (m, 3H), 4.58 (t, 1H), 4.33 (AB, 2H), 3.90 (s, 3H), 3.78 (m, 1H), 3.42 (m, 1H), 3.08 (m, 2H), 1.95 (m, 1H), 1.78 (m, 1H), 0.88 (m, 1H), 0.71 (m, 3H). FAB MS, [M+H]$^+$=583. Elemental analysis calculated with 0.5 mole of excess TFA and 0.5 mmol of $H_2O$ cal. C=56.69%, H=4.82%, N=7.35%, found C=56.83%, H=4.94%, N=7.46%.

EXAMPLE 84

3'-Methyl-biphenyl-4-sulfonic acid {1-[3-(aminoiminomethyl)benzyl]-2-oxopyrrolidin-3(S)-yl}amide trifluoroacetate A. 4-(3-Methylphenyl)-bromobenzene The title compound is prepared as described in EXAMPLE 53, Part A substituting 3-bromotoluene for 2-bromoanisole. The crude product is purified by column chromatography eluting with hexanes to afford the title compound as a crystalline solid.

$^1$H NMR (CDCl$_3$, 300 MHz) δ7.55 (m, 2H), 7.40 (m, 2H), 7.31 (m, 3H), 7.18 (m, 1H), 2.39 (s, 3H).

B. 3'-Methylbiphenyl-4-sulfonyl chloride

The title compound is prepared as described in EXAMPLE 53, Part B substituting 4-(2-methylphenyl)-bromobenzene for 4-(2-methoxyphenyl)-bromobenzene. The title compound is obtained as a white solid.

EI MS, [M]$^+$=266.

C. 3'-Methylbiphenyl-4-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B using 2'-methyl-biphenyl-4-sulfonyl chloride in place of 6-methoxynaphthalene-2-sulfonyl chloride. The crude product is purified by column chromatography eluting with a gradient of 15% EtOAc/$CH_2Cl_2$ to 20% EtOAc/$CH_2Cl_2$ to give the title compound as a white foam.

$^1$H NMR (CDCl$_3$, 300 MHz) δ7.98 (m, 2H), 7.70 (m, 2H), 7.58 (m, 1H), 7.40 (m, 1H), 7.21 (m, 1H), 5.32 (bs, 1H) 4.42 (AB, 2H), 3.78 (t, 3H), 3.18 (m, 2H), 2.60 (m, 1H), 2.41 (s, 3H), 2.09 (m, 1H).

D. 3'-Methyl-biphenyl-4-sulfonic acid {1-[3-(aminoiminomethyl)benzyl]-2-oxopyrrolidin-3(S)-yl}amide trifluoroacetate 3'-Methyl-biphenyl-4-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.27 (bs, 2H), 9.09 (bs, 2H), 8.18 (d, 1H), 7.86 (m, 4H), 7.62 (m, 1H), 7.50 (m, 5H), 7.33 (m, 1H), 7.19 (m, 1H), 4.41 (AB, 2H), 4.11 (m, 1H), 3.10 (m, 2H), 2.32 (s, 3H), 2.04 (m, 1H), 1.58 (m, 1H). FAB MS, [M+H]$^+$=463. Elemental analysis calculated with 2 mmol of H$_2$O cal. C=52.94%, H=5.10%, N=9.15%, found C=53.04%, H=4.80%, N=8.93%.

EXAMPLE 85

3-[{1-[3-(Aminoiminomethyl)benzyl]-2-oxopyrrolidin-3(S)-3-yl}-(7-methoxynaphthalene-2-sulfonyl)amino]acetamide trifluoroacetate A. 3-[{1-(3-Cyanobenzyl)-2-oxopyrrolidin-3-(S)-yl}-7-methoxynaphthalene-2-sulfonylamino]-acetamide The title compound is prepared as described in EXAMPLE 67, Part C substituting 3-[{1-(3-cyanobenzyl)-2-oxopyrrolidin-3-(S)-yl}-7-methoxynaphthalene-2-sulfonylamino]-N-acetic acid, for 3-[{1-(3-cyanobenzyl)-2-oxopyrrolidin-3-(S)-yl}-7-methoxynaphthalene-2-sulfonylamino]-N-propionic acid. The title compound (0.39 g, 0.77 mmol) is obtained as a white foam.

$^1$H NMR (CDCl$_3$, 300 MHz) δ8.38 (s, 1H), 7.88 (m, 2H), 7.77 (m, 2H), 7.53 (m, 4H), 7.28 (m, 1H), 7.22 (m, 1H), 5.34 (bs, 1H), 4.61 (m, 2H), 4.46 (AB, 1H), 3.93 (s, 3H), 3.75 (m, 2H), 3.28 (m, 2H), 2.39 (m, 1H), 2.21 (m, 1H).

B. 3-[{1-[3-(Aminoiminomethyl)benzyl]-2-oxopyrrolidin-3(S)-3-yl}-(7-methoxynaphthalene-2-sulfonyl)amino] acetamide trifluoroacetate 3-[{1-(3-Cyanobenzyl)-2-oxopyrrolidin-3-(S)-yl}-7-methoxynaphthalene-2-sulfonylamino]acetamide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.29 (bs, 2H), 8.98 (bs, 2H), 8.42 (s, 1H), 8.03 (d, 1H), 7.97 (d, 1H), 7.78 (d, 1H), 7.65 (m, 1H), 7.55 (m, 5H), 7.31 (dd, 1H), 7.19 (m, 1H), 4.84 (t, 1H), 4.42 (AB, 2H), 3.89 (s, 3H), 3.52 (m, 1H), 3.41 (m, 2H), 3.15 (m, 1H), 2.26 (m, 1H), 2.00 (m, 1H). FAB MS, [M+H]$^+$=510.

EXAMPLE 86

3-[{1-[3-(Aminoiminomethyl)benzyl]-2-oxopyrrolidin-3(S)-3-yl}-(7-methoxynaphthalene-2-sulfonyl)amino]-2-methylacetamide trifluoroacetate A. 3-[{1-(3-Cyanobenzyl)-2-oxopyrrolidin-3-(S)-yl}-7-methoxynaphthalene-2-sulfonylamino]-N-2-methylacetic acid t-butyl ester The title compound is prepared as described in EXAMPLE 26, Part A substituting 7-methoxynaphthalene-2-sulfonic acid [1-(3-cyanobenzyl)-2-oxopyrrolidin-3-(S)-yl]amide, prepared as described in EXAMPLE 43, part A, for 6-methoxynaphthalene-2-sulfonic acid [1-(3-cyanobenzyl)-2-oxopyrrolidin-3-(S)-yl]amide and α-bromo-t-butyl propionic acid for t-butyl-bromoacetate. The crude product is purified by column chromatography eluting with a gradient of 20% EtOAc/hexanes to 30% EtOAc/hexanes. The two compounds obtained, a higher rf spot (minor) and a lower rf spot (major), are enantiomerically pure and are diastereomeric at the carbon of the acetamide. The absolute stereochemistry is not determined, but each diastereomer is treated as below. The compounds are obtained as a white foams.

lower rf spot (major product)

$^1$H NMR (CDCl$_3$, 300 MHz) δ8.48 (s, 1H), 7.95 (dd, 1H), 7.86 (d, 1H), 7.78 (d, 1H), 7.58 (m, 3H), 7.44 (d, 1H), 7.19 (m, 2H), 4.51 (AB, 2H), 4.30 (t, 1H), 4.05 (m, 1H), 3.93 (s, 3H), 3.36 (m, 1H), 3.18 (m, 1H), 2.64 (m, 1H), 1.33 (d, 3H), 1.29 (s, 3H).

higher rf (minor product)

$^1$H NMR (CDCl$_3$, 300 MHz) δ8.60 (s, 1H), 8.21 (d, 1H), 7.83 (d, 1H), 7.79 (d, 1H), 7.51 (m, 2H), 7.24 (m, 2H), 4.82 (AB, 1H), 4.32 (m, 2H), 4.14 (m, 1H), 3.91 (s, 3H), 3.39 (m, 1H), 3.19 (m, 1H), 2.50 (m, 1H), 1.48 (s, 3H), 1.14 (s, 9H).

B. 3-[{1-(3-Cyanobenzyl)-2-oxopyrrolidin-3-(S)-yl}-7-methoxynaphthalene-2-sulfonylamino]-N-2-methylacetic acid The title compound is prepared as described in EXAMPLE 26, Part B, using 3-[{1-(3-cyanobenzyl)-2-oxopyrrolidin-3-(S)-yl}-7-methoxynaphthalene-2-sulfonylamino]-N-2-methylacetic acid t-butyl ester as the starting material.

major product from EXAMPLE 86, Part A
FAB MS, [M+H]$^+$=508.

minor product from EXAMPLE 86, Part A
FAB MS, [M+H]$^+$=508.

C. 3-[{1-(3-Cyanobenzyl)-2-oxopyrrolidin-3-(S)-yl}-6-methoxynaphthalene-2-sulfonylamino]-2-methylacetamide The title compound is prepared as described in EXAMPLE 67, Part C substituting 3-[{1-(3-cyanobenzyl)-2-oxopyrrolidin-3-(S)-yl}-7-methoxynaphthalene-2-sulfonylamino]-N-2-methylacetic acid for 3-[{1-(3-cyanobenzyl)-2-oxopyrrolidin-3-(S)-yl}-7-methoxynaphthalene-2-sulfonylamino]-N-propionic acid. The title compound is obtained as a white foam.

major product from EXAMPLE 86, Part B
FAB MS, [M+H]$^+$=507.

minor product from EXAMPLE 86, Part B
FAB MS, [M+H]$^+$=507.

D. 3-[{1-[3-(Aminoiminomethyl)benzyl]-2-oxopyrrolidin-3(S)-3-yl}-(7-methoxynaphthalene-2-sulfonyl)amino]-2-methylacetamide trifluoroacetate 3-[{1-(3-Cyanobenzyl)-2-oxopyrrolidin-3-(S)-yl}-7-methoxynaphthalene-2-sulfonylamino]-2-methylacetamide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

major product from EXAMPLE 86, Part C $^1$H NMR (DMSO-d$_6$, 300 MHz) δ9.21 (bs, 2H), 8.90 (bs, 2H), 8.48 (s, 1H), 7.96 (m, 3H), 7.55 (m, 5H), 7.30 (m, 1H), 7.18 (m, 1H), 7.00 (m, 1H), 4.58 (m, 2H), 4.47 (m, 1H), 4.07 (m, 1H), 3.91 (s, 3H), 3.26 (m, 2H), 2.48 (m, 2H), 1.18 (d, 3H). FAB MS, [M+H]$^+$=524.

minor product from EXAMPLE 86, Part C

¹H NMR (DMSO-d₆, 300 MHz) δ9.21 (bs, 2H), 8.90 (bs, 2H), 8.48 (s, 1H), 8.35 (m, 1H), 8.05 (m, 1H), 7.90 (m, 3H), 7.72 (m, 4H), 7.36 (dd, 1H), 7.20 (m, 1H), 4.71 (AB, 1H), 4.46 (m, 2H), 4.05 (m, 1H), 3.85 (s, 3H), 3.40 (m, 2H), 2.52 (m, 1H), 2.32 (m, 1H), 1.21 (d, 3H).
FAB MS, [M+H]⁺=524.

EXAMPLE 87

7-Methoxynaphthalene-2-sulfonic acid {1-[3-(aminoiminomethyl)benzyl]-2-oxo-azetidin-3(S)-yl}amide trifluoroacetate A. (2-Oxoazetidin-3-(S)-yl)-carbamic acid tert-butyl ester To a solution of Boc-L-serine (10.3 g, 50 mmol) in 75 mL of H₂O:t-BuOH (2:1) is added methoxyamine hydrochloride (23 g, 75 mmol) and 1-(3-dimethyl-aminopropyl)-3-ethylcarbodiimide hydrochloride (9.6 g, 50 mmol). After 2 hours, the solution is saturated with NaCl. The solution is extracted with EtOAc. The organic layer is dried over MgSO₄, filtered and concentrated. The resulting crude material is dissolved in 50 mL of pyridine and cooled to 0° C. To the solution is added methane sulfonyl chloride (7.44 g, 65 mmol). After 1 hour, the solution is poured into 100 mL of cold 1 N HCl (aq.). The solution is diluted with EtOAc. The layers are separated and the organic layer is washed with 1 N HCl, saturated NaHCO₃ and saturated NaCl. The organic layer is dried over MgSO₄, filtered and concentrated. The resulting crude material is dissolved in 50 mL of acetone and added dropwise to a solution of K₂CO₃ (20.7 g, 150 mmol) in 900 mL of acetone at reflux. After 1 hour, the solution is cooled to ambient temperatures. The solution is filtered through Celite. The collected organic solution is washed with 1 N HCl, saturated NaHCO₃ and saturated NaCl. The organic layer is dried over MgSO₄, filtered and concentrated. The resulting solid is dissolved in 20 mL of THF and added dropwise to an ammonia solution containing sodium (2.6 g, 113 mmol) at −78° C. After the blue color has dissipated, the solution is stirred for an additional 10 minutes. To the reaction mixture is added NH₄Cl (13.4 g, 250 mmol) and the solution is allowed to warm to ambient temperatures. The solution is filtered. The collected solution is concentrated. The resulting residue is recrystallized from EtOAc to give the title compound (2 g, 11 mmol) as a white solid.

¹H NMR (d₆-acetone, 300 MHz) δ6.96 (bs, 1H), 6.63 (bs, 12H), 4.81 (bs, 1H), 3.40 (m, 1H), 3.21 (m, 1H), 1.40 (s, 9H).

B. [1-(3-Cyanobenzyl)-2-oxoazetidin-3-(S)-yl]carbamic acid tert-butyl ester

The title compound is prepared as described in EXAMPLE 23, Part B substituting (2-oxoazetidin-3-(S)-yl)-carbamic acid tert-butyl ester for (2-oxopyrrolidin-3-(S)-yl)-carbamic acid tert-butyl ester. The crude product is purified by column chromatography eluting with a gradient of 20% EtOAc/CH₂Cl₂ to 30% EtOAc/CH₂Cl₂ to give the title compound as a white solid.

¹H NMR (CDCl₃, 300 MHz) δ7.59 (m, 2H), 7.41 (m, 2H), 5.18 (bs, 1H), 4.72 (m, 1H), 4.41 (AB, 2H), 3.41 (m, 1H), 3.23 (m, 1H), 1.41 (s, 9H).

C. 3-(3-(S)-Amino-2-oxoazetidin-1-ylmethyl)benzonitrile hydrochloride

The title compound is prepared as described in EXAMPLE 23, Part C using [1-(3-cyanobenzyl)-2-oxoazetidin-3-(S)-yl]carbamic acid tert-butyl ester as the starting material.

EI MS, [M]⁺=187.

D. 7-Methoxynaphthalene-2-sulfonic acid [1-(3-cyanobenzyl)-2-oxoazetidin-3-(S)-yl]amide The title compound is prepared as in EXAMPLE 24, Part B substituting 3-(3-(S)-Amino-2-oxo-azetidin-1-ylmethyl) benzonitrile hydrochloride for 3-(3-(S)-amino-2-oxopyrrolidin-1-ylmethyl)benzonitrile hydrochloride and using 7-methoxynaphthalene-2-sulfonyl chloride in place of 6-methoxynaphthalene-2-sulfonyl chloride. The crude product is purified by column chromatography eluting with a gradient of 20% EtOAc/CH₂Cl₂ to 30% EtOAc/CH₂Cl₂ to give the title compound as a white solid.

¹H NMR (CDCl₃, 300 MHz) δ8.31 (s, 1H), 7.89 (d, 1H), 7.78 (d, 1H), 7.66 (m, 2H), 7.61 (d, 3H), 7.55 (m, 2H), 7.26 (m, 1H), 5.76 (d, 1H), 5.02 (m, 1H), 3.91 (s, 3H), 3.42 (m, 1H), 3.15 (dd, 1H).

E. 7-Methoxynaphthalene-2-sulfonic acid {1-[3-(aminoiminomethyl)benzyl]-2-oxoazetidin-3(S)-yl}amide trifluoroacetate 7-Methoxynaphthalene-2-sulfonic acid [1-(3-cyanobenzyl)-2-oxoazetidin-3-(S)-yl]amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.22 (bs, 2H), 8.90 (bs, 2H), 8.71 (d, 1H), 8.30 (s, 3H), 8.05 (d, 1H), 7.91 (d, 1H), 7.62 (m, 2H), 7.51 (m, 4H), 7.31 (dd, 1H), 4.66 (m, 1H), 4.31 (AB, 2H), 3.87 (s, 3H), 3.25 (m, 2H). FAB MS, [M+H]⁺=439.

EXAMPLE 88

7-Methoxynaphthalene-2-sulfonic acid {1-[3-(aminoiminomethyl)benzyl]-2-oxo-azetidin-3(S)-yl}benzylamide trifluoroacetate A. 7-Methoxy-2-napthalenesulfonic acid [1-(3-cyanobenzyl)-2-oxoazetidin-3-(S)-yl]benzylamide The title compound is prepared as described in EXAMPLE 25, Part A using 7-methoxynaphthalene-2-sulfonic acid [1-(3-cyanobenzyl)-2-oxoazetidin-3-(S)-yl] amide, prepared as described in Example 65, part D, and benzyl bromide. The crude product is purified by column chromatography eluting with gradient of 30% EtOAc/hexanes to 40% EtOAc/hexanes to afford the title compound as a white foam.

¹H NMR (CDCl₃, 300 MHz) δ8.39 (s, 1H), 7.93 (d, 1H), 7.79 (m, 2H), 7.59 (d, 1H), 7.44 (m, 2H), 7.29 (m, 9H), 5.08 (m, 1H), 4.29 (m, 4H), 3.89 (s, 3H), 3.23 (m, 1H), 2.87 (m, 1H).

B. 7-Methoxy-2-napthalenesulfonic acid {1-[3-(aminoiminomethyl)benzyl]-2-oxoazetidin-3(S)-yl}benzylamide trifluoroacetate 7-Methoxy-2-napthalenesulfonic acid [1-(3-cyanobenzyl)-2-oxoazetidin-3-(S)-yl]benzylamide is converted to the title compound as described in EXAMPLE 24, Part C The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.27 (bs, 2H), 8.99 (bs, 2H), 8.42 (s, 3H), 8.05 (d, 1H), 7.95 (d, 1H), 7.73 (d, 1H), 7.66 (d, 1H), 7.53 (m, 3H), 7.42 (m, 1H), 7.23 (m, 6H), 5.30 (m, 1H), 4.35 (AB, 2H), 4.28 (AB, 2H), 3.29 (m, 1H), 2.83 (m, 1H). FAB MS, [M+H]⁺=529.

EXAMPLE 89

5,6,7,8-Tetrahydronaphthalene-2-sulfonic acid {1-[3-(aminoiminomethyl)-benzyl]-2-oxopyrrolidin-3(S)-yl}amide trifluoroacetate A. 5,6,7,8-Tetrahydronaphthalene-2-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B, substituting 5,6,7,8-tetrahydronaphthalene-2-sulfonyl chloride for 6-methoxynaphthalene-2-sulfonyl chloride. The crude product is purified by column chromatography eluting with 70% EtOAc/hexanes afford the title compound as a white solid.

$^1$H NMR (CDCl$_3$, 300 MHz) δ7.60 (m, 3H), 7.48 (m, 2H), 7.45 (d, 1H), 7.22 (d, 1H), 5.20 (d, 1H), 4.46 (AB, 2H), 3.72 (m, 1H), 3.21 (m, 2H), 2.85 (m, 4H), 2.60 (m, 1H), 1.82 (m, 4H).

B. 5,6,7,8-Tetrahydronaphthalene-2-sulfonic acid {1-[3-(aminoiminomethyl)-benzyl]-2-oxo-3(S)-pyrrolidin-3-yl}amide trifluoroacetate 5,6,7,8-Tetrahydronaphthalene-2-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.31 (bs, 2H), 9.10 (bs, 2H), 8.05 (bs, 1H), 7.69 (m, 1H), 7.55 (m, 5H), 7.25 (m, 1H), 4.46 (AB, 2H), 4.08 (m, 1H), 3.12 (m, 2H), 2.78 (m, 4H), 2.02 (m, 1H), 1.76 (m, 1H), 1.60 (m, 1H). FAB MS, [M+H]$^+$=427. Elemental analysis calculated with 1.375 mmol of H$_2$O cal. C=50.99%, H=5.30%, N=9.91%, found C=50.98%, H=4.93%, N=9.62%.

EXAMPLE 90

7-Methoxy-2-napthalenesulfonic acid {1-[3-(aminoiminomethyl)benzyl]-2-oxo-3(S)-pyrrolidin-3-yl}-(2-methoxybenzyl)amide trifluoroacetate A. 7-Methoxy-2-napthalenesulfonic acid [1-(3-cyanobenzyl)-2-oxopyrrolidin-3-(S)-yl]-(2-methoxybenzyl)amide To a solution of 7-methoxynaphtalene-2-sulfonic acid [1-(3-cyanobenzyl)-2-oxopyrrolidin-3-(S)-yl]amide (0.12 g, 0.26 mmol), prepared as described in EXAMPLE 43, part A, in 20 mL of acetone is added K$_2$CO$_3$ (0.07 g, 0.53 mmol), 2-methoxybenzyl chloride (0.09 g, 0.28 mmol) and tetrabutylammonium iodide (0.02 g, 0.05 mmol). The resulting mixture is stirred for 48 hours, then diluted with CH$_2$Cl$_2$ and washed with saturated NaHCO$_3$, H$_2$O and saturated NaCl. The organic layer is dried over MgSO$_4$, filtered, and concentrated. The crude product is purified by column chromatography eluting with 3% MeOH/CH$_2$Cl$_2$ to afford the title compound as a white foam.

$^1$H NMR (CDCl$_3$, 300 MHz) δ8.50 (s, 1H), 7.98 (dd, 1H), 7.90 (d, 1H), 7.80 (d, 1H), 7.55 (m, 2H), 7.45 (m, 3H), 7.20 (m, 3H), 6.90 (m, 1H), 6.75 (d, 1H), 4.63 (m, 1H), 4.44 (AB, 2H), 4.43 (AB, 2H), 3.90 (s, 3H), 3.71 (s, 3H), 3.09 (m, 2H), 2.30 (m, 1H), 2.10 (m, 1H).

B. 7-Methoxy-2-napthalenesulfonic acid {1-[3-(aminoiminomethyl)benzyl]-2-oxo-3(S)-pyrrolidin-3-yl}-(2-methoxybenzyl)amide trifluoroacetate 7-Methoxy-2-napthalenesulfonic acid [1-(3-cyanobenzyl)-2-oxopyrrolidin-3-(S)-yl]-(2-methoxybenzyl)amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 9.02 (bs, 2H), 8.42 (s, 1H), 8.00 (d, 1H), 7.95 (d, 1H), 7.83 (dd, 1H), 7.65 (d, 1H), 7.45 (m, 5H), 7.34 (dd, 1H), 7.20 (m, 1H), 6.90 (m, 2H), 4.82 (m, 1H), 4.30 (AB, 2H), 3.90 (s, 3H), 3.70 (s, 3H), 3.15 (m, 1H), 3.05 (m, 1H), 2.26 (m, 1H), 1.70 (m, 1H). FAB MS, [M+H]$^+$=573. Elemental analysis calculated with 1.5 mmol of H$_2$O cal. C=54.91%, H=4.54%, N=7.53%, found C=54.97%, H=4.63%, N=7.49%.

EXAMPLE 91

7-Methoxy-2-napthalenesulfonic acid {1-[3-(aminoiminomethyl)benzyl]-2-oxo-3(S)-pyrrolidin-3-yl}-(3-methoxybenzyl)amide trifluoroacetate A. 7-Methoxy-2-napthalenesulfonic acid [1-(3-cyanobenzyl)-2-oxopyrrolidin-3-(S)-yl]-(3-methoxybenzyl)amide The title compound is prepared as described in EXAMPLE 68, Part A using 7-methoxynaphthalene-2-sulfonic acid [1-(3-cyanobenzyl)-2-oxopyrrolidin-3-(S)-yl]amide, prepared as described in EXAMPLE 43, part A, and 3-methoxybenzyl bromide. The crude product is purified by column chromatography eluting with 50% EtOAc/hexanes to afford the title compound as a white foam.

$^1$H NMR (CDCl$_3$, 300 MHz) δ8.43 (s, 1H), 7.91 (m, 2H), 7.75 (d, 1H), 7.40 (m, 4H), 7.20 (m, 2H), 7.13 (m, 1H), 6.92 (bs, 1H), 6.82 (d, 1H), 6.70 (d, 1H), 4.60 (m, 1H), 4.45 (AB, 2H), 4.40 (AB, 2H), 3.90 (s, 3H), 3.65 (s, 3H), 3.00 (m, 2H), 2.28 (m, 1H), 2.00 (m, 1H).

B. 7-Methoxy-2-napthalenesulfonic acid {1-[3-(aminoiminomethyl)benzyl]-2-oxo-3(S)-pyrrolidin-3-yl}-(3-methoxybenzyl)amide trifluoroacetate 7-Methoxy-2-napthalenesulfonic acid [1-(3-cyanobenzyl)-2-oxopyrrolidin-3-(S)-yl]-(3-methoxybenzyl)amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 9.10 (bs, 2H), 8.45 (s, 1H), 8.05 (d, 1H), 7.95 (d, 1H), 7.85 (d, 1H), 7.67 (d, 1H), 7.52 (m, 4H), 7.40 (dd, 1H), 7.19 (m, 1H), 6.90 (m, 2H), 6.78 (dd, 1H), 4.75 (m, 1H), 4.35 (m, 4H), 3.90 (s, 3H), 3.62 (s, 3H), 3.12 (m, 1H), 3.00 (m, 1H), 2.19 (m, 1H), 1.78 (m, 1H). FAB MS, [M+H]$^+$=573. Elemental analysis calculated with 0.675 mmol of H$_2$O cal. C=56.72%, H=4.95%, N=8.02%, found C=56.72%, H=5.08%, N=7.95%.

EXAMPLE 92

7-Methoxy-2-napthalenesulfonic acid {1-[3-(aminoiminomethyl)benzyl]-2-oxo-3(S)-pyrrolidin-3-yl}-(4-methoxybenzyl)amide trifluoroacetate A. 7-Methoxy-2-napthalenesulfonic acid [1-(3-cyanobenzyl)-2-oxopyrrolidin-3-(S)-yl]-(4-methoxybenzyl)amide The title compound is prepared as described in EXAMPLE 90, Part A using 7-methoxynaphthalene-2-sulfonic acid [1-(3-cyanobenzyl)-2-oxopyrrolidin-3-(S)-yl]amide, prepared as described in EXAMPLE 43, part A, and 4-methoxybenzyl chloride. The crude product is purified by column chromatography eluting with 50% EtOAc/hexanes to afford the title compound as a white foam.

¹H NMR (CDCl₃, 300 MHz) δ8.38 (s, 1H), 7.90 (m, 2H), 7.80 (d, 1H), 7.50 (m, 1H), 7.40 (m, 2H), 7.27 (m, 1H), 6.70 (d, 2H), 6.60 (d, 2H), 4.50 (m, 1H), 4.45 (AB, 2H), 4.40 (AB, 2H), 3.90 (s, 3H), 3.65 (s, 3H), 3.00 (m, 2H), 2.30 (m, 1H), 2.00 (m, 1H).

B. 7-Methoxy-2-napthalenesulfonic acid {1-[3-(aminoiminomethyl)benzyl]-2-oxo-3(S)-pyrrolidin-3-yl}-(4-methoxybenzyl)amide trifluoroacetate 7-Methoxy-2-napthalenesulfonic acid [1-(3-cyanobenzyl)-2-oxopyrrolidin-3-(S)-yl]-(4-methoxybenzyl) amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 2H), 9.05 (bs, 2H), 8.33 (s, 1H), 8.02 (d, 1H), 7.95 (d, 1H), 7.80 (dd, 1H), 7.70 (d, 1H), 7.55 (m, 4H), 7.35 (dd, 1H), 7.20 (d, 2H), 6.80 (d, 2H), 4.70 (m, 1H), 4.35 (AB, 2H), 3.85 (s, 3H), 3.70 (s, 3H), 3.10 (m, 1H), 2.95 (m, 1H), 2.10 (m, 1H), 1.70 (m, 1H). FAB MS, [M+H]⁺=573. Elemental analysis calculated with 0.5 mmol of excess TFA cal. C=54.91%, H=4.54%, N=7.53%, found C=55.04%, H=4.39%, N=7.64%.

EXAMPLE 93

7-Methoxy-2-napthalenesulfonic acid {1-[3-(aminoiminomethyl)benzyl]-2-oxo-3(S)-pyrrolidin-3-yl}(pyridin-2-ylmethyl)amide trifluoroacetate A. 7-Methoxy-2-napthalenesulfonic acid [1-(3-cyanobenzyl)-2-oxopyrrolidin-3-(S)-yl](pyridin-2-ylmethyl)amide The title compound is prepared as described in EXAMPLE 90, Part A using 7-methoxynaphthalene-2-sulfonic acid [1-(3-cyanobenzyl)-2-oxopyrrolidin-3-(S)-yl]amide, prepared as described in EXAMPLE 43, part A, and pyridin-2-yl-methyl chloride. The crude product is purified by column chromatography eluting with 2% MeOH/CH₂Cl₂ to afford the title compound as a white foam.

¹H NMR (CDCl₃, 300 MHz) δ8.45 (s, 1H), 7.91 (s, 1H), 7.80 (d, 1H), 7.50 (m, 4H), 7.20 (m, 7H), 4.70 (m, 1H), 4.50 (m, 4H), 3.91 (s, 3H), 3.10 (m, 2H), 2.25 (m, 1H), 2.00 (m, 1H).

B. 7-Methoxy-2-napthalenesulfonic acid {1-[3-(aminoiminomethyl)benzyl]-2-oxo-3(S)-pyrrolidin-3-yl}(pyridin-2-ylmethyl)amide trifluoroacetate 7-Methoxy-2-napthalenesulfonic acid [1-(3-cyanobenzyl)-2-oxopyrrolidin-3-(S)-yl](pyridin-2-ylmethyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (CDCl₃, 300 MHz) δ8.50 (s, 1H), 8.15 (d, 1H), 7.90 (s, 2H), 7.80 (m, 2H), 7.70 (m, 2H), 7.45 (m, 2H), 7.25 (m, 3H), 7.15 (m, 1H), 5.10 (m, 1H), 4.55 (AB, 2H), 4.30 (AB, 2H), 3.91 (s, 3H), 3.10 (m, 2H), 2.95 (m, 1H), 2.25 (m, 1H), 1.95 (m, 1H, 1.90 (bs, 4H). FAB MS, [M+H]⁺=544. Elemental analysis calculated with 0.35 mmol of H₂O cal. C=56.08%, H=4.66%, N=10.55%, found C=56.07%, H=5.23%, N=10.50%.

EXAMPLE 94

7-Methoxy-2-napthalenesulfonic acid {1-[3-(aminoiminomethyl)benzyl]-2-oxo-3(S)-pyrrolidin-3-yl}(pyridin-3-ylmethyl)amide trifluoroacetate A. 7-Methoxy-2-napthalenesulfonic acid [1-(3-cyanobenzyl)-2-oxopyrrolidin-3-(S)-yl](pyridin-3-yl-methyl)amide The title compound is prepared as described in EXAMPLE 90, Part A using 7-methoxynaphthalene-2-sulfonic acid [1-(3-cyanobenzyl)-2-oxopyrrolidin-3-(S)-yl]amide, prepared as described in EXAMPLE 43, part A, and pyridin-3-yl-methyl bromide. The crude product is purified by column chromatography eluting with 5% MeOH/CH₂Cl₂ to afford the title compound as a white foam.

¹H NMR (CDCl₃, 300 MHz) δ8.50 (m, 1H), 8.40 (m, 1H), 7.90 (m, 3H), 7.82 (d, 1H), 7.60 (m, 1H), 7.48 (dd, 1H), 7.45 (s, 1H), 7.23 (m, 5H), 4.60 (m, 1H), 4.50 (AB, 2H), 4.45 (AB, 2H), 3.91 (s, 3H), 3.10 (m, 2H), 2.30 (m, 1H), 1.97 (m, 1H).

B. 7-Methoxy-2-napthalenesulfonic acid {1-[3-(aminoiminomethyl)benzyl]-2-oxo-3(S)-pyrrolidin-3-yl}(pyridin-3-ylmethyl)amide trifluoroacetate 7-Methoxy-2-napthalenesulfonic acid [1-(3-cyanobenzyl)-2-oxopyrrolidin-3-(S)-yl](pyridin-3-ylmethyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 2H), 9.00 (bs, 2H), 8.75 (s, 1H), 8.60 (m, 1H), 8.48 (s, 1H), 8.15 (d, 1H), 8.05 (d, 1H), 8.00 (d, 1H), 7.82 (dd, 1H), 7.65 (d, 1H), 7.55 (m, 5H), 7.38 (dd, 1H), 7.20 (m, 1H), 4.95 (m, 1H), 4.50 (s, 2H), 4.40 (AB, 2H), 3.90 (s, 3H), 3.10 (m, 2H), 2.10 (m, 1H), 1.75 (m, 1H). FAB MS, [M+H]⁺=544.

EXAMPLE 95

7-Methoxy-2-napthalenesulfonic acid {1-[3-(aminoiminomethyl)benzyl]-2-oxo-3(S)-pyrrolidin-3-yl}-(pyridin-4-yl-methyl)amide trifluoroacetate A. 7-Methoxy-2-napthalenesulfonic acid [1-(3-cyanobenzyl)-2-oxopyrrolidin-3-(S)-yl](pyridin-4-ylmethyl)amide The title compound is prepared as described in EXAMPLE 90, Part A using 7-methoxynaphthalene-2-sulfonic acid [1-(3-cyanobenzyl)-2-oxopyrrolidin-3-(S)-yl]amide, prepared as described in EXAMPLE 43, part A, and pyridin-4-yl-methyl chloride. The crude product is purified by column chromatography eluting with 2% MeOH/CH₂Cl₂ to afford the title compound as a white foam.

¹H NMR (CDCl₃, 300 MHz) δ8.52 (d, 2H), 8.40 (s, 1H), 7.90 (m, 2H), 7.80 (d, 1H), 7.60 (m, 1H), 7.48 (d, 1H), 7.40 (d, 1H), 7.30 (m, 5H), 4.60 (m, 1H), 4.45 (m, 4H), 3.95 (s, 3H), 3.10 (m, 2H), 2.30 (m, 1H), 1.97 (m, 1H).

B. 7-Methoxy-2-napthalenesulfonic acid {1-[3-(aminoiminomethyl)benzyl]-2-oxo-3(S)-pyrrolidin-4-yl}(pyridin-4-ylmethyl)amide trifluoroacetate 7-Methoxy-2-napthalenesulfonic acid [1-(3-cyanobenzyl)-2-oxopyrrolidin-3-(S)-yl](pyridin-4-yl-methyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.25 (bs, 2H), 9.10 (bs, 2H), 8.70 (d, 1H), 8.45 (s, 1H), 8.08 (d, 1H), 8.00 (d, 1H), 7.95 (d, 2H), 7.80 (dd, 1H), 7.65 (m, 1H), 7.53 (m, 4H), 7.40 (dd, 1H), 4.97 (m, 1H), 4.60 (AB, 2H), 4.38 (AB, 2H), 3.98 (s, 3H), 3.10 (m, 2H), 2.10 (m, 1H), 1.70 (m, 1H). FAB MS, [M+H]⁺=544. Elemental analysis calculated with 1.275 mmol of H₂O cal. C=46.26%, H=3.83%, N=7.71%, found C=46.27%, H=3.93%, N=7.61%.

EXAMPLE 96

7-Methoxy-2-napthalenesulfonic acid {1-[3-(aminoiminomethyl)benzyl]-2-oxo-3(S)-pyrrolidin-3-yl}-(1-benzyl-1H-imidazol-2-ylmethyl)amide trifluoroacetate A. 7-Methoxy-2-napthalenesulfonic acid [1-(3-cyanobenzyl)-2-oxopyrrolidin-3-(S)-yl]-(1-benzyl-1H-imidazol-2-ylmethyl)amide The title compound is prepared as described in EXAMPLE 90, Part A using 7-methoxynaphthalene-2-sulfonic acid [1-(3-cyanobenzyl)-2-oxopyrrolidin-3-(S)-yl] amide, prepared as described in EXAMPLE 43, part A, and 1-benzyl-1H-imidazol-2-ylmethyl chloride. The crude product is purified by column chromatography eluting with 2% MeOH/CH₂Cl₂ to afford the title compound as a white foam.

¹H NMR (CDCl₃, 300 MHz) δ7.88 (s, 1H), 7.77 (d, 1H), 7.65 (dd, 2H), 7.50 (s, 1H), 7.40 (m, 2H), 7.28 (m, 1H), 7.19 (m, 4H), 7.10 (d, 1H), 7.00 (dd, 2H), 6.82 (s, 1H), 5.20 (AB, 2H), 4.70 (m, 1H), 4.55 (AB, 2H), 4.20 (AB, 2H), 3.75 (s, 3H), 2.95 (m, 1H), 1.90 (m, 1H).

B. 7-Methoxy-2-napthalenesulfonic acid {1-[3-(aminoiminomethyl)benzyl]-2-oxo-3(S)-pyrrolidin-4-yl}-(1-benzyl-1H-imidazol-2-ylmethyl)amide trifluoroacetate 7-Methoxy-2-napthalenesulfonic acid [1-(3-cyanobenzyl)-2-oxopyrrolidin-3-(S)-yl]-(1-benzyl-1H-imidazol-2-ylmethyl)amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 2H), 9.10 (bs, 2H), 8.30 (s, 1H), 8.05 (d, 1H), 8.00 (d, 1H), 7.65 (m, 14H), 5.50 (s, 2H), 5.10 (m, 1H), 4.75 (AB, 2H), 4.45 (AB, 2H), 3.95 (s, 3H), 3.10 (m, 2H), 2.05 (m, 1H), 1.80 (m, 1H). FAB MS, [M+H]⁺=623. Elemental analysis calculated with 2.5 mmol of H₂O cal. C=50.11%, H=4.26%, N=8.99%, found C=50.34%, H=4.08%, N=8.60%.

EXAMPLE 97

(1-Methyl-1H-imidazol-2-yl)benzene-4-sulfonic acid {1-[3-(aminoiminomethyl)benzyl]-2-oxopyrrolidin-3(S)-yl}amide trifluoroacetate A. 4-(1-Methyl-1H-imidazol-2-yl)bromobenzene The title compound is prepared as described in EXAMPLE 53, Part A substituting 1-methyl-1H-imidazole for 2-bromoanisole. The crude product is purified by column chromatography eluting with 5% MeOH/CH₂Cl₂ to afford the title compound as a white foam.

EI MS, [M]⁺=237.

B. (1-Methyl-1H-imidazol-2-yl)benzene-4-sulfonyl chloride

The title compound is prepared as described in EXAMPLE 53, Part B using 4-(1-methyl-1H-imidazol-2-yl)bromobenzene as the starting material.

EI MS, [M]⁺=256.

C. (1-Methyl-1H-imidazol-2-yl)benzene-4-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B using (1-methyl-1H-imidazol-2-yl)benzene-4-sulfonyl chloride in place of 6-methoxynaphthalene-2-sulfonyl chloride. The crude product is purified by column chromatography eluting with 5% MeOH/CH₂Cl₂ to give the title compound as a white foam.

¹H NMR (CDCl₃, 300 MHz) δ7.60 (m, 3H), 7.45 (m, 5H), 7.15 (s, 1H), 6.98 (s, 1H), 4.48 (AB, 2H), 3.95 (s, 3H), 3.75 (m, 1H), 3.20 (m, 2H), 2.60 (m, 1H), 2.00 (m, 1H).

D. (1-Methyl-1H-imidazol-2-yl)benzene-4-sulfonic acid {1-[3-(aminoiminomethyl)benzyl]-2-oxopyrrolidin-3(S)-yl}amide trifluoroacetate (1-Methyl-1H-imidazol-2-yl)benzene-4-sulfonic acid [1-(3-cyanobenzyl)-2-oxopyrrolidin-3-(S)-yl]amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.30 (bs, 2H), 8.89 (bs, 2H), 8.70 (d, 1H), 7.90 (m, 1H), 7.69 (m, 4H), 7.55 (m, 5H), 4.45 (s, 2H), 4.10 (m, 1H), 3.90 (s, 3H), 3.20 (m, 2H), 2.20 (m, 1H), 1.80 (m, 1H). FAB MS, [M+H]⁺=453. Elemental analysis calculated with 0.8 mmol of H₂O cal. C=44.93%, H=4.00%, N=12.09%, found C=45.02%, H=4.04%, N=11.79%.

EXAMPLE 98

7-Methoxy-2-napthalenesulfonic acid {1-[3-(aminoiminomethyl)benzyl]-2-oxo-3(S)-pyrrolidin-3-yl}-(3-hydroxybenzyl)amide trifluoroacetate A. 3-[(1,1-Dimethylethyl)dimethylsilyl]oxytoluene To a solution of 3-hydroxytoluene (2 g, 8.5 mmol) in 20 mL of CH₂Cl₂ is added DBU (3.32 mL, 22.2 mmol) and 1,1-dimethylethyl)dimethylsilyl chloride (3.07 g, 20.34 mmol). After 1.5 hours, the solution is diluted with EtOAc. The organic solution is washed with 1 N HCl, 10% Na₂CO₃ and saturated NaCl. The organic layer is dried over MgSO₄, filtered, and concentrated. The crude product is purified by column chromatography eluting with 5% EtOAc/hexanes to afford the title compound (4.1 g, 18.5 mmol) as an oil.

¹H NMR (CDCl₃, 300 MHz) δ7.10 (dd, 1H), 6.70 (d, 1H), 6.65 (s, 1H), 6.63 (d, 1H), 2.30 (s, 3H), 1.00 (s, 9H), 0.20 (s, 6H).

B. α-Bromo-m-3-[(1,1-dimethylethyl)dimethylsilyl]oxytoluene

To a solution of 3-[(1,1-dimethylethyl)dimethylsilyl]oxytoluene (1 g, 4.5 mmol) in 40 mL of CCl₄ is added N-bromo succinimide (0.92 g, 5.17 mmol) and benzoyl peroxide (0.16 g, 0.45 mmol). The solution is heated to reflux. After 16 hours, the solution is diluted with EtOAc. The organic solution is washed with 1 N HCl, 10% NaCO₃ and saturated NaCl. The organic layer is dried over MgSO₄, filtered, and concentrated. The title compound (1.33 g, 4.4 mmol) is obtained as an oil.

EI MS, [M]⁺=301.

C. 7-Methoxy-2-napthalenesulfonic acid [1-(3-cyanobenzyl)-2-oxopyrrolidin-3-(S)-yl]-(3-hydroxybenzyl)amide The title compound is prepared as described in EXAMPLE 90, Part A using 7-methoxynaphthalene-2-sulfonic acid [1-(3-cyanobenzyl)-2-oxopyrrolidin-3-(S)-yl] amide, prepared as described in EXAMPLE 43, part A, and α-bromo-m-3-[(1,1-dimethylethyl)dimethylsilyl]oxytoluene. The crude product is purified by column chromatography eluting with 45% EtOAc/hexanes to afford the title compound as a white foam.

$^1$H NMR (CDCl$_3$, 300 MHz) δ8.45 (s, 1H), 7.90 (s, 1H), 7.80 (m, 1H), 7.58 (m, 3H), 7.45 (m, 3H), 7.15 (m, 1H), 6.90 (m, 1H), 6.72 (dd, 1H), 5.60 (bs, 1H), 4.65 (m, 1H), 4.62 (AB, 2H), 4.30 (s, 2H), 3.90 (s, 3H), 3.05 (m, 2H), 2.30 (m, 1H), 2.00 (m, 1H).

D. 7-Methoxy-2-napthalenesulfonic acid {1-[3-(aminoiminomethyl)benzyl]-2-oxo-3(S)-pyrrolidin-3-yl}-(3-hydroxybenzyl)amide trifluoroacetate 7-Methoxy-2-napthalenesulfonic acid [1-(3-cyanobenzyl)-2-oxopyrrolidin-3-(S)-yl]-(3-hydroxybenzyl)amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

1H NMR (DMSO-d$_6$, 300 MHz) δ9.30 (bs, 2H), 9.00 (bs, 2H), 8.45 (s, 1H), 8.00 (d, 1H), 7.95 (d, 1H), 7.85 (dd, 1H), 7.65 (d, 1H), 7.50 (m, 4H), 7.35 (dd, 1H), 7.02 (m, 1H), 6.80 (bs, 1H), 6.65 (m, 2H), 4.75 (m, 1H), 4.37 (AB, 2H), 4.30 (AB, 2H), 3.90 (s, 3H), 3.15 (m, 1H), 2.95 (m, 1H), 2.10 (m, 1H), 1.70 (m, 1H). FAB MS, [M+H]$^+$=559. Elemental analysis calculated with 0.5 mmol of excess TFA cal. C=54.32%, H=4.35%, N=7.68%, found C=54.53%, H=4.56%, N=7.82%.

EXAMPLE 99

7-Methoxy-2-napthalenesulfonic acid {1-[3-(aminoiminomethyl)benzyl]-2-oxo-3(S)-pyrrolidin-3-yl}-(2-hydroxybenzyl)amide trifluoroacetate A. 2-[(1,1-Dimethylethyl)dimethylsilyl]oxytoluene The title compound is prepared as in EXAMPLE 76, Part A substituting 2-hydroxytoluene for 3-hydroxytoluene. The crude product is purified by column chromatography eluting with 10% EtOAc/hexanes to afford the title compound as an oil.

$^1$H NMR (CDCl$_3$, 300 MHz) δ7.14 (d, 1H), 7.08 (m, 1H), 6.85 (m, 1H), 6.75 (d, 1H), 2.20 (s, 3H), 1.00 (s, 9H), 0.20 (s, 6H).

B. α-Bromo-m-2-[(1,1-dimethylethyl)dimethylsilyl]oxytoluene

The title compound is prepared as in EXAMPLE 98, Part B substituting 2-[(1,1-dimethylethyl)dimethylsilyl]oxytoluene for 3-[(1,1-dimethylethyl)dimethylsilyl]oxytoluene. The crude product is purified by column chromatography eluting with 5% EtOAc/hexanes to afford the title compound as an oil.

$^1$H NMR (CDCl$_3$, 300 MHz) δ7.30 (dd, 1H), 7.19 (m, 1H), 6.90 (m, 1H), 6.80 (d, 1H), 4.50 (s, 2H), 1.05 (s, 9H), 0.30 (s, 6H).

C. 7-Methoxy-2-napthalenesulfonic acid [1-(3-cyanobenzyl)-2-oxopyrrolidin-3-(S)-yl]-(2-[(1,1-dimethylethyl)dimethylsilyl]oxybenzyl)amide To a solution of 7-methoxynaphthalene-2-sulfonic acid [1-(3-cyanobenzyl)-2-oxopyrrolidin-3-(S)-yl]amide (0.20 g, 0.46 mmol), prepared as described in EXAMPLE 43, part A, in 20 mL of acetone is added α-bromo-m-2-[(1,1-dimethylethyl)dimethylsilyl]oxytoluene (0.145 g, 0.48 mmol) and K$_2$CO$_3$ (0.13 g, 0.92 mmol). The crude product is purified by column chromatography eluting with a gradient of 40% EtOAc/hexanes to 80% EtOAc/hexanes afford the title compound (0.20 g, 0.37 mmol) as a white solid.

$^1$H NMR (CDCl$_3$, 300 MHz) δ7.80 (m, 3H), 7.45 (m, 4H), 7.20 (m, 1H), 7.10 (m, 1H), 6.95 (m, 1H), 6.70 (m, 1H), 6.50 (d, 1H), 4.90 (m, 1H), 4.40 (m, 4H), 3.90 (s, 3H), 3.10 (m, 2H), 2.30 (m, 1H), 2.00 (m, 1H).

D. 7-Methoxy-2-napthalenesulfonic acid {1-[3-(aminoiminomethyl)benzyl]-2-oxo-3(S)-pyrrolidin-3-yl}-(2-hydroxybenzyl)amide trifluoroacetate 7-Methoxy-2-napthalenesulfonic acid [1-(3-cyanobenzyl)-2-oxopyrrolidin-3-(S)-yl]-(2-[(1,1-dimethylethyl)dimethylsilyl]oxybenzyl)amide is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 8.95 (bs, 2H), 8.45 (s, 1H), 8.05 (d, 1H), 7.95 (d, 1H), 7.85 (dd, 1H), 7.68 (dd, 1H), 7.55 (m, 4H), 7.38 (m, 2H), 7.05 (m, 2H), 6.75 (m, 2H), 4.80 (m, 1H), 4.35 (bs, 2H), 4.30 (AB, 2H), 3.90 (s, 3H), 3.15 (m, 1H), 3.00 (m, 1H), 2.20 (m, 1H), 1.95 (m, 1H). FAB MS, [M+H]$^+$=559. Elemental analysis calculated with 0.5 mmol of excess TFA cal. C=53.66%, H=4.43%, N=7.53%, found C=53.94%, H=4.43%, N=7.59%.

EXAMPLE 100

7-Methoxy-2-napthalenesulfonic acid {1-[3-(aminoiminomethyl)benzyl]-2-oxo-3(S)-pyrrolidin-3-yl}(pyrazol-3-ylmethyl)amide trifluoroacetate A. N-t-Butyloxycarbonylpyrazol-3-ylmethyl bromide 3-Methylpyrazole (2.04 g, 2.49 mmol) is dissolved in 25 mL acetonitrile under nitrogen, cooled in a ice bath, and treated with BOC anhydride (6.5 g, 2.98 mmol) followed by DMAP (0.303 g, 2.48 mmol). The reaction is warmed to room temperature over about two hours and diluted with ethyl acetate. The organic solution is washed with 1 N HCl, saturated NaHCO$_3$ and saturated NaCl solution dried over Na$_2$SO$_4$, filtered, and concentrated to obtain N-t-butyloxycarbonyl-3-methylpyrazole (2.5 g, 13.7 mmol), EI MS, [M]$^+$=182. A portion of this material (1 g, 5.8 mmol) is dissolved in CCl$_4$ (20 mL), treated with N-bromosuccinimide (1.47 g, 8.26 mmol) and benzoyl peroxide (0.2 g, 0.83 mmol) and heated to reflux. After 4 hours, the solution is diluted with EtOAc washed with saturated NaHCO$_3$, dried over Na$_2$SO$_4$ and concentrated. The residue is chromatographed with 10% EtOAc/hexane to yield the title compound (0.74 g, 2.85 mmol), EI MS, [M]$^+$=259/261.

B. 7-Methoxy-2-napthalenesulfonic acid {1-[3-cyanobenzyl]-2-oxo-3(S)-pyrrolidin-3-yl}-(N-t-butyloxycarbonylpyrazol-3-ylmethyl)amide A solution of 6-methoxynaphthalene-2-sulfonic acid [1-(3-cyanobenzyl)-2-oxopyrrolidin-3-(S)-yl]amide (0.30 g, 0.69 mmol) in refluxing acetone (25 mL) is treated with N-t-butyloxycarbonyl-pyrazol-3-ylmethyl bromide (0.28 g, 1.07 mmol) as described in EXAMPLE 90, Part A. Chromatographic purification (50% EtOAc/hexane to 60% EtOAc/hexane) yielded the title compound as a white solid (0.37 g, 0.6 mmol).

$^1$H NMR (CDCl$_3$, 300 MHz) δ8.50 (s, 1H), 7.90–8.02 (m, 3H), 7.79 (d, 1H), 7.46-1.60 (m, 4H), 7.30 (dd, 1H), 7.27 (s, 1H), 6.50 (d, 1H), 4.62 (t, 1H), 4.47 (AB, 2H), 4.45 (AB, 2H), 3.94 (s, 3H), 3.24 (m, 1H), 3.14 (m, 1H), 2.26 (m, 2H), 1.63 (s, 9H). FAB MS [M+H]$^+$=616.

C. 7-Methoxy-2-napthalenesulfonic acid {1-[3-(aminoiminomethyl)benzyl]-2-oxo-3(S)-pyrrolidin-3-yl}(pyrazol-3-ylmethyl)amide trifluoroacetate 7-Methoxy-2-napthalenesulfonic acid {1-[3-cyanobenzyl]-2-oxo-3(S)-pyrrolidin-3-yl}(pyrazol-3-ylmethyl)amide (0.37 g, 0.6 mmol) is converted to the title compound as described in EXAMPLE 32, Part C. The crude product is converted to the hydrochloride salt with methanolic HCl then purified by RP-HPLC eluting with a gradient of 5% $CH_3CN/H_2O$ to 50% $CH_3CN/H_2O$; the appropriate product fractions are lyophilized to provide the title compound as a white solid (0.045 g, 0.08 mmol).

$^1$H NMR (DMSO-$d_6$, 300 MHz) δ9.35 (bs, 2H), 9.07 (bs, 2H), 8.46 (s, 1H), 8.03 (d, 1H), 7.98 (d, 1H), 7.72 (d, 1H), 7.58 (d, 1H), 7.55–7.64 (m, 5H), 7.36 (dd, 1H), 6.12 (s, 1H), 4.80 (t, 1H), 4.40 (two AB, 4H), 3.90 (s, 3H), 3.14 (m, 1H), 3.03 (m, 1H), 2.12 (m, 1H), 1.69 (m, 1H). FAB MS, $[M+H]^+$=533. Elemental analysis calculated with 1.6 mmol of $H_2O$: C=54.24%, H=5.43%, N=14.06%, found C=54.22%, H=5.19%, N=13.74%.

EXAMPLE 101

Quinoline-6-sulfonic acid {1-[3-(aminoiminomethyl)benzyl]-2-oxopyrrolidin-3-(S)-yl}amide trifluoroacetate A. Quinoline-6-sulfonyl chloride The title compound is prepared from 6-bromoquinoline as described in EXAMPLE 53, Part B. The solid product is collected, washed with copious amounts of hexane and ether and used without further purification.

EI MS, $[M]^+$=227.

B. Quinoline-6-sulfonic acid {1-[3-cyanobenzyl]-2-oxopyrrolidin-3-(S)-yl}amide 3-(3-(S)-Amino-2-oxopyrrolidin-1-ylmethyl)benzonitrile hydrochloride (0.32 g, 1.26 mmol) is suspended in 15 mL of $CH_3CN$. To the solution is added triethylamine (0.384 g, 3.78 mmol) followed by quinoline-6-sulfonyl chloride (0.25 g, 0.99 mmol). After stirring for 1.5 hours, the solution is diluted with EtOAc and washed with 0.1 N aqueous HCl, water and saturated NaCl solution. The organic layer is dried over $Na_2SO_4$, filtered and concentrated. The crude residue is purified by column chromatography (4% $MeOH/CH_2Cl_2$) to afford the title compound (0.146 g, 0.36 mmol) and as a solid.

$^1$H NMR (CDCl$_3$, 300 MHz) δ9.04 (d, 1H), 8.53 (s, 1H), 8.30 (d, 1H), 8.24 (m, 2H), 7.48–7.55 (m, 5H), 6.46 (brs, 1H), 5.29 (s, 1H), 4.45 (AB, 2H), 3.98 (t, 1H), 3.75 (m, 1H), 3.20 (m, 2H), 2.56 (m, 1H), 2.06 (m, 1H). FAB MS, $[M+H]^+$=407.

A minor component is also isolated: 2-n-Butylquinoline-6-sulfonic acid {1-[3-cyanobenzyl]-2-oxopyrrolidin-3-(S)-yl}amide (0.056 g, 0.12 mmol); FAB MS, $[M=H]^+$=463.

C. Quinoline-6-sulfonic acid {1-[3-(aminoiminomethyl)benzyl]-2-oxopyrrolidin-3-(S)-yl}amide trifluoroacetate Quinoline-6-sulfonic acid {1-[3-cyanobenzyl]-2-oxopyrrolidin-3-(S)-yl}amide (0.146 g, 0.36 mmol) is converted to the title compound as described in EXAMPLE 24, Part C. The crude product is purified by RP-HPLC eluting with a gradient of $H_2O$ (0.1% TFA) to 100% $CH_3CN$ over 35 minutes and the appropriate product fractions are lyophilized to provide the title compound as a white solid (0.050 g, 0.077 mmol) as well as unreacted starting material (0.10 g, 0.25 mmol).

$^1$H NMR (DMSO-$d_6$, 300 MHz) δ9.30 (bs, 2H), 9.05–9.10 (m, 3H), 8.61 (d, 1H), 8.58 (s, 1H), 8.40 (d, 1H), 8.16 (AB, 2H), 7.65–7.72 (m, 2H), 7.50–7.60 (m, 3H), 4.42 (AB, 2H), 4.20 (q, 1H), 3.09 (m, 2H), 2.03 (m, 1H), 1.60 (m, 1H). Ion Spray MS, $[M+H]^+$=424. Elemental analysis calculated with 2 mole of $H_2O$: C=43.67%, H=3.96%, N=10.19%; found C=43.87%, H=3.63%, N=10.08%.

EXAMPLE 102

4-Pyridin-4-ylbenzene sulfonic acid {1-[3-(aminoiminomethyl)benzyl]-2-oxopyrrolidin-3(S)-yl}amide bistrifluoroacetate A. 4-(Pyridin-4-yl)-bromobenzene 4-Bromopyridine hydrochloride is free based with saturated $NaHCO_3$ solution and extracted into methylene chloride. The organic solution is concentrated at room temperature and used immediately without further purification. A portion of the solid obtained (3 g, 19 mmol) is treated as described in EXAMPLE 53, Part A with n-butyl lithium (14.25 mL of a 1.6 M solution in TIF, 22.8 mmol) and iodobromobenzene (5.39 g, 19 mmol). The crude product is purified by chromatography (30% EtOAc/hexanes to 60% EtOAc/hexanes) to obtain the title compound (2.59 g, 11.06 mmol).

EI MS, $[M]^+$=233/235.

B. 4-Pyridin4-ylbenzene sulfonyl chloride

The title compound is prepared from 4-(pyridin-4-yl)-bromobenzene as described in EXAMPLE 53, Part B, except that 2 equivalents of t-butyl lithium is used to generate the starting anion. The crude solid product is purified by washing with copious amounts of hexane and ether. EI MS, $[M]^+$=253 and is used without further purification.

C. 4-Pyridin-4-ylbenzene sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride (0.2 g, 0.79 mmol) as in EXAMPLE 24, Part B using 4-pyridin-4-ylbenzene sulfonyl chloride (0.50 g, 1.98 mmol) in place of 6-methoxynaphthalene-2-sulfonyl chloride. The crude product is purified by chromatography (2.5 to 5% MeOH/$CH_2Cl_2$) to obtain a white solid (0.25 g, 0.58 mmol).

$^1$H NMR (CDCl$_3$, 300 MHz) δ8.78 (m, 2H), 8.11 (d, 2H), 7.66 (m, 2H), 7.47–7.58 (m, 5H), 5.48 (s, 1H), 4.50 (AB, 2H), 3.88 (t, 1H), 3.29 (dd, 2H), 2.58 (m, 1H), 2.17 (m, 1H). FAB MS, $[M+H]^+$=433.

D. 4-Pyridin-4-ylbenzene sulfonic acid {1-[3-(aminoiminomethyl)benzyl]-2-oxopyrrolidin-3(S)-yl}amide bistrifluoroacetate 4-Pyridin-4-ylbenzene sulfonic acid [1-(3-cyanobenzyl)-2-oxopyrrolidin-3-(S)-yl]amide 0.14 g, 0.32 mmol) is converted to the title compound as described in EXAMPLE 24, Part C. The crude product is purified by RP-HPLC eluting with a gradient of 5% $CH_3CN/H_2O$ (0.1% TFA) to 40% $CH_3CN/H_2O$ (0.1% TFA) and the appropriate product fractions are lyophilized to provide the title compound as a white solid (0.132 g, 0.19 mmol).

$^1$H NMR (DMSO-$d_6$, 300 MHz) δ9.28 bs, 2H), 9.13 (bs, 2H), 8.80 (bs, 1H), 8.33 (m, 1H), 7.97 (m, 5H), 7.62 (m, 1H), 7.51 (m, 3H), 4.40 (m, 2H), 4.15 (m, 1H), 3.10 (m, 2H), 2.05 (m, 1H), 1.60 (m, 1H). FAB MS, $[M+H]^+$=450. Elemental analysis cal. C=47.86%, H=3.72%, N=10.34%, found C=47.94%, H=3.84%, N=10.40%.

EXAMPLE 103

7-Methoxy-2-napthalenesulfonic acid {1-[3-(aminoiminomethyl)benzyl]-2-oxo-3(S)-pyrrolidin-3-yl}(thiophene-2-ylmethyl)amide trifluoroacetate A. 7-Methoxy-2-napthalenesulfonic acid [1-(3-cyanobenzyl)-2-oxopyrrolidin-3-(S)-yl](thiophene-2-ylmethyl)amide The title compound is prepared as described in EXAMPLE 90, Part A using 7-methoxynaphthalene-2-sulfonic acid [1-(3-cyanobenzyl)-2-oxopyrrolidin-3-(S)-yl]

amide (0.100 g, 0.23 mmol), prepared as described in EXAMPLE 43, part A, and thiophene-2-ylmethyl bromide (0.10 g, 0.56 mmol). The crude product is triturated with hexane/ether and used without further purification.

$^1$H NMR (CDCl$_3$, 300 MHz) δ8.49 (s, 1H), 7.93 (bs 2H), 7.70 (d, 1H), 7.50 (m, 3H), 7.28 (m, 3H), 7.10 (d, 1H), 6.90 (m, 2H), 4.65 (m, 3H), 4.45 (AB, 2H), 3.93 (s, 3H), 3.09 (m, 2H), 2.28 (m, 1H), 2.04 (m, 1H). FAB MS, [M+H]$^+$=532.

B. 7-Methoxy-2-napthalenesulfonic acid {1-[3-(aminoiminomethyl)benzyl]-2-oxo-3(S)-pyrrolidin-3-yl-(thiophene-2-ylmethyl)amide trifluoroacetate 7-Methoxy-2-napthalenesulfonic acid [1-(3-cyanobenzyl)-2-oxopyrrolidin-3-(S)-yl-(thiophene-2-ylmethyl)amide (0.12 g, 0.23 mmol) is converted to the title compound as described in EXAMPLE 24, Part C. The crude product is purified by RP-HPLC eluting with a gradient of 10% CH$_3$CN/H$_2$O (0.1% TFA) to 100% CH$_3$CN and the appropriate product fractions are lyophilized to provide the title compound as a white solid (0.045 g, 0.064 mmol).

$^1$H NMR (CD$_3$OD, 300 MHz) δ8.49 (s, 1H), 7.95 (d, 1H), 7.87 (m, 2H), 7.62 (m, 4H), 7.43 (d, 1H), 7.31 (m, 2H), 6.96 (m, 1H), 6.85 (m, 1H), 4.66 (m, 4H), 3.92 (s, 3H), 3.23 (m, 2H), 2.23 (m, 1H), 2.05 (m, 1H). FAB MS, [M+H]$^+$=549. Elemental analysis calculated with 2 mmol of H$_2$O cal. C=51.57%, H=4.76%, N=8.02%, found C=51.70%, H=4.41%, N=7.79%.

EXAMPLE 104

4-Pyridin-3-ylbenzene sulfonic acid {1-[3-(aminoiminomethyl)benzyl]-2-oxopyrrolidin-3(S)-yl}amide bistrifluoroacetate A. 4-(Pyridin-3-yl)bromobenzene 3-Bromopyridine (6 g, 38 mmol) is treated as described in EXAMPLE 53, Part A with n-butyl lithium (28.5 mL of a 1.6 M solution in THF, 45.6 mmol) and iodobromobenzene (8.96 g, 31.7 mmol). The crude product is purified by chromatography (30% EtOAc/hexanes) to obtain the title compound (3.5 g, 14.9 mmol).

EI MS, [M]$^+$=233/235.

B. 4-Pyridin-3-ylbenzene sulfonylchloride

The title compound is prepared from 4-(pyridin-3-yl)-bromobenzene (1.75 g, 7.5 mmol) as described in EXAMPLE 53, Part B except that 2 equivalents of t-butyl lithium is used to generate the starting anion. The crude solid product is purified by washing with copious amounts of hexane followed by 100 mL of hot anhydrous CH$_2$Cl$_2$ and is used without further purification (1.98 g, 7.8 mmol).

EI MS, [M]$^+$=253.

C. 4-Pyridin-3-ylbenzene sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride (0.3 g, 1.2 mmol) as in EXAMPLE 24, Part B using 4-pyridin-3-ylbenzenesulfonyl chloride (0.57 g, 2.4 mmol) in place of 6-methoxynaphthalene-2-sulfonyl chloride. The crude product is purified by chromatography (2.5% MeOH/CH$_2$Cl$_2$ to 5% MeOH/CH$_2$Cl$_2$) to obtain a white solid (0.08 g, 0.18 mmol).

$^1$H NMR (CD$_3$OD, 300 MHz) δ8.85 (bs, 2H), 8.57 (bs, 2H), 8.16 (d, 1H), 7.94 (AB, 4H), 7.46–7.65 (m, 5H), 4.44 (AB, 2H), 4.23 (t, 1H), 3.20 (m, 2H), 2.33 (m, 1H), 1.87 (m, 1H).

D. 4-Pyridin-3-ylbenzene sulfonic acid {1-[3-(aminoiminomethyl)benzyl]-2-oxopyrrolidin-3(S)-yl}amide bistrifluoroacetate 4-Pyridin-3-ylbenzene sulfonic acid [1-(3-cyanobenzyl)-2-oxopyrrolidin-3-(S)-yl]amide (0.08 g, 0.18 mmol) is converted to 4-pyridin-3-ylbenzene-4-sulfonic acid {1-[3-(aminoiminomethyl)benzyl]-2-oxopyrrolidin-3(S)-yl}amide bistrifluoroacetate as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid (0.016 g, 0.024 mmol).

$^1$H NMR (DMSO-d$_6$, 300 MHz) δ9.27 (bs, 2H), 9.05 (bs, 2H), 8.23 (m, 2H), 7.93 (m, 4H), 7.62 (m, 2H), 7.51 (m, 3H), 4.40 (m, 2H), 4.15 (m, 1H), 3.10 (m, 2H), 2.05 (m, 1H), 1.60 (m, 1H). FAB MS, [M+H]$^+$=450.

EXAMPLE 105

N-Methylpyrid-4-ylphenyl-4-sulfonic acid {1-[3-(aminoiminomethyl)benzyl]-2-oxopyrrolidin-3(S)-yl}amide trifluoro acetate Pyrid-4-ylbenzene sulfonic acid {1-[3-cyanobenzyl]-2-oxopyrrolidin-3(S)-yl}amide (0.25 g, 0.58 mmol), prepared as described in EXAMPLE 80, Part C is converted to the title compound as described in EXAMPLE 32, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a yellow solid (0.055, 0.08 mmol).

$^1$H NMR (CD$_3$OD, 300 MHz) δ8.42, 8.98 (AB, 4H), 8.16 (s, 4H) 7.56–7.73 (m, 3H), 7.59 (s, 1H), 4.50 (AB, 2H), 4.43 (s, 3H), 4.27 (t, 1H), 3.26 (m, 2H), 2.33 (m, 1H), 1.80 (m, 1H). FAB MS, [M+H]$^+$=464.

EXAMPLE 106

2-Methoxyquinoline-7-sulfonic acid {1-[3-(aminoiminomethyl)benzyl]-2-oxopyrrolidin-3-(S)-yl}amide trifluoroacetate A. 2-Methoxyquinoline-7-sulfonyl chloride 7-Bromo-2-methoxyquinoline (1.75 g, 7.5 mmol) is treated as described in EXAMPLE 53, Part B. The crude solid product is collected, washed with hexane and used without further purification (0.66 g, 2.6 mmol).

EI MS, [M]$^+$=257.

B. 2-Methoxyquinoline-7-sulfonic acid {1-[3-cyanobenzyl]-2-oxopyrrolidin-3-(S)-yl}amide The title compound is prepared from 3-(3-(S)-amino-2-oxopyrrolidin-1-ylmethyl)benzonitrile hydrochloride (0.305, 1.2 mmol) as in EXAMPLE 24, Part B using 2-methoxyquinoline-7-sulfonyl chloride (0.30 g, 1.16 mmol) in place of 6-methoxynaphthalene-2-sulfonyl chloride. 2-Methoxy-quinoline-7-sulfonic acid {1-[3-cyanobenzyl]-2-oxopyrrolidin-3-(S)-yl}amide is obtained as a solid (0.27 g, 0.62 mmol) upon chromatography (CH$_2$Cl$_2$ to 3% MeOH/CH$_2$Cl$_2$).

$^1$H NMR (CDCl$_3$, 300 MHz) δ8.43 (m, 2H), 8.03 (d, 2H), 7.80–7.91 (m, 2H), 7.58 (d, 1H), 7.43 (m, 3H), 7.06 (d, 1H), 5.43 (s, 1H), 4.43 (s, 2H), 4.08 (s, 3H), 3.80 (t, 1H), 3.20 (dd, 2H), 2.62 (m, 1H), 2.10 (m, 1H). EI MS, [M]$^+$=436.

C. -Methoxyquinoline-7-sulfonic acid {1-[3-cyanobenzyl]-2-oxopyrrolidin-3-(S)-yl}methylamide 2-Methoxy-quinoline-7-sulfonic acid {1-[3-cyanobenzyl]-2-oxopyrrolidin-3-(S)-yl}amide (0.15 g, 0.35 mmol) is converted to the title compound (0.157 g, 0.35 mmol) as described in EXAMPLE 90, Part A except that acetone is replaced with anhydrous DMF (4 mL) and a catalytic amount of tert-butyl ammonium iodide is added.

EI MS, [M]$^+$=450.

D. 2-Methoxyquinoline-7-sulfonic acid {1-[3-(aminoiminomethyl)benzyl]-2-oxopyrrolidin-3-(S)-yl}amide trifluoroacetate 2-Methoxy-quinoline-7-sulfonic acid {1-[3-cyanobenzyl]-2-oxopyrrolidin-3-(S)-yl}methylamide is converted to the title compound as described in EXAMPLE 24, Part C. The crude product is purified by RP-HPLC eluting with a gradient of 10% $CH_3CN/H_2O$ (0.1% TFA) to 100% $CH_3CN$ and the appropriate product fractions are lyophilized to provide the title compound as a white solid (0.038 g, 0.065 mmol).

$^1$H NMR ($CD_3OD$, 300 MHz) δ8.35 (s, 1H), 8.25 (d, 1H), 7.98 (d, 3H), 7.84 (dd, 1H), 7.69 (m, 1H), 7.50–7.68 (m, 3H), 7.10 (s, 1H), 5.0 (t, 1H), 4.53 (AB, 2H), 4.08 (s, 3H), 3.30 (m, 2H), 2.80 (s, 3H), 2.15 (m, 1H), 1.93 (m, 1H). FAB MS, $[M+H]^+$=468. Elemental analysis calculated with 1.5 mmol of TFA and 0.5 mmol of $H_2O$: C=48.2%, H=4.28%, N=10.81%, found C=48.16%, H=4.37%, N=10.67%.

EXAMPLE 107

4-(6-Methoxypyridin-2-yl)benzene-4-sulfonic acid {1-[3-(aminoiminomethyl)benzyl]-2-oxopyrrolidin-3 (S)-yl}amide bistrifluoroacetate A. 4-(6-Methoxypyridin-2-yl)bromobenzene 2-Bromo-6-methoxypyridine (3 g, 17 mmol) is treated as described in EXAMPLE 53, Part A with n-butyl lithium (10.6 mL of a 1.6 M solution in THF, 17 mmol) and iodobromobenzene (4.8 g, 17 mmol). The crude product is purified by chromatography (5% EtOAc/hexanes) to obtain the title compound (2 g, 7.6 mmol).

EI MS, $[M]^+$=263/265.

B. 4-(6-Methoxypyridin-2-yl)benzene sulfonyl chloride

The title compound is prepared from 4-(pyridin-4-yl)-bromobenzene (1.92 g, 7.5 mmol) as described in EXAMPLE 53, Part B. The crude product is purified by chromatography to give 4-(6 methoxypyridin-2-yl)benzene sulfonyl chloride.

EI MS, $[M]^+$=283.

C. 4-(6-Methoxypyridin-2-yl)benzene-4-sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride (0.59 g, 2.3 mmol) as in EXAMPLE 24, Part B using 4-(6-methoxypyridin-2-yl)benzene sulfonyl chloride (0.63 g, 2.2 mmol) in place of 6-methoxynaphthalene-2-sulfonyl chloride. The crude product (1.1 g, 2.4 mmol) is used without further purification.

$^1$H NMR ($CDCl_3$, 300 MHz) δ8.20 (d, 2H), 7.98 (d, 2H), 7.66 (t, 1H), 7.57 (m, 1H), 7.35–7.45 (m, 4H), 6.88 (d, 1H), 7.07 (dd, 1H), 5.36 (bs, 1H), 4.45 (s, 2H), 3.78 (t, 1H), 3.21 (m, 2H), 2.61 (m, 1H), 2.10 (m, 1H).

D. 4-(6-Methoxypyridin-2-yl)benzene-4-sulfonic acid {1-[3-(aminoiminomethyl)benzyl]-2-oxopyrrolidin-3(S)-yl}amide bistrifluoroacetate 4-(6-Methoxypyridin-2-yl)benzene-4-sulfonic acid [1-(3-cyanobenzyl)-2-oxopyrrolidin-3-(S)-yl]amide (0.26 g, 0.57 mmol) is converted to the title compound as described in EXAMPLE 24, Part C. The crude product is purified by RP-HPLC eluting with a gradient of 10% $CH_3CN/H_2O$ (0.1% TFA) to 100% $CH_3CN$ and the appropriate product fractions are lyophilized to provide the title compound as a white solid (0.168 g, 0.24 mmol).

$^1$H NMR ($CD_3OD$, 300 MHz) δ8.25 (m, 2H), 7.05 (m, 3H), 7.97 (m, 2H), 7.72 (m, 2H), 7.54 (m, 4H), 6.78 (d, 1H), 4.51 (AB, 2H), 4.20 (t, 1H), 4.00 (s, 3H), 3.22 (m, 2H), 2.29 (m, 1H), 1.78 (m, 1H). FAB MS, $[M+H]^+$=480.

EXAMPLE 108

4-(3-Chloropyridin-2-yloxy)benzene-4-sulfonic acid {1-[3-(aminoiminomethyl)benzyl]-2-oxopyrrolidin-3 (S)-yl}amide trifluoroacetate A. 4-(3-Chloropyridin-2-yloxy)bromobenzene Bromophenol (3.74 g, 22 mmol) is stirred with 50% sodium hydroxide solution (16 mL) for about 1 hour then treated with hexadecyltributylphosphonium bromide (3.25 g, 6.4 mmol), 2.3-dichloro-pyridine (3.2 g, 21.6 mmol) and toluene (15 mL). The mixture is heated to 100° C. for 18 hours, cooled and diluted with ethyl acetate and water. The organic layer is separated, washed with dilute NaOH and saturated NaCl, dried ($MgSO_4$) and concentrated. Flash chromatography (5% EtOAc/hexanes) yielded the title compound (4.4 g, 15 mmol).

EI MS, $[M]^+$=285.

B. 4-(3-Chloropyridin-2-yloxy)benzene sulfonyl chloride 4-(3-Chloropyridin-2-yloxy)bromobenzene (2 g, 7.03 mmol) is converted to the title compound as described in EXAMPLE 53, Part B. The crude product, a gummy solid, is purified by chromatography ($CH_2Cl_2$) to yield 4-(3-chloropyridin-2-yloxy)benzene sulfonyl chloride (0.76 g, 2.5 mmol).

EI MS, $[M]^+$=303.

C. 4-(3-Chloropyridin-2-yloxy)benzene sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride as in EXAMPLE 24, Part B using 4-(3-chloropyridin-2-yloxy) benzene sulfonyl chloride in place of 6-methoxynaphthalene-2-sulfonyl chloride.

$^1$H NMR ($CDCl_3$, 300 MHz) δ8.07 (d, 1H), 7.96 (d, 2H), 7.82 (d, 1H), 7.58 (m, 1H), 7.46 (m, 3H), 7.32 (d, 2H), 7.07 (dd, 1H), 5.35 (s, 1H), 4.46 (s, 2H), 3.78 (t, 1H), 3.21 (dd, 2H), 2.58 (m, 1H), 2.08 (m, 1H).

D. 4-(3-Chloropyridin-2-yloxy)benzene-4-sulfonic acid {1-[3-(aminoiminomethyl)benzyl]-2-oxopyrrolidin-3(S)-yl}amide trifluoroacetate 4-(3-Chloropyridin-2-yloxy)benzene sulfonic acid [1-(3-cyanobenzyl)-2-oxopyrrolidin-3-(S)-yl]amide (0.47 g, 0.97 mmol) is converted to the title compound as described in EXAMPLE 24, Part C. The crude product is purified by RP-HPLC eluting with a gradient of 15% $CH_3CN/H_2O$ (0.1% TFA) to 70% $CH_3CN/H_2O$ (0.1% TFA) and the appropriate product fractions are lyophilized to provide the title compound as a white solid (0.4 g, 0.64 mmol).

$^1$H NMR (DMSO-$d_6$, 300 MHz) δ9.26 (bs, 2H), 9.15 (bs, 2H), 8.16 (d, 1H), 8.05 (m, 2H), 7.85 (m, 2H), 7.62 (m, 1H), 7.51 (m, 3H), 7.30 (m, 2H), 7.22 (m, 1H), 4.41 (AB, 2H), 4.13 (m, 1H), 3.08 (m, 2H), 2.04 (m, 1H), 1.60 (m, 1H). FAB MS, $[M+H]^+$=500. Elemental analysis calculated with 0.5 mmol of $H_2O$: C=48.20%, H=3.88%, N=11.24%, found C=48.23%, H=3.56%, N=10.97%.

EXAMPLE 109

4-(N-Oxidopyridin-3-yl)benzene-4-sulfonic acid {1-[3-(aminoiminomethyl)benzyl]-2-oxopyrrolidin-3 (S)-yl}amide trifluoroacetate A. 4-(N-Oxidopyridin-3-yl)benzene sulfonic acid [1-(3-cyanobenzyl)-2-oxopyrrolidin-3-(S)-yl]amide 4-Pyridin-3-ylbenzene sulfonic acid [1-(3-cyanobenzyl)-2-oxopyrrolidin-3-(S)-yl]amide (0.125 g, 0.29 mmol) is treated with m-chloroperbenzoic acid (0.55 g, 3.2 mmol) in chloroform (4 mL) for 20 hours. The reaction is diluted with methylene chloride, washed with saturated $NaHCO_3$ and saturated NaCl, dried ($Na_2SO_4$) and concentrated to yield 4-(N-oxidopyridin-3-yl)benezene sulfonic acid [1-(3-cyanobenzyl)-2-oxopyrrolidin-3-(S)-yl]amide (0.12 g, 0.27 mmol). The crude product is used without further purification.

$^1$H NMR (CDCl$_3$, 300 MHz) δ8.50 (bs, 1H), 8.28 (d, 1H), 8.06 (d, 2H), 7.68 (d, 2H), 7.36–7.60 (m, 5H), 6.00 (m, 1H), 4.46 (AB, 2H), 3.90 (m, 1H), 3.25 (m, 2H), 2.60 (m, 1H), 2.08 (m, 1H). FAB MS, [M+H]$^+$=449.

B. 4-(N-Oxidopyridin-3-yl)benzene-4-sulfonic acid {1-[3-(aminoiminomethyl)benzyl]-2-oxopyrrolidin-3(S)-yl}amide trifluoroacetate 4-(N-Oxidopyridin-3-yl)benzene-4-sulfonic acid [1-(3-cyanobenzyl)-2-oxopyrrolidin-3-(S)-yl]amide (0.12 g, 0.27 mmol) is converted to the title compound as described in EXAMPLE 24, Part C. The crude product is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound as a white solid (0.045 g, 0.07 mmol).

$^1$H NMR (DMSO-d$_6$, 300 MHz) δ9.26 (bs, 2H), 9.00 (bs, 2H), 8.62 (m, 1H), 8.38 (m, 2H), 7.94 (m, 4H), 7.65 (m, 2H), 7.50 (m, 4H), 4.40 (AB, 2H), 4.13 (m, 1H), 3.10 (m, 2H), 2.05 (m, 1H), 1.59 (m, 1H). FAB MS, [M+H]$^+$=466.

EXAMPLE 110

4-Phenoxybenzene-4-sulfonic acid {1-[3-(aminoiminomethyl)benzyl]-2-oxopyrrolidin-3(S)-yl}amide trifluoroacetate A. 4-Phenoxybenzene sulfonyl chloride 4-(Phenoxy)bromobenzene (6 g, 24 mmol) is converted to the title compound as described in EXAMPLE 53, Part B. The final suspension is concentrated and the residue is purified by chromatography (2% ether/hexane) to yield 4-phenoxybenzene sulfonyl chloride (3.92 g, 14.6 mmol).

EI MS, [M]$^+$=468.

B. 4-Phenoxybenzene sulfonic acid [1-(3-cyanobenzyl)-2-oxopyrrolidin-3-(S)-yl]amide The title compound is prepared from 3-(3-(S)-amino-2-oxopyrrolidin-1-ylmethyl)benzonitrile hydrochloride (0.35 g, 1.39 mmol) as in EXAMPLE 24, Part B using 4-phenoxybenzene-4-sulfonyl chloride (0.38 g, 1.41 mmol) in place of 6-methoxynaphthalene-2-sulfonyl chloride. Standard work-up and chromatography gave 4-phenoxybenzene sulfonic acid [1-(3-cyanobenzyl)-2-oxopyrrolidin-3-(S)-yl] amide (0.37 g, 0.83 mmol). The crude product is triturated with hexane/ether and used without further purification.

$^1$H NMR (CDCl$_3$, 300 MHz) δ7.86 (d, 2H), 7.63 (d, 1H), 7.40–7.50 (m, 5H), 7.22 (t, 1H), 7.09 (t, 4H), 5.24 (s, 1H), 4.47 (AB, 2H), 3.77 (t, 1H), 3.20 (dd, 2H), 2.58 (m, 1H), 2.09 (m, 1H). FAB MS, [M+H]$^+$=447.

C. 4-Phenoxybenzene sulfonic acid {1-[3-(aminoiminomethyl)benzyl]-2-oxopyrrolidin-3(S)-yl}amide trifluoroacetate 4-Phenoxybenzene sulfonic acid [1-(3-cyanobenzyl)-2-oxopyrrolidin-3-(S)-yl]amide (0.37 g, 0.83 mmol) is converted to the title compound as described in EXAMPLE 24, Part C. The crude product is purified by RP-HPLC eluting with a gradient of 25% CH$_3$CN/H$_2$O (0.1% TFA) to 100% CH$_3$CN and the appropriate product fractions are lyophilized to provide the title compound as a white solid (0.25 g, 0.426 mmol).

$^1$H NMR (DMSO-d$_6$, 300 MHz) δ7.78 (d, 2H), 7.55–7.75 (m, 4H), 7.40 (t, 2H), 7.23 (t, 1H), 7.07 (m, 4H), 4.42 (AB, 2H), 4.14 (t, 1H), 3.25 (m, 2H), 2.25 (m, 1H), 1.87 (m, 1H). FAB MS, [M+H]$^+$=465. Elemental analysis calculated with 1 mmol of TFA and 0.5 mmol of H$_2$O: C=53.15%, H=4.46%, N=9.50%, found C=53.10%, H=4.21%, N=9.40%.

EXAMPLE 111

7-Methoxy-2-napthalenesulfonic acid {1-[3-(aminoiminomethyl)benzyl]-2-oxo-3(S)-pyrrolidin-3-yl}(thiophene-3-ylmethyl)amide trifluoroacetate A. 7-Methoxy-2-napthalenesulfonic acid [1-(3-cyanobenzyl)-2-oxopyrrolidin-3-(S)-yl](thiophene-3-ylmethyl)amide The title compound is prepared as described in EXAMPLE 90, Part A using 7-methoxynaphthalene-2-sulfonic acid [1-(3-cyanobenzyl)-2-oxopyrrolidin-3-(S)-yl] amide (0.193 g, 0.44 mmol), prepared as described in EXAMPLE 43, part A, and thiophen-3-ylmethyl bromide (0.30 g, 1.68 mmol). The crude product is triturated with hexane/ether and used without further purification (0.25 g, 0.48 mmol).

$^1$H NMR (CDCl$_3$, 300 MHz) δ8.45 (s, 1H), 7.94 (AB, 2H), 7.80 (d, 1H), 7.06 (d, 1H), 7.40–7.65 (m, 2H), 7.18–7.32 (m, 4H), 7.05–7.13 (m, 2H), 4.4–4.6 (m, 3H), 4.38 (AB, 2H), 3.93 (s, 3H), 3.07 (m, 2H), 2.27 (m, 1H), 1.99 (m, 1H). FAB MS, [M+H]$^+$=532.

B. 7-Methoxy-2-napthalenesulfonic acid {1-[3-(aminoiminomethyl)benzyl]-2-oxo-3(S)-pyrrolidin-3-yl}(thiophene-3-ylmethyl)amide trifluoroacetate 7-Methoxy-2-napthalenesulfonic acid [1-(3-cyanobenzyl)-2-oxopyrrolidin-3-(S)-yl](thiophen-3-ylmethyl)amide (0.25 g, 0.48 mmol) is converted to the title compound as described in EXAMPLE 24, Part C. The crude product is purified by RP-HPLC eluting with a gradient of 10% CH$_3$CN/H$_2$O (0.1% TFA) to 100% CH$_3$CN and the appropriate product fractions are lyophilized to provide the title compound as a white solid (0.150 g, 0.218 mmol).

$^1$H NMR (CD$_3$OD, 300 MHz) δ8.48 (s, 1H), 7.97 (d, 1H), 7.88 (m, 2H), 7.6–7.72 (m, 4H), 7.43 (d, 1H), 7.30 (m, 2H), 7.24 (bs, 1H), 6.98 (d, 1H), 4.69 (t, 1H), 4.52 (AB, 2H), 4.45 (AB, 2H) 3.93 (s, 3H), 3.22 (m, 2H), 2.23 (m, 1H), 2.02 (m, 1H). FAB MS, [M+H]$^+$=549. Elemental analysis calculated with 1 mmol of H$_2$O cal. C=52.93%, H=4.59%, N=8.23%, found C=52.68%, H=4.51%, N=7.97%.

EXAMPLE 112

6-Methoxynaphthalene-2-sulfonic acid {1-[3-(methoxyaminoiminomethyl)-benzyl]-2-oxopyrrolidin-3-(S)-yl}-methylamide trifluoroacetate 6-Methoxynaphthalene-2-sulfonic acid [1-(3-cyanobenzyl)-2-oxopyrrolidin-3-(S)-yl]methylamide, prepared as described in EXAMPLE 25, Part A, (0.096 g, 0.21 mmol) is dissolved in 15 mL of a 2:1 mixture of EtOH/CH$_2$Cl$_2$. The solution is cooled to 0° C. and HCl gas is bubbled through the solution for 10 minutes. The ice bath is removed and the reaction mixture is stirred at room temperature for 18 hours. After this time, the solution is concentrated and pumped under high vacuum until dry. The residue is dissolved in 10 mL of ethanol, and treated with methoxyamine hydrochloride (0.18 g, 2.14 mmol) and triethylamine (0.24 g, 2.38 mmol). The reaction mixture is stirred at room temperature for 24 hours and diluted with ethyl acetate. The organic layer is washed with water and brine dried (Na$_2$SO$_4$) and concentrated. The residue is purified by flash chromatography eluting with a gradient of 0.25% MeOH/CH$_2$Cl$_2$ to 1% MeOH/CH$_2$Cl$_2$. The appropriate product fractions are collected, concentrated and converted to the TFA salt to give the title compound (0.41 g, 0.19 mmol) as an amorphous white solid.

$^1$H NMR (CDCl$_3$, 300 MHz) δ8.39 (s, 1H), 7.89 (d, 1H), 7.78 (m, 2H), 7.58 (m, 2H), 7.30 (m, 4H), 6.20 (bs, 2H), 4.88

(t, 1H), 4.42 (AB, 2H), 3.92 (m, 3H), 3.90 (m, 3H), 3.21 (m, 2H), 2.75 (m, 3H), 2.22 (m, 1H), 1.95 (m, 1H). FAB MS, [M+H]$^+$=497. Elemental analysis calculated with 1.7 mmol of H$_2$O cal. C=50.57%, H=5.09%, N=8.74%, found C=50.58%, H=4.55%, N=8.29%.

EXAMPLE 113

6-Methoxynaphthalene-2-sulfonic acid {1-[3-(cyanoaminoiminomethyl)benzyl]-2-oxopyrrolidin-3-(S)-yl}methylamide trifluoroacetate 6-Methoxynaphthalene-2-sulfonic acid {1-[3-(aminoiminomethyl)benzyl]-2-oxopyrrolidin-3-(S)-yl}methylamide (0.2 g, 0.4 mmol), prepared as described in EXAMPLE 25, Part B, is dissolved in ethanol (10 mL), and treated with triethyl amine (0.202 g, 2 mmol) and cyanogen bromide (0.4 mL of a 5 M solution, 2 mmol) portionwise over 48 hours. The solution is cooled during the addition of reagents. Upon completion (TLC analysis) the solution is concentrated and the residue purified by chromatography (5% MeOH/CH$_2$Cl$_2$), followed by RP-HPLC eluting with a gradient of 20% CH$_3$CN/H$_2$O (0.1% TFA) to 100% CH$_3$CN. The title compound is isolated as a white solid (0.043 g, 0.086 mmol).

$^1$H NMR (CD$_3$OD, 300 MHz) δ8.42 (s, 1H), 7.97 (d, 1H), 7.85 (d, 1H), 7.72 (m, 3H), 7.42 (m, 3H), 7.30 (d, 1H), 5.00 (m, 1H), 4.48 (AB, 2H), 3.92 (s, 3H), 3.24 (m, 2H), 2.10 (m, 1H), 1.85 (m, 1H). FAB MS, [M+H]$^+$=492. Elemental analysis calculated with 0.6 mmol of H$_2$O cal. C=59.77%, H=5.26%, N=13.94%, found C=59.75%, H=4.96%, N=13.84%.

EXAMPLE 114

6-Methoxynaphthalene-2-sulfonic acid {1-[3-(hydroxyaminoiminomethyl)-benzyl]-2-oxopyrrolidin-3-(S)-yl}-methylamide trifluoroacetate 6-Methoxynaphthalene-2-sulfonic acid [1-(3-cyanobenzyl)-2-oxopyrrolidin-3-(S)-yl]methylamide, prepared as described in EXAMPLE 25, Part A, (0.10 g, 0.22 mmol) is dissolved in 10 mL of methanol, treated with Hydroxylamine hydrochloride (0.078 g, 1.1 mmol) and K$_2$CO$_3$ (0.154 g, 1.1 mmol) and heated to reflux for 18 hours. The solution is cooled, concentrated and the residue purified by RP-HPLC eluting with a gradient of 10% CH$_3$CN/H$_2$O (0.1% TFA) to 100% CH$_3$CN. The title compound is isolated as a white solid (0.080 g, 0.126 mmol).

$^1$H NMR (CD$_3$OD, 300 MHz) δ8.46 (s, 1H), 8.05 (d, 1H), 7.90 (d, 1H), 7.78 (dd, 1H), 7.62 (m, 3H), 7.58 (m, 1H), 7.50 (m, 1H), 7.38 (dd, 1H), 5.00 (t, 1H), 4.58 (s, 2H), 3.95 (s, 3H), 3.30 (m, 2H), 2.70 (s, 3H), 2.20 (m, 1H), 1.95 (m, 1H). FAB MS, [M+H]$^+$=483. Elemental analysis calculated with 2.1 mmol of H$_2$O cal. C=48.22%, H=4.90%, N=8.83%, found C=48.86%, H=4.30%, N=8.61%.

EXAMPLE 115

4-Amino-3-[3-(S)-(7-methoxynaphthalene-2-sulfonylamino)-2-oxopyrrolidin-1-yl-methyl] benzamidine dihydrochloride A. 4-Amino-3-methylbenzonitrile To a solution of 3-methyl-4-nitrobenzonitrile (2 g, 12.3 mmol) in 100 mL of EtOH is added SnCl$_2$ (13.9 g, 61.7 mmol). The resulting solution is refluxed. After 2 hours, the solution is cooled to ambient temperatures. The solution is poured into 150 mL of ice water. The pH of the solution is adjusted to >7 with a solution of saturated NaHCO$_3$. The solution is diluted with EtOAc and the resulting mixture is filtered through Celite. The filtered solution is separated. The organic layer is dried over MgSO$_4$, filtered and concentrated to give the title compound (1.57 g, 8.7 mmol) as an off-white solid.

$^1$H NMR (CDCl$_3$, 300 MHz) δ7.30 (m, 2H), 6.63 (d, 1H), 4.10 (bs, 2H), 2.15 (m, 2H). EI MS, [M]$^+$=132.

B. 4-(Benzhydrylidenylamino)-3-methylbenzonitrile

To a solution of 4-amino-3-methybenzonitrile (1.2 g, 9.08 mmol) in 75 mL of toluene is added benzophenone (1.74 g, 9.53 mmol) and p-toluenesulfonic acid (0.43 g, 2.1 mmol). The reaction vessel is fitted with a Dean-Stark trap and the solution is heated to reflux. After 24 hours, the solution is cooled to ambient temperatures. The solution is concentrated. The crude material is purified by column chromatography eluting with a gradient of 3% EtOAc/hexanes to 10% EtOAc/hexanes. The title compound (2.43 g, 8.2 mmol) is obtained as an oil.

$^1$H NMR (CDCl$_3$, 300 MHz) δ7.80 (m, 2H), 7.40 (m, 6H), 7.30 (s, 1H), 7.15 (d, 1H), 7.05 (bs, 2H), 6.50 (d, 1H), 2.20 (s, 3H). EI MS, [M]$^+$=296.

C. 4-(Benzhydrylidenylamino)-3-bromomethylbenzonitrile

To a solution of 4-(benzhydrylidenylamino)-3-methylbenzonitrile (1.36 g, 4.27 mmol) in 40 mL of CCl$_4$ is added N-bromosuccinimide (0.84 g, 4.7 mmol) and benzoyl peroxide (0.22 g, 0.64 mmol). The solution is refluxed for 16 hours. The solution is cooled to ambient temperatures. The solution is diluted with CH$_2$Cl$_2$. The solution is washed with 1 N NaOH and saturated NaCl. The organic layer is dried over MgSO$_4$, filtered and concentrated. The crude material is purified by column chromatography eluting with a gradient of 5% EtOAc/hexanes to 10% EtOAc/hexanes. The title compound (0.91 g, 2.43 mmol) is obtained as an oil.

$^1$H NMR (CDCl$_3$, 300 MHz) δ7.80 (m, 2H), 7.60 (d, 1H), 7.35 (m, 8H), 7.15 (dd, 1H), 6.35 (d, 1H), 4.55 (s, 2H). EI MS, [M]$^+$=374.

D. {1-[2-(Benzhydrylidenylamino)-5-cyano-benzyl]-2-oxopyrrolidin-3-yl}-carbamic acid tert-butyl ester The title compound is prepared as described in EXAMPLE 23, Part B substituting 4-(benzhydrylidenylamino)-3-bromomethylbenzonitrile for α-bromo-m-toluyl nitrile. The crude material is purified by column chromatography eluting with a gradient of 30% EtOAc/hexanes to 40% EtOAc/hexanes. The title compound is obtained as a yellow solid.

$^1$H NMR (CDCl$_3$, 300 MHz) δ7.70 (bs, 2H), 7.40 (s, 1H), 7.38 (bs, 6H), 7.30 (d, 1H), 7.15 (bs, 2H), 6.48 (d, 1H), 5.00 (d, 1H, 4.45 (AB, 2H), 4.15 (m, 1H), 3.30 (m, 2H), 2.61 (m, 1H), 1.90 (m, 1H), 1.45 (s, 9H).

E. 7-Methoxynaphthalene-2-sulfonic acid [1-(2-amino-5-cyanobenzyl)-2-oxopyrrolidin-3-yl]amide Hydrogen chloride gas is bubbled through a solution of {1-[2-(benzhydrylidenylamino)-5-cyanobenzyl]-2-oxopyrrolidin-3-yl}carbamic acid tert-butyl ester (0.70 g, 1.42 mmol) in 75 mL of EtOAc at 0° C. for 5 minutes. After 1 hour, the solution is concentrated. The resulting residue is dissolved in 50 mL of CH$_3$CN. To the solution is added triethyl amine (0.79 mL, 5.68 mmol) and 7-methoxynaphthalene sulfonyl chloride (0.38 g, 1.49 mmol). After 5 hours, the reaction mixture is diluted with EtOAc. The resulting solution is washed with saturated NaHCO$_3$ and saturated NaCl. The organic layer is dried over MgSO$_4$, filtered and concentrated. The crude material is purified by column chromatography eluting with 5% CH$_3$OH/CH$_2$Cl$_2$. The title compound (0.60 g, 1.21 mmol) is obtained as a yellow solid.

¹H NMR (CDCl₃, 300 MHz) δ8.30 (s, 1H), 7.90 (d, 1H), 7.80 (d, 1H), 7.70 (d, 1H), 7.35 (m, 4H), 6.55 (d, 1H), 5.25 (d, 1H), 4.90 (s, 2H), 4.30 (AB, 2H), 3.95 (s, 3H), 3.75 (m, 1H), 3.20 (m, 2H), 2.55 (m, 1H), 2.00 (m, 1H).

F 4-Amino-3-[3-(S)-(7-methoxynaphthalene-2-sulfonylamino)-2-oxopyrrolidin-1-yl-methyl]benzamidine dihydrochloride 7-Methoxynaphthalene-2-sulfonic acid [1-(2-amino-5-cyano-benzyl)-2-oxopyrrolidin-3-yl]amide is converted to the title compound as described in EXAMPLE 24, Part C. The crude product is purified by RP-HPLC eluting with a gradient of 10% CH₃CN/H₂O to 60% CH₃CN/H₂O and the appropriate product fractions are lyophilized to provide the title compound as a white solid.

¹H NMR (DMSO-d₆, 300 MHz) δ8.80 (bs, 2H), 8.45 (bs, 2H), 8.35 (s, 1H), 8.10 (d, 1H), 8.00 (d, 1H), 7.90 (d, 1H), 7.70 (dd, 1H), 7.50 (m, 2H), 7.40 (d, 1H), 7.35 (dd, 1H), 6.70 (d, 1H), 6.20 (bs, 2H), 4.15 (AB, 2H), 4.10 (m, 1H), 3.90 (s, 3H), 3.12 (m, 2H), 1.98 (m, 1H), 1.55 (m, 1H). Elemental analysis calculated with 2 mmol of H₂O cal. C=47.92%, H=5.42%, N=12.15%, found C=48.00%, H=5.27%, N=12.29%.

EXAMPLE 116

4-Amino-3-[3-(S)-(7-methoxynaphthalene-2-sulfonyl-methylamino)-2-oxopyrrolidin-1-yl-methyl]benzamidine trifluoroacetate A. {1-[2-(Benzhydrylidenylamino)-5-cyano-benzyl]-2-oxopyrrolidin-3-yl}-N-methylcarbamic acid tert-butyl ester To a solution of {1-[2-(benzhydrylidenylamino)-5-cyanobenzyl]-2-oxopyrrolidin-3-yl}carbamic acid tert-butyl ester (3.94 g, 7.98 mmol) in 8 mL of DMF at 0° C. is added a 60% mineral oil dispersion of NaH (0.35 g, 8.77 mmol). After 20 minutes, methyl iodide (0.99 mL, 15.9 mmol) is added. After 2 hours, the solution is diluted with saturated NH₄Cl and EtOAc. The layers are separated. The organic layer is washed with H₂O and saturated NaCl. The organic layer is dried over MgSO₄, filtered and concentrated. The crude material is purified by column chromatography eluting with a gradient of 30% EtOAc/hexanes to 50% EtOAc/hexanes. The title compound (3.72 g, 7.31 mmol) is obtained as a yellow solid.

¹H NMR (CDCl₃, 300 MHz) δ7.70 (bs, 2H), 7.45 (m, 8H), 7.10 (bs, 2H), 6.45 (dd, 1H), 4.70 (m, 1H), 4.49 (AB, 2H), 3.30 (m, 2H), 2.83 (s, 3H), 2.35 (m, 1H), 2.10 (m, 1H), 1.50 (s, 9H). FAB MS, [M+H]⁺=509.

B. 7-Methoxynaphthalene-2-sulfonic acid [1-(2-amino-5-cyanobenzyl)-2-oxopyrrolidin-3-yl]methylamide The title compound is prepared as described in EXAMPLE 115, Part E substituting {1-[2-(benzhydrylidenylamino)-5-cyanobenzyl]-2-oxopyrrolidin-3-yl}-N-methylcarbamic acid tert-butyl ester for {1-[2-(benzhydrylidenylamino)-5-cyanobenzyl]-2-oxopyrrolidin-3-yl}carbamic acid tert-butyl ester. The title compound is obtained as a yellow solid.

¹H NMR (CDCl₃, 300 MHz) δ8.38 (s, 1H), 7.87 (d, 1H), 7.78 (d, 1H), 7.72 (dd, 1H), 7.32 (dd, 1H), 7.30 (dd, 1H), 7.28 (d, 1H), 7.23 (dd, 1H), 6.55 (d, 1H), 4.98 (s, 2H), 4.25 (AB, 2H), 4.15 (m, 1H), 3.98 (s, 3H), 3.20 (m, 2H), 2.70 (s, 3H), 1.95 (m, 1H).

C. 4-Amino-3-[3-(S)-(7-methoxynaphthalene-2-sulfonylmethylamino)-2-oxopyrrolidin-1-ylmethyl]benzamidine trifluoroacetate 7-Methoxynaphthalene-2-sulfonic acid [1-(2-amino-5-cyano-benzyl)-2-oxopyrrolidin-3-yl]methylamide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ8.90 (bs, 2H), 8.75 (bs, 2H), 8.40 (s, 1H), 8.050 (d, 1H), 7.95 (d, 1H), 7.70 (dd, 1H), 7.60 (d, 1H), 7.55 (dd, 1H), 7.48 (d, 1H), 7.39 (dd, 1H), 6.70 (d, 1H), 6.00 (bs, 1H), 4.98 (m, 1H), 4.20 (AB, 2H), 3.90 (s, 3H), 3.15 (m, 2H), 2.67 (s, 3H), 2.05 (m, 1H), 1.70 (m, 1H). FAB MS, [M+H]⁺=482. Elemental analysis calculated with 1.3 mmol of H₂O cal. C=50.49%, H=4.98%, N=11.32%, found C=50.50%, H=4.50%, N=10.99%.

EXAMPLE 117

N-(4-Carbamimidoyl-2-{3-[(7-methoxynaphthalene-2-sulfonyl)methylamino]-2-oxopyrrolidin-1-(S)-ylmethyl}phenyl)acetamide trifluroacetate A. N-(4-Cyano-2-{3-[(7-methoxynaphthalene-2-sulfonyl)methylamino]-2-oxopyrrolidin-1-ylmethyl}phenyl)acetamide To a solution of 7-methoxynaphthalene-2-sulfonic acid [1-(2-amino-5-cyano-benzyl)-2-oxopyrrolidin-3-yl]methylamide (0.28 g, 0.61 mmol), prepared as described in EXAMPLE 116, Part B, in 25 mL of CH₂Cl₂ is added triethyl amine (0.25 mL, 1.81 mmol), dimethylamino pyridine (0.01 g, 0.061 mmol), and acetyl chloride (0.43 g, 6.05 mmol). The solution is heated to 60° C. After 16 hours, The solution is cooled to ambient temperatures and diluted with EtOAc. The solution is washed with saturated NaHCO₃ and saturated NaCl. The organic layer is dried over MgSO₄, filtered and concentrated. The crude material is purified by column chromatography eluting with 20% EtOAc/CH₂Cl₂. The title compound (0.232 g, 0.49 mmol) is obtained as a white solid.

¹H NMR (CDCl₃, 300 MHz) δ9.50 (s, 1H), 8.50 (d, 1H), 8.30 (s, 1H), 7.89 (d, 1H), 7.80 (d, 1H), 7.76 (dd, 1H), 7.60 (d, 1H), 7.40 (d, 1H), 7.20 (m, 2H), 4.90 (m, 1H), 4.30 (AB, 2H), 3.90 (s, 3H), 3.30 (m, 2H), 2.75 (s, 3H), 2.35 (m, 1H), 2.05 (m, 1H), 1.90 (s, 3H).

B. N-(4-Carbamimidoyl-2-{3-[(7-methoxynaphthalene-2-sulfonyl)methyl-amino]-2-oxopyrrolidin-1-(S)-ylmethyl}phenyl)acetamide trifluroacetate N-(4-Cyano-2-{3-[(7-methoxynaphthalene-2-sulfonyl)methylamino]-2-oxopyrrolidin-1-ylmethyl}phenyl)acetamide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.70 (s, 1H), 9.23 (bs, 2H), 9.00 (bs, 1H), 8.40 (s, 1H), 8.00 (d, 1H), 7.98 (d, 1H), 7.70 (m, 2H), 7.60 (m, 2H), 7.35 (dd, 1H), 4.97 (m, 1H), 4.40 (AB, 2H), 3.90 (s, 3H), 3.20 (m, 2H), 2.68 (s, 3H), 2.10 (m, 1H), 2.00 (s, 3H), 1.80 (m, 1H). FAB MS, [M+H]⁺=524. Elemental analysis calculated with 1.5 mmol of H₂O cal. C=50.60%, H=5.00%, N=10.54%, found C=50.48%, H=4.61%, N=10.17%.

EXAMPLE 118

4-Amino-3-[3-(S)-(4-tert-butylbenzenesulfonylamino)-2-oxopyrrolidin-1-yl-methyl]benzamidine trifluoroacetate A. 4-tert-Butylbenzene-2-sulfonic acid [1-(2-amino-5-cyano-benzyl)-2-oxopyrrolidin-3-yl]amide The title compound is prepared as described in EXAMPLE 115, Part E, using 4 tert-butylbenzene sulfonyl chloride in place of 7-methoxynaphthalene sulfonyl chloride. The title compound is obtained as a yellow solid.

¹H NMR (CDCl₃, 300 MHz) δ7.80 (d, 2H), 7.55 (d, 2H), 7.35 (dd, 1H), 7.25 (d, 1H), 6.60 (d, 1H), 5.15 (s, 1H), 4.90 (s, 2H), 4.28 (AB, 2H), 3.75 (m, 1H), 3.20 (m, 2H), 2.55 (m, 1H), 2.03 (m, 1H), 1.30 (s, 9H).

B. 4-Amino-3-[3-(S)-(4-tert-butylbenzenesulfonylamino)-2-oxopyrrolidin-1-yl-methyl]benzamidine trifluoroacetate 4-tert-Butylbenzene-2-sulfonic acid [1-(2-amino-5-cyanobenzyl)-2-oxopyrrolidin-3-yl]amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ8.80 (s, 1H), 8.30 (bs, 2H), 8.05 (d, 1H), 7.80 (d, 2H), 7.60 (d, 2H), 7.50 (d, 1H), 7.40 (s, 1H), 6.70 (d, 1H), 6.20 (bs, 2H), 4.20 (AB, 2H), 4.10 (m, 1H), 3.15 (m, 2H), 2.05 (m, 1H), 1.50 (m, 1H), 1.25 (s, 9H). FAB MS, [M+H]⁺=444. Elemental analysis calculated with 0.5 mmol of excess TFA cal. C=48.86%, H=5.00%, N=11.39%, found C=49.10%, H=5.21%, N=11.56%.

EXAMPLE 119

3-Amino-5-[3-(S)-(7-methoxynaphthalene-2-sulfonylamino)-2-oxopyrrolidin-1-yl-methyl]benzamidine bistrifluoroacetate A. 3-Amino-5-methylbenzonitrile The title compound is prepared as described in EXAMPLE 115, Part A using 3-methyl-5-nitro-benzonitrile as the starting material.

¹H NMR (CDCl₃, 300 MHz) δ6.83 (s, 1H), 6.70 (s, 1H), 6.68 (s, 1H), 3.70 (bs, 2H), 2.30 (s, 3H).

B. 3-(Benzhydrylidenylamino)-5-methylbenzonitrile

The title compound is prepared as described in EXAMPLE 115, Part B, using 3-amino-5-methylbenzonitrile in place of 4-amino-3-methylbenzonitrile.

¹H NMR (CDCl₃, 300 MHz) δ7.73 (d, 2H), 7.45 (m, 2H), 7.30 (m, 4H), 7.05 (dd, 2H), 7.00 (s, 1H), 6.78 (s, 2H), 6.71 (s, 1H), 2.20 (s, 3H). EI MS, [M]⁺=296.

C. 3-(Benzhydrylidenylamino)-5-bromomethylbenzonitrile

The title compound is prepared as described in EXAMPLE 115, Part C using 3-(benzhydrylidenylamino)-5-methylbenzonitrile as the starting material.

¹H NMR (CDCl₃, 300 MHz) δ7.75 (d, 2H), 7.50 (m, 1H), 7.40 (m, 2H), 7.30 (m, 4H), 7.05 (m, 2H), 6.95 (s, 1H), 6.89 (s, 1H), 4.30 (s, 2H). EI MS, [M]⁺=374.

D. {1-[3-(Benzhydrylidenylamino)-5-cyano-benzyl]-2-oxopyrrolidin-3-yl}-carbamic acid tert-butyl ester The title compound is prepared as described in EXAMPLE 23, Part B substituting 3-(benzhydrylidenylamino)-5-bromomethylbenzonitrile for α-bromo-m-toluyl nitrile. The crude material is purified by column chromatography eluting with a gradient of 30% EtOAc/hexanes to 40% EtOAc/hexanes. The title compound is obtained as a yellow solid.

¹H NMR (CDCl₃, 300 MHz) δ7.75 (d, 2H), 7.50 (m, 1H), 7.40 (m, 2H), 7.30 (m, 4H), 7.10 (m, 1H), 6.95 (s, 1H), 6.65 (s, 1H), 5.10 (bs, 1H), 4.30 (AB, 2H), 4.05 (m, 1H), 3.85 (m, 2H), 2.55 (m, 1H), 1.75 (m, 1H), 1.40 (s, 9H). EI MS, [M]⁺=495.

E. 7-Methoxynaphthalene-2-sulfonic acid [1-(3-benzhydrylidenylamino-5-cyanobenzyl)-2-oxopyrrolidin-3-yl]amide The title compound is prepared as in EXAMPLE 115, Part E, substituting {1-[3-(benzhydrylidenylamino)-5-cyanobenzyl]-2-oxopyrrolidin-3-yl}carbamic acid tert-butyl ester for {1-[2-(benzhydrylidenylamino)-5-cyanobenzyl]-2-oxopyrrolidin-3-yl}carbamic acid tert-butyl ester.

¹H NMR (CDCl₃, 300 MHz) δ8.35 (s, 1H), 7.90 (d, 1H), 7.80 (d, 1H), 7.75 (dd, 1H), 7.70 (d, 2H), 7.50 (m, 1H), 7.40 (m, 2H), 7.25 (m, 5H), 7.00 (m, 4H), 6.55 (s, 1H), 5.25 (s, 1H), 4.25 (AB, 2H), 3.95 (s, 3H), 3.65 (m, 1H), 2.80 (m, 2H), 2.45 (m, 1H), 1.95 (m, 1H). FAB MS, [M+H]⁺=615.

F. 3-Amino-5-[3-(S)-(7-methoxynaphthalene-2-sulfonylamino)-2-oxopyrrolidin-1-yl-methyl]benzamidine bistrifluoroacetate 7-Methoxynaphthalene-2-sulfonic acid [1-(3-benzhydrylidenylamino-5-cyano-benzyl)-2-oxopyrrolidin-3-yl]amide is converted to the title compound as described in EXAMPLE 24, Part C. The crude product is purified by RP-HPLC eluting with a gradient of 10% CH₃CN/H₂O (0.1% TFA) to 60% CH₃CN/H₂O (0.1% TFA) and the appropriate product fractions are lyophilized to provide the title compound as a white solid.

¹H NMR (DMSO-d₆, 300 MHz) δ9.15 (s, 1H), 9.00 (bs, 2H), 8.35 (s, 1H), 8.20 (d, 1H), 8.05 (d, 1H), 7.95 (d, 1H), 7.70 (dd, 1H), 7.60 (d, 1H), 7.20 (dd, 1H), 6.70 (s, 1H), 6.65 (s, 1H), 6.60 (s, 1H), 5.80 (bs, 2H), 4.20 (AB, 2H), 4.10 (m, 1H), 3.90 (s, 3H), 3.00 (m, 2H), 2.00 (m, 1H), 1.50 (m, 1H). FAB MS, [M+H]⁺=468. Elemental analysis calculated with 1 mmol of excess TFA cal. C=43.02%, H=3.49%, N=8.65%, found C=43.51%, H=3.82%, N=8.89%.

EXAMPLE 120

{4-(Aminoiminomethyl)-2-[3-(7-methoxynaphthalene-2-sulfonylamino)-2-oxopyrrolidin-1-ylmethyl]phenoxy}acetic acid methyl ester trifluoroacetate A. 4-Hydroxy-3-methylbenzonitrile To a solution of 4-bromo-3-methylbenzonitrile (7.07 g, 36.1 mmol) in 225 mL of THF at −78° C. is added a 1.7 M solution of tert-butyl lithium (45.6 mL, 77.6 mmol) in pentane. After 5 minutes, CuBr.SMe₂ (15.9 g, 77.6 mmol) is added. The resulting solution is stirred for 10 minutes, then O₂ is slowly bubbled through the reaction mixture for 30 minutes. After this time, the solution is allowed to warm to ambient temperatures. The solution is stirred for 16 hours. The solution is then poured into 100 mL of H₂O. The solution is diluted with EtOAc. The layers are separated. The organic layer is washed with saturated (NH₄)₂SO₄ solution. The organic layer is then extracted with 10 N NaOH. The collected aqueous basic layers are acidified to pH=6 with 6N HCl. The solution is then extracted with EtOAc. The combined organic layers are dried over MgSO₄, filtered and concentrated. The title compound is obtained as a solid.

¹H NMR (CDCl₃, 300 MHz) δ9.00 (s, 1H), 7.45 (s, 1H), 7.40 (d, 1H), 6.80 (d, 1H), 2.26 (s, 3H). EI MS, [M]⁺=133.

B. (4-Cyano-2-methylphenoxy)acetic acid methyl ester

Methyl bromoacetate (0.56 mL, 5.92 mmol) is added to a solution of phenol (0.70 g, 5.29 mmol), K₂CO₃ (1.6 g, 11.6 mmol) and tetrabutyl ammonium iodide (0.57 g, 1.53 mmol) in 30 mL of DMF. The resulting solution is heated to 80° C. for 16 hours. The solution is then cooled to ambient temperatures. The solution is diluted with EtOAc. The resulting solution is washed with H₂O and saturated NaCl. The organic layer is dried over MgSO₄, filtered and concentrated. The crude product is purified by column chromatography eluting with a gradient of 10% EtOAc/hexanes to 50% EtOAc/hexanes to afford the title compound (1.4 g, 0.8 mmol).

¹H NMR (CDCl₃, 300 MHz) δ7.45 (m, 2H), 6.70 (d, 1H), 4.68 (s, 2H), 3.80 (s, 2H), 2.25 (s, 3H). EI MS, [M]⁺=205.

C. (2-Bromomethyl-4-cyanophenoxy)acetic acid methyl ester

The title compound is prepared as described in EXAMPLE 115, Part C, substituting (4-cyano-2-methylphenoxy)acetic acid methyl ester for 4-(benzhydrylidenylamino)-3-methylbenzonitrile. The title compound is obtained as a white solid.

$^1$H NMR (CDCl$_3$, 300 MHz) δ7.65 (d, 1H), 7.55 (dd, 1H), 6.80 (d, 1H), 4.80 (s, 2H), 4.55 (s, 2H), 3.80 (s, 3H). EI MS, [M]$^+$=283.

D. [2-(3-tert-Butyoxycarbonylamino-2-oxopyrrolidin-1-ylmethyl)-4-cyano-phenoxy]acetic acid methyl ester The title compound is prepared as described in EXAMPLE 23, Part B, substituting (2-bromomethyl-4-cyanophenoxy)acetic acid methyl ester for α-bromo-m-toluylnitrile. The title compound is obtained as a white solid.

$^1$H NMR (CDCl$_3$, 300 MHz) δ7.55 (m, 2H), 6.78 (d, 1H), 5.10 (bs, 1H), 4.70 (s, 2H), 4.55 (AB, 2H), 4.15 (m, 1H), 3.80 (s, 3H), 3.20 (m, 2H), 2.60 (s, 2H), 1.90 (m, 1H), 1.58 (s, 9H).

E. {4-Cyano-2-[3-(7-methoxynaphthalene-2-sulfonylamino)-2-oxopyrrolidin-1-ylmethyl]phenoxy}acetic acid methyl ester The title compound is prepared as described in Example 115, Part E substituting (2-bromomethyl-4-cyanophenoxy)acetic acid methyl ester for {1-[2-(benzhydrylidenylamino)-5-cyanobenzyl]-2-oxopyrrolidin-3-yl}carbamic acid tert-butyl ester. The title compound is obtained as a white foam.

$^1$H NMR (CDCl$_3$, 300 MHz) δ8.35 (s, 1H), 7.90 (d, 1H), 7.75 (dd, 1H), 7.55 (dd, 1H), 7.42 (d, 1H), 7.30 (dd, 1H), 7.20 (m, 1H), 6.70 (d, 1H), 5.40 (d, 1H), 4.65 (s, 2H), 3.95 (s, 3H), 3.70 (m, 1H), 3.20 (m, 2H), 2.50 (m, 1H), 2.05 (m, 1H). FAB MS, [M+H]$^+$=524.

F. {4-(Aminoiminomethyl)-2-[3-(7-methoxynaphthalene-2-sulfonylamino)-2-oxopyrrolidin-1-ylmethyl]phenoxy}acetic acid methyl ester trifluoroacetate The title compound is prepared as described in EXAMPLE 32, Part C, substituting {4-cyano-2-[3-(7-methoxynaphthalene-2-sulfonylamino)-2-oxopyrrolidin-1-ylmethyl]phenoxy}acetic acid methyl ester for of 7-benzyloxynaphthalene-2-sulfonic acid [1-(3-cyanobenzyl)-2-oxopyrrolidin-3-(S)-yl]amide. The title compound is obtained as a white solid.

1H NMR (DMSO-d$_6$, 300 MHz) δ9.00 (bs, 4H), 8.30 (s, 1H), 7.97 (d, 1H), 7.90 (d, 1H), 7.65 (m, 2H), 7.50 (s, 1H), 7.37 (s, 1H), 7.25 (dd, 1H), 7.10 (d, 1H), 4.95 (AB, 2H), 4.30 (AB, 2H), 4.05 (m, 1H), 3.80 (s, 3H), 3.60 (s, 3H), 3.15 (m, 2H), 1.95 (m, 1H), 1.55 (m, 1H). FAB MS, [M+H]$^+$=541. Elemental analysis calculated with 3.4 mmol of H$_2$O cal. C=46.98%, H=5.04%, N=7.83%, found C=46.99%, H=4.84%, N=8.10%.

EXAMPLE 121

{4-(Aminoiminomethyl)-2-[3-(7-methoxynaphthalene-2-sulfonylamino)-2-oxopyrrolidin-1-ylmethyl]phenoxy}acetic acid trifluoroacetate To a solution of {4-(aminoiminomethyl)-2-[3-(7-methoxynaphthalene-2-sulfonylamino)-2-oxopyrrolidin-1-ylmethyl]-phenoxy}-acetic acid methyl ester trifluoroacetate (0.1 g, 0.18 mmol), prepared as in EXAMPLE 120, Part F, in 2 mL of EtOH is added 10 N NaOH (0.05 mL). The solution is stirred for 5 hours. After this time, the solution is concentrated. The residue is dissolved in 2 mL of H$_2$O and the pH is adjusted to 3 using 1 N HCl. The solid which forms is collected by filtration. The solid is purified by RP-HPLC eluting with a gradient of 10% CH$_3$CN/H$_2$O (0.1% TFA) to 100% CH$_3$CN. The appropriate fraction are lyophilized to afford the title compound (0.05 g, 0.7 mmol) as a white solid.

$^1$H NMR (DMSO-d$_6$, 300 MHz) δ9.10 (bs, 2H), 8.70 (bs, 2H), 8.35 (s, 1H), 8.15 (d, 1H), 8.00 (d, 1H), 7.90 (d, 1H), 7.70 (m, 2H), 7.50 (s, 1H), 7.45 (s, 1H), 7.30 (m, 1H), 7.10 (m, 1H), 4.85 (s, 1H), 4.30 (AB, 2H), 4.05 (m, 1H), 3.80 (s, 3H), 3.10 (m, 2H), 1.95 (m, 1H), 1.55 (m, 1H). FAB MS, [M+H]$^+$=527. Elemental analysis cal., C=46.16%, H=3.74%, N=7.42%, found C=45.98%, H=3.87%, N=7.75%.

EXAMPLE 122

4-(3-Amino-2-oxo-pyrrolidine-1-ylmethyl)thiophene-2-carbonitrile hydrochloride

A. 5-Iodothiophene-3-carboxaldehyde

To a solution of thiophene-3-carboxaldehyde (36 g, 321 mmol) in 80 mL of CCl$_4$ and 60 mL of H$_2$O is added 2.5 mL of conc. H$_2$SO$_4$ in 160 mL of acetic acid. To the resulting solution is added HIO$_3$ (14 g, 80 mmol) and I$_2$ (38 g, 150 mmol). The solution is refluxed for 6 hours. After this time, the reaction is cooled to ambient temperatures and 200 mL of CHCl$_3$ is added. The layers are separated. The aqueous layer is extracted with CHCl$_3$. The organic layers are combined and washed with 0.5 M Na$_2$S$_2$O$_3$, sat. NaHCO$_3$ and sat. NaCl. The organic layer is dried over MgSO$_4$, filtered and concentrated. The crude product is purified by column chromatography eluting with gradient of 2% EtOAc/hexanes to 5% EtOAc/hexanes to afford the title compound (20 g, 84 mmol) as a white solid.

$^1$H NMR (CDCl$_3$, 300 MHz) δ9.78 (s, 1H), 8.10 (s, 1H), 7.69 (s, 1H).

B. (5-Iodothiophene-3-yl)methanol

To a solution of 5-odothiophene-3-carboxaldehyde (42 g, 176 mmol) in 800 mL of THF is added NaBH$_4$ (7 g, 185 mmol). After 1 hour, the reaction is quenched by the addition of 100 mL of sat. NH$_4$Cl. The resulting solution is diluted with 1 L of EtOAc. The layers are separated. The organic layer is washed with H$_2$O and sat. NaCl. The organic layer is dried over MgSO$_4$, filtered and concentrated. The title compound (42 g, 175 mmol) is obtained as an oil.

$^1$H NMR (CDCl$_3$, 300 MHz) δ7.18 (s, 2H), 4.63 (s, 2H), 1.92 (bs, 1H).

C. 4-Hydroxymethylthiophene-2-carbonitrile

To a solution of (5-iodothiophene-3-yl)methanol (42 g, 176 mmol) in 150 mL of DMF is added Zn(CN)$_2$ (12.4 g, 106 mmol) and Pd(PPh$_3$)$_4$ (8.13 g, 7.04 mmol). The solution is heated to 80° C. After 6 hours, the solution is diluted with 3 L of EtOAc. The resulting solution is washed with 1 N NH$_4$OH, H$_2$O and sat. NaCl. The organic layer is dried over MgSO$_4$, filtered and concentrated. The crude product is purified by column chromatography eluting with gradient of 20% EtOAc/hexanes to 30% EtOAc/hexanes to afford the title compound (10 g, 72 mmol) as a clear oil.

$^1$H NMR (CDCl$_3$, 300 MHz) δ7.59 (s, 1H), 7.46 (s, 1H), 4.67 (s, 2H), 2.42 (bs, 1H).

D. 4-Bromomethylthiophene-2-carbonitrile

To a solution of 4-hydroxymethylthiophene-2-carbonitrile (10 g, 72 mmol), in 360 mL of THF is added triphenyl phosphine (18.3 g, 76 mmol) and CBr$_4$ (25 g, 76 mmol). After 3 hours, the solution is filtered and concentrated. The crude product is purified by column chromatography eluting with gradient of 5% EtOAc/hexanes to 10% EtOAc/hexanes to afford the title compound (14 g, 69 mmol) as a white solid.

$^1$H NMR (CDCl$_3$, 300 MHz) δ7.62 (s, 1H), 7.49 (s, 1H), 4.42 (s, 2H).

E. (2-Oxopyrrolidin-3-(S)-yl)carbamic acid tert-butyl ester (S)-Boc-Diaminobutyric acid (25 g, 115 mmol), triethyl amine (35 g, 344 mmol), and hydroxybenzotriazole (19.3 g, 143 mmol) are dissolved in 300 mL of THF. 1-(3-Dimethylaminopropyl)-3-ethylcarbodiiimide hydrochloride (27.4 g, 143 mmol) is added to the solution. The solution is heated to 60° C. over 15 minutes. A white precipitate forms and the solution is kept at 60° C. for 4 hours. After this time, the solution is filtered and the collected liquid is concentrated. The crude product is purified by column chromatography in a gradient of 1% MeOH/CH$_2$Cl$_2$ to 3% MeOH/CH$_2$Cl$_2$ to afford the title compound (19.6 g, 98 mmol) as a white solid.

$^1$H NMR (CDCl$_3$, 300 MHz) δ6.17 (bs, 1H), 5.08 (bs, 1H), 4.12 (m, 1H), 3.33 (m, 2H), 2.65 (m, 1H), 2.00 (m, 1H), 1.42 (s, 9H).

F. [1-(5-Cyanothiophene-3-ylmethyl)-2-oxopyrrolidin-3-yl] carbamic acid tert-butyl ester To a solution of (2-oxopyrrolidin-3-(S)-yl)carbamic acid tert-butyl ester (3.2 g, 16 mmol) in 80 mL of THF:DMF (10:1) at 0° C. is added 4-bromomethylthiophene-2-carbonitrile (3.23 g, 16 mmol) and sodium hydride (60%) (0.67 g, 16.8 mmol). After addition, the solution is allowed to warm to ambient temperatures. After 2 hours, the solution is quenched by the addition of sat NH$_4$Cl. The solution is diluted with H$_2$O and EtOAc. The layers are separated. The organic layer is washed with H$_2$O and sat. NaCl. The organic layer is dried over MgSO$_4$, filtered and concentrated. The crude product is purified by column chromatography eluting with gradient of 20% EtOAc/CH$_2$Cl$_2$ to 30% EtOAc/CH$_2$Cl$_2$ to afford the title compound (4 g, 13.8 mmol) as a white solid.

$^1$H NMR (CDCl$_3$, 300 MHz) δ7.51 (s, 1H), 7.45 (s, 1H), 5.12 (bs, 1H), 4.42 (AB, 2H), 4.12 (m, 1H), 3.27 (m, 2H), 2.58 (m, 1H), 1.93 (m, 1H), 1.42 (s, 9H).

G. 4-(3-Amino-2-oxopyrrolidine-1-ylmethyl)thiophene-2-carbonitrile hydrochloride

[1-(5-Cyanothiophene-3-ylmethyl)-2-oxopyrrolidin-3-yl] carbamic acid tert-butyl ester (4 g, 13.8 mmol) is added to a solution of 100 mL of EtOAc sat. with HCl gas at 0° C. After 3 hours, the solution is concentrated. The title compound (3.3 g, 13.5 mmol) is obtained as a white solid.

$^1$H NMR (DMSO-d$_6$, 300 MHz) δ8.61 (bs, 3H), 7.96 (s, 1H), 7.82 (s, 1H), 5.12 (bs, 1H), 4.42 (AB, 2H), 4.00 (m, 1H), 3.27 (m, 2H), 2.31 (m, 1H), 2.03 (m, 1H).

EXAMPLE 123

5-(3-Amino-2-oxopyrrolidine-1-ylmethyl)thiophene-2-carbonitrile hydrochloride

A. (5-Bromothiophene-2-yl)methanol

To a solution of 5-bromothiophene-2-carboxaldehyde (15 g, 79 mmol) in 250 mL of THF is added NaBH$_4$ (3 g, 86 mmol). After 1 hour, the reaction is quenched by the addition of 100 mL of sat. NH$_4$Cl. The resulting solution is diluted with Et$_2$O. The layers are separated. The organic layer is washed with H$_2$O and sat. NaCl. The organic layer is dried over MgSO$_4$, filtered and concentrated. The crude product is purified by column chromatography eluting with gradient of 5% EtOAc/hexanes to 10% EtOAc/hexanes to afford the title compound (13.7 g, 71 mmol) as an oil.

$^1$H NMR (CDCl$_3$, 300 MHz) δ6.91 (d, 1H), 6.74 (d, 1H), 4.72 (s, 2H), 2.16 (bs, 1H).

B. 5-Hydroxymethylthiophene-2-carbonitrile

The title compound is prepared as described in EXAMPLE 122, Part C using (5-bromothiophene-2-yl) methanol as the starting material. The crude product is purified by column chromatography eluting with gradient of 20% EtOAc/hexanes to 30% EtOAc/hexanes to afford the title compound as a clear oil.

$^1$H NMR (CDCl$_3$, 300 MHz) δ7.52 (d, 1H), 6.97 (d, 1H), 4.87 (s, 2H), 2.26 (bs, 1H).

C. 5-Bromomethylthiophene-2-carbonitrile

The title compound is prepared as described in EXAMPLE 122, Part D using 5-hydroxymethylthiophene-2-carbonitrile as the starting material. The crude product is purified by column chromatography eluting with gradient of 10% EtOAc/hexanes to 20% EtOAc/hexanes to afford the title compound as a white solid.

$^1$H NMR (CDCl$_3$, 300 MHz) δ7.49 (d, 1H), 7.09 (d, 1H), 4.66 (s, 2H).

D. [1-(5-Cyanothiophene-2-ylmethyl)-2-oxopyrrolidin-3-yl]carbamic acid tert-butyl ester The title compound is prepared as described in EXAMPLE 122, Part F using 5-bromomethylthiophene-2-carbonitrile in place of 4-bromomethylthiophene-2-carbonitrile. The crude product is purified by column chromatography eluting with gradient of 10% EtOAc/CH$_2$Cl$_2$ to 30% EtOAc/CH$_2$Cl$_2$ to afford the title compound as a white solid.

$^1$H NMR (CDCl$_3$, 300 MHz) δ7.51 (d, 1H), 6.98 (d, 1H), 5.09 (bs, 1H), 4.64 (AB, 2H), 4.17 (m, 1H), 3.30 (m, 2H), 2.62 (m, 1H), 1.93 (m, 1H), 1.43 (s, 9H).

E. 5-(3-Amino-2-oxopyrrolidine-1-ylmethyl)thiophene-2-carbonitrile hydrochloride The title compound is prepared as described in EXAMPLE 122, Part G using [1-(5-cyanothiophene-2-ylmethyl)-2-oxopyrrolidin-3-yl]carbamic acid tert-butyl ester as the starting material. The title compound is obtained as a white solid.

$^1$H NMR (DMSO-d$_6$, 300 MHz) δ8.59 (bs, 3H), 7.90 (d, 1H), 7.62 (d, 1H), 5.10 (bs, 1H), 4.63 (AB, 2H), 4.10 (m, 1H), 3.25 (m, 2H), 2.28 (m, 1H), 2.05 (m, 1H).

EXAMPLE 124

5-(3-Amino-2-oxopyrrolidine-1-ylmethyl)thiophene-3-carbonitrile hydrochloride

A. (4-Bromothiophene-2-yl)methanol

The title compound is prepared as described in EXAMPLE 123, Part A using 4-bromothiophene-2-carboxaldehyde as the starting material. The title compound is obtained as a clear oil.

EI MS, [M]$^+$=192.

B. 5-Hydroxymethylthiophene-3-carbonitrile

The title compound is prepared as described in EXAMPLE 122, Part C using (4 bromothyiophene-2-yl) methanol as the starting material. The crude product is purified by column chromatography eluting with gradient of 20% EtOAc/hexanes to 40% EtOAc/hexanes to afford the title compound as a clear oil.

$^1$H NMR (CDCl$_3$, 300 MHz) δ7.83 (s, 1H), 7.12 (s, 1H), 4.80 (AB, 2H), 2.27 (bs, 1H). EI MS, [M]$^+$=139.

C. 5-Bromomethylthiophene-3-carbonitrile

The title compound is prepared as described in EXAMPLE 122, Part D using 5-hydroxymethylthiophene-3-carbonitrile as the starting material. The crude product is purified by column chromatography eluting with gradient of 5% EtOAc/ hexanes to 15% EtOAc/hexanes to afford the title compound as a white solid.

$^1$H NMR (CDCl$_3$, 300 MHz) δ7.91 (d, 1H), 7.27 (d, 1H), 4.65 (s, 2H).

D. [1-(4-Cyanothiophene-2-ylmethyl)-2-oxopyrrolidin-3-yl]carbamic acid tert-butyl ester The title compound is prepared as described in EXAMPLE 122, Part F using 5-bromomethylthiophene-3- carbonitrile in place of 4-bromomethylthiophene-2-carbonitrile. The crude product is purified by column chromatography eluting with gradient of 20% EtOAc/CH$_2$Cl$_2$ to 40% EtOAc/CH$_2$Cl$_2$ to afford the title compound as a white solid.

$^1$H NMR (CDCl$_3$, 300 MHz) δ7.86 (s, 1H), 7.14 (s, 1H), 5.09 (bs, 1H), 4.62 (AB, 2H), 4.16 (m, 1H), 3.30 (m, 2H), 2.62 (m, 1H), 1.90 (m, 1H), 1.42 (s, 9H).

E. 5-(3-Amino-2-oxopyrrolidine-1-ylmethyl)thiophene-3-carbonitrile hydrochloride The title compound is prepared as described in EXAMPLE 122, Part G using [1-(4-cyanothiophene-2-ylmethyl)-2-oxopyrrolidin-3-yl]carbamic acid tert-butyl ester as the starting material. The title compound is obtained as a white solid.

$^1$H NMR (CDCl$_3$, 300 MHz) δ8.72 (bs, 3H), 7.81 (s, 1H), 7.35 (s, 1H), 5.10 (bs, 1H), 4.63 (AB, 2H), 4.40 (m, 1H), 3.38 (m, 2H), 2.62 (m, 1H), 2.50 (m, 1H).

EXAMPLE 125

4-[3-(S)-(7-Methoxynaphthalene-2-sulfonylamino)-2-oxopyrrolidin-1-ylmethyl]thiophene-2-carboxamidine trifluoroacetate A. 7-Methoxynaphthalene-2-sulfonic acid, sodium salt To a suspension of 7-hydroxynaphthalene-2-sulfonic acid, sodium salt (10 g, 40.2 mmol) in 150 mL of 2:1 H$_2$O/ethanol is added solid NaOH (1.79 g, 44.7 mmol) at room temperature. The mixture is stirred until a homogenous solution forms, and dimethyl sulfate (4.23 mL, 44.7 mmol) is then added. A precipitate eventually forms and the mixture is stirred over a period of 16 hours. The crude mixture is concentrated in vacuo and the residue is stirred in 100 mL of absolute EtOH as a slurry for 2 hours. The precipitate is filtered and dried. The solid is heated at reflux in 100 mL of 95% EtOH for 2 hours, allowed to cool to room temperature, filtered and dried to give 8.12 g of the title compound.

$^1$H NMR (DMSO-d$_6$, 300 MHz) δ8.07 (s, 1H), 7.78 (m, 2H), 7.54 (dd, 1H), 7.38 (s, 1H), 7.14 (dd, 1H), 3.86 (s, 3H)

B. 7-Methoxynaphthalene-2-sulfonyl chloride

A mixture of 7-methoxynaphthalene-2-sulfonic acid, sodium salt (8.12 g, 31.1 mmol) in 80 mL of thionyl chloride is heated at 80° C. for 3 hours. A few drops of DMF is added with vigorous bubbling resulting and the mixture is heated for an additional 1.5 hours. The mixture is allowed to cool to room temperature and concentrated in vacuo. The residue is diluted in EtOAc and washed successively with water (2×), 1 N HCl solution and saturated NaCl. The organic layer is dried over anhydrous MgSO$_4$, filtered and concentrated. The crude product is purified by column chromatography eluting with 20% EtOAc/hexanes to afford the title compound (5.2 g, 20.2 mmol) as a white solid.

$^1$H NMR (CDCl$_3$, 300 MHz) d 8.49 (d, 1H), 7.96 (d, 1H), 7.85 (d, 2H), 7.39 (dd, 1H), 7.29 (d, 1H), 3.99 (s, 3H). EI MS, [M]$^+$=256.

C. 7-Methoxynaphthalene-2-sulfonic acid-[1-(5-cyanothiophen-3-ylmethyl)-2-oxopyrrolidin-3-(S)-yl]amide To a solution of 4-(3-Amino-2-oxopyrrolidine-1-ylmethyl)thiophene-2-carbonitrile hydrochloride (0.43 g, 1.8 mmol), prepared as in EXAMPLE 122, in 10 mL of CH$_2$Cl$_2$is added 7-methoxynaphthalene-2-sulfonyl chloride (0.51 g, 2 mmol) and triethyl amine (0.55 g, 5.4 mmol). After 16 hours, the solution is diluted with EtOAc and H$_2$O. The layers are separated. The organic layer is washed with 1 N HCl, sat. NaHCO$_3$ and sat. NaCl. The organic layer is dried over MgSO$_4$, filtered and concentrated. The crude product is purified by column chromatography eluting with gradient of 10% EtOAc/CH$_2$Cl$_2$ to 20% EtOAc/CH$_2$Cl$_2$ to afford the title compound (0.50 g, 1.22 mmol) as a white solid.

$^1$H NMR (CDCl$_3$, 300 MHz) δ8.32 (s, 1H), 7.90 (d, 1H), 7.82 (d, 1H), 7.73 (dd, 1H), 7.42 (s, 1H), 7.36 (s, 1H), 7.30 (dd, 1H), 7.26 (m, 1H), 5.33 (bs, 1H), 4.29 (AB, 2H), 3.95 (s, 3H), 3.70 (m, 1H), 3.22 (m, 2H), 2.61 (m, 1H), 2.08 (m, 1H).

D. 4-[3-(S)-(7-Methoxynaphthalene-2-sulfonylamino)-2-oxopyrrolidin-1-ylmethyl]thiophene-2-carboxamidine trifluoroacetate To a solution of 7-methoxynaphthalene-2-sulfonic acid-[1-(5-cyanothiophen-3-ylmethyl)-2-oxopyrrolidin-3-(S)-yl]amide (0.3 g, 0.73 mmol) in 20 mL of EtOAc:CH$_2$Cl$_2$ (2:1) at 0° C. is bubbled HCl gas for 5 minutes. After 5 hours, the solution is concentrated. The resulting residue is dissolved in 20 mL of MeOH and cooled to 0° C. Ammonia gas is bubbled into the solution for 5 minutes. After this time the solution is heated to 50° C. for 3 hours. The solution is then concentrated. The resulting crude material is purified by RP-HPLC eluting with a gradient of 10% CH$_3$CN/H$_2$O (0.1% TFA) to 60% CH$_3$CN/H$_2$O (0.1% TFA) and the appropriate product fractions are lyophilized to provide the title compound (0.13 g, 0.23 mmol) as a white solid.

$^1$H NMR (DMSO-d$_6$, 300 MHz) δ9.26 (bs, 2H), 9.07 (bs, 2H), 8.33 (bs, 1H), 8.16 (d, 1H), 7.98 (d, 1H), 7.91 (d, 1H), 7.82 (s, 1H), 7.69 (dd, 1H), 7.53 (s, 1H), 7.30 (dd, 1H), 4.31 (AB, 2H), 4.08 (m, 1H), 3.87 (s, 3H), 3.06 (m, 2H), 3.06 (m, 2H), 1.95 (m, 1H), 1.55. FAB MS, [M+H]$^+$=458. Elemental analysis calculated with 1 mmol of H$_2$O and 1.5 mmol of excess TFA cal. C=45.64%, H=4.07%, N=8.87%, found C=45.88%, H=3.97%, N=9.12%.

EXAMPLE 126

4-{3-(S)-[(7-Methoxynaphthalene-2-sulfonyl)methylamino]-2-oxopyrrolidin-1-ylmethyl}thiophene-2-carboxamidine trifluoroacetate A. 7-Methoxynaphthalene-2-sulfonic acid-[1-(5-cyanothiophen-3-ylmethyl)-2-oxopyrrolidin-3-(S)-yl]methylamide To a solution of 7-methoxynaphthalene-2-sulfonic acid-[1-(5-cyanothiophen-3-ylmethyl)-2-oxopyrrolidin-3-(S)-yl]amide (2.36 g, 5.35 mmol), prepared as in EXAMPLE 125, Part C, in 16 mL of DMF is added MeI (1.14 g, 8.03 mmol) and K$_2$CO$_3$ (1.11 g, 8.03 mmol). After 16 hours, the solution is diluted with EtOAc and H$_2$O. The layers are separated. The organic layer is washed with H$_2$O and sat. NaCl. The organic layer is dried over MgSO$_4$, filtered and concentrated. The crude product is purified by column chromatography eluting with gradient of 5% EtOAc/CH$_2$Cl$_2$ to 15% EtOAc/CH$_2$Cl$_2$to afford the title compound (2.30 g, 5.05 mmol) as a white solid.

$^1$H NMR (CDCl$_3$, 300 MHz) δ8.40 (s, 1H), 7.91 (d, 1H), 7.82 (s, 1H), 7.78 (s, 1H), 7.46 (s, 1H), 7.39 (s, 1H), 7.27 (m, 2H), 4.88 (t, 1H), 4.40 (AB, 2H), 3.95 (s, 3H), 3.26 (m, 2H), 2.80 (s, 3H), 2.38 (m, 1H), 2.05 (m, 1H).

B. 4-{3-(S)-[(7-Methoxynaphthalene-2-sulfonyl)methylamino]-2-oxopyrrolidin-1-ylmethyl}thiophene-2-carboxamidine trifluoroacetate 7-Methoxynaphthalene-2-sulfonic acid-[1-(5-cyanothiophen-3-ylmethyl)-2-oxopyrrolidin-3-(S)-yl] methylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.24 (bs, 2H), 8.97 (bs, 2H), 8.39 (s, 1H), 8.02 (d, 1H), 7.95 (d, 1H), 7.91 (s, 1H), 7.80 (s, 1H), 7.68 (dd, 1H), 7.55 (s, 1H), 7.32 (dd, 1H), 4.86 (t, 1H), 4.37 (AB, 2H), 3.87 (s, 3H), 3.46 (m, 1H), 3.14 (m, 1H), 2.46 (s, 3H), 1.95 (m, 1H), 1.74 (m, 1H). FAB MS, [M+H]$^+$=473. Elemental analysis calculated with 1.5 mmol of H$_2$O cal. C=46.98%, H=4.60%, N=9.13%, found C=46.86%, H=3.97%, N=4.29%.

EXAMPLE 127

2-[[1-(5-Carbamimidoylthiophene-3-ylmethyl)-2-oxopyrrolidin-3-(S)-yl](7-methoxynaphthalene-2-sulfonyl)amino]acetamide trifluoroacetate A. 2-[[1-(5-Cyanothiophene-3-ylmethyl)-2-oxopyrrolidin-3-(S)-yl](7-methoxynaphthalene-2-sulfonyl)amino]acetic acid tert-butyl ester The title compound is prepared as in EXAMPLE 126, Part A using tert-butyl-bromoacetate in place of MeI to give the title compound as a white foam.

$^1$H NMR (CDCl$_3$, 300 MHz) δ8.42 (s, 1H), 7.78 (m, 3H), 7.48 (s, 1H), 7.39 (s, 1H), 7.25 (m, 2H), 4.52 (t, 1H), 4.40 (AB, 2H), 4.22 (AB, 2H), 3.95 (s, 3H), 3.26 (m, 2H), 2.52 (m, 1H), 2.42 (m, 1H), 1.43 (s, 9H).

B. 2-[[1-(5-Cyanothiophene-3-ylmethyl)-2-oxopyrrolidin-3-(S)-yl](7-methoxynaphthalene-2-sulfonyl)amino]acetic acid To a solution of 2-[[1-(5-cyanothiophene-3-ylmethyl)-2-oxopyrrolidin-3-(S)-yl]-(7-methoxynaphthalene-2-sulfonyl)amino]acetic acid tert-butyl ester (0.40 g, 0.72 mmol) in 15 mL of CH$_2$Cl$_2$ is added 5 mL of TFA. After 2 hours, the solution is concentrated to give the title compound as a white foam.

$^1$H NMR (CDCl$_3$, 300 MHz) δ8.36 (s, 1H), 7.91 (d, 1H), 7.80 (d, 1H), 7.68 (d, 1H), 7.50 (s, 2H), 7.31 (m, 1H), 7.25 (m, 1H), 7.14 (m, 1H), 4.73 (t, 1H), 4.47 (s, 2H), 3.95 (s, 3H), 3.92 (AB, 2H), 3.32 (m, 2H), 2.42 (m, 1H), 2.13 (m, 1H).

C. 2-[[1-(5-Cyanothiophene-3-ylmethyl)-2-oxopyrrolidin-3-(S)-yl](7-methoxynaphthalene-2-sulfonyl)amino]acetamide To a solution of 2-[[1-(5-cyanothiophene-3-ylmethyl)-2-oxopyrrolidin-3-(S)-yl]-(7-methoxynaphthalene-2-sulfonyl)amino]acetic acid (0.40 g, 0.80 mmol) in 6 mL of THF at −15° C. is added triethyl amine (0.10 g, 0.96 mmol) and ethyl chloroformate (0.09 g, 0.84 mmol). The solution is stirred for 1 hour. After this time, NH$_4$OH (0.07 mL, 0.90 mmol) is added and the solution is allowed to warm to ambient temperatures. After 16 hours, the solution is diluted with EtOAc. The solution is washed with 1 N HCl, sat. NaHCO$_3$ and sat. NaCl. The organic layer is dried over MgSO$_4$, filtered and concentrated. The title compound (0.28 g, 0.56 mmol) is obtained as a white foam.

$^1$H NMR (CDCl$_3$, 300 MHz) δ8.38 (s, 1H), 7.88 (m, 3H), 7.38 (m, 4H), 4.51 (AB, 2H), 4.12 (m, 1H), 3.95 (s, 3H), 3.78 (AB, 2H), 3.26 (m, 2H), 2.32 (m, 2H).

D. 2-[[1-(5-Carbamimidoylthiophene-3-ylmethyl)-2-oxopyrrolidin-3-(S)-yl](7-methoxynaphthalene-2-sulfonyl)amino]acetamide trifluoroacetate 2-[[1-(5-Cyanothiophene-3-ylmethyl)-2-oxopyrrolidin-3-(S)-yl]-(7-methoxynaphthalene-2-sulfonyl)amino]acetamide is converted to the title compound as described in EXAMPLE 125, Part D. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.23 (bs, 2H), 8.91 (bs, 2H), 8.41 (s, 1H), 7.92 (m, 3H), 7.78 (m, 2H), 7.58 (m, 2H), 7.32 (dd, 1H), 7.20 (m, 1H), 4.78 (t, 1H), 4.38 (AB, 2H), 3.90 (s, 3H), 3.67 (AB, 12H), 3.18 (m, 2H), 2.04 (m, 2H). FAB MS, [M+H]$^+$=516.

EXAMPLE 128

4-{3-(S)-[(7-Methoxynaphthalene-2-sulfonyl)benzylamino]-2-oxopyrrolidin-1-ylmethyl}thiophene-2-carboxamidine trifluoroacetate A. 7-Methoxynaphthalene-2-sulfonic acid-[1-(5-cyanothiophen-3-ylmethyl)-2-oxopyrrolidin-3-(S)-yl]benzylamide The title compound is prepared as in EXAMPLE 126, Part A using benzyl bromide in place of MeI to give the title compound as a white foam.

$^1$H NMR (CDCl$_3$, 300 MHz) δ8.44 (s, 1H), 8.00 (s, 1H), 7.91 (m, 1H), 7.79 (d, 1H), 7.53 (d, 1H), 7.23 (m, 8H) 4.52 (m, 3H), 4.36 (AB, 2H), 3.95 (s, 3H), 3.08 (dd, 2H), 2.28 (m, 1H), 2.05 (m, 1H).

B. 4-{3-(S)-[(7-Methoxynaphthalene-2-sulfonyl)benzylamino]-2-oxo-pyrrolidin-1-ylmethyl}thiophene-2-carboxamidine trifluoroacetate 7-Methoxynaphthalene-2-sulfonic acid-[1-(5-cyanothiophen-3-ylmethyl)-2-oxopyrrolidin-3-(S)-yl]-benzylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.22 (bs, 2H), 9.08 (bs, 2H), 8.41 (s, 1H), 8.00 (d, 1H), 7.96 (d, 1H), 7.87 (s, 1H), 7.80 (m, 2H), 7.52 (s, 1H), 7.21 (m, 6H), 4.71 (t, 1H), 4.40 (AB, 2H), 4.24 (AB, 2H), 3.88 (s, 3H), 3.11 (m, 1H), 2.93 (m, 1H), 2.12 (m, 1H), 1.62 (m, 1H). FAB MS, [M+H]$^+$=549. Elemental analysis cal. C=54.37%, H=4.41%, N=8.45%, found C=53.80%, H=4.45%, N=8.11%

EXAMPLE 129

4-[3-(S)-(5-Chloro-3-methylbenzo[b]thiophene-2-sulfonylamino)-2-oxo-pyrrolidin-1-ylmethyl]thiophene-2-carboxamidine trifluoroacetate A. 5-Chloro-3-methylbenzo[b]thiophene -2-sulfonic acid-[1-(5-cyanothiophen-3-ylmethyl)-2-oxopyrrolidin-3-(S)-yl]amide The title compound is prepared as in EXAMPLE 125, Part C using 5-chloro-3-methylbenzo[b]thiophene-2-sulfonyl chloride in place of 7-methoxy-naphthalene-2-sulfonyl chloride to give the title compound as a white foam.

$^1$H NMR (CDCl$_3$, 300 MHz) δ7.89 (m, 2H), 7.43 (m, 3H), 5.69 (bs, 1H), 4.42 (s, 2H), 3.90 (m, 1H), 3.26 (m, 2H), 2.70 (s, 3H), 2.62 (m, 1H), 1.89 (m, 1H).

B. 4-[3-(S)-(5-Chloro-3-methylbenzo[b]thiophene-2-sulfonylamino)-2-oxopyrrolidin-1-ylmethyl]-thiophene-2-carboxamidine trifluoroacetate 5-Chloro-3-methylbenzo[b]thiophene-2-sulfonic acid-[1-(5-cyanothiophen-3-ylmethyl)-2-oxopyrrolidin-3-(S)-yl]amide is converted to the title compound as described in EXAMPLE 125, Part D. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are lyophilized to provide the title compound as a white solid.

$^1$H NMR (DMSO-d$_6$, 300 MHz) δ9.21 (bs, 2H), 8.87 (bs, 2H), 8.69 (d, 1H), 8.04 (m, 2H), 7.80 (m, 2H), 7.54 (d, 1H), 4.31 (AB, 2H), 4.12 (m, 1H), 3.11 (m, 2H), 2.58 (s, 3H), 2.03 (m, 1H), 1.60 (m, 1H). FAB MS, [M+H]$^+$=483.

EXAMPLE 130

5-{3-(S)-[(7-Methoxynaphthalene-2-sulfonyl)methylamino]-2-oxopyrrolidin-1-ylmethyl}thiophene-3-carboxamidine trifluoroacetate A. 7-Methoxynaphthalene-2-sulfonic acid [1-(4-cyanothiophen-2-ylmethyl)-2-oxopyrrolidin-3-(S)-yl]amide The title compound is prepared as in EXAMPLE 125, Part C using 5-(3-amino-2-oxopyrrolidine-1-ylmethyl) thiophene-3-carbonitrile hydrochloride, prepared as in EXAMPLE 124, in place of 4-(3-amino-2-oxopyrrolidine-1-ylmethyl)-thiophene-2-carbonitrile hydrochloride. The crude product is purified by column chromatography eluting with gradient of 10% EtOAc/CH$_2$Cl$_2$ to 20% EtOAc/CH$_2$Cl$_2$ to afford the title compound as a white solid.

FAB MS, [M+H]$^+$=442.

B. 7-Methoxynaphthalene-2-sulfonic acid [1-(4-cyanothiophen-2-ylmethyl)-2-oxopyrrolidin-3-(S)-yl]methylamide The title compound is prepared as in EXAMPLE 126, Part A using 7-methoxynaphthalene-2-sulfonic acid [1-(4-cyanothiophen-2-ylmethyl)-2-oxopyrrolidin-3-(S)-yl]amide in place of 7-methoxynaphthalene-2-sulfonic acid [1-(5-cyanothiophen-3-ylmethyl)-2-oxopyrrolidin-3-(S)-yl] amide. The crude product is purified by column chromatography eluting with gradient of 5% EtOAc/CH$_2$Cl$_2$ to 15% EtOAc/CH$_2$Cl$_2$ to afford the title compound as a white solid.

$^1$H NMR (CDCl$_3$, 300 MHz) δ8.41 (s, 1H), 8.00 (m, 1H), 7.90 (d, 1H), 7.82 (s, 1H), 7.76 (m, 2H), 7.24 (m, 2H), 7.10 (s, 1H), 4.92 (t, 1H), 4.58 (AB, 2H), 3.91 (s, 3H), 3.29 (m, 2H), 2.73 (s, 3H), 2.37 (m, 1H), 2.03 (m, 1H).

C. 5-{3-(S)-[(7-Methoxynaphthalene-2-sulfonyl)methylamino]-2-oxopyrrolidin-1-ylmethyl}thiophene-3-carboxamidine trifuuoroacetate 7-Methoxynaphthalene-2-sulfonic acid [1-(4-cyanothiophen-2-ylmethyl)-2-oxopyrrolidin-3-(S)-yl]-methylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA and the appropriate product fractions are lyophilized to provide the title compound as a white solid.

$^1$H NMR (DMSO-d$_6$, 300 MHz) δ8.88 (bs, 4H), 8.41 (s, 1H), 8.35 (s, 1H), 8.00 (d, 1H), 7.92 (d, 1H), 7.68 (dd, 1H), 7.57 (s, 1H), 7.48 (s, 1H), 7.32 (dd, 1H), 4.82 (t, 1H), 4.50 (AB, 2H), 3.88 (s, 3H), 3.21 (m, 2H), 2.63 (s, 3H), 2.00 (m, 1H), 1.72 (m, 1H). FAB MS, [M+H]$^+$=473. Elemental analysis calculated with 0.75 mmol of H$_2$O cal. C=50.57%, H=5.11%, N=10.72%, Cl=6.78%, found C=50.52%, H=4.96%, N=10.46%, Cl=6.91%.

EXAMPLE 131

4-{3-(S)-[(5-Chloro-3-methylbenzo[b]thiophene-2-sulfonyl)benzylamino]-2-oxopyrrolidin-1-ylmethyl}thiophene-2-carboxamidine trifluoroacetate A. 5-Chloro-3-methylbenzo[b]thiophene-2-sulfonic acid [1-(5-cyanothiophen-3-ylmethyl)-2-oxopyrrolidin-3-(S)-yl]-benzylamide The title compound is prepared as in EXAMPLE 126, Part A using 5-chloro-3-methylbenzo[b]thiophene-2-sulfonic acid [1-(5-cyanothiophen-3-ylmethyl)-2-oxopyrrolidin-3-(S)-yl]amide, prepared as in EXAMPLE 129, Part A, in place of 7-methoxynaphthalene-2-sulfonic acid [1-(5-cyanothiophen-3-ylmethyl)-2-oxopyrrolidin-3-(S)-yl]amide and benzyl bromide in place of MeI. The crude product is purified by column chromatography eluting with gradient of 40% EtOAc/hexanes to 50% EtOAc/hexanes to afford the title compound as a white solid.

$^1$H NMR (CDCl$_3$, 300 MHz) δ7.82 (s, 1H), 7.75 (d, 2H), 7.43 (dd, 2H), 7.40 (s, 1H), 7.32 (m, 2H), 7.28 (m, 2H), 4.88 (AB, 1H), 4.64 (t, 1H), 4.38 (AB, 2H), 4.22 (AB, 1H), 3.06 (m, 1H), 2.90 (m, 1H), 2.71 (s, 3H), 2.28 (m, 1H), 1.81 (m, 1H).

B. 4-{3-(S)-[(5-Chloro-3-methylbenzo[b]thiophene-2-sulfonyl)benzylamino]-2-oxopyrrolidin-1-ylmethyl}thiophene-2-carboxamidine trifluoroacetate 5-Chloro-3-methylbenzo[b]thiophene-2-sulfonic acid [1-(5-cyanothiophen-3-ylmethyl)-2-oxopyrrolidin-3-(S)-yl] benzylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.30 (bs, 2H), 9.25 (bs, 2H), 8.05 (s, 1H), 8.03 (s, 1H), 7.82 (s, 1H), 7.80 (s, 1H), 7.55 (dd, 1H), 7.28 (m, 2H), 7.21 (m, 3H), 4.82 (t, 1H), 4.62 (AB, 1H), 4.25 (AB, 2H), 4.20 (AB, 1H), 3.13 (m, 1H), 2.91 (m, 1H), 2.60 (s, 3H), 2.15 (m, 1H), 1.62 (m, 1H). FAB MS, [M+H]$^+$=573. Elemental analysis cal. C=48.94%, H=3.81%, N=8.15%, found C=48.60%, H=3.71%, N=7.90%.

EXAMPLE 132

4-{3-(S)-[(Methanesulfonyl)-(3-phenylpropyl)amino]-2-oxopyrrolidin-1-ylmethyl}thiophiene-2-carboxamidine trifluoro acetate A. Methanesulfonic acid [1-(5-cyanothiophen-3-ylmethyl)-2-oxopyrrolidin-3-(S)-yl]amide The title compound is prepared as in EXAMPLE 125, Part C using methane sulfonyl chloride in place of 7-methoxynaphthalene-2-sulfonyl chloride to give the title compound as a white foam.

$^1$H NMR (CDCl$_3$, 300 MHz) δ7.52 (s, 1H), 7.43 (s, 1H), 5.10 (bs, 1H), 4.44 (AB, 2H), 4.18 (m, 1H), 3.39 (m, 2H), 3.15 (s, 3H), 2.60 (m, 1H), 2.00 (m, 1H).

B. Methanesulfonic acid [1-(5-cyanothiophen-3-ylmethyl)-2-oxopyrrolidin-3-(S)-yl]-(3-phenylpropyl)amide The title compound is prepared as in EXAMPLE 126, Part A using methanesulfonic acid [1-(5-cyanothiophen-3-ylmethyl)-2-oxopyrrolidin-3-(S)-yl]amide in place of 7-methoxynaphthalene-2-sulfonic acid [1-(5-cyanothiophen-3-ylmethyl)-2-oxopyrrolidin-3-(S)-yl]amide and phenethyl bromide in place of MeI to give the title compound as a white foam.

$^1$H NMR (CDCl$_3$, 300 MHz) δ7.48 (s, 1H), 7.40 (s, 1H), 7.23 (m, 5H), 4.52 (AB, 1H), 4.30 (m, 1H), 4.26 (AB, 1H), 3.22 (m, 4H), 3.12 (s, 3H), 2.63 (m, 2H), 2.15 (m, 2H), 1.94 (m, 2H).

C. 4-{3-(S)-[(Methanesulfonyl)-(3-phenylpropyl)amino]-2-oxopyrrolidin-1-ylmethyl}thiophene-2-carboxamidine trifluoro acetate Methanesulfonic acid-[1-(5-cyanothiophen-3-ylmethyl)-2-oxopyrrolidin-3-(S)-yl]-(3-phenylpropyl)amide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.28 (bs, 2H), 9.07 (bs, 2H), 7.90 (m, 1H), 7.85 (m, 1H), 7.23 (m, 2H), 7.15 (m, 3H), 4.55 (t, 1H), 4.40 (AB, 2H), 3.20 (m, 3H), 3.12 (s, 3H), 3.07 (m, 1H), 2.56 (m, 2H), 2.31 (m, 1H), 1.91 (m, 3H). FAB MS, [M+H]$^+$=435.

EXAMPLE 133

4-{3-(S)-[(Methanesulfonyl)(naphthalene-2-yl) amino]-2-oxopyrrolidin-1-ylmethyl}thiophene-2-carboxamidine trifluoroacetate A. Methanesulfonic acid-[1-(5-cyanothiophen-3-ylmethyl)-2-oxopyrrolidin-3-(S)-yl](naphthalene-2-yl)amide The title compound is prepared as in EXAMPLE 126, Part A using methanesulfonic acid-[1-(5-cyanothiophen-3-ylmethyl)-2-oxopyrrolidin-3-(S)-yl]amide, prepared as in EXAMPLE 132, Part A, in place of 7-methoxy-naphthalene-2-sulfonic acid-[1-(5-cyanothiophen-3-ylmethyl)-2-oxopyrrolidin-3-(S)-yl]amide and 2-naphthyl bromide in place of MeI to give the title compound as a white foam.

$^1$H NMR (CDCl$_3$, 300 MHz) δ7.79 (m, 4H), 7.50 (m, 5H), 4.70 (m, 1H), 4.53 (m, 2H), 4.40 (m, 1H), 4.32 (m, 1H), 3.26 (s, 3H), 3.04 (m, 2H), 2.00 (m, 2H).

B. 4-{3-(S)-[(Methanesulfonyl)(naphthalene-2-yl)amino]-2-oxopyrrolidin-1-ylmethyl}thiophene-2-carboxamidine trifluoroacetate Methanesulfonic acid-[1-(5-cyanothiophen-3-ylmethyl)-2-oxopyrrolidin-3-(S)-yl](naphthalene-2-yl)amide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.25 (bs, 2H), 9.12 (bs, 2H), 7.86 (m, 5H), 7.49 (m, 4H), 4.70 (m, 2H), 4.36 (m, 3H), 3.23 (s, 3H), 3.02 (m, 2H), 2.10 (m, 1H), 1.71 (m, 1H). FAB MS, [M+H]$^+$=457.

EXAMPLE 134

4-{3-(S)-[(4,5-Dichlorothiophene-2-sulfonyl) benzylamino]-2-oxopyrrolidin-1-ylmethyl}thiophene-2-carboxamidine trifluoroacetate A. 4,5-Dichlorothiophene-2-sulfonic acid [1-(5-cyanothiophen-3-ylmethyl)-2-oxopyrrolidin-3-(S)-yl]amide The title compound is prepared as in EXAMPLE 125, Part C using 4,5-dichlorothiophene-2-sulfonyl chloride in place of 7-methoxynaphthalene-2-sulfonyl chloride to give the title compound as a white foam.

$^1$H NMR (CDCl$_3$, 300 MHz) δ7.62 (m, 1H), 7.45 (m, 4H), 5.52 (s, 1H), 4.49 (s, 2H), 3.92 (m, 1H), 3.26 (m, 2H), 2.61 (m, 1H), 2.08 (m, 2H).

B. 4,5-Dichlorothiophene-2-sulfonic acid-[1-(5-cyanothiophen-3-ylmethyl)-2-oxopyrrolidin-3-(S)-yl] benzylamide The title compound is prepared as in EXAMPLE 126, Part A using 4,5-dichlorothiophene-2-sulfonic acid [1-(5-cyanothiophen-3-ylmethyl)-2-oxopyrrolidin-3-(S)-yl]amide in place of 7-methoxynaphthalene-2-sulfonic acid [1-(5-cyanothiophen-3-ylmethyl)-2-oxopyrrolidin-3-(S)-yl]amide and benzyl bromide in place of MeI to give the title compound as a white foam.

$^1$H NMR (CDCl$_3$, 300 MHz) δ7.61 (s, 1H), 7.46 (m, 2H), 7.32 (m, 2H), 7.26 (m, 3H), 4.56 (m, 2H), 4.40 (t, 1H), 4.37 (AB, 2H), 3.04 (m, 2H), 2.15 (m, 1H), 1.90 (m, 2H).

C. 4-{3-(S)-[(4,5-Dichlorothiophene-2-sulfonyl) benzylamino]-2-oxopyrrolidin-1-ylmethyl}thiophene-2-carboxamidine trifluoroacetate 4,5-Dichlorothiophene-2-sulfonic acid [1-(5-cyanothiophen-3-ylmethyl)-2-oxopyrrolidin-3-(S)-yl] benzylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.21 (bs, 2H), 9.00 (bs, 2H), 7.92 (m, 1H), 7.89 (m, 4H), 7.81 (m, 1H), 7.26 (m, 5H), 4.76 (m, 1H), 4.58 (m, 1H), 4.32 (AB, 2H), 4.19 (m, 1H), 3.11 (m, 1H), 3.00 (m, 1H), 2.10 (m, 1H), 1.62 (m, 1H). FAB MS, [M+H]$^+$=543. Elemental analysis cal. C=42.01%, H=3.22%, N=8.52%, found C=41.73%, H=3.23%, N=8.29%.

EXAMPLE 135

4-{3-(S)-[(5-Chloro-3-methylbenzo[b]thiophene-2-sulfonyl)methylamino]-2-oxopyrrolidin-1-ylmethyl}thiophene-2-carboxamidine trifluoroacetate A. 5-Chloro-3-methylbenzo[b]thiophene-2-sulfonic acid[1-(5-cyanothiophen-3-ylmethyl)-2-oxopyrrolidin-3-(S)-yl]-methylamide The title compound is prepared as in EXAMPLE 126, Part A using 5-chloro-3-methylbenzo[b]thiophene-2-sulfonic acid [1-(5-cyanothiophen-3-ylmethyl)-2-oxopyrrolidin-3-(S)-yl]-benzylamide in place of 7-methoxynaphthalene-2-sulfonic acid [1-(5-cyanothiophen-3-ylmethyl)-2-oxopyrrolidin-3-(S)-yl]amide to afford the title compound as a white solid.

$^1$H NMR (CDCl$_3$, 300 MHz) δ7.79 (m, 2H), 7.42 (m, 3H), 4.87 (t, 1H), 4.40 (AB, 2H), 3.26 (m, 2H), 2.88 (s, 2H), 2.70 (s, 3H), 2.41 (m, 1H), 2.05 (m, 1H).

B. 4-{3-(S)-[(5-Chloro-3-methylbenzo[b]thiophene-2-sulfonyl)methylamino]-2-oxopyrrolidin-1-ylmethyl}thiophene-2-carboxamidine trifluoroacetate 5-Chloro-3-methylbenzo[b]thiophene-2-sulfonic acid-[1-(5-cyanothiophen-3-ylmethyl)-2-oxopyrrolidin-3-(S)-yl]-methylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.21 (bs, 2H), 8.85 (bs, 2H), 8.10 (m, 2H), 7.91 (s, 1H), 7.81 (s, 1H), 7.60 (m, 1H), 4.88 (t, 1H), 4.37 (AB, 2H), 3.21 (m, 2H), 2.75 (s, 3H), 2.65 (s, 3H), 2.09 (m, 1H), 1.92 (m, 1H). FAB MS, [M+H]$^+$=497.

EXAMPLE 136

2-[[1-(5-Carbamimidoylthiophene-3-ylmethyl)-2-oxopyrrolidin-3-(S)-yl]-(7-methoxynaphthalene-2-sulfonyl)amino]-N-phenethylacetamide trifluoroacetate A. 2-[[1-(5-Cyanothiophene-3-ylmethyl)-2-oxopyrrolidin-3-(S)-yl]-(7-methoxynaphthalene-2-sulfonyl)amino]-N-phenethylacetamide The tiltle compound is prepared as described in EXAMPLE 127, Part C, substituting phenethyl amine for NH$_4$OH. The title compound is obtained as a white foam.

$^1$H NMR (CDCl$_3$, 300 MHz) δ8.38 (s, 1H), 7.89 (m, 1H), 7.78 (m, 1H), 7.55 (s, 1H), 7.21 (m, 6H), 4.47 (AB, 2H), 4.30 (m, 1H), 3.92 (s, 3H), 3.76 (AB, 2H), 3.31 (m, 2H), 2.61 (m, 2H), 2.28 (m, 1H).

B. 2-[[1-(5-Carbamimidoylthiophene-3-ylmethyl)-2-oxopyrrolidin-3-(S)-yl]-(7-methoxynaphthalene-2-sulfonyl) amino]-N-phenethylacetamide trifluoroacetate 2-[[1-(5-Cyanothiophene-3-ylmethyl)-2-oxopyrrolidin-3-(S)-yl]-(7-methoxynaphthalene-2-sulfonyl)amino]-N- phenethylacetamide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.21 (bs, 2H), 8.99 (bs, 2H), 8.41 (s, 1H), 8.15 (m, 1H), 7.95 (m, 2H), 7.78 (m, 2H), 7.55 (m, 1H), 7.35 (m, 1H), 7.18 (m, 5H), 4.78 (t, 1H), 4.38 (AB, 2H), 3.89 (s, 3H), 3.86 (m, 1H), 3.62 (m, 3H), 3.18 (m, 2H), 2.51 (m, 2H), 2.02 (m, 2H). FAB MS, [M+H]$^+$=620.

EXAMPLE 137

2-[[1-(5-Carbamimidoylthiophene-3-ylmethyl)-2-oxopyrrolidin-3-(S)-yl]-(4,5-dichlorothiophene-2-sulfonyl)amino]-N-phenethylacetamide trifluoroacetate A. 2-[[1-(5-Cyanothiophene-3-ylmethyl)-2-oxopyrrolidin-3-(S)-yl]-(4,5-dichlorothiophene-2-sulfonyl)amino]acetic acid tert-butyl ester The title compound is prepared as in EXAMPLE 126, Part A using tert-butyl-bromoacetate in place of MeI to give the title compound as a white foam.

$^1$H NMR (CDCl$_3$, 300 MHz) δ7.60 (s, 1H), 7.49 (s, 1H), 7.42 (s, 1H), 4.42 (m, 3H), 3.89 (AB, 2H), 3.72 (m, 1H), 3.27 (m, 2H), 2.55 (m, 1H), 2.34 (m, 1H), 1.44 (s, 9H).

B. 2-[[1-(5-Cyanothiophene-3-ylmethyl)-2-oxopyrrolidin-3-(S)-yl]-(4,5-dichlorothiophene-2-sulfonyl)amino]acetic acid To a solution of 2-[[1-(5-cyanothiophene-3-ylmethyl)-2-oxopyrrolidin-3-(S)-yl]-(4,5-dichlorothiophene-2-sulfonyl)amino]acetic acid tert-butyl ester (0.40 g, 0.72 mmol) in 15 mL of $CH_2Cl_2$ is added 5 mL of TFA. After 2 hours, the solution is concentrated to give the title compound as a white foam.

$^1$H NMR (CDCl$_3$, 300 MHz) δ7.98 (s, 1H), 7.89 (s, 1H), 7.81 (s, 1H), 4.80 (t, 1H), 4.32 (AB, 2H), 3.88 (AB, 2H), 3.19 (m, 2H), 2.22 (m, 1H), 2.08 (m, 1H).

C. 2-[[1-(5-Cyanothiophene-3-ylmethyl)-2-oxopyrrolidin-3-(S)-yl]-(4,5-dichlorothiophene-2-sulfonyl)amino]-N-phenethylacetamide The title compound is prepared as described in EXAMPLE 127, Part C, substituting 2-[[1-(5-Cyanothiophene-3-ylmethyl)-2-oxopyrrolidin-3-(S)-yl]-(4,5-dichlorothiophene-2-sulfonyl)amino]acetic acid for 2-[[1-(5-cyanothiophene-3-ylmethyl)-2-oxopyrrolidin-3-(S)-yl]-(7-methoxynaphthalene-2-sulfonyl)amino]acetic acid and substituting phenethyl amine for NH$_4$OH. The title compound is obtained as a white foam.

$^1$H NMR (CDCl$_3$, 300 MHz) δ7.50 (m, 3H), 7.25 (m, 5H), 4.45 (AB, 2H), 4.40 (t, 1H), 3.86 (AB, 2H), 3.39 (m, 1H), 3.22 (m, 1H), 2.42 (m, 1H), 2.22 (m, 1H).

D. 2-[[1-(5-Carbamimidoylthiophene-3-ylmethyl)-2-oxopyrrolidin-3-(S)-yl]-(4,5-dichlorothiophene-2-sulfonyl)amino]-N-phenethyl acetamide trifluoroacetate 2-[[1-(5-Cyanothiophene-3-ylmethyl)-2-oxopyrrolidin-3-(S)-y]-(7-methoxynaphthalene-2-sulfonyl)amino]-N-phenethylacetamide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.22 (bs, 2H), 9.11 (bs, 2H), 8.56 (m, 1H), 7.92 (s, 1H), 7.89 (s, 1H), 7.78 (s, 1H), 7.26 (m, 4H), 4.79 (t, 1H), 4.39 (m, 2H), 3.89 (AB, 2H), 3.18 (m, 2H), 2.28 (m, 1H), 2.10 (m, 1H). FAB MS, [M+H]$^+$=600. Elemental analysis calculated C=41.50%, H=3.48%, N=9.68%, found C=41.48%, H=3.21%, N=8.68.

EXAMPLE 138

2-[[1-(5-Carbamimidoylthiophene-3-ylmethyl)-2-oxopyrrolidin-3-(S)-yl]-(7-methoxynaphthalene-2-sulfonyl)amino]-N-benzylacetamide trifluoroacetate A. 2-[[1-(5-Cyanothiophene-3-ylmethyl)-2-oxopyrrolidin-3-(S)-yl]-(7-methoxynaphthalene-2-sulfonyl)amino]-N-benzylacetamide The tiltle compound is prepared as described in EXAMPLE 127, Part C, substituting benzyl amine for NH$_4$OH. The title compound is obtained as a white foam.

$^1$H NMR (CDCl$_3$, 300 MHz) δ8.35 (s, 1H), 7.76 (m, 2H), 7.49 (m, 1H), 7.23 (m, 9H), 4.40 (m, 5H), 3.94 (s, 3H), 3.86 (AB, 2H), 3.36 (m, 1H), 3.24 (m, 1H), 2.31 (m, 2H).

B. 2-[[1-(5-Carbamimidoylthiophene-3-ylmethyl)-2-oxopyrrolidin-3-(S)-yl]-(7-methoxynaphthalene-2-sulfonyl)amino]-N-benzylacetamide trifluoroacetate 2-[[1-(5-Cyanothiophene-3-ylmethyl)-2-oxopyrrolidin-3-(S)-yl]-(7-methoxy-naphthalene-2-sulfonyl)amino]-N-benzylacetamide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (CD$_3$OD, 300 MHz) δ8.80 (m, 1H), 8.42 (s, 1H), 7.87 (m, 5H), 7.36 (m, 2H), 7.20 (m, 5H), 4.82 (m, 1H), 4.50 (AB, 2H), 4.32 (m, 2H), 3.92 (m, 5H), 3.30 (m, 2H), 2.30 (m, 1H), 2.05 (m, 1H). FAB MS, [M+H]$^+$=606.

EXAMPLE 139

2-[[1-(4-Carbamimidoylthiophene-2-ylmethyl)-2-oxopyrrolidin-3-(S)-yl]-(7-methoxynaphthalene-2-sulfonyl)amino]acetamide trifluoroacetate A. 2-[[1-(4-Cyanothiophene-2-ylmethyl)-2-oxopyrrolidin-3-(S)-yl]-(7-methoxynaphthalene-2-sulfonyl)amino]acetic acid tert-butyl ester The title compound is prepared as in EXAMPLE 126, Part A substituting 7-methoxynaphthalene-2-sulfonic acid [1-(4-cyanothiophen-2-ylmethyl)-2-oxopyrrolidin-3-(S)-yl]amide for 7-methoxynaphthalene-2-sulfonic acid [1-(5-cyanothiophen-3 ylmethyl)-2-oxopyrrolidin-3-(S)-yl]amide and tert-butyl-bromoacetate in place of MeI to give the title compound as a white foam.

$^1$H NMR (CDCl$_3$, 300 MHz) δ8.42 (s, 1H), 7.82 (m, 4H), 7.27 (m, 2H), 7.15 (s, 1H), 4.66 (m, 1H), 4.15 (m, 1H), 3.92 (s, 3H), 3.68 (m, 1H), 3.28 (m, 2H), 2.56 (m, 1H), 2.40 (m, 1H), 1.41 (s, 9H).

B. 2-[[1-(4-Cyanothiophene-2-ylmethyl)-2-oxopyrrolidin-3-(S)-yl]-(7-methoxynaphthalene-2-sulfonyl)amino]acetic acid The title compound is prepared as described in EXAMPLE 127, Part B using 2-[[1-(4-cyanothiophene-2-ylmethyl)-2-oxopyrrolidin-3-(S)-yl]-(7-methoxynaphthalene-2-sulfonyl)amino]acetic acid tert-butyl ester.

FAB MS, [M+H]$^+$=500.

C. 2-[[1-(4-Cyanothiophene-2-ylmethyl)-2-oxopyrrolidin-3-(S)-yl]-(7-methoxynaphthalene-2-sulfonyl)amino]acetamide The tiltle compound is prepared as described in EXAMPLE 127, Part C, substituting 2-[[1-(4-cyanothiophene-2-ylmethyl)-2-oxopyrrolidin-3-(S)-yl]-(7-methoxynaphthalene-2-sulfonyl)amino]acetic acid for 2-[[1-(5-cyanothiophene-3-ylmethyl)-2-oxopyrrolidin-3-(S)-yl-(7-methoxynaphthalene-2-sulfonyl)amino]acetic acid. The title compound is obtained as a white foam.

$^1$H NMR (CDCl$_3$, 300 MHz) δ8.35 (s, 1H), 7.80 (m, 5H), 7.28 (m, 2H), 5.42 (m, 1H), 4.64 (m, 3H), 3.94 (s, 3H), 3.72 (AB, 2H), 3.36 (AB, 2H), 2.35 (m, 1H), 2.16 (m, 1H).

D. 2-[[1-(4-Carbamimidoylthiophene-2-ylmethyl)-2-oxopyrrolidin-3-(S)-yl]-(7-methoxynaphthalene-2-sulfonyl)amino]acetamide trifluoroacetate 2-[[1-(4-Cyanothiophene-2-ylmethyl)-2-oxopyrrolidin-3-(S)-yl]-(7-methoxynaphthalene-2-sulfonyl)amino]-N-benzylacetamide is converted to the title compound as described in EXAMPLE 125, Part D. The crude product is purified by RP-HPLC eluting in a gradient of 10% CH$_3$CN/H$_2$O to 80% CH$_3$CN/H$_2$O and the appropriate product fractions are lyophilized to provide the title compound as a white solid.

$^1$H NMR (DMSO-d$_6$, 300 MHz) δ9.11 (bs, 4H), 8.48 (m, 2H), 7.98 (m, 2H), 7.74 (m, 1H), 7.54 (m, 3H), 7.35 (m, 1H), 7.21 (m, 1H), 4.79 (t, 1H), 4.53 (AB, 2H), 3.89 (s, 3H), 3.64 (AB, 2H), 3.21 (m, 2H), 2.04 (m, 2H). FAB MS, [M+H]$^+$= 516. Elemental analysis calculated with 1.75 mmol of H$_2$O cal. C=47.34%, H=5.10%, N=12.00%, Cl=6.08%, found C=47.30%, H=4.82%, N=11.75, Cl=6.02%.

EXAMPLE 140

2-[[1-(5-Cyanothiophene-3-ylmethyl)-2-oxopyrrolidin-3-(S)-yl]-(5-chloro-3-methyl benzo[b]thiophene-2-sulfonyl)amino]acetic acid methyl ester A. 2-[[1-(5-Cyanothiophene-3-ylmethyl)-2-oxopyrrolidin-3-(S)-yl]-(7-methoxynaphthalene-2-sulfonyl)amino]acetic acid methyl ester The title compound is prepared as in EXAMPLE 126, Part A substituting 5-chloro-3-methyl-benzo[b]thiophene-2-sulfonic acid-[1-(5-cyanothiophen-3-ylmethyl)-2-oxopyrrolidin-3-(S)-yl]amide for 7-methoxynaphthalene-2-sulfonic acid-[1-(5-cyanothiophen-3-ylmethyl)-2-oxopyrrolidin-3-(S)-yl]amide and substituting methylbromoacetate for MeI to give the title compound as a white foam.

$^1$H NMR (CDCl$_3$, 300 MHz) δ7.80 (s, 1H), 7.76 (d, 1H), 7.45 (m, 2H), 7.39 (s, 1H), 4.64 (t, 1H), 4.40 (m, 2H), 4.18 (m, 2H), 3.52 (s, 3H), 3.33 (m, 2H), 2.69 (s, 3H), 2.55 (m, 1H), 2.38 (m, 1H).

2-[[1-(5-Cyanothiophene-3-ylmethyl)-2-oxopyrrolidin-3-(S)-yl]-(5-chloro-3-methyl benzo[b]thiophene-2-sulfonyl)amino]acetic acid methyl ester 2-[[1-(5-Cyanothiophene-3-ylmethyl)-2-oxopyrrolidin-3-(S)-yl]-(7-methoxynaphthalene-2-sulfonyl)amino]acetic acid methyl ester is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.26 (bs, 2H), 9.18 (bs, 2H), 8.06 (m, 2H), 7.90 (s, 2H), 7.81 (s, 1H), 7.60 (m, 1H), 4.75 (t, 1H), 4.30 (AB, 2H), 4.01 (AB, 2H), 3.58 (s, 3H), 3.20 (m, 2H), 2.62 (s, 3H), 2.28 (m, 1H), 2.07 (m, 1H). FAB MS, [M+H]$^+$=555.

EXAMPLE 141

4-{3-(S)-[(7-Aminonaphthalene-2-sulfonyl)benzylamino]-2-oxopyrrolidin-1-ylmethyl}thiophene-2-carboxamidine bistrifluoroacetate A. N-Cbz-7-aminonaphthalene-2-sulfonic acid, sodium salt To a suspension of 7-aminonaphthalene-2-sulfonic acid, sodium salt (10.1 g, 41.2 mmol) in 200 mL of water is added solid NaOH (3.29 g, 82.4 mmol) at room temperature. The mixture is stirred for 1 hour, and then benzyl chloroformate (11.8 mL, 82.4 mmol) is added. A precipitate forms after 30 min and the resulting mixture is stirred over a period of 18 hours. The crude mixture is concentrated in vacuo and the residue is stirred in 100 mL of absolute EtOH as a slurry for 2 hours. The precipitate is filtered and dried. The solid is heated at reflux in 100 mL of 95% EtOH for 2 hours, allowed to cool to room temperature, filtered and dried to give 15.4 g of the title compound.

$^1$H NMR (DMSO-d$_6$, 300 MHz) d 8.06 (s, 1H), 7.97 (s, 1H), 7.82 (d, 1H), 7.77 (d, 1H), 7.61 (dd, 1H), 7.58 (dd, 1H), 7.41 (m, 5H), 5.18 (s, 2H).

B. N-Cbz-7-aminonaphthalene-2-sulfonyl chloride

N-Cbz-7-aminonaphthalene-2-sulfonic acid, sodium salt (15.4 g, 40.7 mmol) is converted to the title compound as described in EXAMPLE 125, Part B. The crude product is purified by column chromatography in a gradient of hexanes to 20% EtOAc/hexanes to afford the title compound (5 g, 13.3 mmol) as a beige solid.

$^1$H NMR (CDCl$_3$, 300 MHz) d 8.38 (s, 1H), 8.12 (s, 1H), 7.88 (d, 1H), 7.80 (d, 2H), 7.60 (dd, 1H), 7.34 (m, 5H), 7.27 (s, 1H), 5.21 (s, 2H).

C. N-Cbz-7-aminonaphthalene-2-sulfonic acid-[1-(5-cyanothiophen-3-ylmethyl)-2-oxopyrrolidin-3-(S)-yl]amide The title compound is prepared from 4-(3-(S)-amino-2-oxopyrrolidin-1-ylmethyl)thiophene-2-carbonitrile hydrochloride as described in EXAMPLE 125, Part C using N-Cbz-7-aminonaphthalene-2-sulfonyl chloride in place of 7-methoxynaphthalene-2-sulfonyl chloride. The crude product is purified by column chromatography eluting with a gradient of 10% EtOAc/CH$_2$Cl$_2$ to 25% EtOAc/CH$_2$Cl$_2$ to provide the title compound as a solid.

$^1$H NMR (CDCl$_3$, 300 MHz) δ8.68 (s, 1H), 8.28 (s, 1H), 7.71 (m, 2H), 7.61 (m, 2H), 7.45 (d, 1H), 7.35 (m, 7H), 6.05 (d, 1H), 5.20 (AB, 2H), 4.35 (AB, 2H), 3.86 (m, 1H), 3.14 (m, 2H), 2.47 (m, 1H), 1.99 (m, 1H).

D. N-Cbz-7-aminonaphthalene-2-sulfonic acid-[1-(5-cyanothiophen-3-ylmethyl)-2-oxopyrrolidin-3-(S)-yl]benzylamide N-Cbz-7-aminonaphthalene-2-sulfonic acid-[1-(5-cyanothiophen-3-ylmethyl)-2-oxopyrrolidin-3-(S)-yl]amide (0.56 g, 1.01 mmol) is dissolved in 10 mL of DMF and cooled to 0° C. Sodium hydride (42 mg of a 60% dispersion in mineral oil, 1.06 mmol) is added and the solution is stirred for 20 minutes. To the mixture is added benzyl bromide (0.18 g, 1.06 mmol). The reaction mixture is stirred at 0° C. for 20 minutes and then at room temperature for 1.5 hours. The solution is poured into a separatory funnel and diluted with 100 mL of EtOAc. The organic layer is washed with water, 1 N HCl and saturated NaCl solution, then dried over MgSO$_4$, filtered and concentrated. The crude residue is purified by column chromatography eluting with a gradient of 25% EtOAc/CH$_2$Cl$_2$ to 50% EtOAc/CH$_2$Cl$_2$ to give the title compound (0.34 g, 0.53 mmol) as a solid.

$^1$H NMR (CDCl$_3$, 300 MHz) δ8.39 (s, 1H), 8.08 (s, 1H), 7.86 (d, 1H), 7.78 (d, 1H), 7.74 (s, 1H), 7.60 (d, 1H), 7.37 (m, 8H), 7.25 (m, 5H), 5.19 (AB, 2H), 4.52 (m, 1H), 4.39 (AB, 2H), 4.34 (AB, 2H), 2.92 (m, 2H), 2.16 (m, 1H), 1.87 (m, 1H).

E. 4-{3-(S)-[(7-Aminonaphthalene-2-sulfonyl) benzylamino]-2-oxopyrrolidin-1-ylmethyl}thiophene-2-carboxamidine bistrifluoroacetate N-Cbz-7-aminonaphthalene-2-sulfonic acid-[1-(5-cyanothiophen-3-ylmethyl)-2-oxopyrrolidin-3-(S)-yl]-benzylamide is converted to the title compound as described in EXAMPLE 125, Part D. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.26 (bs, 2H), 9.04 (bs, 2H), 8.14 (s, 1H), 7.81 (m, 3H), 7.73 (d, 1H), 7.55 (dd, 1H), 7.32 (m, 2H), 7.25 (m, 3H), 7.11 (dd, 1H), 7.01 (s, 1H), 4.73 (m, 1H), 4.35 (AB, 2H), 4.29 (AB, 2H), 3.13 (m, 1H), 2.94 (m, 1H), 2.08 (m, 1H), 1.63 (m, 1H). FAB MS, $[M+H]^+$=534. Elemental analysis calculated with 0.4 mol of $H_2O$: C=48.42%, H=3.91%, N=9.11%; found C=48.42%, H=4.06%, N=9.11%.

EXAMPLE 142

4-{3-(S)-[(7-Aminonaphthalene-2-sulfonyl) methylamino]-2-oxopyrrolidin-1-ylmethyl}thiophene-2-carboxamidine bistrifluoroacetate A. N-Cbz-7-aminonaphthalene-2-sulfonic acid [1-(5-cyanothiophen-3-ylmethyl)-2-oxopyrrolidin-3-(S)-yl] methylamide The title compound is prepared from N-Cbz-7-aminonaphthalene-2-sulfonic acid [1-(5-cyanothiophen-3-ylmethyl)-2-oxopyrrolidin-3-(S)-yl]amide as described in EXAMPLE 141, Part D using methyl iodide in place of benzyl bromide. The crude product is purified by column chromatography eluting with 10% $EtOAc/CH_2Cl_2$ to afford the title compound as a solid.

$^1$H NMR (CDCl$_3$, 300 MHz) δ8.38 (s, 1H), 8.08 (s, 1H), 7.85 (d, 1H), 7.80 (dd, 1H), 7.77 (d, 1H), 7.40 (m, 8H), 7.21 (s, 1H), 5.24 (AB, 2H), 4.87 (m, 1H), 4.35 (AB, 2H), 3.22 (m, 2H), 2.79 (s, 3H), 2.35 (m, 1H), 2.05 (m, 1H).

B. 4-{3-(S)-[(7-Aminonaphthalene-2-sulfonyl) methylamino]-2-oxopyrrolidin- 1-ylmethyl}thiophene-2-carboxamidine bistrifluoroacetate N-Cbz-7-aminonaphthalene-2-sulfonic acid [1-(5-cyanothiophen-3-ylmethyl)-2-oxopyrrolidin-3-(S)-yl] methylamide is converted to the title compound as described in EXAMPLE 125, Part D. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.26 (bs, 2H), 9.01 (bs, 2H), 8.07 (s, 1H), 7.90 (s, 1H), 7.82 (d, 1H), 7.80 (s, 1H), 7.73 (d, 1H), 7.43 (d, 1H), 7.12 (dd, 1H), 7.01 (s, 1H), 4.86 (m, 1H), 4.37 (AB, 2H), 3.15 (m, 2H), 2.64 (s, 3H), 1.95 (m, 1H), 1.74 (m, 1H). FAB MS, $[M+H]^+$=458. Elemental analysis calculated: C=43.80%, H=3.68%, N=10.21%; found C=43.40%, H=3.75%, N=10.00%.

EXAMPLE 143

2-[[1-(5-Carbamimidoylthiophene-3-ylmethyl)-2-oxopyrrolidin-3-(S)-yl]-(7-aminonaphthalene-2-sulfonyl)amino]acetamide bistrifluoroacetate A. 2-[[1-(5-Cyanothiophene-3-ylmethyl)-2-oxopyrrolidin-3-(S)-yl]-(N-Cbz-7-aminonaphthalene-2-sulfonyl)amino] acetic acid tert-butyl ester The title compound is prepared from N-Cbz-7-aminonaphthalene-2-sulfonic acid [1-(5-cyanothiophen-3-ylmethyl)-2-oxopyrrolidin-3-(S)-yl]amide as described in EXAMPLE 141, Part D using tert-butyl bromoacetate in place of benzyl bromide. The crude product is purified by column chromatography eluting with a gradient of 5% $EtOAc/CH_2Cl_2$ to 10% $EtOAc/CH_2Cl_2$ to provide the title compound as a solid.

$^1$H NMR (CDCl$_3$, 300 MHz) δ8.45 (s, 1H), 8.10 (s, 1H), 7.87 (m, 2H), 7.80 (d, 1H), 7.55 (dd, 1H), 7.45 (m, 7H), 7.01 (m, 1H), 5.30 (s, 2H), 4.55 (m, 1H), 4.40 (AB, 2H), 3.92 (AB, 2H), 3.32 (m, 1H), 3.21 (m, 1H), 2.60 (m, 1H), 2.45 (m, 1H), 1.50 (s, 9H).

B. 2-[[1-(5-Cyanothiophene-3-ylmethyl)-2-oxopyrrolidin-3-(S)-yl]-(N-Cbz-7-aminonaphthalene-2-sulfonyl)amino] acetic acid 2-[[1-(5-Cyanothiophene-3-ylmethyl)-2-oxopyrrolidin-3-(S)-yl]-(N-Cbz-7-aminonaphthalene-2-sulfonyl)amino] acetic acid tert-butyl ester is converted to the title compound as described in EXAMPLE 127, Part B. The product is azeotroped with toluene/$CH_2Cl_2$ to give a white foam which is used directly in the next step.

FAB MS, $[M+H]^+$=619.

C. 2-[[1-(5-Cyanothiophene-3-ylmethyl)-2-oxopyrrolidin-3-(S)-yl]-(N-Cbz-7-aminonaphthalene-2-sulfonyl)amino] acetamide The title compound is prepared as described in EXAMPLE 127, Part C using 2-[[1-(5-cyanothiophene-3-ylmethyl)-2-oxopyrrolidin-3-(S)-yl]-(N-Cbz-7-aminonaphthalene-2-sulfonyl)amino]acetic acid in place of 2-[[1-(5-cyanothiophene-3-ylmethyl)-2-oxopyrrolidin-3-(S)-yl]-(7-methoxynaphthalene-2-sulfonyl)amino]acetic acid. The crude product is purified by column chromatography eluting with 2% MeOH/50% $EtOAc/CH_2Cl_2$ to provide the title compound as a white solid.

$^1$H NMR (CDCl$_3$, 300 MHz) δ8.40 (s, 1H), 8.09 (s, 1H), 7.82 (m, 2H), 7.75 (m, 2H), 7.60 (dd, 1H), 7.50 (m, 2H), 7.38 (m, 6H), 5.63 (bs, 1H), 5.25 (s, 2H), 4.51 (s, 1H), 4.43 (AB, 2H), 3.77 (AD, 2H), 3.38 (m, 1H), 3.25 (m, 1H), 2.39 (m, 1H), 2.21 (m, 1H).

D. 2-[[1-(5-Carbamimidoylthiophene-3-ylmethyl)-2-oxopyrrolidin-3-(S)-yl]-(7-aminonaphthalene-2-sulfonyl)amino]acetamide bistrifluoroacetate 2-[[1-(5-Cyanothiophene-3-ylmethyl)-2-oxopyrrolidin-3-(S)-yl]-(N-Cbz-7-aminonaphthalene-2-sulfonyl)amino] acetamide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.26 (bs, 2H), 9.00 (bs, 2H), 8.12 (s, 1H), 7.92 (s, 1H), 7.82 (d, 1H), 7.81 (s, 1H), 7.73 (d, 1H), 7.58 (s, 1H), 7.48 (dd, 1H), 7.24 (s, 1H), 7.13 (dd, 1H), 7.01 (s, 1H), 4.78 (m, 1H), 4.38 (AB, 2H), 3.64 (AB, 2H), 3.20 (m, 2H), 2.09 (m, 1H), 1.97 (m, 1H). FAB MS, $[M+H]^+$=501.

EXAMPLE 144

4-[3-(S)-(6-Amino-5-chloro-2-sulfonylamino)-2-oxopyrrolidin-1-ylmethyl]-thiophene-2-carboxamidine trifluoroacetate A. N-Cbz-6-aminonaphthalene-2-sulfonic acid, sodium salt The title compound is prepared as described in EXAMPLE 141, Part A using 6-aminonaphthalene-2-sulfonic acid, sodium salt in place of 7-amino-naphthalene-2-sulfonic acid, sodium salt. The crude product is isolated from 95% EtOH.

$^1$H NMR (DMSO-$d_6$, 300 MHz) d 8.06 (m, 2H), 7.88 (d, 1H), 7.72 (d, 1H), 7.66 (d, 1H), 7.55 (dd, 1H), 7.41 (m, 5H), 5.19 (s, 2H).

B. N-Cbz-6-amino-5-chloro-naphthalene-2-sulfonyl chloride and N-Cbz-6-aminonaphthalene-2-sulfonyl chloride N-Cbz-6-aminonaphthalene-2-sulfonic acid, sodium salt is converted to the title compounds as described in EXAMPLE 125, Part B. The crude mixture is purified by column chromatography in a gradient of hexanes to 10% EtOAc/hexanes to provide N-Cbz-6-amino-5-chloro-naphthalene-2-sulfonyl chloride as the major component as a beige solid.

¹H NMR (CDCl₃, 300 MHz) d 8.71 (d, 1H), 8.59 (s, 1H), 8.38 (d, 1H), 8.09 (dd, 1H), 7.96 (d, 1H), 7.65 (s, 1H), 7.41 (m, 5H), 5.30 (s, 2H). EI MS, [M]⁺=409.

The N-Cbz-6-aminonaphthalene-2-sulfonyl chloride is also isolated as a minor component from the above procedure as a solid.

¹H NMR (CDCl₃, 300 MHz) d 8.52 (s, 1H), 8.23 (m, 1H), 7.96 (m, 3H), 7.55 (dd, 1H), 7.43 (m, 5H), 7.01 (s, 1H), 5.30 (s, 2H). FAB MS, [M+H]⁺=376.

C. N-Cbz-6-amino-5-chloro-naphthalene-2-sulfonic acid-[1-(5-cyanothiophen-3-ylmethyl)-2-oxopyrrolidin-3-(S)-yl] amide The title compound is prepared from 4-(3-(S)-amino-2-oxopyrrolidin-1-ylmethyl)thiophene-2-carbonitrile hydrochloride as described in EXAMPLE 125, Part C using N-Cbz-6-amino-5-chloro-naphthalene-2-sulfonyl chloride in place of 7-methoxynaphthalene-2-sulfonyl chloride. The crude product is concentrated from EtOAc to afford the title compound as a white solid.

¹H NMR (CDCl₃, 300 MHz) δ8.61 (d, 1H), 8.44 (s, 1H), 8.29 (d, 1H), 7.96 (dd, 1H), 7.90 (d, 1H), 7.60 (s, 1H), 7.43 (m, 6H), 7.39 (d, 1H), 5.55 (s, 1H), 5.29 (s, 2H), 4.42 (AB, 2H), 3.78 (m, 1H), 3.25 (m, 2H), 2.60 (m, 1H), 2.09 (m, 1H).

D. 4-[3-(S)-(6-Amino-5-chloro-2-sulfonylamino)-2-oxopyrrolidin-1-ylmethyl]-thiophene-2-carboxamidine trifluoroacetate N-Cbz-6-amino-5-chloro-naphthalene-2-sulfonic acid [1-(5-cyanothiophen-3-ylmethyl)-2-oxopyrrolidin-3-(S)-yl] amide is converted to the title compound as described in EXAMPLE 125, Part D. The crude product is purified by RP-HPLC eluting in a gradient of 10% CH₃CN/H₂O to 60% CH₃CN/H₂O and the appropriate product fractions are lyophilized to provide the title compound as a white solid.

¹H NMR (DMSO-d₆, 300 MHz) δ9.25 (bs, 2H), 9.13 (bs, 2H), 8.25 (dd, 1H), 8.07 (d, 1H), 7.95 (d, 1H), 7.86 (s, 1H), 7.83 (dd, 1H), 7.80 (m, 2H), 7.22 (d, 1H), 4.34 (AB, 2H), 4.05 (m, 1H), 3.09 (m, 2H), 1.97 (m, 1H), 1.55 (m, 1H). FAB MS, [M+H]⁺=478. Elemental analysis calculated with 1.3 mol of H₂O: C=42.20%, H=3.78%, N=11.18%; found C=42.20%, H=3.36%, N=10.70%.

EXAMPLE 145

4-{3-(S)-[(6-Amino-5-chloro-naphthalene-2-sulfonyl)methylamino]-2-oxopyrrolidin- 1-ylmethyl}thiophene-2-carboxamidine trifluoroacetate A. N-Cbz-6-amino-5-chloro-naphthalene-2-sulfonic acid [1-(5-cyanothiophen-3-ylmethyl)-2-oxopyrrolidin-3-(S)-yl]-methylamide The title compound is prepared from N-Cbz-6-amino-5-chloro-naphthalene-2-sulfonic acid [1-(5-cyanothiophen-3-ylmethyl)-2-oxopyrrolidin-3-(S)-yl]amide as described in EXAMPLE 141, Part D using methyl iodide in place of benzyl bromide. The crude product is purified by column chromatography eluting in a gradient of 10% EtOAc/CH₂Cl₂ to 25% EtOAc/CH₂Cl₂ to afford the title compound as a solid.

¹H NMR (CDCl₃, 300 MHz) δ8.60 (d, 1H), 8.49 (d, 1H), 8.25 (d, 1H), 8.05 (dd, 1H), 7.95 (d, 1H), 7.60 (s, 1H), 7.44 (m, 7H), 5.30 (s, 2H), 4.93 (m, 1H), 4.40 (AB, 2H), 3.30 (m, 2H), 2.80 (s, 3H), 2.40 (m, 1H), 2.08 (m, 1H).

B. 4-{3-(S)-[(6-Amino-5-chloro-naphthalene-2-sulfonyl)methylamino]-2-oxopyrrolidin-1-ylmethyl}thiophene-2-carboxamidine trifluoroacetate N-Cbz-6-amino-5-chloro-naphthalene-2-sulfonic acid [1-(5-cyanothiophen-3-ylmethyl)-2-oxopyrrolidin-3-(S)-yl]-methylamide is converted to the title compound as described in EXAMPLE 125, Part D. The crude product is purified by RP-HPLC eluting in a gradient of 10% CH₃CN/H₂O (0.1% TFA) to 80% CH₃CN/H₂O (0.1% TFA) and the appropriate product fractions are lyophilized to provide the title compound as a white solid.

¹H NMR (DMSO-d₆, 300 MHz) δ9.26 (bs, 2H), 9.06 (bs, 2H), 8.29 (s, 1H), 7.94 (d, 1H), 7.90 (s, 1H), 7.84 (d, 1H), 7.81 (d, 1H), 7.79 (s, 1H), 7.23 (d, 1H), 4.85 (m, 1H), 4.36 (AB, 2H), 3.13 (m, 2H), 2.63 (s, 3H), 1.97 (m, 1H), 1.73 (m, 1H). FAB MS, [M+H]⁺=492. Elemental analysis calculated with 1.3 mol of H₂O: C=43.89%, H=4.10%, N=11.13%; found C=43.90%, H=3.71%, N=10.62%.

EXAMPLE 146

2-[[1-(5-Carbamimidoylthiophene-3-ylmethyl)-2-oxopyrrolidin-3-(S)-yl]-(6-amino-5-chloronaphthalene-2-sulfonyl)amino]acetamide trifluoroacetate A. 2-[[1-(5-Cyanothiophene-3-ylmethyl)-2-oxopyrrolidin-3-(S)-yl]-(N-Cbz-6-amino-5-chloronaphthalene-2-sulfonyl)amino]acetic acid tert-butyl ester The title compound is prepared from N-Cbz-6-amino-5-chloro-naphthalene-2-sulfonic acid-[1-(5-cyanothiophen-3-ylmethyl)-2-oxopyrrolidin-3-(S)-yl]amide as described in EXAMPLE 141, Part D using tert-butyl bromoacetate in place of benzyl bromide. The crude product is purified by column chromatography eluting with a gradient of 5% EtOAc/CH₂Cl₂ to 10% EtOAc/CH₂Cl₂ to provide the title compound as a solid.

¹H NMR (CDCl₃, 300 MHz) for rotamers present: δ8.63-8.40 (m, 2H), 8.30-7.75 (m, 3H), 7.60-7.30 (m, 5H), 7.28-7.12 (m, 2H), 5.31-5.08 (m, 2H), 4.89-3.62 (m, 6H), 3.30 (m, 1H), 3.22 (m, 1H), 2.60 (m, 1H), 2.42 (m, 1H), 1.47 (s, 9H).

B. 2-[[1-(5-Cyanothiophene-3-ylmethyl)-2-oxopyrrolidin-3-(S)-yl]-(N-Cbz-6-amino-5-chloronaphthalene-2-sulfonyl)amino]acetic acid.

2-[[1-(5-Cyanothiophene-3-ylmethyl)-2-oxopyrrolidin-3-(S)-yl]-(N-Cbz-6-amino-5-chloronaphthalene-2-sulfonyl)amino]acetic acid tert-butyl ester is converted to the title compound as described in EXAMPLE 127, Part B. The product is azeotroped with toluene to give a foam which is used directly in the next step.

C. 2-[[1-(5-Cyanothiophene-3-ylmethyl)-2-oxopyrrolidin-3-(S)-yl]-(N-Cbz-6-amino-5-chloronaphthalene-2-sulfonyl)amino]acetamide The title compound is prepared as described in EXAMPLE 127, Part C using 2-[[1-(5-cyanothiophene-3-ylmethyl)-2-oxopyrrolidin-3-(S)-yl]-(N-Cbz-6-amino-5-chloronaphthalene-2-sulfonyl)amino]acetic acid in place of 2-[[1-(5-cyanothio-phene-3-ylmethyl)-2-oxopyrrolidin-3-(S)-yl]-(7-methoxynaphthalene-2-sulfonyl)amino]acetic acid. The crude product is purified by column chromatography eluting in a gradient of 50% EtOAc/CH₂Cl₂ to 2% MeOH/50% EtOAc/CH₂Cl₂ to provide the title compound as a solid.

¹H NMR (CDCl₃, 300 MHz) δ8.63 (d, 1H), 8.46 (s, 1H), 8.30 (d, 1H), 8.04 (d, 1H), 7.93 (d, 1H), 7.86 (s, 1H), 7.60 (s, 1H), 7.54 (m, 2H), 7.42 (m, 5H), 5.37 (s, 1H), 5.27 (s,

2H), 4.52 (m, 1H), 4.50 (AB, 2H), 3.78 (AB, 2H), 3.42 (m, 1H), 3.32 (m, 1H), 2.50 (m, 1H), 2.35 (m, 1H).

D. 2-[[1-(5-Carbamimidoylthiophene-3-ylmethyl)-2-oxopyrrolidin-3-(S)-yl]-(6-amino-5-chloronaphthalene-2-sulfonyl)amino]acetamide trifluoroacetate 2-[[1-(5-Cyanothiophene-3-ylmethyl)-2-oxopyrrolidin-3-(S)-yl]-(N-Cbz-6-amino-5-chloronaphthalene-2-sulfonyl) amino]acetamide is converted to the title compound as described in EXAMPLE 125, Part D. The crude product is purified by RP-HPLC eluting in a gradient of 10% $CH_3CN/H_2O$ (0.1% TFA) to 60% $CH_3CN/H_2O$ (0.1% TFA) and the appropriate product fractions are lyophilized to provide the title compound as a white solid.

$^1$H NMR (DMSO-$d_6$, 300 MHz) δ9.25 (bs, 2H), 8.95 (bs, 2H), 8.32 (s, 1H), 7.93 (d, 1H), 7.91 (s, 1H), 7.86 (d, 1H), 7.80 (m, 2H), 7.56 (s, 1H), 7.22 (m, 2H), 6.28 (bs, 2H), 4.75 (m, 1H), 4.34 (AB, 2H), 3.62 (AB, 2H), 3.16 (m, 2H), 2.07 (m, 1H), 1.95 (m, 1H). FAB MS, $[M+H]^+$=615.

EXAMPLE 147

4-[3-(S)-(6-Aminonaphthalene-2-sulfonylamino)-2-oxopyrrolidin-1-ylmethyl]-thiophene-2-carboxamidine dihydrochloride A. N-Cbz-6-aminonaphthalene-2-sulfonic acid-[1-(5-cyanothiophen-3-ylmethyl)-2-oxopyrrolidin-3-(S)-yl]amide The title compound is prepared from 4-(3-(S)-amino-2-oxopyrrolidin-1-ylmethyl)thiophene-2-carbonitrile hydrochloride as described in EXAMPLE 125, Part C using N-Cbz-6-aminonaphthalene-2-sulfonyl chloride in place of 7-methoxynaphthalene-2-sulfonyl chloride. The crude product is purified by column chromatography eluting with a gradient of 10% $EtOAc/CH_2Cl_2$ to 25% $EtOAc/CH_2Cl_2$ to provide the title compound as a solid.

$^1$H NMR (CDCl$_3$, 300 MHz) δ8.34 (s, 1H), 8.04 (s, 1H), 7.80 (d, 1H), 7.77 (d, 1H), 7.70 (d, 1H), 7.50 (s, 1H), 7.47 (d, 1H), 7.40 (m, 7H), 5.98 (d, 1H), 5.23 (s, 2H), 4.40 (AB, 2H), 3.82 (m, 1H), 3.25 (m, 2H), 2.58 (m, 1H), 2.08 (m, 1H).

B. 4-[3-(S)-(6-Aminonaphthalene-2-sulfonylamino)-2-oxopyrrolidin-1-ylmethyl]-thiophene-2-carboxamidine dihydrochloride N-Cbz-6-aminonaphthalene-2-sulfonic acid-[1-(5-cyanothiophen-3-ylmethyl)-2-oxopyrrolidin-3-(S)-yl]amide is converted to the title compound as described in EXAMPLE 125, Part D. The crude product is purified by RP-HPLC eluting in a gradient of 10% $CH_3CN/H_2O$ to 80% $CH_3CN/H_2O$ and the appropriate product fractions are lyophilized to provide the title compound as a white solid.

$^1$H NMR (DMSO-$d_6$, 300 MHz) δ9.32 (bs, 2H), 8.99 (bs, 2H), 8.15 (s, 1H), 7.99 (d, 1H), 7.86 (m, 2H), 7.76 (d, 1H), 7.62 (m, 2H), 7.03 (dd, 1H), 6.86 (s, 1H), 4.35 (AB, 2H), 4.03 (m, 1H), 3.10 (m, 2H), 1.90 (m, 1H), 1.53 (m, 1H). FAB MS, $[M+H]^+$=444.

EXAMPLE 148

5-[3-(S)-(7-Methoxynaphthalene-2-sulfonylamino)-2-oxopyrrolidin-1-ylmethyl]-thiophene-2-carboxamidine trifluoroacetate A. 7-Methoxynaphthalene-2-sulfonic acid [1-(5-cyanothiophen-2-ylmethyl)-2-oxopyrrolidin-3-(S)-yl]amide The title compound is prepared as in EXAMPLE 125, Part C using 5-(3-amino-2-oxopyrrolidin-1-ylmethyl)thiophene-2-carbonitrile hydrochloride, prepared as in EXAMPLE 123, in place of 4-(3-amino-2-oxopyrrolidine-1-ylmethyl) thiophene-2-carbonitrile hydrochloride. The crude product is purified by column chromatography eluting with gradient of 10% $EtOAc/CH_2Cl_2$ to 20% $EtOAc/CH_2Cl_2$ to afford the title compound as a white solid.

$^1$H NMR (CDCl$_3$, 300 MHz) δ8.36 (s, 1H), 7.89 (d, 1H), 7.75 (m, 2H), 7.43 (d, 1H), 7.30 (m, 1H), 7.22 (m, 2H), 6.90 (d, 1H), 5.44 (bs, 1H), 4.59 (AB, 2H), 3.90 (s, 3H), 3.74 (m, 1H), 3.28 (m, 2H), 2.61 (m, 1H), 2.10 (m, 1H).

B. 5-[3-(S)-(7-Methoxynaphthalene-2-sulfonylamino)-2-oxopyrrolidin-1-ylmethyl]thiophene-2-carboxamidine trifluoroacetate 7-Methoxynaphthalene-2-sulfonic acid-[1-(5-cyanothiophen-2-ylmethyl)-2-oxopyrrolidin-3-(S)-yl]amide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (CD$_3$OD, 300 MHz) δ8.41 (s, 1H), 7.96 (d, 1H), 7.87 (d, 1H), 7.74 (m, 1H), 7.40 (d, 1H), 7.31 (dd, 1H), 7.18 (d, 1H), 4.64 (s, 2H), 4.10 (t, 1H), 3.91 (s, 3H), 3.28 (m, 2H), 2.21 (m, 1H), 1.76 (m, 1H). FAB MS, $[M+H]^+$=459.

EXAMPLE 149

5-{3-(S)-[(7-Methoxynaphthalene-2-sulfonyl)methylamino]-2-oxopyrrolidin-1-ylmethyl}thiophene-2-carboxamidine trifluoroacetate A. 7-Methoxynaphthalene-2-sulfonic acid [1-(5-cyanothiophen-2-ylmethyl)-2-oxopyrrolidin-3-(S)-Yl]-methylamide The title compound is prepared as in EXAMPLE 126, Part A using 7-methoxynaphthalene-2-sulfonic acid [1-(5-cyanothiophen-2-ylmethyl)-2-oxopyrrolidin-3-(S)-yl] amide, prepared as in EXAMPLE 148, Part A, in place of 7-methoxynaphthalene-2-sulfonic acid [1-(5-cyanothiophen-3-ylmethyl)-2-oxopyrrolidin-3-(S)-yl] amide.

$^1$H NMR (CDCl$_3$, 300 MHz) δ8.41 (s, 1H), 7.91 (d, 1H), 7.78 (dd, 2H), 7.46 (m, 1H), 7.25 (m, 3H), 6.93 (d, 1H), 4.91 (t, 1H), 4.60 (AB, 2H), 3.92 (s, 3H), 3.31 (m, 2H), 2.74 (s, 3H), 2.36 (m, 1H), 2.03 (m, 1H).

B. 5-{3-(S)-[(7-Methoxynaphthalene-2-sulfonyl)methylamino]-2-oxopyrrolidin-1-ylmethyl}thiophene-2-carboxamidine trifluoroacetate 7-Methoxynaphthalene-2-sulfonic acid [1-(5-cyanothiophen-2-ylmethyl)-2-oxopyrrolidin-3-(S)-yl] methylamide is converted to the title compound as described in EXAMPLE 125, Part D. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.20 (bs, 2H), 8.82 (bs, 2H), 8.38 (s, 1H), 8.04 (d, 1H), 7.96 (d, 1H), 7.83 (d, 1H), 7.69 (dd, 1H), 7.57 (d, 1H), 7.34 (dd, 1H), 7.21 (d, 1H), 4.83 (t, 1H), 4.61 (AB, 2H), 3.89 (s, 3H), 3.19 (m, 2H), 2.62 (s, 3H), 2.04 (m, 1H), 1.82 (m, 1H). FAB MS, $[M+H]^+$=473.

EXAMPLE 150

5-{3-(S)-[(7-Methoxynaphthalene-2-sulfonyl)benzylamino]-2-oxopyrrolidin-1-ylmethyl}thiophene-2-carboxamidine trifluoroacetate A. 7-Methoxynaphthalene-2-sulfonic acid [1-(5-cyanothiophen-2-ylmethyl)-2-oxopyrrolidin-3-(S)-yl]-benzylamide The title compound is prepared as in EXAMPLE 126, Part A using 7-methoxynaphthalene-2-sulfonic acid[1-(5- cyanothiophen-2-ylmethyl)-2-oxopyrrolidin-3-(S)-yl] amide, prepared as in EXAMPLE 148, Part A, in place of 7-methoxynaphthalene-2-sulfonic acid [1-(5-cyanothiophen-3-ylmethyl)-2-oxopyrrolidin-3-(S)-yl]amide and benzyl bromide for methyl iodide.

$^1$H NMR (CDCl$_3$, 300 MHz) δ8.43 (s, 1H), 7.92 (m, 2H), 7.80 (d, 1H), 7.47 (m, 1H), 7.31 (m, 3H), 7.22 (m, 4H), 6.93 (d, 1H), 4.55 (m, 4H), 4.26 (m, 1H), 3.93 (s, 3H), 3.12 (m, 2H), 2.28 (m, 1H), 1.96 (m, 1H).

B. 5-{3-(S)-[(7-Methoxynaphthalene-2-sulfonyl) benzylamino]-2-oxopyrrolidin-1-ylmethyl}thiophene-2-carboxamidine trifluoroacetate 7-Methoxynaphthalene-2-sulfonic acid [1-(5-cyanothiophen-2-ylmethyl)-2-oxopyrrolidin-3-(S)-yl]-benzylamide is converted to the title compound as described in EXAMPLE 125, Part D. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.22 (bs, 2H), 9.05 (bs, 2H), 8.42 (s, 1H), 8.05 (d, 1H), 7.96 (d, 1H), 7.88 (d, 1H), 7.80 (m, 1H), 7.53 (s, 1H), 7.28 (m, 6H), 7.15 (d, 1H), 4.72 (t, 1H), 4.52 (m, 3H), 4.19 (m, 1H), 3.88 (s, 3H), 3.14 (m, 1H), 3.05 (m, 1H), 2.13 (m, 1H), 1.74 (m, 1H). FAB MS, [M+H]$^+$=549.

EXAMPLE 151

[Amino-(4-{3-(S)-(7-methoxynaphthalene-2-sulfonyl)methylamino]-2-oxopyrrolidin-1-ylmethyl}thiophene-2-yl)methylene]carbamic acid methyl ester trifluoroacetate A. [Amino-(4-{3-(S)-(7-methoxynaphthalene-2-sulfonyl)methylamino]-2-oxopyrrolidin-1-ylmethyl}thiophene-2-yl)methylene]carbamic acid methyl ester trifluoroacetate To a solution of 4-{3-(S)-[(7-methoxynaphthalene-2-sulfonyl)methylamino]-2-oxopyrrolidin-1-ylmethyl}thiophene-2-carboxamidine trifluoroacetate (0.7 g, 1.20 mmol) in 12 mL of CH$_2$Cl$_2$ and 1 mL of DMF at 0° C. is added N-methyl piperidine (0.42 g, 4.2 mmol) and methyl chloroformate (0.12 g, 1.26 mmol). After 0.5 hour, the solution is diluted EtOAc. The organic solution is washed with H$_2$O and sat. NaCl. The organic layer is dried over MgSO$_4$, filtered and concentrated. The crude product is purified by RP-HPLC eluting in a gradient of 10% CH$_3$CN/ H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.58 (bs, 2H), 8.39 (s, 1H), 8.05 (d, 1H), 7.96 (d, 1H), 7.82 (d, 1H), 7.74 (s, 1H), 7.68 (d, 1H), 7.58 (d, 1H), 7.35 (dd, 1H), 7.15 (d, 1H), 4.86 (t, 1H), 4.32 (AB, 2H), 3.86 (s, 3H), 3.66 (s, 3H), 3.13 (m, 2H), 2.64 (s, 3H), 1.96 (m, 1H), 1.71 (m, 1H). FAB MS, [M+H]$^+$=531. Elemental analysis calculated with 1.75 mmol of H$_2$O cal. C=46.22%, H=4.54%, N=8.29%, found C=46.00%, H=4.02%, N=7.93%.

EXAMPLE 152

4-{3-(S)-[(7-Methoxynaphthalene-2-sulfonyl) methylamino]-2-oxopyrrolidin-1-ylmethyl}thiophene-2-N-hydroxycarboxamidine trifluoroacetate A. 4-{3-(S)-[(7-Methoxynaphthalene-2-sulfonyl) methylamino]-2-oxopyrrolidin-1-ylmethyl}thiophene-2-N-hydroxycarboxamidine trifluoroacetate To a solution of 7-methoxynaphthalene-2-sulfonic acid [1-(5-cyanothiophen-3-ylmethyl)-2-oxopyrrolidin-3-(S)-yl] methylamide (0.48 g, 1 mmol) in 10 mL of EtOH is added hydroxylamine hydrochloride (0.11 g, 1.54 mmol) and triethyl amine (0.25 g, 2.5 mmol). The solution is heated to reflux. After 1 hour, the solution is concentrated. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (CDCl$_3$, 300 MHz) δ8.49 (s, 1H), 7.84 (d, 1H), 7.76 (m, 2H), 7.60 (s, 1H), 7.35 (s, 1H), 7.28 (m, 1H), 7.20 (m, 1H), 6.75 (bs, 2H), 4.96 (t, 1H), 4.87 (bs, 1H), 4.40 (AB, 2H), 3.90 (s, 3H), 3.23 (m, 2H), 2.77 (s, 3H), 2.28 (m, 1H), 1.93 (m, 1H). FAB MS, [M+H]$^+$=489. Elemental analysis calculated with 1.75 mmol of H$_2$O cal. C=45.64%, H=4.53%, N=8.84%, found C=45.33%, H=4.05%, N=8.36%.

EXAMPLE 153

4-(3-(S)-Amino-2-oxopyrrolidin-1-ylmethyl) pyridine-2-carbonitrile trifluoroacetate A. 2-Cyano-4-[{(tert-butyldimethylsilyl)oxy}methyl] pyridine The title compound is prepared according to the procedure described in *J. Heterocyclic Chem.* 30, 631 (1993). The crude residue obtained is purified by column chromatography eluting with gradient of 5% EtOAc/hexanes to 20% EtOAc/hexanes to afford the title compound as a yellow oil.

$^1$H NMR (CDCl$_3$, 300 MHz) δ8.66 (d, 1H), 7.69 (s, 1H), 7.48 (m, 1H), 4.80 (s, 2H), 1.00 (s, 9H), 0.19 (s, 6H).

B. 2-Cyano-4-(hydroxymethyl)pyridine

A solution of 2-cyano-4-[{(tert-butyldimethylsilyl) oxy}methyl]pyridine (10.1 g, 40.5 mmol) in 200 mL of anhydrous MeOH is stirred over 12 g of Dowex-50W-H$^+$ ion-exchange resin (pre-washed with MeOH) for a period of 18 hours. After this time, the mixture is filtered and washed with MeOH twice. The combined filtrates are concentrated in vacuo. The crude residue is purified by column chromatography eluting with 50% EtOAc/hexanes to afford the title compound (4.82 g, 35.9 mmol) as an oil.

$^1$H NMR (CDCl$_3$, 300 MHz) δ8.70 (m, 1H), 7.75 (s, 1H), 7.55 (d, 1H), 4.87 (d, 2H), 2.31 (bs, 1H).

C. 2-Cyano4-(bromomethyl)pyridine

Bromine (6.88 g, 43.1 mmol) is added dropwise to a solution of triphenylphosphine (11.3 g, 43.1 mmol) in 280 mL of CH$_2$Cl$_2$ at 0° C. The mixture is tirred for 30 minutes at 0° C. At this time, 2-cyano-4-(hydroxymethyl)-pyridine (4.82 g, 35.9 mmol) is added and the resulting mixture is stirred for 2 hours at room temperature. The reaction mixture is diluted with CH$_2$Cl$_2$ and washed with water (2x) and saturated NaCl solution. The organic layer is dried with MgSO$_4$, filtered and concentrated. The crude product is purified by column chromatography eluting in a gradient of 20% EtOAc/hexanes to 30% EtOAc/hexanes to afford the title compound (6.40 g, 32.5 mmol) as an oil.

$^1$H NMR (CDCl$_3$, 300 MHz) δ8.75 (d, 1H), 7.79 (s, 1H), 7.60 (d, 1H), 4.49 (s, 2H).

D. [1-(2-Cyano-pyridin-4-ylmethyl)-2-oxopyrrolidin-3-(S)-yl]carbamic acid tert-butyl ester The title compound is prepared from (2-oxopyrrolidin-3-(S)-yl)-carbamic acid tert-butyl ester as described in EXAMPLE 122, Part F using 2-cyano-4-(bromomethyl) pyridine in place of 4-bromomethylthiophene-2-carbonitrile. The crude product is purified by column chromatography eluting with gradient of 25% EtOAc/CH$_2$Cl$_2$ to 50% EtOAc/CH$_2$Cl$_2$ to afford the title compound as a solid.

$^1$H NMR (CDCl$_3$, 300 MHz) δ8.69 (d, 1H), 7.70 (s, 1H), 7.46 (d, 1H), 5.42 (bs, 1H), 4.57 (AB, 2H), 4.22 (m, 1H), 3.35 (m, 2H), 2.62 (m, 1H), 2.10 (m, 1H), 1.50 (s, 9H)

E. 4-(3-(S)-Amino-2-oxopyrrolidin-1-ylmethyl)pyridine-2-carbonitrile trifluoroacetate To a solution of [1-(2-cyano-pyridin-4-ylmethyl)-2-oxopyrrolidin-3-(S)-yl]carbamic acid tert-butyl ester (3.34 g, 10.6 mmol) in 50 mL of $CH_2Cl_2$ is added 5 mL of TFA. The reaction mixture is stirred for 18 hours and then concentrated to give the title compound (3.40 g, 10.3 mmol) as a white foam.

$^1$H NMR (DMSO-$d_6$, 300 MHz) δ7.90 (d, 1H), 7.70 (bs, 3H), 7.09 (s, 1H), 6.80 (m, 1H), 3.78 (AB, 2H), 3.35 (m, 1H), 2.55 (m, 2H), 1.62 (m, 1H), 1.20 (m, 1H).

EXAMPLE 154

4-[3-(S)-(7-Methoxynaphthalene-2-sulfonylamino)-2-oxopyrrolidin-1-ylmethyl]-pyridine-2-carboxamidine trifluoroacetate A. 7-Methoxynaphthalene-2-sulfonic acid-[1-(2-cyanopyridin-4-ylmethyl)-2-oxopyrrolidin-3-(S)-yl]amide The title compound is prepared as described in EXAMPLE 125, Part C using 4-(3-(S)-amino-2-oxopyrrolidin-1-ylmethyl)pyridine-2-carbonitrile trifluoroacetate in place of 4-(3-(S)-amino-2-oxopyrrolidine-1-ylmethyl)thiophene-2-carbonitrile hydrochloride. The crude product is purified by column chromatography eluting with a gradient of 25% EtOAc/$CH_2Cl_2$ to 50% EtOAc/$CH_2Cl_2$ to provide the title compound as a white solid.

$^1$H NMR (CDCl$_3$, 300 MHz) δ8.60 (d, 1H), 8.37 (s, 1H), 7.84 (d, 1H), 7.75 (m, 2H), 7.50 (s, 1H), 7.30 (dd, 1H), 7.26 (dd, 1H), 7.22 (m, 1H), 6.12 (d, 1H), 4.47 (AB, 2H), 3.96 (m, 1H), 3.90 (s, 3H), 3.22 (m, 2H), 2.52 (m, 1H), 2.10 (m, 1H).

B. 4-[3-(S)-(7-Methoxynaphthalene-2-sulfonylamino)-2-oxopyrrolidin-1-ylmethyl]pyridine-2-carboxamidine trifluoroacetate Hydrogen sulfide gas is bubbled for 5 minutes through a solution of 7-methoxynaphthalene-2-sulfonic acid-[1-(2-cyanopyridin-4-ylmethyl)-2-oxopyrrolidin-3-(S)-yl]amide (0.22 g, 0.50 mmol) in 10 mL of a 10:1 mixture of pyridine/triethylamine. After stirring the pale green solution for a period of 18 hours, the reaction mixture is concentrated in vacuo. The residue is diluted in acetone and concentrated to give the crude thioamide. To a solution of thioamide in 10 mL of acetone is added iodomethane (1 mL, 16 mmol). The resulting mixture is heated at reflux for 1 hour, allowed to cool to room temperature and concentrated in vacuo to provide the crude thioimidate hydroiodide. To a solution of thioimidate hydroiodide in 10 mL of MeOH is added ammonium acetate (0.15 g, 1.9 mmol). The resulting mixture is heated at reflux for 2 hours, allowed to cool to room temperature and stirred overnight. The resulting mixture is concentrated in vacuo to provide the crude amidine salt. The crude product is purified by RP-HPLC eluting in a gradient of 15% $CH_3CN/H_2O$ (0.1% TFA) to 80% $CH_3CN/H_2O$ (0.1% TFA) and the appropriate product fractions are lyophilized to provide the title compound (0.10 g, 0.18 mmol) as a white amorphous solid.

$^1$H NMR (DMSO-$d_6$, 300 MHz) δ9.51 (bs, 2H), 9.40 (bs, 2H), 8.73 (d, 1H), 8.37 (s, 1H), 8.25 (d, 1H), 8.02 (d, 1H), 7.92 (m, 2H), 7.72 (dd, 1H), 7.58 (d, 1H), 7.53 (s, 1H), 7.32 (dd, 1H), 4.49 (AB, 2H), 4.18 (m, 1H), 3.86 (s, 3H), 3.15 (m, 2H), 2.02 (m, 1H), 1.64 (m, 1H). FAB MS, [M+H]$^+$=454.

EXAMPLE 155

4-{3-(S)-[(7-Methoxynaphthalene-2-sulfonyl)benzylamino]-2-oxopyrrolidin-1-ylmethyl}pyridine-2-carboxamidine trifluoroacetate A. 7-Methoxynaphthalene-2-sulfonic acid-[1-(2-cyanopyridin-4-ylmethyl)-2-oxopyrrolidin-3-(S)-yl]-benzylamide The title compound is prepared as described in EXAMPLE 141, Part D using 7-methoxynaphthalene-2-sulfonic acid-[1-(2-cyanopyridin-4-ylmethyl)-2-oxopyrrolidin-3-(S)-yl]amide in place of N-Cbz-7-aminonaphthalene-2-sulfonic acid-[1-(5-cyanothiophen-3-ylmethyl)-2-oxopyrrolidin-3-(S)-yl]amide. The crude product is purified by column chromatography eluting with gradient of $CH_2Cl_2$ to 3% MeOH/$CH_2Cl_2$ to afford the title compound as a white solid.

$^1$H NMR (CDCl$_3$, 300 MHz) δ8.66 (d, 1H), 8.48 (s, 1H), 7.98 (m, 2H), 7.80 (d, 1H), 7.53 (s, 1H), 7.41 (d, 1H), 7.29 (m, 7H), 4.47 (AB, 2H), 4.45 (AB, 2H), 4.45 (m, 1H), 3.94 (s, 3H), 3.11 (m, 2H), 2.30 (m, 1H), 2.19 (m, 1H).

B. 4-{3-(S)-[(7-Methoxynaphthalene-2-sulfonyl)benzylamino]-2-oxopyrrolidin-1-ylmethyl}pyridine-2-carboxamidine trifluoroacetate 7-Methoxynaphthalene-2-sulfonic acid [1-(2-cyanopyridin-4-ylmethyl)-2-oxopyrrolidin-3-(S)-yl]-benzylamide is converted to the title compound as described in EXAMPLE 154, Part B. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.50 (bs, 2H), 9.29 (bs, 2H), 8.75 (d, 1H), 8.48 (s, 1H), 8.02 (d, 1H), 7.96 (d, 1H), 7.93 (s, 1H), 7.83 (dd, 1H), 7.56 (m, 2H), 7.35 (m, 3H), 7.29 (m, 3H), 4.84 (m, 1H), 4.44 (AB, 2H), 4.42 (AB, 2H), 3.90 (s, 3H), 3.20 (m, 1H), 3.05 (m, 1H), 2.19 (m, 1H), 1.80 (m, 1H). FAB MS, [M+H]$^+$=544.

EXAMPLE 156

4-{3-(S)-[(7-Methoxynaphthalene-2-sulfonyl)methylamino]-2-oxopyrrolidin-1-ylmethyl}pyridine-2-carboxamidine trifluoroacetate A. 7-Methoxynaphthalene-2-sulfonic acid-[1-(2-cyanopyridin-4-ylmethyl)-2-oxopyrrolidin-3-(S)-yl]-methylamide The title compound is prepared from 7-methoxynaphthalene-2-sulfonic acid-[1-(2-cyanopyridin-4-ylmethyl)-2-oxopyrrolidin-3-(S)-yl]amide as described in EXAMPLE 141, Part D using methyl iodide in place of benzyl bromide. The crude product is purified by column chromatography eluting with gradient of 20% EtOAc/$CH_2Cl_2$ to 40% EtOAc/$CH_2Cl_2$ to afford the title compound as a white solid.

$^1$H NMR (CDCl$_3$, 300 MHz) δ8.65 (d, 1H), 8.41 (s, 1H), 7.90 (d, 1H), 7.79 (m, 2H), 7.53 (s, 1H), 7.37 (m, 1H), 7.29 (m, 2H), 4.97 (m, 1H), 4.47 (AB, 2H), 3.93 (s, 3H), 3.29 (m, 2H), 2.83 (s, 3H), 2.40 (m, 1H), 2.10 (m, 1H).

B. 4-{3-(S)-[(7-Methoxynaphthalene-2-sulfonyl)methylamino]-2-oxopyrrolidin-1-ylmethyl}pyridine-2-carboxamidine trifluoroacetate 7-Methoxynaphthalene-2-sulfonic acid-[1-(2-cyanopyridin-4-ylmethyl)-2-oxopyrrolidin-3-(S)-yl]methylamide is converted to the title compound as described in EXAMPLE 154, Part B. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-d$_6$, 300 MHz) δ9.54 (bs, 2H), 9.31 (bs, 2H), 8.74 (d, 1H), 8.40 (s, 1H), 8.04 (d, 1H), 7.97 (s, 1H), 7.95 (d, 1H), 7.70 (dd, 1H), 7.59 (m, 2H), 7.37 (m, 1H), 4.99 (m, 1H), 4.50 (AB, 2H), 3.89 (s, 3H), 3.24 (m, 2H), 2.71 (s, 3H), 2.05 (m, 1H), 1.88 (m, 1H). FAB MS, [M+H]$^+$=468.

EXAMPLE 157

4-[3-(S)-(5-Chloro-3-methylbenzo[b]thiophene-2-sulfonylamino)-2-oxopyrrolidin-1-ylmethyl] pyridine-2-carboxamidine trifluoroacetate A. 5-Chloro-3-methylbenzo[b]thiophene-2-sulfonic acid [1-(2-cyanopyridin-4-ylmethyl)-2-oxopyrrolidin-3-(S)-yl] amide The title compound is prepared as described in EXAMPLE 125, Part C using 4-(3-(S)-amino-2-oxopyrrolidin-1-ylmethyl)pyridine-2-carbonitrile trifluoroacetate in place of 4-(3-(S)-amino-2-oxopyrrolidine-1-ylmethyl)-thiophene-2-carbonitrile hydrochloride and with 5-chloro-3-methyl-benzo[b]thiophene-2-sulfonyl chloride in place of 7-methoxynaphthalene-2-sulfonyl chloride. The crude product is purified by column chromatography eluting with gradient of 25% EtOAc/CH$_2$Cl$_2$ to 50% EtOAc/CH$_2$Cl$_2$ to afford the title compound as a white solid.

$^1$H NMR (CDCl$_3$, 300 MHz) δ8.67 (d, 1H), 7.82 (s, 1H), 7.76 (d, 1H), 7.51 (s, 1H), 7.48 (dd, 1H), 7.32 (d, 1H), 5.65 (d, 1H), 4.49 (AB, 2H), 4.00 (m, 1H), 3.29 (m, 2H), 2.71 (s, 3H), 2.66 (m, 1H), 2.19 (m, 1H).

B. 4-[3-(S)-(5-Chloro-3-methylbenzo[b]thiophene-2-sulfonylamino)-2-oxopyrrolidin-1-ylmethyl]pyridine-2-carboxamidine trifluoroacetate 5-Chloro-3-methylbenzo[b]thiophene-2-sulfonic acid [1-(2-cyano-pyridin-4-ylmethyl)-2-oxopyrrolidin-3-(S)-yl] amide is converted to the title compound as described in EXAMPLE 154, Part B. The crude product is purified by RP-HPLC eluting in a gradient of 10% CH$_3$CN/H$_2$O (0.1% TFA) to 80% CH$_3$CN/H$_2$O (0.1 % TFA) and the appropriate product fractions are lyophilized to provide the title compound as a white solid.

$^1$H NMR (DMSO-d$_6$, 300 MHz) δ9.51 (bs, 2H), 9.42 (bs, 2H), 8.78 (d, 1H), 8.76 (s, 1H), 8.09 (d, 1H), 8.05 (s, 1H), 7.94 (s, 1H), 7.59 (s, 1H), 7.57 (d, 1H), 4.50 (AB, 2H), 4.27 (m, 1H), 3.17 (m, 2H), 2.63 (s, 3H), 2.10 (m, 1H), 1.72 (m, 1H). FAB MS, [M+H]$^+$=478. Elemental analysis calculated with 1.4 mole of H$_2$O: C=42.81%, H=3.89%, N=11.35%; found C=42.82%, H=3.30%, N=10.84%.

EXAMPLE 158

4-{3-(S)-[(5-Chloro-3-methylbenzo[b]thiophene-2-sulfonyl)methylamino]-2-oxopyrrolidin-1-ylmethyl}pyridine-2-carboxamidine trifluoroacetate A. 5-Chloro-3-methylbenzo[b]thiophene-2-sulfonic acid [1-(2-cyanopyridin-4-ylmethyl)-2-oxopyrrolidin-3-(S)-yl]-methylamide The title compound is prepared from 5-chloro-3-methylbenzo[b]thiophene-2-sulfonic acid [1-(2-cyanopyridin-4-ylmethyl)-2-oxopyrrolidin-3-(S)-yl]amide as described in EXAMPLE 141, Part D using methyl iodide in place of benzyl bromide. The crude product is purified by column chromatography eluting with gradient of 10% EtOAc/CH$_2$Cl$_2$ to 25% EtOAc/CH$_2$Cl$_2$ to afford the title compound as a white solid.

$^1$H NMR (CDCl$_3$, 300 MHz) δ8.66 (d, 1H), 7.80 (s, 1H), 7.74 (d, 1H), 7.53 (s, 1H), 7.43 (dd, 1H), 7.35 (d, 1H), 4.95 (m, 1H), 4.47 (AB, 2H), 3.29 (m, 2H), 2.91 (s, 3H), 2.70 (s, 3H), 2.41 (m, 1H), 2.15 (m, 1H).

B. 4-{3-(S)-[(5-Chloro-3-methylbenzo[b]thiophene-2-sulfonyl)methylamino]-2-oxopyrrolidin-1-ylmethyl}pyridine-2-carboxamidine trifluoroacetate 5-Chloro-3-methylbenzo[b]thiophene-2-sulfonic acid-[1-(2-cyanopyridin-4-ylmethyl)-2-oxopyrrolidin-3-(S)-yl] methylamide is converted to the title compound as described in EXAMPLE 154, Part B. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are lyophilized to provide the title compound as a white solid.

$^1$H NMR (DMSO-d$_6$, 300 MHz) δ9.52 (bs, 2H), 9.34 (bs, 2H), 8.74 (d, 1H), 8.08 (m, 2H), 7.95 (s, 1H), 7.63 (s, 1H), 7.61 (dd, 1H), 4.99 (m, 1H), 4.50 (AB, 2H), 3.31 (m, 1H), 3.21 (m, 1H), 2.80 (s, 3H), 2.66 (s, 3H), 2.14 (m, 1H), 2.03 (m, 1H). FAB MS, [M+H]$^+$=493.

EXAMPLE 159

2-{[1-(2-Carbamimidoylpyridine-4-ylmethyl)-2-oxopyrrolidin-3-(S)-yl]-(7-methoxynaphthalene-2-sulfonyl)amino}acetamide trifluoroacetate A. 2-[[1-(2-Cyanopyridine-4-ylmethyl)-2-oxopyrrolidin-3-(S)-yl]-(7-methoxynaphthalene-2-sulfonyl)amino]acetic acid tert-butyl ester The title compound is prepared from 7-methoxynaphthalene-2-sulfonic acid-[1-(2-cyanopyridin-4-ylmethyl)-2-oxopyrrolidin-3-(S)-yl]amide as described in EXAMPLE 141, Part D using tert-butyl bromoacetate in place of benzyl bromide. The crude product is purified by column chromatography eluting with gradient of 10% EtOAc/CH$_2$Cl$_2$ to 25% EtOAc/CH$_2$Cl$_2$ to afford the title compound as a white solid.

$^1$H NMR (CDCl$_3$, 300 MHz) δ8.66 (d, 1H), 8.44 (s, 1H), 7.90 (d, 1H), 7.85 (d, 1H), 7.79 (d, 1H), 7.58 (s, 1H), 7.42 (d, 1H), 7.29 (dd, 1H), 7.28 (m, 1H), 4.56 (m, 1H), 4.49 (AB, 2H), 3.99 (AB, 2H), 3.94 (s, 3H), 3.31 (m, 2H), 2.63 (m, 1H), 2.54 (m, 1H), 1.43 (s, 9H).

B. 2-[[1-(2-Cyanopyridine-4-ylmethyl)-2-oxopyrrolidin-3-(S)-yl]-(7-methoxynaphthalene-2-sulfonyl)amino]acetic acid 2-[[1-(2-Cyanopyridine-4-ylmethyl)-2-oxopyrrolidin-3-(S)-yl]-(7-methoxynaphthalene-2-sulfonyl)amino]acetic acid tert-butyl ester is converted to the title compound as described in EXAMPLE 127, Part B. The product is azeotroped with toluene to give a white foam.

$^1$H NMR (CDCl$_3$, 300 MHz) δ9.61 (bs, 1H), 8.70 (d, 1H), 8.39 (s, 1H), 7.90 (d, 1H), 7.79 (d, 1H), 7.70 (d, 1H), 7.68 (s, 1H), 7.51 (m, 1H), 7.30 (m, 1H), 7.20 (d, 1H), 4.80 (m, 1H), 4.59 (AB, 2H), 4.01 (s, 2H), 3.95 (s, 3H), 3.40 (m, 2H), 2.48 (m, 1H), 2.31 (m, 1H). FAB MS, [M+H]$^+$=495.

C. 2-[[1-(2-Cyanopyridine-4-ylmethyl)-2-oxopyrrolidin-3-(S)-yl]-(7-methoxynaphthalene-2-sulfonyl)amino]acetamide The title compound is prepared as described in EXAMPLE 127, Part C using 2-[[1-(2-cyanopyridine-4-ylmethyl)-2-oxopyrrolidin-3-(S)-yl]-(7-methoxynaphthalene-2-sulfonyl)amino]acetic acid in place of 2-[[1-(5-cyanothiophene-3-ylmethyl)-2-oxopyrrolidin-3-(S)-yl]-(7-methoxynaphthalene-2-sulfonyl)amino]acetic acid. The crude product is concentrated from EtOAc to afford the title compound as a white solid.

$^1$H NMR (CDCl$_3$, 300 MHz) δ8.73 (d, 1H), 8.40 (s, 1H), 7.91 (d, 1H), 7.80 (m, 2H), 7.69 (s, 1H), 7.50 (d, 1H), 7.32 (m, 1H), 7.29 (m, 1H), 5.45 (bs, 2H), 4.58 (m, 1H), 4.57 (AB, 2H), 3.98 (s, 3H), 3.82 (AB, 2H), 3.40 (m, 1H), 3.32 (m, 1H), 2.51 (m, 1H), 2.42 (m, 1H).

141

D. 2-{[1-(2-Carbamimidoyl-pyridine-4-ylmethyl)-2-oxopyrrolidin-3-(S)-yl]-(7-methoxynaphthalene-2-sulfonyl)amino}acetamide trifluoroacetate 2-[[1-(2-Cyanopyridine-4-ylmethyl)-2-oxopyrrolidin-3-(S)-yl]-(7-methoxynaphthalene-2-sulfonyl)amino]acetamide is converted to the title compound as described in EXAMPLE 154, Part B. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.52 (bs, 2H), 9.33 (bs, 2H), 8.75 (d, 1H), 8.45 (s, 1H), 8.04 (d, 1H), 7.99 (s, 1H), 7.95 (d, 1H), 7.77 (d, 1H), 7.64 (d, 1H), 7.58 (bs, 2H), 7.35 (dd, 1H), 7.25 (s, 1H), 4.88 (m, 1H), 4.50 (AB, 2H), 3.90 (s, 3H), 3.73 (AB, 2H), 3.25 (m, 2H), 2.11 (m, 2H). FAB MS, [M+H]$^+$=511.

EXAMPLE 160

2-{[1-(2-Carbamimidoyl-pyridine-4-ylmethyl)-2-oxopyrrolidin-3-(S)-yl]-(7-methoxynaphthalene-2-sulfonyl)amino}-N-phenethylacetamide trifluoroacetate A. 2-[[1-(2-Cyanopyridine-4-ylmethyl)-2-oxopyrrolidin-3-(S)-yl]-(7-methoxynaphthalene-2-sulfonyl)amino]-N-phenethylacetamide The title compound is prepared as described in EXAMPLE 127, Part C using 2-[[1-(2-cyan-pyridine-4-ylmethyl)-2-oxopyrrolidin-3-(S)-yl]-(7-methoxy-naphthalene-2-sulfonyl)amino]acetic acid in place of 2-[[1-(5-cyanothiophene-3-ylmethyl)-2-oxopyrrolidin-3-(S)-yl]-(7-methoxynaphthalene-2-sulfonyl)amino-]acetic acid and with phenethylamine instead of $NH_4OH$. The crude product is purified by column chromatography eluting with gradient of 50% $EtOAc/CH_2Cl_2$ to 2% $MeOH/50\%$ $EtOAc/CH_2Cl_2$ to afford the title compound as a white solid.

$^1$H NMR (CDCl$_3$, 300 MHz) δ8.70 (d, 1H), 8.39 (s, 1H), 7.89 (d, 1H), 7.80 (d, 1H), 7.69 (s, 1H), 7.50 (d, 1H), 7.25 (m, 7H), 7.11 (d, 1H), 4.55 (AB, 2H), 4.31 (bs, 1H), 3.94 (m, 1H), 3.90 (s, 3H), 3.81 (AB, 2H), 3.38 (m, 2H), 3.26 (m, 2H), 2.65 (m, 2H), 2.35 (m, 1H), 1.85 (m, 1H).

B. 2-{[1-(2-Carbamimidoyl-pyridine-4-ylmethyl)-2-oxopyrrolidin-3-(S)-yl]-(7-methoxynaphthalene-2-sulfonyl)amino}-N-phenethylacetamide trifluoroacetate 2-[[1-(2-Cyanopyridine-4-ylmethyl)-2-oxopyrrolidin-3-(S)-yl]-(7-methoxynaphthalene-2-sulfonyl)amino]-N-phenethylacetamide is converted to the title compound as described in EXAMPLE 154, Part B. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.52 (bs, 2H), 9.37 (bs, 2H), 8.75 (d, 1H), 8.44 (s, 1H), 8.19 (m, 1H), 8.03 (d, 1H), 7.99 (s, 1H), 7.97 (d, 1H), 7.77 (dd, 1H), 7.65 (d, 1H), 7.57 (s, 1H), 7.36 (dd, 1H), 7.25 (m, 2H), 7.19 (m, 3H), 4.88 (m, 1H), 4.51 (AB, 2H), 3.88 (s, 3H), 3.79 (AB, 2H), 3.22 (m, 4H), 2.64 (m, 2H), 2.18 (m, 1H), 2.09 (m, 1H). FAB MS, [M+H]$^+$=615.

EXAMPLE 161

4-{3-(S)-[(7-Methoxynaphthalene-2-sulfonyl)-thiophen-3-ylmethylamino]-2-oxopyrrolidin-1-ylmethyl}pyridine-2-carboxamidine trifluoroacetate A. 7-Methoxynaphthalene-2-sulfonic acid-[1-(2-cyanopyridin-4-ylmethyl)-2-oxopyrrolidin-3-(S)-yl]thiophen-3-ylmethylamide The title compound is prepared from 7-methoxynaphthalene-2-sulfonic acid [1-(2-cyanopyridin-4-ylmethyl)-2-oxopyrrolidin-3-(S)-yl]amide as described in EXAMPLE 141, Part D using 3-bromomethylthiophene in place of benzyl bromide. The crude product is purified by column chromatography eluting with gradient of 10% $EtOAc/CH_2Cl_2$ to 25% $EtOAc/CH_2Cl_2$ to afford the title compound as a white solid.

$^1$H NMR (CDCl$_3$, 300 MHz) δ8.65 (d, 1H), 8.47 (s, 1H), 7.95 (m, 2H), 7.80 (d, 1H), 7.57 (s, 1H), 7.43 (d, 1H), 7.25 (m, 4H), 7.08 (d, 1H), 4.49 (AB, 2H), 4.45 (m, 3H), 3.94 (s, 3H), 3.19 (m, 2H), 2.34 (m, 1H), 2.20 (m, 1H).

B. 4-{3-(S)-[(7-Methoxynaphthalene-2-sulfonyl)thiophen-3-ylmethylamino]-2-oxopyrrolidin-1-ylmethyl}pyridine-2-carboxamidine trifluoroacetate 7-Methoxynaphthalene-2-sulfonic acid [1-(2-cyanopyridin-4-ylmethyl)-2-oxopyrrolidin-3-(S)-yl]thiophen-3-ylmethylamide is converted to the title compound as described in EXAMPLE 154, Part B. The crude product is purified by RP-HPLC eluting in a gradient of 10% $CH_3CN/H_2O$ (0.1% TFA) to 80% $CH_3CN/H_2O$ (0.1% TFA) and the appropriate product fractions are lyophilized to provide the title compound as a white solid.

$^1$H NMR (DMSO-$d_6$, 300 MHz) δ9.43 (bs, 2H), 9.17 (bs, 2H), 8.66 (d, 1H), 8.35 (s, 1H), 7.94 (d, 1H), 7.88 (s, 1H), 7.87 (d, 1H), 7.73 (d, 1H), 7.51 (d, 1H), 7.45 (s, 1H), 7.34 (m, 1H), 7.29 (m, 2H), 6.92 (d, 1H), 4.70 (m, 1H), 4.34 (s, 2H), 4.30 (AB, 2H), 3.80 (s, 3H), 3.12 (m, 1H), 3.00 (m, 1H), 2.10 (m, 1H), 1.77 (m, 1H). FAB MS, [M+H]$^+$=550.

EXAMPLE 162

4-{3-(S)-[(7-Methoxynaphthalene-2-sulfonyl)thiophen-3-ylmethylamino]-2-oxopyrrolidin-1-ylmethyl}thiophene-2-carboxamidine trifluoroacetate A. 7-Methoxynaphthalene-2-sulfonic acid [1-(2-cyanothiophene-4-ylmethyl)-2-oxopyrrolidin-3-(S)-yl]thiophene-3-ylmethylamide The title compound is prepared from 7-methoxynaphthalene-2-sulfonic acid [1-(2-cyanothiophen-4-ylmethyl)-2-oxopyrrolidin-3-(S)-yl]amide (0.5 g, 1.16 mmol) as described in EXAMPLE 126, Part A, using 3-bromomethylthiophene in place of methyl iodide. The crude product is purified by column chromatography eluting with 60% EtOAc/hexanes to afford 7-methoxy-naphthalene-2-sulfonic acid-[1-(2-cyanothiophene-4-ylmethyl)-2-oxopyrrolidin-3-(S)-yl]thiophene-3-ylmethylamide as a white solid (0.18 g, 0.33 mmol).

$^1$H NMR (CDCl$_3$, 300 MHz) δ8.44 (s, 1H), 7.93 (m, 2H), 7.78 (d, 1H), 7.46 (d, 1H), 7.24 (m, 3H), 7.13 (s, 4H), 7.05 (d, 1H), 4.2–4.6 (2AB, 4H), 4.44 (t, 1H), 3.72 (s, 3H), 3.12 (m, 2H), 2.25 (m, 1H), 2.05 (m, 1H). FAB MS, [M+H]$^+$=538.

B. 4-{3-(S)-[(7-Methoxynaphthalene-2-sulfonyl)thiophen-3-ylmethylamino]-2-oxopyrrolidin-1-ylmethyl}thiophene-2-carboxamidine trifluoroacetate 7-Methoxynaphthalene-2-sulfonic acid [1-(2-cyanothiophen-4-ylmethyl)-2-oxopyrrolidin-3-(S)-yl]thiophene-3-ylmethylamide (0.18, 0.33 mmol) is converted as described in EXAMPLE 125, Part D. The crude product is purified by RP-HPLC eluting in a gradient of 25% $CH_3CN/H_2O$ (0.1% TFA) to 80% $CH_3CN/H_2O$ (0.1% TFA) and the appropriate product fractions are lyophilized to provide the title compound as a white solid (0.083 g, 0.12 mmol).

$^1$H NMR (DMSO-$d_6$, 300 MHz) $\delta$8.43 (s, 1H), 7.92 (d, 1H), 7.83 (m, 4H), 7.39 (s, 1H), 7.28 (m, 2H), 7.17 (s 1H), 6.97 (d, 1H), 4.64 (t 1H), 4.43 (2 AB, 4H), 3.92 (s, 3H), 3.18 (m, 2H), 2.22 (m, 1H), 1.96 (m, 1H). FAB MS, [M+H]$^+$= 555. Elemental analysis calculated with 1 mole of $H_2O$: C=48.97%, H=4.26%, N=8.16%; found C=48.80%, H=4.34%, N=7.88%.

EXAMPLE 163

4-{3-(S)-[(4-(6-Nitro-2-chlorophenoxy) benzenesulfonyl)amino]-2-oxopyrrolidin-1-ylmethyl}thiophene-2-carboxamidine trifluoroacetate A. 4-{3-(S)-[(4-(6-Nitro-2-chlorophenoxy) benzenesulfonyl)amino]-2-oxopyrrolidin-1-ylmethyl}thiophene-2-carbononitrile 4-{3-(S)-[(4-(6-Nitro-2-chlorophenoxy)benzenesulfonyl) amino]-2-oxopyrrolidin-1-ylmethyl}thiophene-2-carbononitrile is prepared as described in EXAMPLE 125, Part C from of 4-(3-Amino-2-oxopyrrolidine-1-ylmethyl) thiophene-2-carbonitrile hydrochloride (0.36 g, 1.4 mmol), and 4-(6-Nitro-2-chlorophenoxy)-benzenesulfonyl chloride (0.63 g, 1.8 mmol) and triethyl amine (0.57 g, 5.7 mmol). After 18 hours, the solution is diluted with $CH_2Cl_2$ and 0.5 N HCl. The layers are separated; the organic layer is dried over $NA_2SO_4$, filtered and concentrated. The crude product is triturated with ether to afford the title compound (0.72 g, 1.35 mmol) as a white foam.

$^1$H NMR (CD$_3$OD, 300 MHz) $\delta$8.03 (d, 1H), 7.91 (two d, 3H), 7.69 (s, 1H), 7.63 (s, 1H), 7.53 (dd, 1H) 7.02 (d, 2H), 4.42 (AB, 2H), 4.11 (t, 1H), 3.23 (m, 2H), 2.23 (m, 1H), 1.71 (m, 1H). FAB MS, [M+H]$^+$=533; 535.

B. 4-{3-(S)-[(4-(6-Nitro-2-chlorophenoxy)benzenesulfonyl) amino]-2-oxopyrrolidin-1-ylmethyl}thiophene-2-carboxamidine trifluoroacetate 4-{3-(S)-[(4-(6-Nitro-2-chlorophenoxy)benzenesulfonyl) amino]-2-oxopyrrolidin-1-ylmethyl}thiophene-2-carbononitrile (0.408 g, 0.75 mmol) is converted to the title compound as described in EXAMPLE 125, Part D. The crude product is purified by repeated RP-HPLC, eluting with a gradient of 10% $CH_3CN$/H2O (0.1% TFA) to 100% $CH_3CN$. The appropriate product fractions are lyophilized to provide the title compound as a white solid (0.22 g, 0.33 mmol).

$^1$H NMR (CD$_3$OD, 300 MHz) $\delta$8.04 (d, 1H), 7.92 (two d, 3H), 7.86 (s, 1H), 7.78 (s, 1H), 7.56 (dd, 1H) 7.02 (d, 2H), 4.46 (AB, 2H), 4.10 (t, 1H), 3.28 (m, 2H), 2.24 (m, 1H), 1.85 (m, 1H). FAB MS, [M+H]$^+$=550; 552.

EXAMPLE 164

5-{3-(S)-[(7-Methoxynaphthalene-2-sulfonylamino]-2-oxopyrrolidin-1-ylmethyl}-furan-2-carboxamidine trifluoroacetate A. 5-Bromomethylfuran-2-carbononitrile 5-Hydoxymethylfuran-2-carbonitrile (1.12 g, 9.1 mmol) is dissolved in THF (75 mL), treated with triphenylphosphine (2.9 g, 11.06 mmol), carbon tetrabromide (3.78 g, 11.4 mmol) and stirred at room temperature for 18 hours. Standard workup yields the title compound (1.45 g, 7.8 mmol).

$^1$H NMR (CDCl$_3$, 300 MHz) $\delta$7.04 (d, 2H), 6.50 (d, 1H), 4.43 (s, 2H).

B. 5-(3-Amino-2-oxopyrrolidine-1-ylmethyl)furan-2-carbonitrile hydrochloride

A solution of (2-oxopyrrolidin-3-(S)-yl)carbamic acid tert-butyl ester (1.56 g, 7.8 mmol) in 80 mL of THF:DMF (5:1) is treated with 5-bromomethylfuran-2-carbo-nitrile (3.23 g, 16 mmol) and sodium hydride (60%) (0.32 g, 8 mmol) as described in EXAMPLE 122, Part F. After addition, the solution is allowed to warm to ambient temperatures. After 5 hours, the solution is quenched by the addition of sat. NH$_4$Cl. The solution is diluted with EtOAc and washed with $H_2O$ (3x) and saturated NaCl. The organic layer is dried over MgSO$_4$, filtered and concentrated. The crude product is purified by column chromatography eluting with gradient of 40% EtOAc/hexanes to 80% EtOAc/hexanes to afford [1-(5-cyanofuran-2-ylmethyl)-2-oxopyrrolidin-3-yl]carbamic acid tert-butyl ester (2.38 g, 7.8 mmol) as a white solid. A portion of this material (1.28 g, 4.2 mmol) is treated as described in EXAMPLE 122, Part G to yield the title compound (1.1 g, 4.55 mmol).

$^1$H NMR (DMSO-$d_6$, 300 MHz) $\delta$8.73 (bs, 3H), 7.45 (d, 1H), 6.73 (d, 1H), 4.50 (s, 2H), 3.95 (m, 1H), 3.30 (m, 2H), 2.31 (m, 1H), 1.98 (m, 1H). EI MS, M$^+$=205.

C. 7-Methoxynaphthalene-2-sulfonic acid [1-(2-cyanofuran-5-ylmethyl)-2-oxopyrrolidin-3-(S)-yl]-amide 7-Methoxynaphthalene-2-sulfonic acid [1-(2-cyanofuran-5-ylmethyl)-2-oxopyrrolidin-3-(S)-yl]amide is prepared as described in EXAMPLE 125, Part C from of 5-(3-amino-2-oxopyrrolidine-1-ylmethyl)furan-2-carbonitrile hydrochloride (1.1 g, 4.55 mmol), and 7-methoxynaphthalene-2-sulfonyl chloride (1.52 g, 5.9 mmol). After 16 hours, the solution is diluted with $CH_2Cl_2$. The organic layer is washed with 0.5 N HCl, water and sat NaCl. The organic layer is dried over Na$_2$SO$_4$, filtered and concentrated. The crude product is purified by column chromatography eluting with 10% EtOAc/$CH_2Cl_2$ to afford the title compound (0.88 g, 2.07 mmol) as a white solid.

$^1$H NMR (CDCl$_3$, 300 MHz) $\delta$8.33 (s, 1H), 7.86 (d, 1H), 7.74 (m, 2H), 7.27 (dd, 1H), 7.22 (d, 1H), 6.97 (d, 1H), 6.35 (d, 1H), 5.61 (d, 1H), 4.40 (AB, 2H), 3.93 (s, 3H), 3.73 (m, 1H), 3.28 (m, 2H), 2.57 (m, 1H), 2.08 (m, 1H). EI MS, [M]$^+$=425.

D. 5-{3-(S)-[(7-Methoxynaphthalene-2-sulfonylamino]-2-oxopyrrolidin-1-ylmethyl}furan-2-carboxamidine trifluoroacetate 7-Methoxynaphthalene-2-sulfonic acid-[1-(2-cyanofuran-5-ylmethyl)-2-oxopyrrolidin-3-(S)-yl]amide (0.355 g, 0.83 mmol) is converted as described in EXAMPLE 125, Part D.

The crude product is purified by RP-HPLC eluting in a gradient of 10% $CH_3CN/H_2O$ (0.1% TFA) to 100% $CH_3CN$ and the appropriate product fractions are lyophilized to provide the title compound as a white solid (0.365 g, 0.625 mmol).

$^1$H NMR (DMSO-$d_6$, 300 MHz) $\delta$8.40 (s, 1H), 7.94 (d, 1H), 7.87 (d, 1H), 7.74 (dd, 1H), 7.48 (d, 1H), 7.38 (d, 1H), 7.28 (dd, 1H), 6.64 (d, 1H), 4.53 (AB, 2H), 4.14 (t, 1H), 3.93 (s, 3H), 3.28 (m, 2H), 2.12 (m, 1H), 1.74 (m, 1H). FAB MS, [M+H]$^+$=443. Elemental analysis calculated with 1.5 mole of $H_2O$: C=47.34%, H=4.49%, N=9.61%; found C=47.25%, H=4.05%, N=9.13%.

EXAMPLE 165

4-[3-(S)-(5-Chloro-3-methylbenzo[b]thiophene-2-sulfonylamino)-2-oxopyrrolidin-1-ylmethyl]furan-2-carboxamidine trifluoroacetate A. 4-Hydroxymethylfuran-2-carbonitrile A solution of furan-3-ylmethanol (9.68 g, 98.7 mmol) in THF (150 mL) at −78° C. is treated with n-butyl lithium (65 mL of 1.6 M solution) for 1 hour followed by and s-butyl lithium (86 mL of 1.3 M solution) for 4 hours. A solution of iodine (29 g, 114 mmol) in THF (250 mL) is added and the solution is slowly warmed to room temperature. After stirring overnight the reaction mixture is diluted with ether, washed with brine, dried (MgSO4) and concentrated. Chromatographic purification (30% ethyl acetate/hexane) yielded the title compound as a dark red oil (13.7 g, 61.2 mmol) contaminated with furan-3-ylmethanol. This material is treated as described in EXAMPLE 122, Part C; the crude product is chromatographed with ethyl acetate/hexane (30–40%) to yield pure title compound (1.25 g, 10.1 mmol).

$^1$H NMR (CDCl$_3$, 300 MHz) δ7.53 (s, 1H), 7.14 (s, 1H), 4.56 (s, 2H); EI MS, M$^+$=123.

B. 3-Bromomethylfuran-5-carbonitrile

The title compound is prepared as described in EXAMPLE 122, Part D except that 4-hydroxymethylthiophene-2-carbonitrile is replaced with 4-hydroxy-methyl-furan-2-carbonitrile (1.24 g, 10.1 mmol); yield: (0.78 g, 3.9 mmol).

$^1$H NMR (CDCl$_3$, 300 MHz) δ7.59 (s, 1H), 7.12 (s, 1H), 4.30 (s, 2H); EI MS, M$^+$=185/187.

C. 3-(3-Amino-2-oxopyrrolidine-1-ylmethyl)furan-2-carbonitrile

A solution of (2-oxopyrrolidin-3-(S)-yl)carbamic acid tert-butyl ester (0.78 g, 3.9 mmol) in 40 mL of THF:DMF (5:1) is treated with 3-bromomethylfuran-5-carbonitrile (0.78 g, 3.9 mmol) and sodium hydride (60%) (0.10 g, 4.2 mmol) as described in EXAMPLE 122, Part F. After addition, the solution is allowed to warm to ambient temperatures. Standard workup folowed by chromatography (5–10% MeOH/CH$_2$Cl$_2$) affords [1-(2-cyanofuran-4-ylmethyl)- 2-oxopyrrolidin-3-yl]carbamic acid tert-butyl ester (1.05 g, 7.8 mmol) as a white solid. This material is treated with trimethylsilyliodide (0.844 g, 4.22 mmol) and free based with Amberlite (OH) resin to yield the title compound (0.926 g, 4.51 mmol).

$^1$H NMR (CD$_3$OD, 300 MHz) δ7.80 (s, 1H), 7.28 (s, 1H), 4.36 (AB, 2H), 3.72 (t, 1H), 3.38 (m, 2H), 2.43 (m, 1H), 1.80 (m, 1H).

D. 5-Chloro-3-methylbenzo[b]thiophene-2-sulfonic acid [1-(2-cyano-furan-4-ylmethyl)-2-oxopyrrolidin-3-(S)-yl]amide The title compound (0.25 g, 0.56 mmol) is prepared as in EXAMPLE 125, Part C, using 5-chloro-3-methylbenzo[b]thiophene-2-sulfonyl chloride (0.39 g, 1.39 mmol) and 3-(3-amino-2-oxopyrrolidin-1-ylmethyl)furan-2-carbononitrile (0.25 g, 1.22 mmol).

$^1$H NMR (CDCl$_3$, 300 MHz) δ7.78 (s, 1H), 7.73 (d, 1H), 7.49 (s, 3H), 7.45 (d, 1H), 5.78 (bs, 1H), 4.28 (s, 2H), 3.87 (m, 1H), 3.23 (m, 2H), 2.66 (s, 3H), 2.55 (m, 1H), 2.05 (m, 1H).

E. 4-[3-(S)-(5-Chloro-3-methylbenzo[b]thiophene-2-sulfonylamino)-2-oxopyrrolidin-1-ylmethyl]furan-2-carboxamidine trifluoroacetate 5-Chloro-3-methylbenzo[b]thiophene-2-sulfonic acid [1-(2-cyano-furan-4-ylmethyl)-2-oxopyrrolidin-3-(S)-yl]amide (0.24 g, 0.53 mmol) is converted to the title compound as described in EXAMPLE 125, Part D. The crude product is purified by RP-HPLC eluting in a gradient of 20% CH$_3$CN/H$_2$O (0.1 % TFA) to 80% CH$_3$CN/H$_2$O (0.1% TFA) and the appropriate product fractions are lyophilized to provide the title compound as a white solid (0.12 g, 0.2 mmol).

$^1$H NMR (DMSO-d$_6$, 300 MHz) δ9.21 (bs, 2H), 9.10 (bs, 2H) 8.68 (d, 1H), 8.09 (m, 3H), 7.54 (m 2H), 4.19 (AB, 2H), 4.14 (m, 1H), 3.15 (m, 2H), 2.60 (s, 3H), 2.02 (m, 1H), 1.63 (m, 1H). FAB MS, [M+H]$^+$=467. Elemental analysis calculated with 1.5 mole of H$_2$O: C=41.48%, H=3.81%, N=9.21%; found C=41.51%, H=3.41%, N=8.84%.

Other compounds prepared according to the procedures above include those encompassed by the following formula:

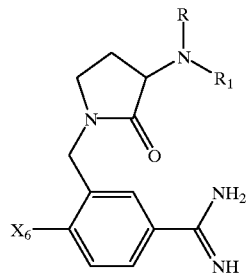

wherein R is hydrogen, methyl, aralkyl, heteroaralkyl, HO$_2$CCH$_2$—, HOC(O)CH$_2$—, H$_2$NC(O)CH$_2$—, (aralkyl)HNC(O)CH$_2$— or (heteroaralkyl)HNC(O)CH$_2$—; X$_6$ is hydrogen or amino; and R$_1$ is selected from the group of formulae

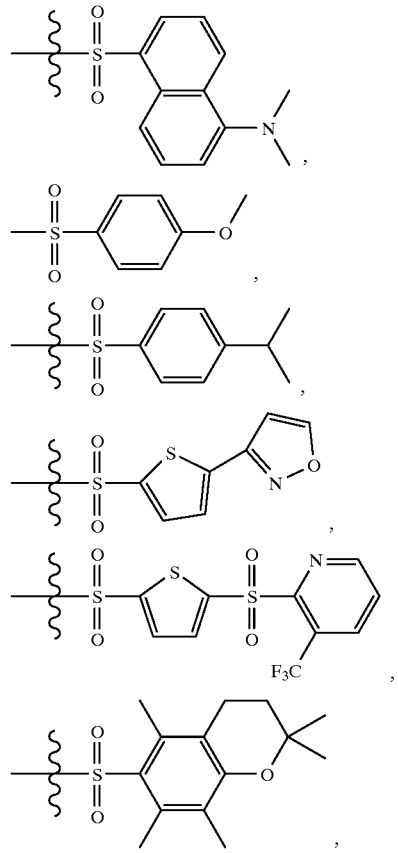

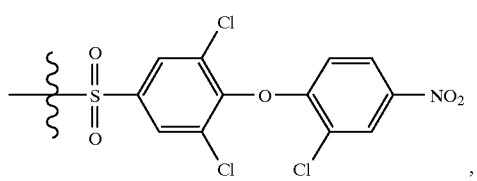,
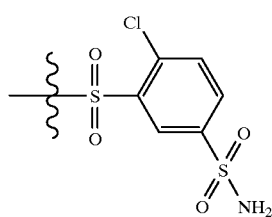,
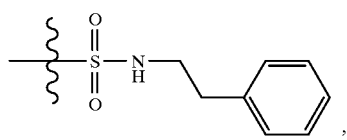,
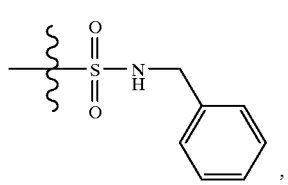,
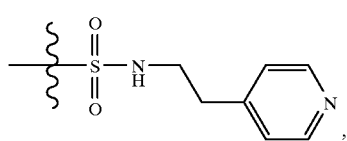,
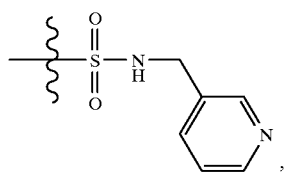,
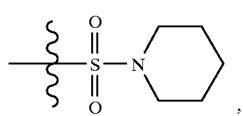,
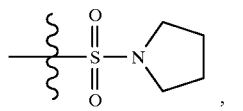,
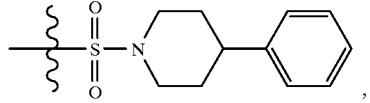,
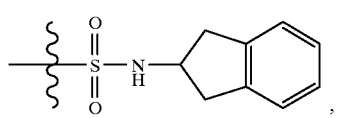,
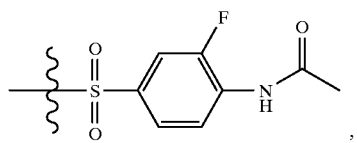,
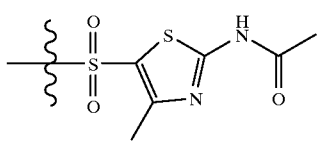,
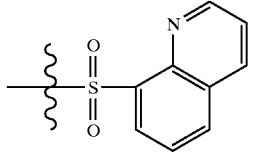,
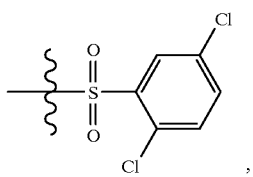,
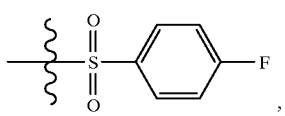,
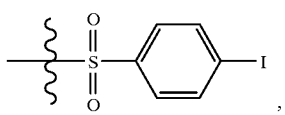,
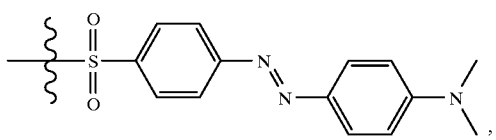,
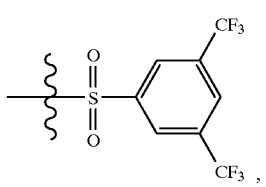,
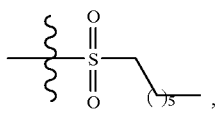,
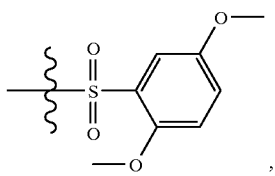,
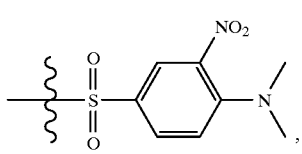,
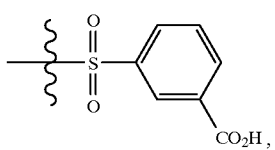,

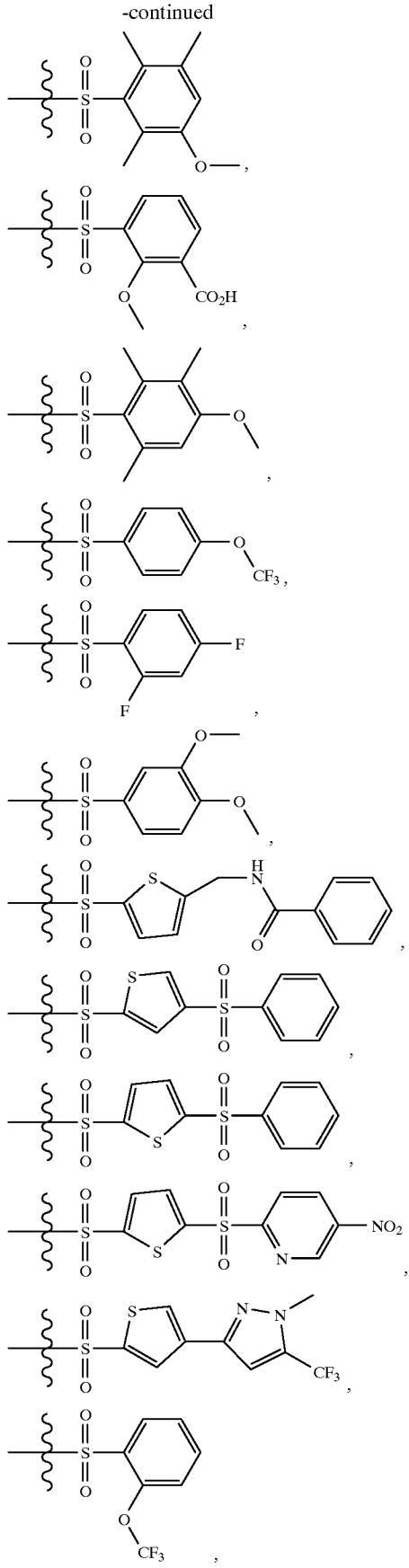
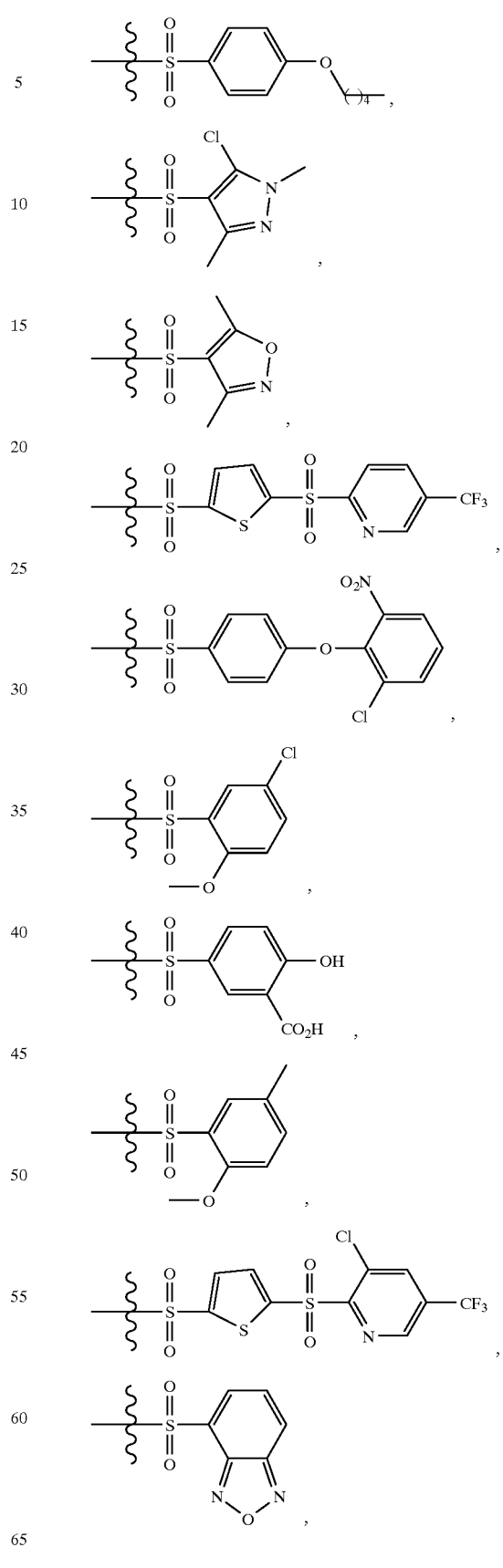

151
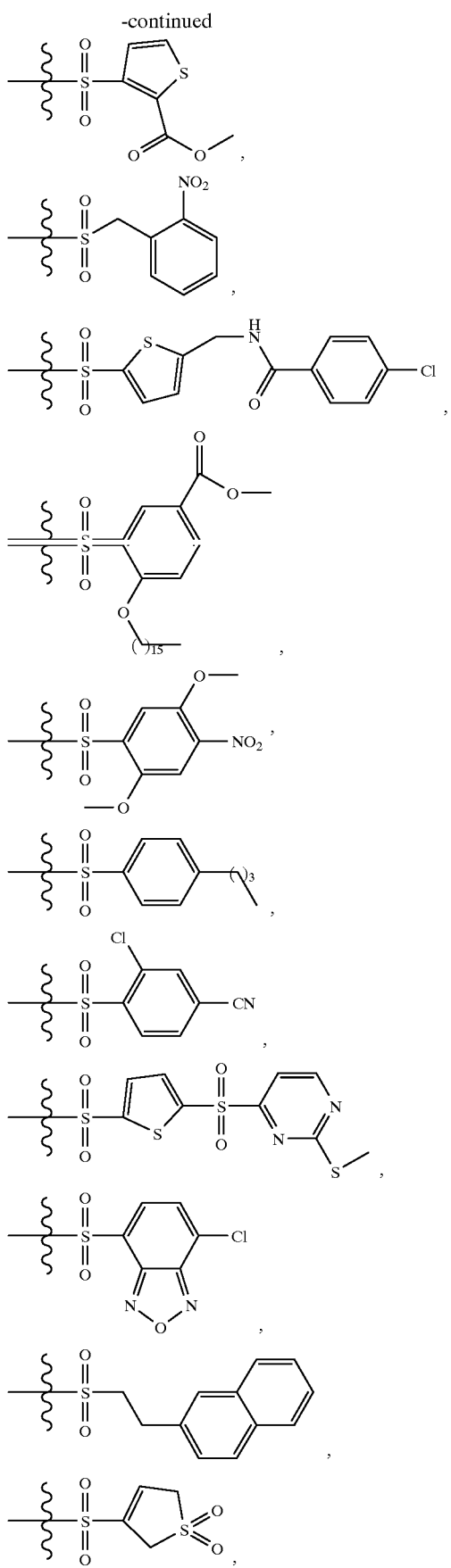
152
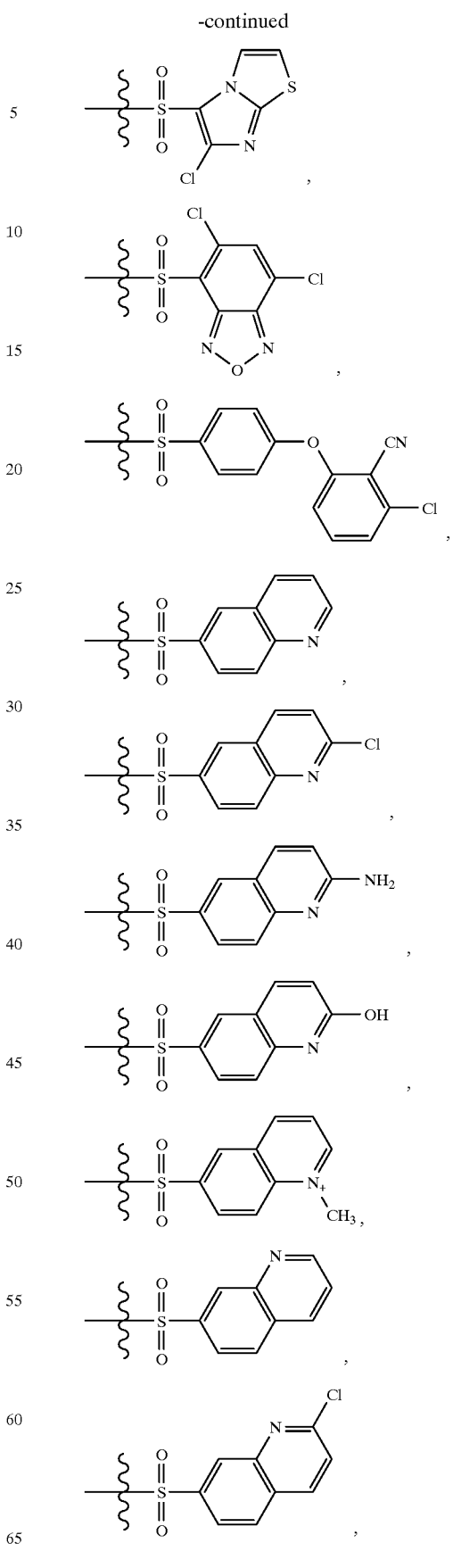

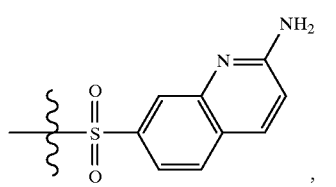,
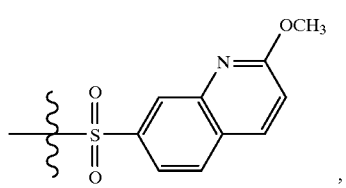,
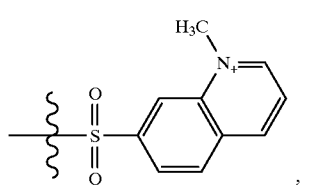,
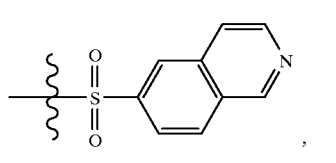,
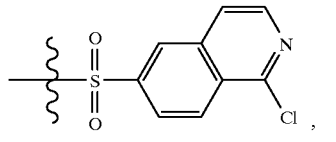,
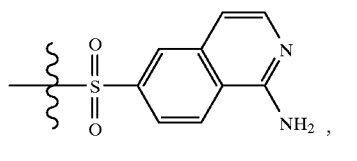,
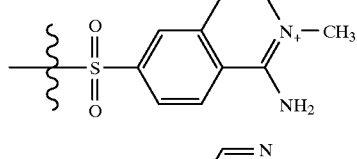,
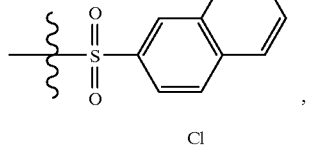,
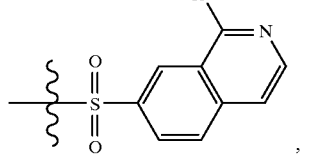,
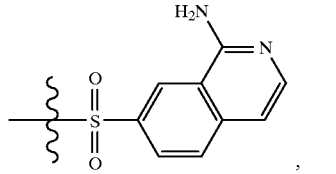,
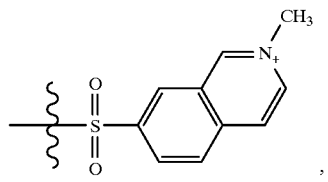,
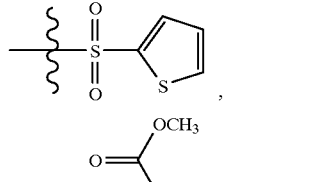,
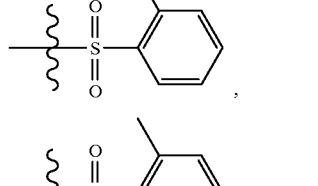,
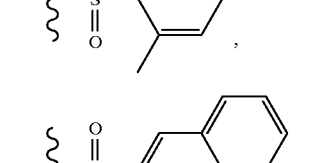,
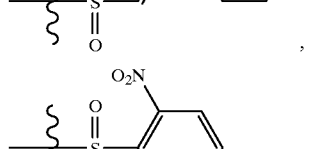,
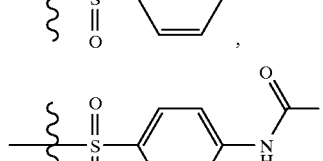,
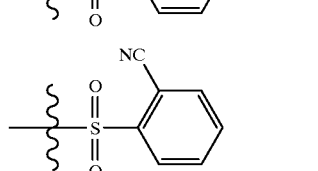,
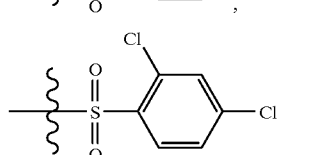,
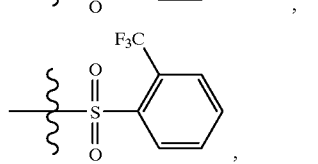,
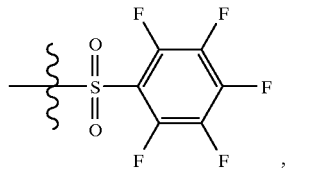, -continued
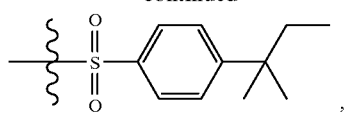,
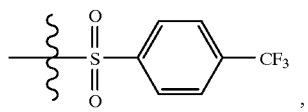,
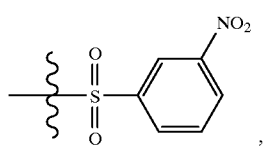,
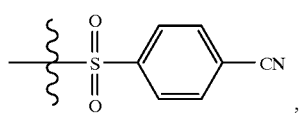,
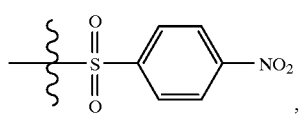,
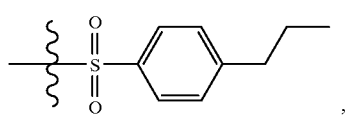,
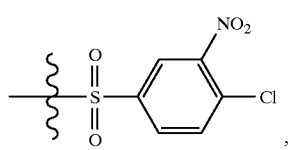,
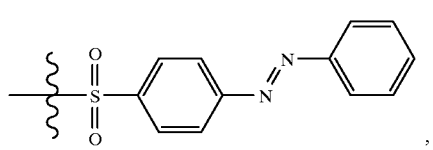,
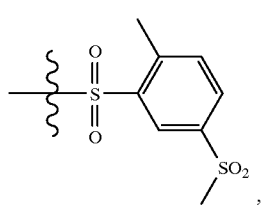,
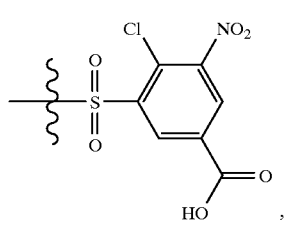,
-continued
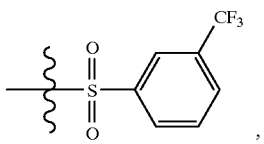,
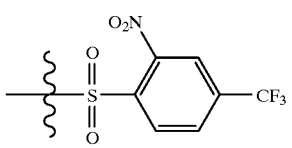,
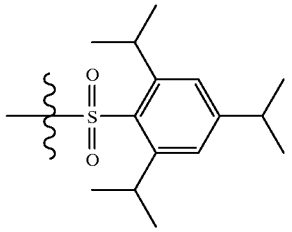,
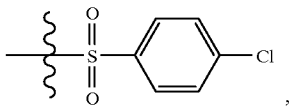,
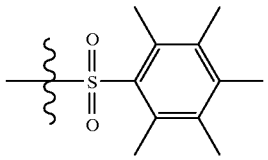,
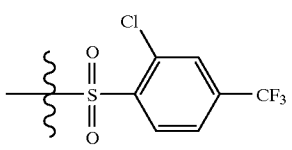,
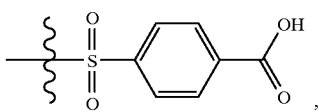,
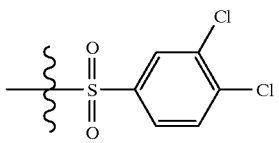,
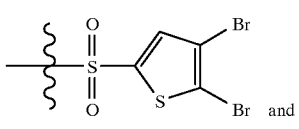 and
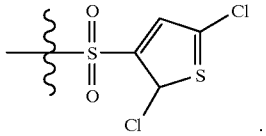.
Other compounds prepared according to the procedures above include those encompassed by the following formula:

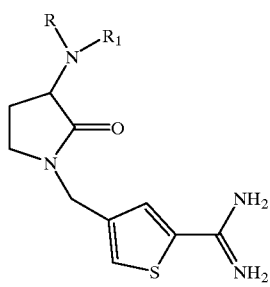
wherein R is hydrogen, methyl, aralkyl, heteroaralkyl, HO$_2$CCH$_2$—, HOC(O)CH$_2$—, H$_2$NC(O)CH$_2$—, (aralkyl)HNC(O)CH$_2$— or (heteroaralkyl)HNC(O)CH$_2$—; and R$_1$ is selected from the group of formulae
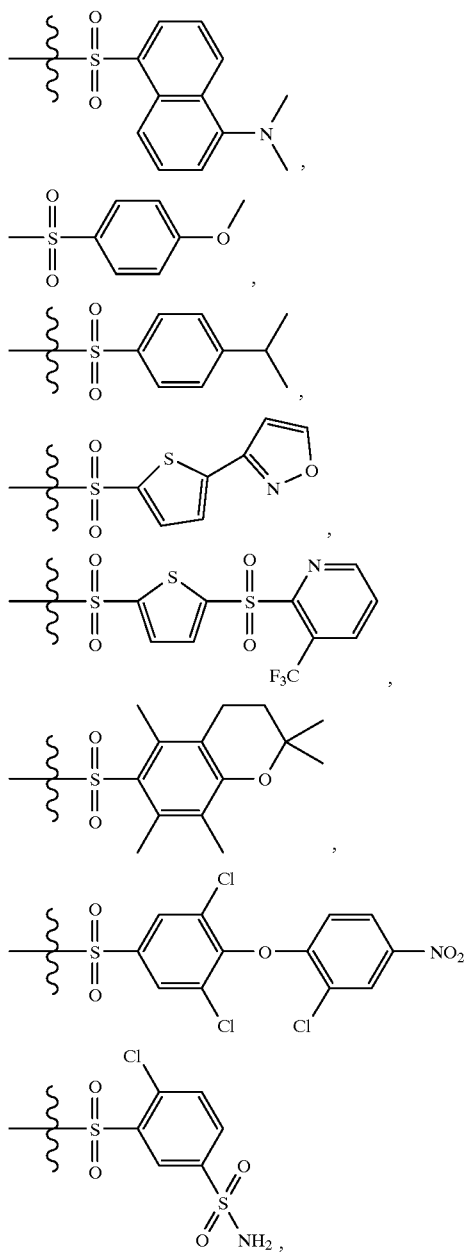
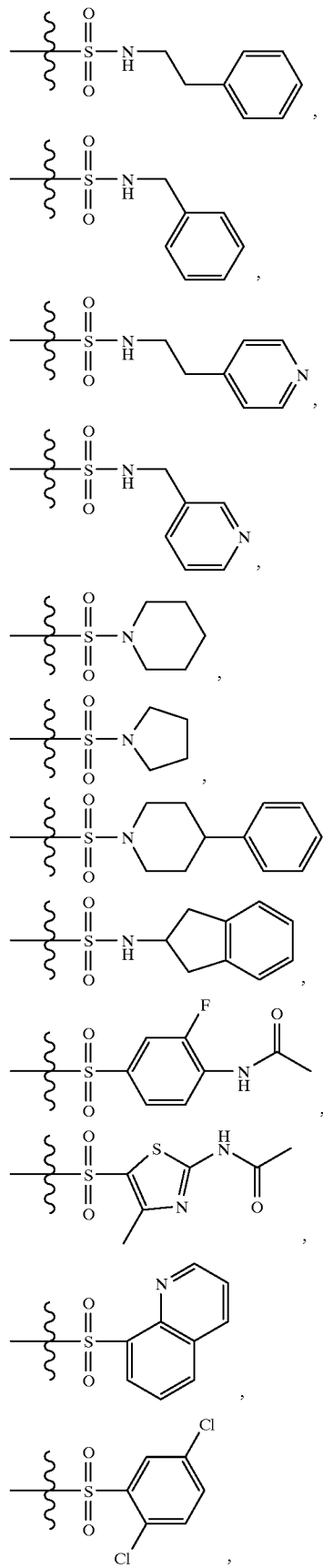

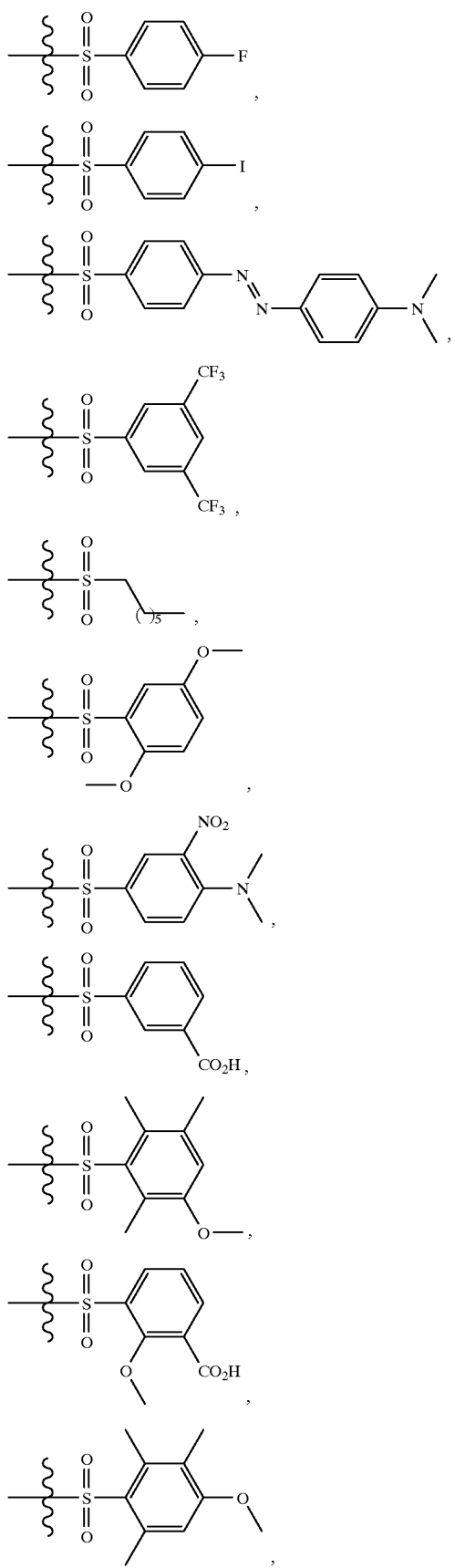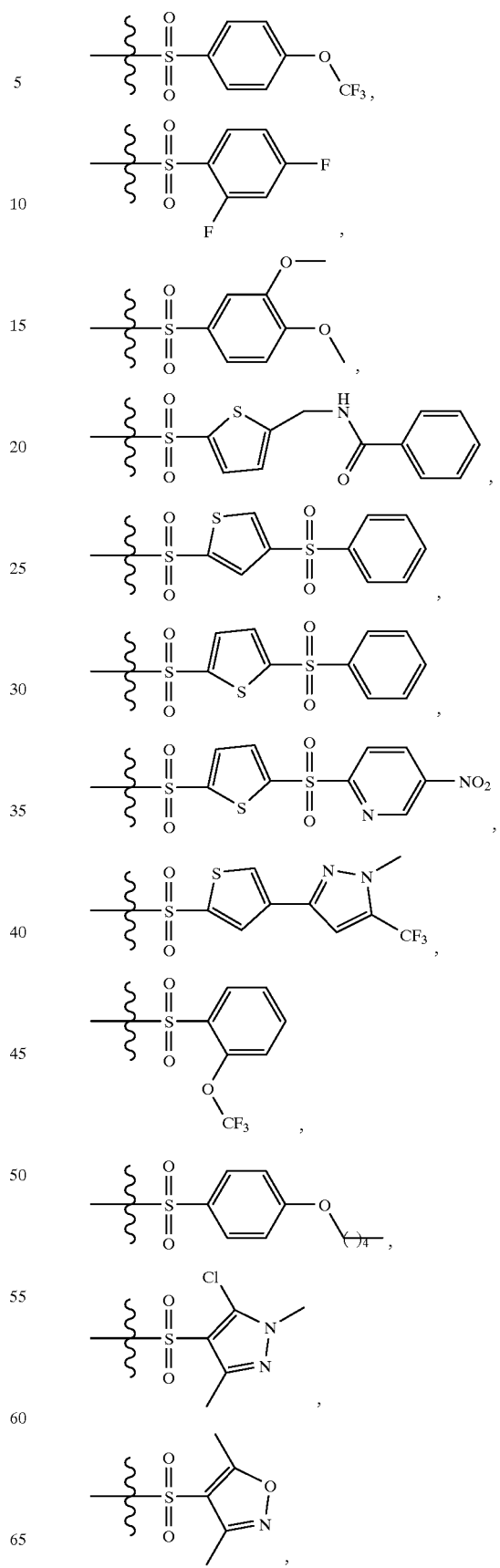

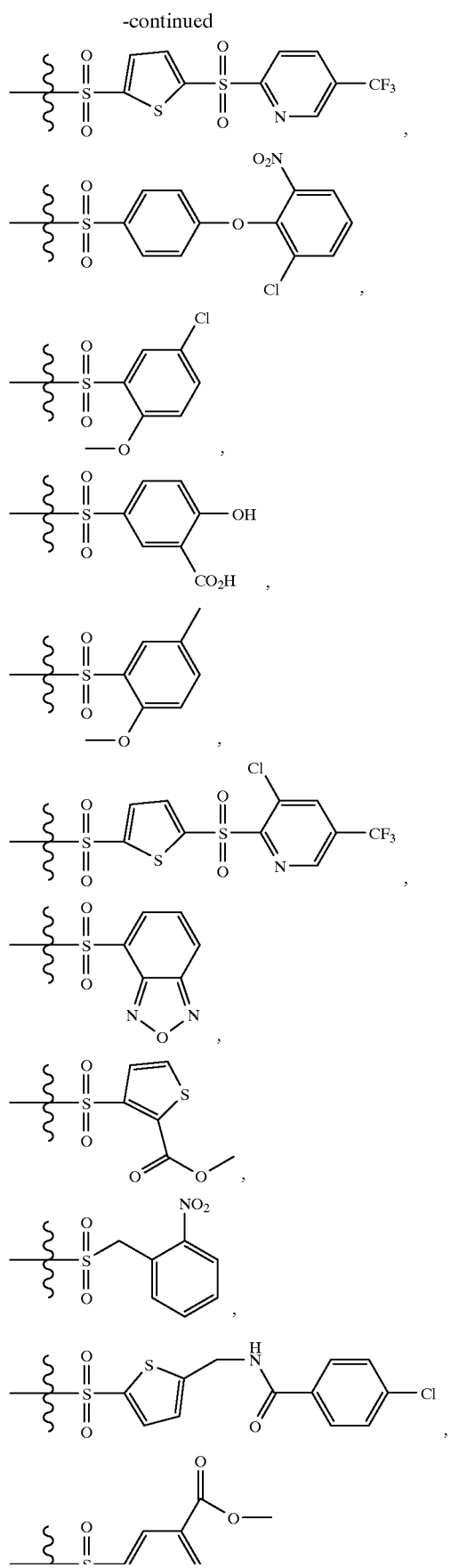
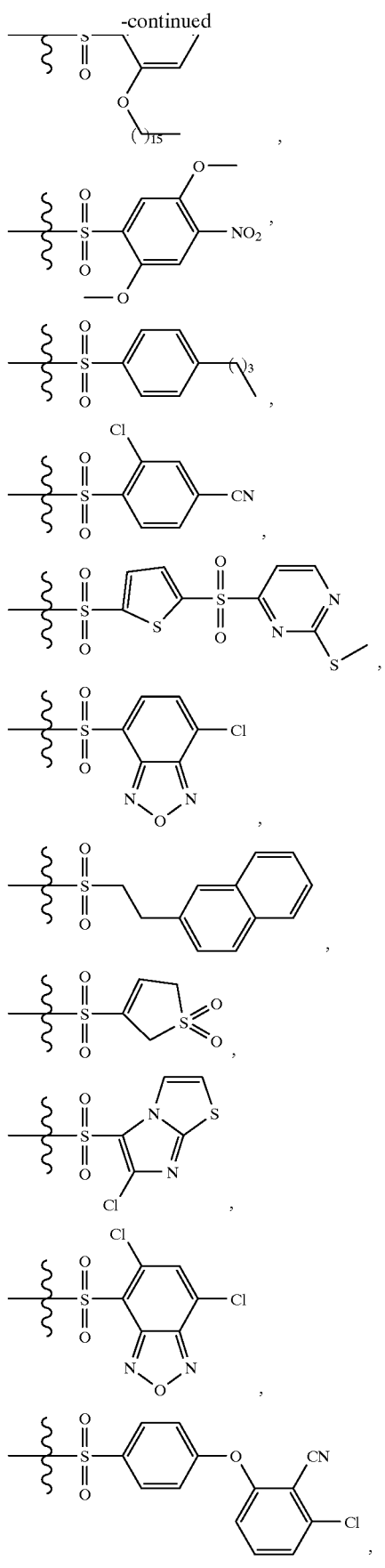

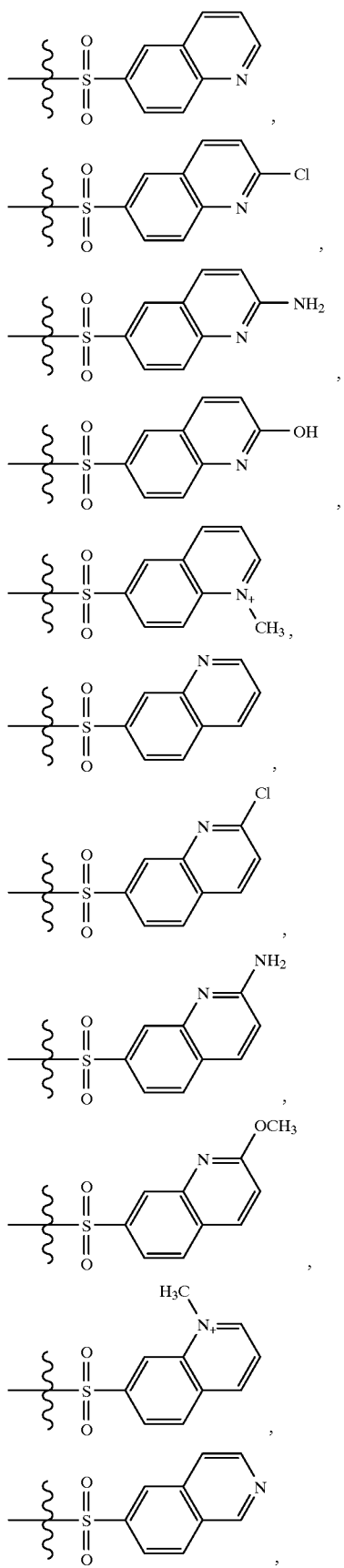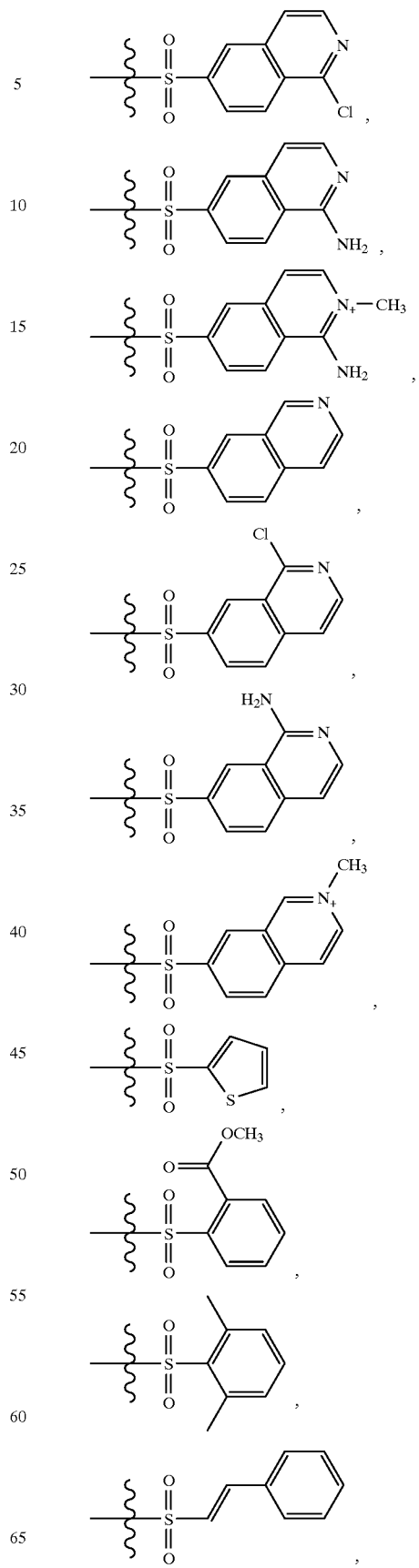

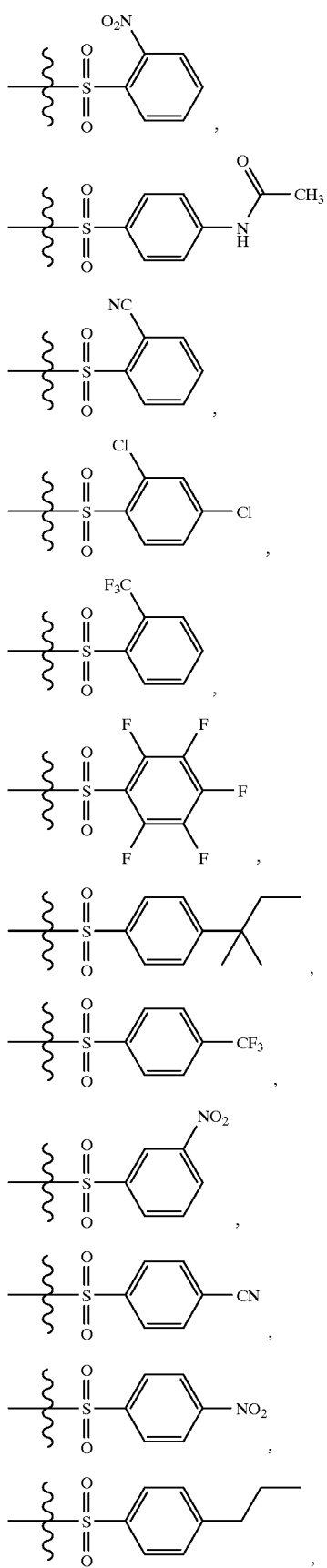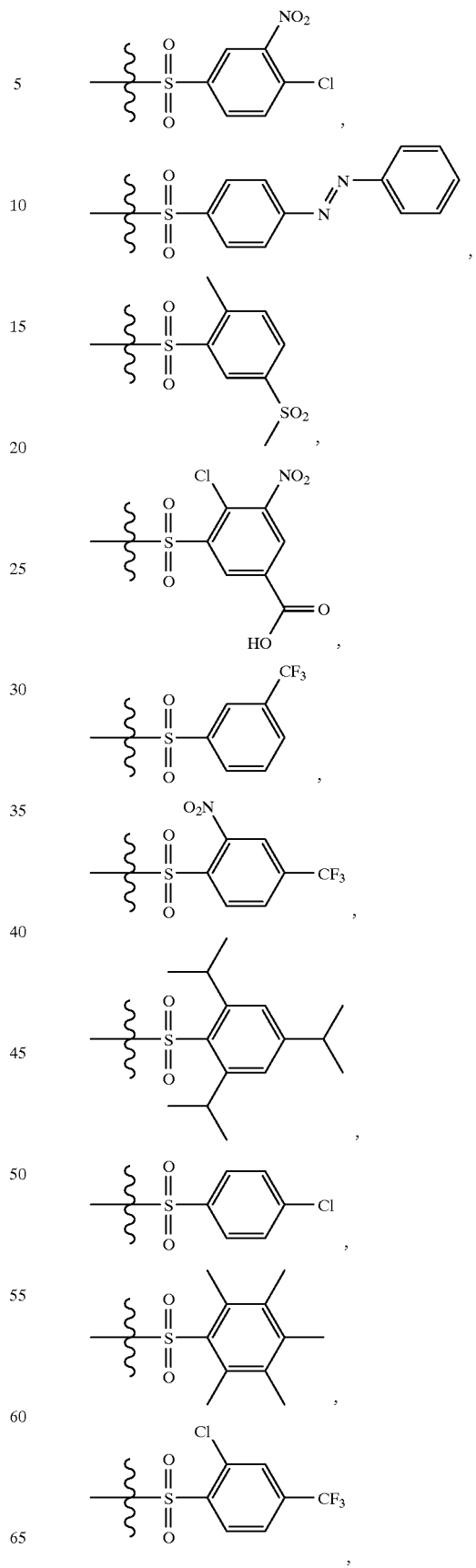

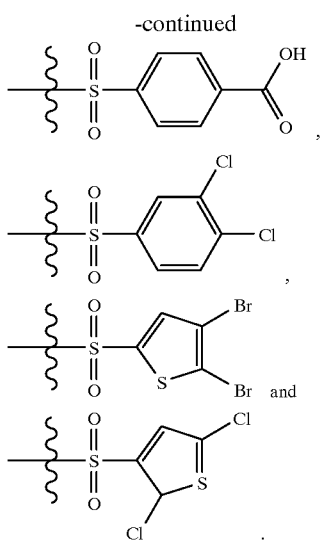

The molecules described herein inhibit blood coagulation by virtue of their ability to inhibit the penultimate enzyme in the coagulation cascade, controlling the activity of Factor Xa. Both the activity of free Factor Xa and Factor Xa assembled in the prothrombinase complex (Factor Xa, Factor Va, calcium and phospholipid) are inhibited by compounds of formula 1. The inhibition of the Factor Xa activity is obtained by direct complex formation between the inhibitor and the enzyme and is therefore independent of the plasma co-factor antithrombin III. Effective inhibition of the Factor Xa activity is achieved by administering the compounds either by oral administration, continuous intravenous infusion, bolus intravenous administration or any other parenteral route such that it achieves the desired effect of preventing the activity of Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of inhibitors of the activity of Factor Xa with standard heparin, low molecular weight heparin, direct thrombin inhibitors (i.e. hirudin), aspirin, fibrinogen receptor antagonists, streptokinase, urokinase and/or tissue plasminogen activator may result in greater antithrombotic or thrombolytic efficacy or efficiency. The compounds described herein may be administered to treat thrombotic complications in a variety of animals such as primates including humans, sheep, horses, cattle, pigs, dogs, rats and mice. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, inhibitors of Factor Xa activity may find utility in the treatment or prevention of other physiological conditions in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of factor Xa activity will effectively block thrombin generation and therefore neutralize any pathologic effects of thrombin on various cell types.

According to a further feature of the invention there is provided a method for the treatment of a human or animal patient suffering from, or subject to, a physiological condition which can be ameliorated by the administration of an inhibitor of the Factor Xa activity, for example conditions as hereinbefore described, which comprises the administration to the patient of a therapeutically effective amount of compound of formula I or a composition containing a compound of formula I. "Effective amount" is meant to describe an amount of compound of the present invention effective in inhibiting the activity of Factor Xa and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Factor Xa Inhibitor: Enzyme Assay Methods

Please find below a section describing the methods used for evaluating the activity of the compounds used in the factor Xa program for insertion into the patent.

Enzyme Assays

The ability of the compounds in the present invention to act as inhibitors of factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50= Ki [1+[S]/Km]) assuming competitive inhibition kinetics.

By way of example, 5-pyrid-2-yl-thiophene-2-sulfonic acid {1-[3-aminoiminomethyl)benzyl]-2-oxopyrrolidin-3-(S)-yl}amide trifluoroacetate has a Ki value of 100 nM.

By way of example, 7-methoxy naphthalene-2-sulfonic acid-1-[3-(aminoiminomethyl)benzyl]-2-oxopyrrolidin-3-(S)-yl}amide trifluoroacetate has a Ki value of 35 nM.

An additional in vitro assay may be used to evaluate the potency of compounds according to the invention in normal human plasma The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

A compound according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1–161) in Experimental Venous Thrombosis—a Comparison with Low Molecular Weight Heparin, J. Holst, B. Lindblad, D. Bergqvist, O. Nordfang, P. B. Ostergaard, J. G. L. Petersen, G. Nielsen and U. Hedner. *Thrombosis and Haemostasis,* 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 ml/kg (i.m.). The right jugular vein is cannulated for infusion of anesthetic (ketamine/xylazine 17/2.5 mg/kg/hr at a rate of approximately 0.5 ml/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 ml of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 ml ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model

The antithrombotic efficacy of factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. *Journal of Cardiovascular Pharmacology,* 22, 526–533 (1993); Rat Model of Arterial Thrombosis Induced by Ferric Chloride, K. D. Kurtz, B. W. Main, and G. E. Sandusky. *Thrombosis Research,* 60, 269–280 (1990); The Effect of Thrombin Inhibition in a Rat Arterial Thrombosis Model, R. J. Broersma, L. W. Kutcher and E. F. Heminger. *Thrombosis Research* 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 ml of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 ml/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of formula I

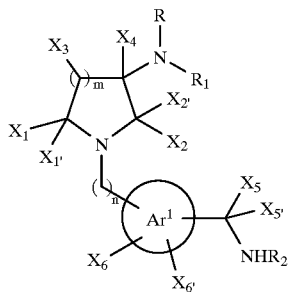

(I)

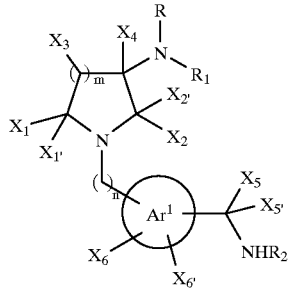

(I)

-continued is phenyl or monocyclic heteroaryl;

R is hydrogen, optionally substituted alkyl, optionally substituted aralkyl, optionally substituted heteroaralkyl or hydroxyalkyl;

$R_1$ is hydrogen, $R_3S(O)_p$— or $R_3R_4NS(O)_p$—;

$R_2$ is hydrogen, or when $X_5$ and $X_{5'}$ taken together are $=NR_5$, then $R_2$ is hydrogen, optionally substituted lower alkyl, optionally substituted aralkyl or optionally substituted heteroaralkyl;

$R_3$ is optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or R and $R_3$ taken together form a 5 to 7 membered ring;

$R_4$ is optionally substituted alkyl, optionally substituted cycloalkyl or optionally substituted aryl, optionally substituted heteroaryl, optionally substituted aralkyl or optionally substituted heteroaralkyl, or $R_3$ and $R_4$ taken together with the nitrogen to which $R_3$ and $R_4$ are attached form an optionally substituted 4 to 7 membered heterocyclyl;

$X_1$ and $X_{1'}$ are independently selected from hydrogen, optionally substituted alkyl, optionally substituted aryl, optionally substituted aralkyl, optionally substituted heteroaryl, optionally substituted heteroaralkyl or hydroxyalkyl, or $X_1$ and $X_{1'}$ taken together form oxo;

$X_2$ and $X_{2'}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1'}$ taken together form a 4 to 7 membered ring;

$X_4$ is hydrogen, optionally substituted alkyl, optionally substituted aralkyl, or hydroxyalkyl;

$X_5$ and $X_{5'}$ are hydrogen or taken together are $=NR_5$;

$R_5$ is hydrogen, $R_6O_2C$—, $R_6O$—, cyano, R6CO-, optionally substituted lower alkyl, nitro or $Y^{1'}Y^{2'}N$—;

$Y^{1'}$ and $Y^{2'}$ are independently hydrogen, alkyl, aralkyl or heteroaralkyl;

$X_6$ and $X_{6'}$ are independently hydrogen, $R_7R_8N$—, $R_9O$—, $R_7R_8NCO$—, $R_7R_8NSO_2$—, $R_9CO$—, halo, cyano or nitro;

$R_6$ is hydrogen, optionally substituted lower alkyl or optionally substituted aralkyl or optionally substituted heteroaralkyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$— or lower acyl;

$R_9$ is hydrogen, optionally substituted lower alkyl, lower acyl or $R_{10}(O)CCH_2$—;

$R_{10}$ is hydrogen, optionally substituted lower alkyl, alkoxy or hydroxy;

m is 0, 1, 2 or 3;

n is 1, 2 or 3; and p is 1 or 2, or a pharmaceutically acceptable salt thereof, an N-oxide thereof, a hydrate thereof or a solvate thereof.

2. The compound of claim 1 wherein $R_3$ is optionally substituted phenyl, optionally substituted naphthyl, optionally substituted thienyl or optionally substituted benzothienyl.

3. The compound of claim 1 wherein n is 1, and m is 1.

4. The compound of claim 1 wherein $X_2$ and $X_{2'}$ taken together are oxo.

5. The compound of claim 1 wherein $X_1$, $X_{1'}$, $X_3$ and $X_4$ are hydrogen.

6. The compound of claim 1 wherein $X_5$ and $X_{5'}$ taken together are =NH.

7. The compound of claim 1 wherein $X_5$ and $X_{5'}$ taken together are =NR$_5$ wherein $R_5$ is $R_6O_2C-$.

8. The compound of claim 1 wherein

is phenyl and the carbon substituted with $X_5$, $X_{5'}$ and $HR_2N-$ is attached to the 3-position of the phenyl moiety relative to the cyclic amino-alkylene substituent.

9. The compound of claim 1 wherein

moiety has the formula

10. The compound of claim 1 wherein $X_1$ is hydrogen and $X_{1'}$ is carboxyalkyl, alkoxycarbonylalkyl or aryl, or $X_1$ and $X_{1'}$ taken together form oxo.

11. The compound of claim 1 wherein $R_1$ is $R_3SO_2$.

12. The compound of claim 1 wherein $R_1$ is $R_3R_4NSO_2-$.

13. The compound of claim 1 wherein one of $X_6$ and $X_{6'}$ is amino in a para position relative to the

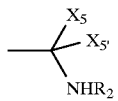

moiety.

14. A compound according to claim 1 which is

6-Methoxynaphthalene-2-sulfonic acid {1-[3-(aminoiminomethyl)benzyl]-2-oxopyrrolidin-3-(S)-yl}amide trifluoroacetate;

6-Methoxynaphthalene-2-sulfonic acid {1-[3-(aminoiminomethyl)benzyl]-2-oxopyrrolidin-3-(S)-yl}methyl amide trifluoroacetate;

2-[{1-[3-(Aminoiminomethyl)benzyl]-2-oxopyrrolidin-3-(S)-yl}-6-methoxynaphthalene-2-sulfonylamino]-N-phenethylacetamide trifluoroacetate;

9,10-Dioxo-8a,9,10,10a-tetrahydroanthracene-2-sulfonic acid {1-[3-(aminoiminomethyl)benzyl]-2-oxopyrrolidin-3-(S)-yl}amide trifluoroacetate;

8-Chloro-7-methoxynaphthalene-2-sulfonic acid {1-[3-(aminoiminomethyl)-benzyl]-2-oxopyrrolidin-3-(S)-yl}amide trifluoroacetate;

7-Methoxynaphthalene-2-sulfonic acid {1-[4-(aminoiminomethyl)benzyl]-2-oxopyrrolidin-3-(S)-yl}amide trifluoroacetate;

6,7-Dimethoxynaphthalene-2-sulfonic acid ({1-[3-(aminoiminomethyl)benzyl]-2-oxopyrrolidin-3-(S)-yl}amide trifluoroacetate;

Naphtho(2,3-d)-(1,3)dioxole-6-sulfonic acid {1-[3-(aminoiminomethyl)benzyl]-2-oxopyrrolidin-3-(S)-yl}amide trifluoroacetate;

7-Benzyloxynaphthalene-2-sulfonic acid {1-[3-(aminoiminomethyl)benzyl]-2-oxopyrrolidin-3-(S)-yl}amide trifluoroacetate;

7-Hydroxynaphthalene-2-sulfonic acid {1-[3-(aminoiminomethyl)benzyl]-2-oxopyrrolidin-3-(S)-yl}amide trifluoroacetate;

6-Hydroxynaphthalene-2-sulfonic acid {1-[3-(aminoiminomethyl)benzyl]-2-oxopyrrolidin-3-(S)-yl}amide trifluoroacetate;

5-Chloro-3-methylbenzo[b]thiophene-2-sulfonic acid {1-[3-(aminoiminomethyl)benzyl]-2-oxopyrrolidin-3-(S)-yl}amide trifluoroacetate;

5-Chloro-3-methylbenzo[b]thiophene-2-sulfonic acid {1-[3-(aminoiminomethyl)benzyl]-2-oxopyrrolidin-3-(S)-yl}methyl amide trifluoroacetate;

7-Methylnaphthalene-2-sulfonic acid {1-[3-(aminoiminomethyl)benzyl]-2-oxopyrrolidin-3-(S)-yl}amide trifluoroacetate;

7-Ethylnaphthalene-2-sulfonic acid {1-[3-(aminoiminomethyl)benzyl]-2-oxopyrrolidin-3-(S)-yl}amide trifluoroacetate;

5-Chloro-6-aminonaphthalene-2-sulfonic acid {1-[3-(aminoiminomethyl)benzyl]-2-oxopyrrolidin-3-(S)-yl}amide bistrifluoroacetate;

7-Methylaminonaphthalene-2-sulfonic acid {1-[3-(aminoiminomethyl)benzyl]-2-oxopyrrolidin-3-(S)-yl}amide bistrifluoroacetate;

2-Methyl-1,2,3,4-tetrahydroisoquinolinyl-7-sulfonic acid {1-[3-(aminoiminomethyl)benzyl]-2-oxopyrrolidin-3-(S)-yl}amide bistrifluoroacetate;

1,2,3,4-Tetrahydroisoquinolinyl-7-sulfonic acid {1-[3-(aminoiminomethyl)benzyl]-2-oxopyrrolidin-3(S)-yl}methyl amide dihydrochloride;

7-Methoxynaphthalene-2-sulfonic acid {1-[3-(aminoiminomethyl)benzyl]-2-oxopyrrolidin-3-(S)-yl}-(4-nitrobenzyl)amide trifluoroacetate;

7-Methoxynaphthalene-2-sulfonic acid {1-[3-(aminoiminomethyl)benzyl]-2-oxopyrrolidin-3-(S)-yl}-(4-aminobenzyl)amide bistrifluoroacetate;

7-Methoxynaphthalene-2-sulfonic acid {1-[3-(aminoiminomethyl)benzyl]-2-oxopyrrolidin-3-(S)-yl} (3-nitrobenzyl)amide trifluoroacetate;

7-Methoxynaphthalene-2-sulfonic acid {1-[3-(aminoiminomethyl)benzyl]-2-oxopyrrolidin-3-(S)-yl} (3-aminobenzyl)amide bistrifluoroacetate;

7-Methoxynaphthalene-2-sulfonic acid {1-[3-(aminoiminomethyl)benzyl]-2-oxopyrrolidin-3-(S)-yl}-(2-nitrobenzyl)amide trifluoroacetate;

3-[2-Oxo-3(S)-(2-phenylethenesulfonylamino) pyrrolidin-1-ylmethyl]-benzamidine trifluoroacetate;

3-[2-Oxo-3(S)-(2-phenylethanesulfonylamino) pyrrolidin-1-ylmethyl]-benzamidine trifluoroacetate;

[Imino-(3-{3-[7-Methoxynaphthalene-2-sulfonyl) methylamino]-2-oxo-3(S)-pyrrolidin-1-ylmethyl] phenyl)methyl]carbamic acid ethyl ester;

3-[2-Oxo-3(S)-{2-(pyridin-4-ylamino)-ethanesulfonylamino}-pyrrolidin-1-ylmethyl]-benzamidine bistrifluoroacetate;

2'-Methoxybiphenyl-4-sulfonic acid {1-[3-(aminoiminomethyl)benzyl]-2-oxopyrrolidin-3(S)-yl}amide trifluoroacetate;

5,6,7,8-Tetrahydrophenanthrene-3-sulfonic acid {1-[3-(aminoiminomethyl)benzyl]-2-oxo-3(S)-pyrrolidin-3-yl}amide trifluoroacetate;

Isoquinolinyl-5-sulfonic acid {1-[3-(aminoiminomethyl)benzyl]-2-oxo-3(S)-pyrrolidin-3-yl}amide bistrifluoroacetate;

5-Chlorothiophene-2-sulfonic acid {1-[3-(aminoiminomethyl)benzyl]-2-oxo-3(S)-pyrrolidin-3-yl}amide trifluoroacetate;

2,4-Diaminoquinazoline-6-sulfonic acid {1-[3-(aminoiminomethyl)benzyl]-2-oxo-3(S)-pyrrolidin-3-yl}amide trifluoroacetate;

7-Methoxy-2-naphthalenesufonic acid {1-[3-(aminoiminomethyl)benzyl]-2-oxo-3(S)-pyrrolidin-3-yl}ethylamide trifluoroacetate;

7-Methoxy-2-naphthalenesulfonic acid {1-[3-(aminoiminomethyl)benzyl]-2-oxo-3(S)-pyrrolidin-3-yl}(3-fluorobenzyl)amide trifluoroacetate;

7-Methoxy-2-naphthalenesulfonic acid {1-[3-(aminoiminomethyl)benzyl]-2-oxo-3(S)-pyrrolidin-3-yl}(4-methylbenzyl)amide trifluoroacetate;

7-Methoxy-2-naphthalenesulfonic acid {1-[3-(aminoiminomethyl)benzyl]-2-oxo-3(S)-pyrrolidin-3-yl}(3-methylbenzyl)amide trifluoroacetate;

7-Methoxy-2-naphthalenesulfonic acid {1-[3-(aminoiminomethyl)benzyl]-2-oxo-3(S)-pyrrolidin-3-yl}naphthalene-2-ylmethylamide trifluoroacetate;

7-Methoxy-2-naphthalenesulfonic acid {1-[3-(aminoiminomethyl)benzyl]-2-oxo-3(S)-pyrrolidin-3-yl}(3-phenylallyl)amide trifluoroacetate;

7-Methoxy-2-naphthalenesulfonic acid {1-[3-(aminoiminomethyl)benzyl]-2-oxo-3(S)-pyrrolidin-3-yl}(3-methylbenzyl)amide trifluoroacetate;

7-Methoxy-2-naphthalenesulfonic acid {1-[3-(aminoiminomethyl)benzyl]-2-oxo-3(S)-pyrrolidin-3-yl}(2-fluorobenzyl)amide trifluoroacetate;

2-Fluorobiphenyl-4-sulfonic acid {1-[3-(aminoiminomethyl)benzyl]-2-oxo-3(S)-pyrrolidin-3-yl}methylamide trifluoroacetate;

3-[{1-[3-(Aminoiminomethyl)benzyl]-2-oxopyrrolidin-3 (S)-3-yl}-(7-methoxynaphthalene-2-sulfonyl)amino] propionamide trifluoroacetate;

2-[{1-[3-(Aminoiminomethyl)benzyl]-2-oxopyrrolidin-3-(S)-yl}naphthalene-2-sulfonylamino]-N-phenethylacetamide trifluoroacetate;

2-[{1-[3-(Aminoiminomethyl)benzyl]-2-oxopyrrolidin-3-(S)-yl}biphenyl-4-sulfonylamino]-N-phenethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-phenethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-ethylacetamide trifluoroacetate;

2-[{1-[3-(Aminoiminomethyl)benzyl]-2-oxopyrrolidin-3-(S)-yl}-7-methoxynaphthalene-2-sulfonylamino]-N,N-dimethylacetamide trifluoroacetate;

2-[{1-[3-(Aminoiminomethyl)benzyl]-2-oxopyrrolidin-3-(S)-yl}-7-methoxynaphthalene-2-sulfonylamino]-N-benzylacetamide trifluoroacetate;

2-[{1-[3-(Aminoiminomethyl)benzyl]-2-oxopyrrolidin-3-yl}-7-methoxynaphthalene-2-sulfonylamino]-N-(2-p-toluylethyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-(3-phenylpropyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-(4-methylbenzyl)acetamide trifluoroacetate;

2-[{1-[3-(Aminoiminomethyl)benzyl]-2-oxopyrrolidin-3-(S)-yl}-7-methoxynaphthalene-2-sulfonylamino]-N-[2-(3-fluorophenyl)ethyl]acetamide trifluoroacetate;

2-[{1-[3-(Aminoiminomethyl)benzyl]-2-oxopyrrolidin-3-(S)-yl}-7-methoxynaphthalene-2-sulfonylamino]-N-indan-2-ylacetamide trifluoroacetate;

2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate;

4,5-Dichlorothiophene-2-sulfonic acid {1-[3-(aminoiminomethyl)benzyl]-2-oxo-3(S)-pyrrolidin-3-yl}amide trifluoroacetate 4,5-Dichlorothiophene-2-sulfonic acid {1-[3 (aminoiminomethyl)benzyl]-2-oxo-3(S)-pyrrolidin-3-yl}-methylamide trifluoroacetate;

4,5-Dichlorothiophene-2-sulfonic acid {1-[3-(aminoiminomethyl)benzyl]-2-oxo-3(S)-pyrrolidin-3-yl}benzylamide trifluoroacetate;

7-Methoxy-2-naphthalenesulfonic acid {1-[3-(aminoiminomethyl)benzyl]-2-oxo-3(S)-pyrrolidin-3-yl}-2-cyclopropylphenethylamide trifluoroacetate;

3'-Methyl-biphenyl-4-sulfonic acid {1-[3-(aminoiminomethyl)benzyl]-2-oxopyrrolidin-3(S)-yl}amide trifluoroacetate;

3-[{1-[3-(Aminoiminomethyl)benzyl]-2-oxopyrrolidin-3 (S)-3-yl}-(7-methoxynaphthalene-2-sulfonyl)amino] acetamide trifluoroacetate;

3-[{1-[3-(Aminoiminomethyl)benzyl]-2-oxopyrrolidin-3 (S)-3-yl}-(7-methoxynaphthalene-2-sulfonyl)amino]-2-methylacetamide trifluoroacetate;

7-Methoxynaphthalene-2-sulfonic acid {1-[3 (aminoiminomethyl)benzyl]-2-oxo-azetidin-3(S)-yl}amide trifluoroacetate;

7-Methoxynaphthalene-2-sulfonic acid {1-[3-(aminoiminomethyl)benzyl]-2-oxo-azetidin-3(S)-yl}benzylamide trifluoroacetate;

5,6,7,8-Tetrahydronaphthalene-2-sulfonic acid {1-[3-(aminoiminomethyl)-benzyl]-2-oxopyrrolidin-3(S)-yl}amide trifluoroacetate;

7-Methoxy-2-naphthalenesulfonic acid {1-[3-(aminoiminomethyl)benzyl]-2-oxo-3(S)-pyrrolidin-3-yl}-(2-methoxybenzyl)amide trifluoroacetate;

7-Methoxy-2-naphthalenesulfonic acid {1-[3-(aminoiminomethyl)benzyl]-2-oxo-3(S)-pyrrolidin-3-yl}-(3-methoxybenzyl)amide trifluoroacetate;

7-Methoxy-2-naphthalenesulfonic acid {1-[3 (aminoiminomethyl)benzyl]-2-oxo-3(S)-pyrrolidin-3-yl}-(4-methoxybenzyl)amide trifluoroacetate;

7-Methoxy-2-naphthalenesulfonic acid {1-[3-(aminoiminomethyl)benzyl]-2-oxo-3(S)-pyrrolidin-3-yl}(pyridin-2-ylmethyl)amide trifluoroacetate;

7-Methoxy-2-napthalenesulfonic acid {1-[3-(aminoiminomethyl)benzyl]-2-oxo-3(S)-pyrrolidin-3-yl}(pyridin-3-ylmethyl)amide trifluoroacetate;

7-Methoxy-2-napthalenesulfonic acid {1-[3-(aminoiminomethyl)benzyl]-2-oxo-3(S)-pyrrolidin-3-yl}(pyridin-4-ylmethyl)amide trifluoroacetate;

7-Methoxy-2-napthalenesulfonic acid {1-[3-(aminoiminomethyl)benzyl]-2-oxo-3(S)-pyrrolidin-3-yl}-(1-benzyl-1H-imidazol-2-ylmethyl)amide trifluoroacetate;

(1-Methyl-1H-imidazol-2-yl)benzene-4-sulfonic acid {1-[3-(aminoiminomethyl)benzyl]-2-oxopyrrolidin-3(S)-yl}amide trifluoroacetate;

7-Methoxy-2-napthalenesulfonic acid {1-[3-(aminoiminomethyl)benzyl]-2-oxo-3(S)-pyrrolidin-3-yl}-(3-hydroxybenzyl)amide trifluoroacetate;

7-Methoxy-2-napthalenesulfonic acid {1-[3-(aminoiminomethyl)benzyl]-2-oxo-3(S)-pyrrolidin-3-yl}-(2-hydroxybenzyl)amide trifluoroacetate;

7-Methoxy-2-napthalenesulfonic acid {1-[3-(aminoiminomethyl)benzyl]-2-oxo-3(S)-pyrrolidin-3-yl}(pyrazol-3-ylmethyl)amide trifluoroacetate;

Quinoline-6-sulfonic acid {1-[3-(aminoiminomethyl) benzyl]-2-oxopyrrolidin-3-(S)-yl}amide trifluoroacetate;

4-Pyridin-4-ylbenzene sulfonic acid {1-[3 (aminoiminomethyl)benzyl]-2-oxopyrrolidin-3(S)-yl}amide bistrifluoroacetate;

7-Methoxy-2-napthalenesulfonic acid {1-[3 (aminoiminomethyl)benzyl]-2-oxo-3(S)-pyrrolidin-3-yl}(thiophene-2-ylmethyl)amide trifluoroacetate;

4-Pyridin-3-ylbenzene sulfonic acid {1-[3-(aminoiminomethyl)benzyl]-2-oxopyrrolidin-3(S)-yl}amide bistrifluoroacetate;

N-Methylpyrid-4-ylphenyl-4-sulfonic acid {1-[3-(aminoiminomethyl)benzyl]-2-oxopyrrolidin-3(S)-yl}amide trifluoroacetate;

2-Methoxyquinoline-7-sulfonic acid {1-[3 (aminoiminomethyl)benzyl]-2-oxopyrrolidin-3(S)-yl}amide trifluoroacetate;

4(6-Methoxypyridin-2-yl)benzene-4-sulfonic acid {1-[3-(aminoiminomethyl)benzyl]-2-oxopyrrolidin-3(S)-yl}amide bistrifluoroacetate;

4(3-Chloropyridin-2-yloxy)benzene-4-sulfonic acid {1-[3-(aminoiminomethyl)benzyl]-2-oxopyrrolidin-3(S)-yl}amide trifluoroacetate;

4(N-Oxidopyridin-3-yl)benzene-4-sulfonic acid {1-[3 (aminoiminomethyl)benzyl]-2-oxopyrrolidin-3(S)-yl}amide trifluoroacetate;

4-Phenoxybenzene-4-sulfonic acid {1-[3-(aminoiminomethyl)benzyl]-2-oxopyrrolidin-3(S)-yl}amide trifluoroacetate;

7-Methoxy-2-napthalenesulfonic acid {1-[3-(aminoiminomethyl)benzyl]-2-oxo-3(S)-pyrrolidin-3-yl}(thiophen-3-ylmethyl)amide trifluoroacetate;

6-Methoxynaphthalene-2-sulfonic acid {1-[3-(methoxyaminoiminomethyl)-benzyl]-2-oxpyrrolidin-3-(S)-yl}methylamide trifluoroacetate;

6-Methoxynaphthalene-2-sulfonic acid {1-[3-(cyanoaminoiminomethyl)benzyl]-2-oxopyrrolidin-3-(S)-yl}methylamide trifluoroacetate;

6-Methoxynaphthalene-2-sulfonic acid [1-3-(hydroxyaminoiminomethyl)-benzyl]-2-oxopyrrolidin-3-(S)-yl]-methylamide trifluoroacetate;

4-Amino-3-[3-(S)-(7-methoxynaphthalene-2-sulfonylamino)-2-oxopyrrolidin-1-yl-methyl] benzamidine dihydrochloride;

4-Amino-3-[3-(S)-(7-methoxynaphthalene-2-sulfonylmethylamino)-2-oxopyrrolidin-1-yl-methyl] benzamidine trifluoroacetate;

N-(4-Carbamimidoyl-2-{3-[(7-methoxynaphthalene-2-sulfonyl)methylamino]-2-oxopyrrolidin-1-(S)-ylmethyl}phenyl)acetamide trifluoroacetate;

4-Amino-3-[3-(S)-(4-tert-butylbenzenesulfonylamino)-2-oxopyrrolidin-1-yl-methyl]benzamidine trifluoroacetate;

3-Amino-5-[3-(S)-(7-methoxynaphthalene-2-sulfonylamino)-2-oxopyrrolidin-1-yl-methyl] benzamidine bistrifluoroacetate;

{4-(Aminoiminomethyl)-2-[3-(7-methoxynaphthalene-2-sulfonylamino)-2-oxopyrrolidin-1-ylmethyl] phenoxy}acetic acid methyl ester trifluoroacetate;

{4-(Aminoiminomethyl)-2-[3-(7-methoxynaphthalene-2-sulfonylamino)2-oxopyrrolidin-1-ylmethyl] phenoxy}acetic acid trifluoroacetate;

2-Chloro-6-nitrophenoxybenzene sulfonic acid {1-[3-(aminoiminomethyl)benzyl]-2-oxopyrrolidin-3(S)-yl}amide trifluoroacetate;

4-[3-(S)-(7-Methoxynaphthalene-2-sulfonylamino)-2-oxopyrrolidin-1-ylmethyl]-thiophene-2-carboxamidine trifluoroacetate;

4-{3-(S)-[(7-Methoxynaphthalene-2-sulfonyl) methylamino]-2-oxopyrrolidin-1-ylmethyl}thiophene-2-carboxyamidine trifluoroacetate;

2-[[1-(5-Carbamimidoylthiophene-3-ylmethyl)-2-oxopyrrolidin-3-(S)-yl](7-methoxynaphthalene-2-sulfonyl)amino]acetamide trifluoroacetate;

4-{3-(S)-[(7-Methoxynaphthalene-2-sulfonyl) benzylamino]-2-oxopyrrolidin-1-ylmethyl}thiophene-2-carboxamidine trifluoroacetate;

4-[3-(S)-(5-Chloro-3-methylbenzo[b]thiophene-2-sulfonylamino)-2-oxo-pyrrolidin-1-ylmethyl] thiophene-2-carboxamidine trifluoroacetate;

5-{3-(S)-[(7-Methoxynaphthalene-2-sulfonyl) methylamino]-2-oxopyrrolidin-1-ylmethyl}thiophene-3-carboxamidine trifluoroacetate;

4-{3-(S)-[(5-Chloro-3-methylbenzo[b]thiophene-2-sulfonyl)benzylamino]-2-oxopyrrolidin-1-ylmethyl}thiophene-2-carboxamidine trifluoroacetate;

4-{3-(S)-[(Methanesulfonyl)-(3-phenylpropyl)amino]-2-oxopyrrolidin-1-ylmethyl}thiophene-2-carboxamidine trifluoroacetate;

4-{3-(S)-[(Methanesulfonyl)(naphthalene-2-yl)amino]-2-oxopyrrolidin-1-ylmethyl}thiophene-2-carboxamidine trifluoroacetate;

4-{3-(S)-[4,5-Dichlorothiophene-2-sulfonyl)
benzylamino]-2-oxopyrrolidin-1-ylmethyl}thiophene-
2-carboxamidine trifluoroacetate;

4-{3-(S)-[(5-Chloro-3-methylbenzo[b]thiophene-2-
sulfonyl)methylamino]-2-oxopyrrolidin-1-
ylmethyl}thiophene-2-carboxamidine trifluoroacetate;

2-[[1-(5-Carbamimidoylthiophene-3-ylmethyl)-2-
oxopyrrolidin-3(S)-yl]-(7-methoxynaphthalene-2-
sulfonyl)amino]-N-phenethylacetamide trifluoroacetate;

2-[[1-(5-Carbamimidoylthiophene-3-ylmethyl)2-
oxopyrrolidin-3-(S)yl]-(4,5-dichlorothiophene-2-
sulfonyl)amino]-N-phenethyl acetamide trifluoroacetate;

2-[[1-(5-Carbamimidoylthiophene-3-ylmethyl)-2-
oxopyrrolidin-3-(S)-yl]-7-methoxynaphthalene-2-
sulfonyl)amino]-N-benzylacetamide trifluoroacetate;

2-[[1-(4-Carbamimidoylthiophene-2-ylmethyl)2-
oxopyrrolidin-3(S)-yl]-(7-methoxynaphthalene-2-
sulfonyl)amino]acetamide trifluoroacetate;

2-[[1-(4-Carbamimidoylthiophene-2-ylmethyl)-2-
oxopyrrolidin-3-(S)-yl]-(5-chloro-3-methylbenzo[b]
thiophene-2-sulfonyl)amino]acetic acid methyl ester;

4-{3(S)-[7-Aminonaphthalene-2-sulfonyl)benzylamino]-
2-oxopyrrolidin-1-ylmethyl}thiophene-2-
carboxamidine bistrifluoroacetate;

4-{3(S)-[(7-Aminonaphthalene-2-sulfonyl)
methylamino]-2-oxopyrrolidin-1-ylmethyl}thiophene-
2-carboxamidine bistrifluoroacetate;

2-[[1-(5-Carbamimidoylthiophene-3-ylmethyl)-2-
oxopyrrolidin-3-(S)-yl]-(7-aminonaphthalene-2-
sulfonyl)amino]acetamide bistrifluoroacetate;

4-[3-(S)-(6-Amino-5-chloro-2-sulfonylamino)-2-
oxopyrrolidin-1-ylmethyl]-thiophene-2-carboxamidine
trifluoroacetate;

4-{3-(S)-[(6-Amino-5-chloro-naphthalene-2-sulfonyl)
methylamino]-2-oxopyrrolidin-1-ylmethyl}thiophene-
2-carboxamidine trifluoroacetate;

2-[[1-(5-Carbamimidoylthiophene-3-ylmethyl)-2-
oxopyrrolidin-3-(S)-yl]-(6-amino-5-
chloronaphthalene-2-sulfonyl)amino]acetamide trifluoroacetate;

4-[3-(S)-(6-Aminonaphthalene-2-sulfonylamino)-2-
oxopyrrolidin-1-ylmethyl]-thiophene-2-carboxamidine
dihydrochloride;

5-[3-(S)-(7-Methoxynaphthalene-2-sulfonylamino)-2-
oxopyrrolidin-1-ylmethyl]-thiophene-2-carboxamidine
trifluoroacetate;

5-{3(S)-[(7-Methoxynaphthalene-2-sulfonyl)
methylamino]-2-oxopyrrolidin-1-ylmethyl}thiophene-
2-carboxamidine trifluoroacetate;

5-{3-(S)-[(7-Methoxynaphthalene-2-sulfonyl)
benzylamino]-2-oxopyrrolidin-1-ylmethyl}thiophene-
2-carboxamidine trifluoroacetate;

[Amino-(4-{3-(S)-(7-methoxynaphthalene-2-sulfonyl)
methylamino]-2-oxopyrrolidin-1-ylmethyl}thiophene-
2-yl)methylene]carbamic acid methyl ester trifluoroacetate;

4-{3-(S)-[(7-Methoxynaphthalene-2-sulfonyl)
methylamino]-2-oxopyrrolidin-1-ylmethyl}thiophene-
2-N-hydroxycarboxamidine trifluoroacetate;

4-[3-(S)-(7-Methoxynaphthalene-2-sulfonylamino)-2-
oxopyrrolidin-1-ylmethyl]-pyridin-2-carboxamidine
trifluoroacetate;

4-{3-(S)-[(7-Methoxynaphthalene-2-sulfonyl)
benzylamino]-2-oxopyrrolidin-1-ylmethyl}pyridine-2-
carboxamidine trifluoroacetate;

4-{3-(S)-[(7-Methoxynaphthalene-2-sulfonyl)
methylamino]-2-oxopyrrolidin-1-ylmethyl}pyridine-2-
carboxamidine trifluoroacetate;

4-[3-(S)-(5-Chloro-3-methylbenzo[b]thiophene-2-
sulfonylamino)-2-oxopyrrolidin-1-ylmethyl]pyridine-
2-carboxamidine trifluoroacetate;

4-{3-(S)-[(5-Chloro-3-methylbenzo[b]thiophene-2-
sulfonyl)methylamino]-2-oxopyrrolidin-1-
ylmethyl}pyridine-2-carboxamidine trifluoroacetate;

2-{[1-(2-Carbamimidoylpyridine-4-ylmethyl)-2-
oxopyrrolidin-3-(S)-yl]-(7-methoxynaphthalene-2-
sulfonyl)amino}acetamide trifluoroacetate;

2-{[1-(2-Carbamimidoyl-pyridine-4-ylmethyl)-2-
oxopyrrolidin-3-(S)-yl]-(7-methoxynaphthalene-2-
sulfonyl)amino}-N-phenethylacetamide trifluoroacetate;

4-{3-(S)-[(7-Methoxynaphthalene-2-sulfonyl)-thiophen-
3-ylmethylamino]-2-oxopyrrolidin-1-
ylmethyl}pyridine-2-carboxamidine trifluoroacetate;

4-{3-(S)-[(7-Methoxynaphthalene-2-sulfonyl)thiophen-
3-ylmethylamino]-2-oxopyrrolidin-1-
ylmethyl}thiophene-2-carboxamidine trifluoroacetate;

4-{3-(S)-[(4-(6-Nitro-2-chlorophenoxy)benzenesulfonyl)
amino]-2-oxopyrrolidin-1-ylmethyl}thiophene-2-
carboxamidine trifluoroacetate;

5-{3-(S)-[(7-Methoxynaphthalene-2-sulfonylamino]-2-
oxopyrrolidin-1-ylmethyl}-furan-2-carboxamidine trifluoroacetate; or 4-[3-(S)-(5-Chloro-3-methylbenzo[b]thiophene-2-
sulfonylamino)-2-oxopyrrolidin-1-ylmethyl]furan-2-
carboxamidine trifluoroacetate.

15. A compound according to claim 14 which is
7-Methoxynaphthalene-2-sulfonic acid {1-[3-
(aminoiminomethyl)benzyl]-2-oxopyrrolidin-3-(S)-
yl}methyl amide trifluoroacetate.

16. A compound according to claim 14 which is
3'-Methoxy-biphenyl-4-sulfonic acid {1-[3-
(aminoiminomethyl)benzyl]-2-oxopyrrolidin-3-(S)-
yl}amide trifluoroacetate.

17. A compound according to claim 14 which is
5-Pyrid-2-ylthiophene-2-sulfonic acid {1-[3-
(aminoiminomethyl)benzyl]-2-oxopyrrolidin-3-(S)-
yl}amide trifluoroacetate.

18. A compound according to claim 14 which is
7-Methoxynaphthalene-2-sulfonic acid {1-[3-
(aminoiminomethyl)benzyl]-2-oxopyrrolidin-3-(S)-
yl}amide trifluoroacetate.

19. A compound according to claim 14 which is
7-Aminonaphthalene-2-sulfonic acid {1-[3-
(aminoiminomethyl)benzyl]-2-oxopyrrolidin-3-(S)-
yl}amide bistrifluoroacetate.

20. A compound according to claim 14 which is
5-Chloro-3-methylbenzo[b]thiophene-2-sulfonic acid {1-
[3-(aminoiminomethyl)benzyl]-2-oxopyrrolidin-3-(S)-
yl}amide trifluoroacetate.

21. A compound according to claim 14 which is
2-[{1-[3-(Aminoiminomethyl)benzyl]-2-oxopyrrolidin-
3-(S)-yl}-7-methoxynaphthalene-2-sulfonylamino]-N-
phenethylacetamide trifluoroacetate.

22. A compound according to claim 14 which is
2-[{1-[3-(Aminoiminomethyl)benzyl]-2-oxopyrrolidin-
3-(S)-yl}-7-methoxynaphthalene-2-sulfonylamino]-N-
benzylacetamide trifluoroacetate.

23. A compound according to claim 14 which is
2-[{1-[3-(Aminoiminomethyl)benzyl]-2-oxopyrrolidin-3-(S)-yl}-7-methoxynaphthalene-2-sulfonylamino]-N-(2-pyridin-3-yl-ethyl)acetamide bistrifluoroacetate.

24. A compound according to claim 14 which is
4,5-Dichlorothiophene-2-sulfonic acid {1-[3-(aminoiminomethyl)benzyl]-2-oxo-3(S)-pyrrolidin-3-yl}amide trifluoroacetate.

25. A compound according to claim 14 which is
3'-Methyl-biphenyl-4-sulfonic acid {1-[3-(aminoiminomethyl)benzyl]-2-oxopyrrolidin-3(S)-yl}amide trifluoroacetate.

26. A compound according to claim 14 which is
3-[{1-[3-(Aminoiminomethyl)benzyl]-2-oxopyrrolidin-3(S)-3-yl}-(7-methoxynaphthalene-2-sulfonyl)amino]acetamide trifluoroacetate.

27. A compound according to claim 14 which is
7-Methoxy-2-napthalenesulfonic acid {1-[3-(aminoiminomethyl)benzyl]-2-oxo-3(S)-pyrrolidin-3-yl}(pyridin-2-ylmethyl)amide trifluoroacetate.

28. A compound according to claim 14 which is
Quinoline-6-sulfonic acid {1-[3-(aminoiminomethyl)benzyl]-2-oxopyrrolidin-3-(S)-yl}amide trifluoroacetate.

29. A compound according to claim 14 which is
4-Amino-3-[3-(S)-(7-methoxynaphthalene-2-sulfonylamino)-2-oxopyrrolidin-1-yl-methyl]benzamidine dihydrochloride.

30. A compound according to claim 14 which is
4-Amino-3-[3-(S)-(7-methoxynaphthalene-2-sulfonylmethylamino)-2-oxopyrrolidin-1-yl-methyl]benzamidine trifluoroacetate.

31. A compound according to claim 14 which is
4-Amino-3-[3-(S)-(4-tert-butylbenzenesulfonylamino)-2-oxopyrrolidin-1-yl-methyl]benzamidine trifluoroacetate.

32. A compound according to claim 14 which is
{4-(Aminoiminomethyl)-2-[3-(7-methoxynaphthalene-2-sulfonylamino)-2-oxopyrrolidin-1-ylmethyl]phenoxy}acetic acid methyl ester trifluoroacetate.

33. A compound according to claim 14 which is
4-[3-(S)-(7-Methoxynaphthalene-2-sulfonylamino)-2-oxopyrrolidin-1-ylmethyl]-thiophene-2-carboxamidine trifluoroacetate.

34. A compound according to claim 14 which is
4-{3-(S)-[(7-Methoxynaphthalene-2-sulfonyl)methylamino]-2-oxopyrrolidin-1-ylmethyl}thiophene-2-carboxamidine trifluoroacetate.

35. A compound according to claim 14 which is
2-[[1-(5-Carbamimidoylthiophene-3-ylmethyl)-2-oxopyrrolidin-3-(S)-yl](7-methoxynaphthalene-2-sulfonyl)amino]acetamide trifluoroacetate.

36. A compound according to claim 14 which is
4-[3-(S)-(5-Chloro-3-methylbenzo[b]thiophene-2-sulfonylamino)-2-oxo-pyrrolidin-1-ylmethyl]thiophene-2-carboxamidine trifluoroacetate.

37. A compound according to claim 14 which is
4-{3-(S)-[(5-Chloro-3-methylbenzo[b]thiophene-2-sulfonyl)methylamino]-2-oxopyrrolidin-1-ylmethyl}thiophene-2-carboxamidine trifluoroacetate.

38. A compound according to claim 14 which is
2-[[1-(5-Carbamimidoylthiophene-3-ylmethyl)-2-oxopyrrolidin-3-(S)-yl]-(7-methoxynaphthalene-2-sulfonyl)amino]-N-phenethylacetamide trifluoroacetate.

39. A compound according to claim 14 which is
[Amino-(4-{3-(S)-(7-methoxynaphthalene-2-sulfonyl)methylamino]-2-oxopyrrolidin-1-ylmethyl}thiophene-2-yl)methylene]carbamic acid methyl ester trifluoroacetate.

40. A compound according to claim 14 which is
4-{3-(S)-[(6-Amino-5-chloro-naphthalene-2-sulfonyl)methylamino]-2-oxopyrrolidin-1-ylmethyl}thiophene-2-carboxamidine trifluoroacetate.

41. A compound according to claim 14 which is
4-[3-(S)-(6-Amino-5-chloro-2-sulfonylamino)-2-oxopyrrolidin-1-ylmethyl]-thiophene-2-carboxamidine trifluoroacetate.

42. A compound according to claim 14 which is
4-{3-(S)-[(7-Aminonaphthalene-2-sulfonyl)benzylamino]-2-oxopyrrolidin-1-ylmethyl}thiophene-2-carboxamidine bistrifluoro acetate.

43. A compound according to claim 14 which is
4-[3-(S)-(7-Methoxynaphthalene-2-sulfonylamino)-2-oxopyrrolidin-1-ylmethyl]-pyridine-2-carboxamidine trifluoroacetate.

44. A compound according to claim 14 which is
4-{3-(S)-[(7-Methoxynaphthalene-2-sulfonyl)benzylamino]-2-oxopyrrolidin-1-ylmethyl}pyridine-2-carboxamidine trifluoroacetate.

45. A compound according to claim 14 which is
2-{[1-(2-Carbamimidoyl-pyridine-4-ylmethyl)-2-oxopyrrolidin-3-(S)-yl]-(7-methoxynaphthalene-2-sulfonyl)amino}-N-phenethylacetamide trifluoroacetate.

46. A compound according to claim 14 which is
4-{3-(S)-[(7-Methoxynaphthalene-2-sulfonyl)thiophen-3-ylmethylamino]-2-oxopyrrolidin-1-ylmethyl}thiophene-2-carboxamidine trifluoroacetate.

47. A compound according to claim 14 which is
4-{3-(S)-[(4-(6-Nitro-2-chlorophenoxy)benzenesulfonyl)amino]-2-oxopyrrolidin-1-ylmethyl}thiophene-2-carboxamidine trifluoroacetate.

48. The compound according to claim 1 of the formula

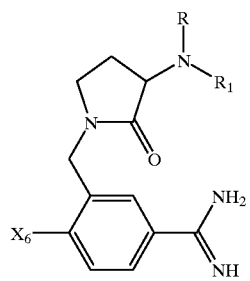

wherein R is hydrogen, methyl, aralkyl, heteroaralkyl, $HO_2CCH_2-$, $HOC(O)CH_2-$, $H_2NC(O)CH_2-$, (aralkyl)$HNC(O)CH_2-$ or (heteroaralkyl)$HNC(O)CH_2-$; $X_6$ is hydrogen or amino; and $R_1$ is selected from the group of formulae

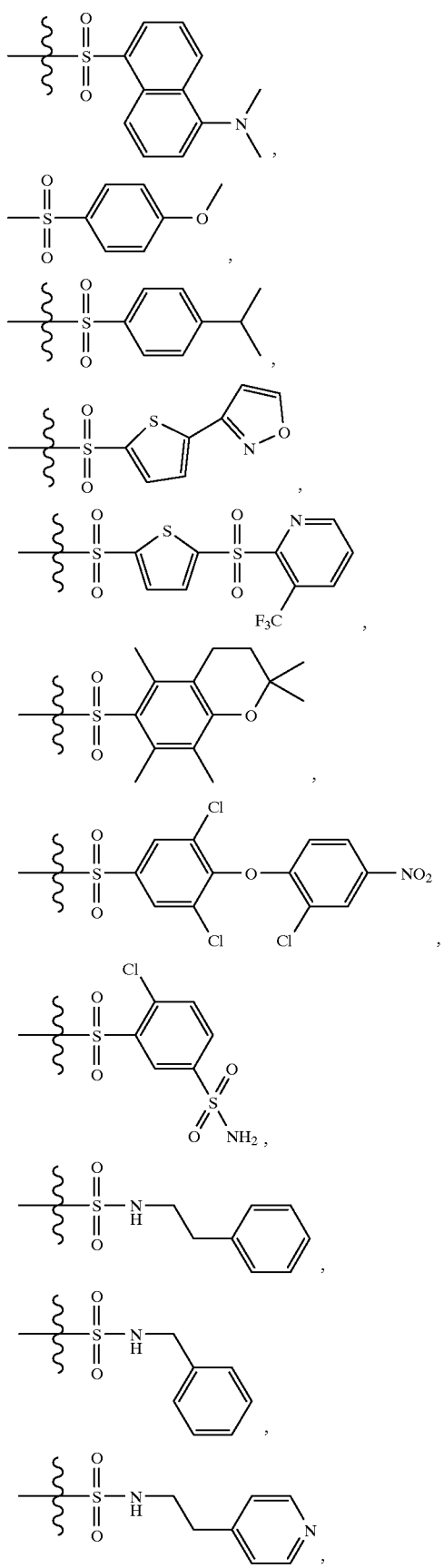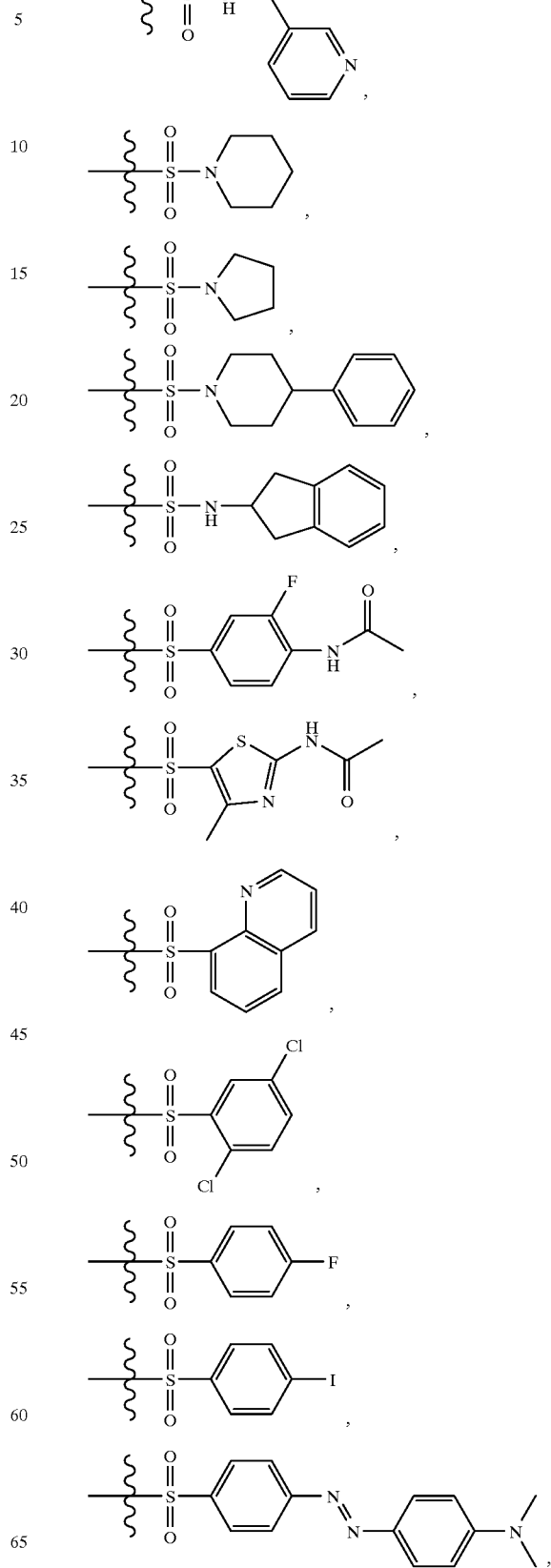

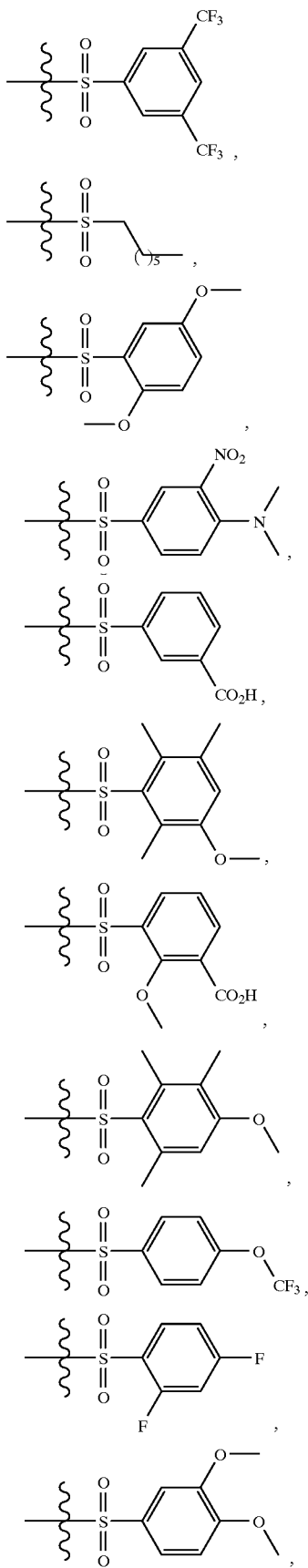
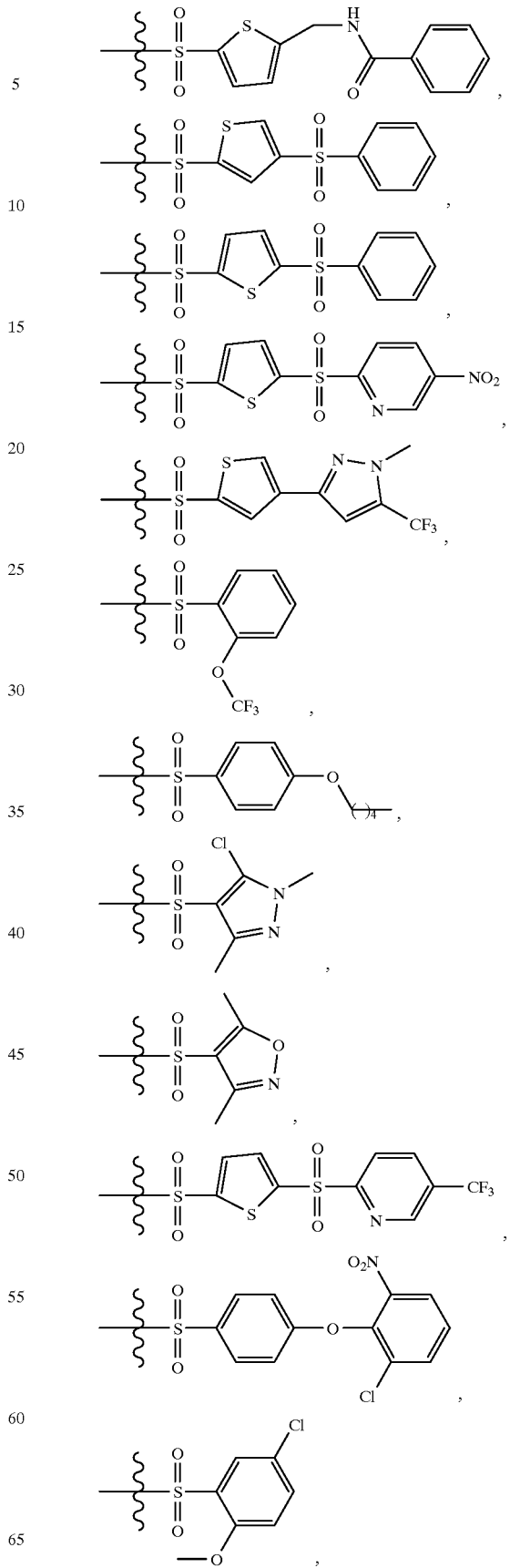

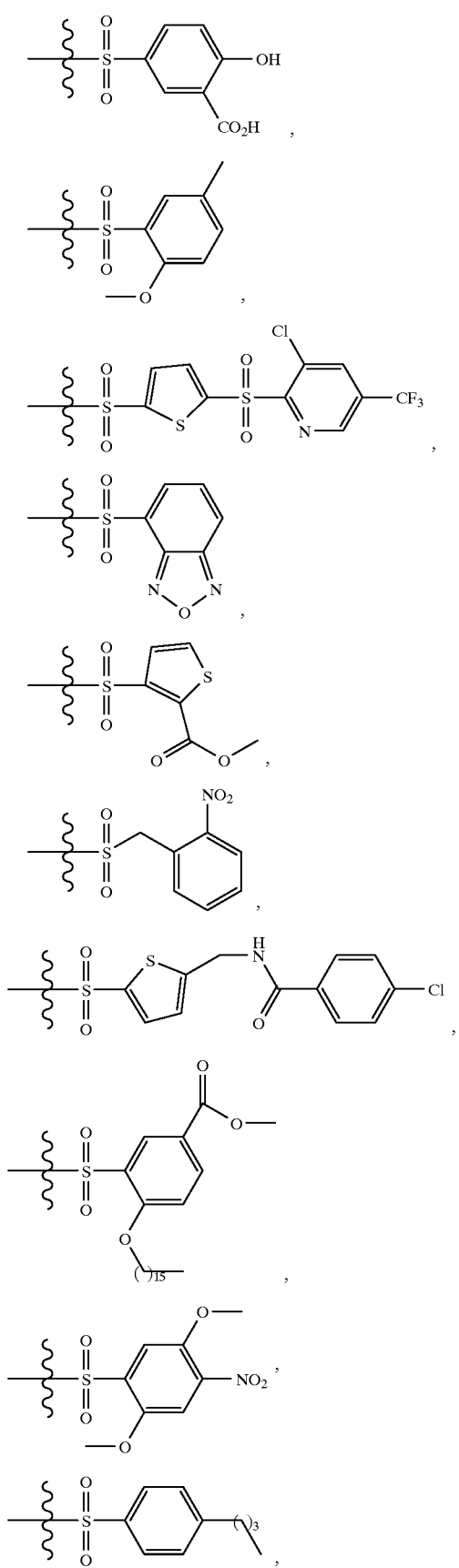
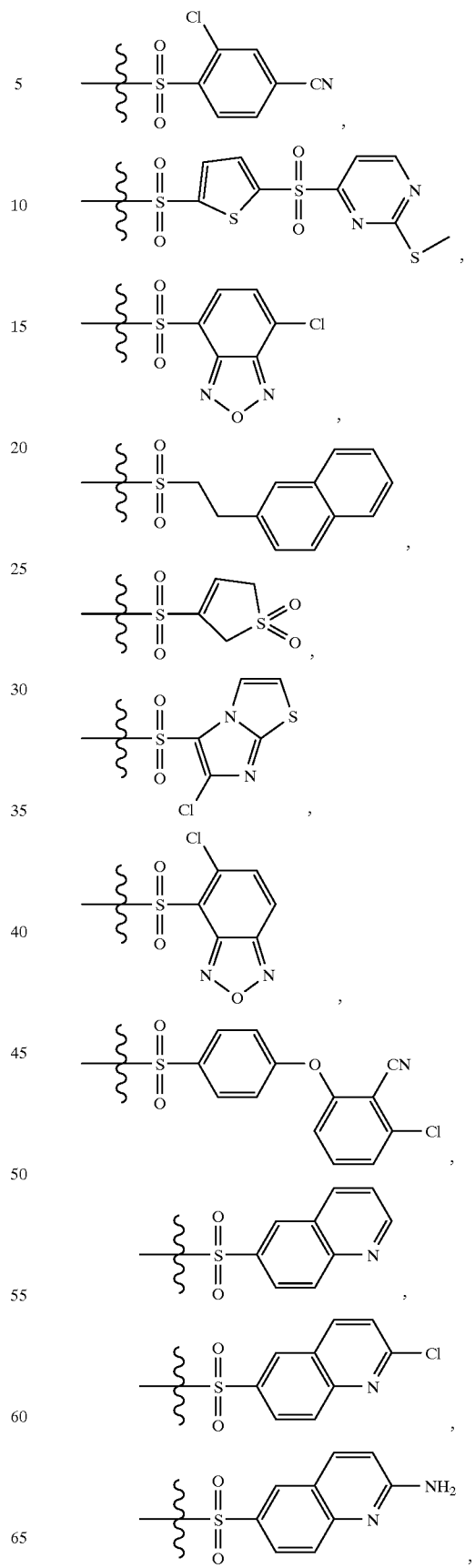

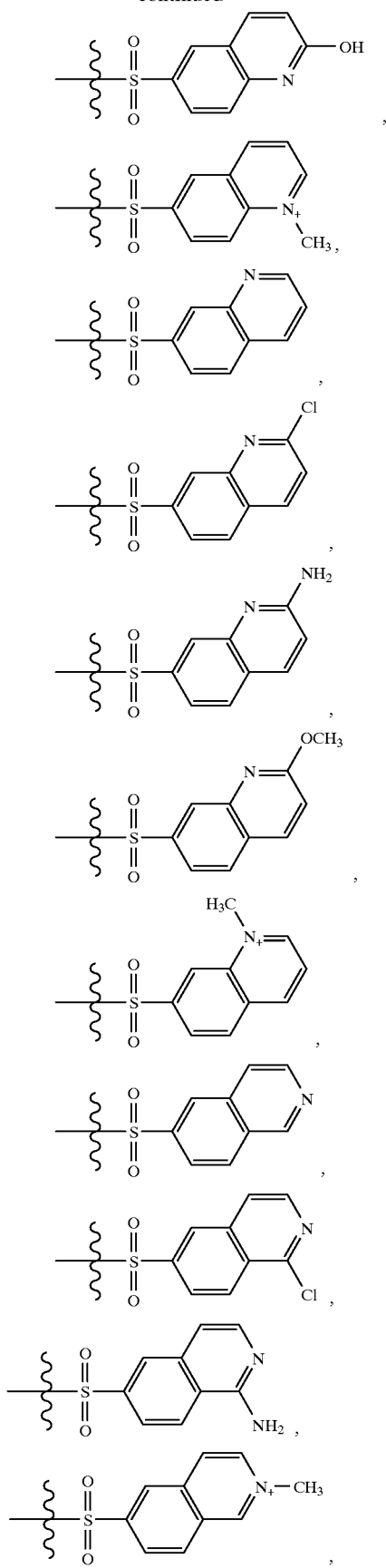
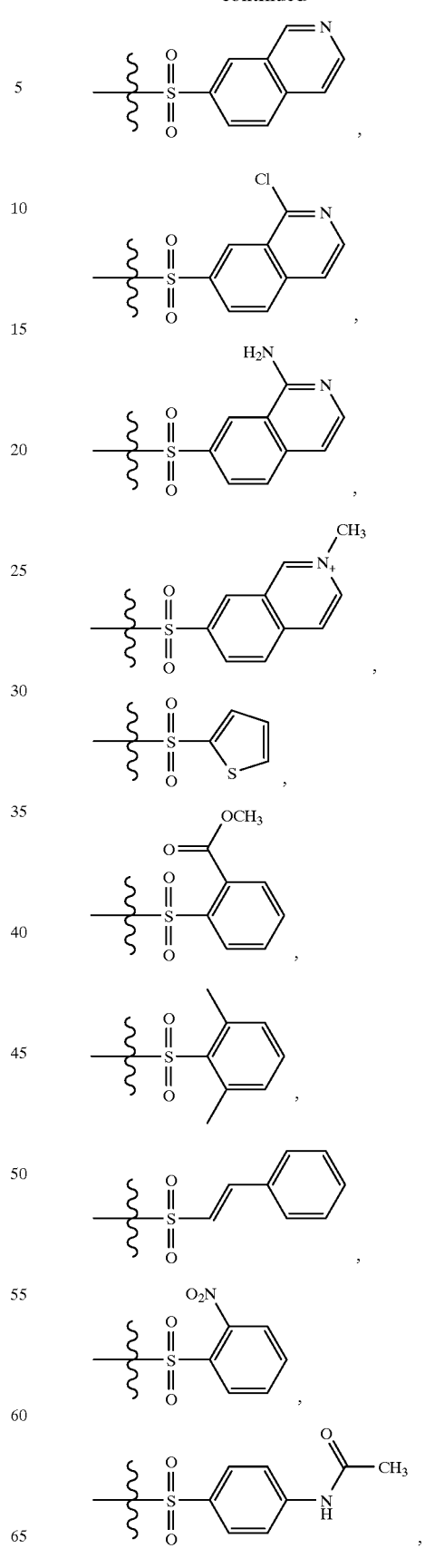

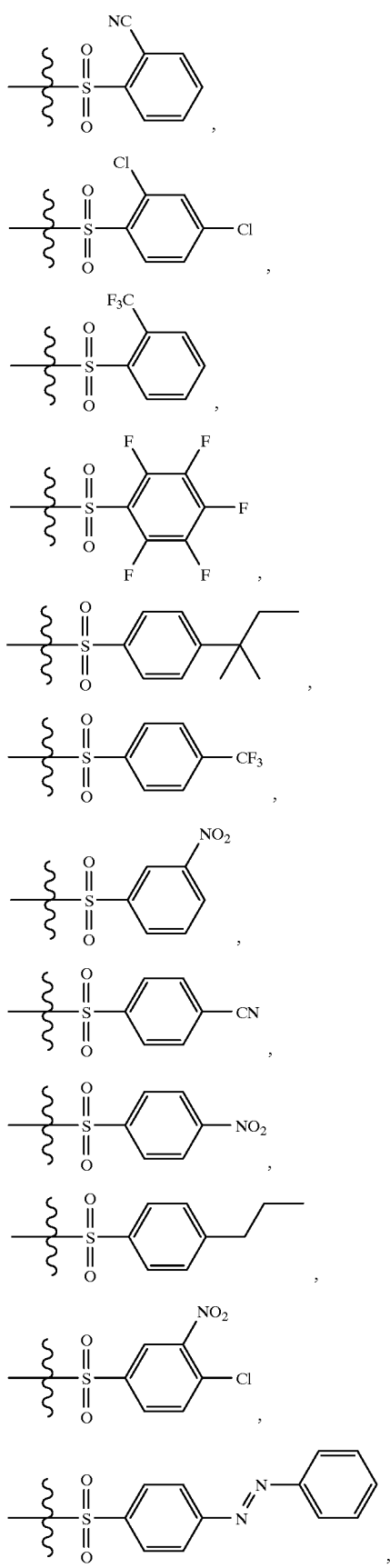
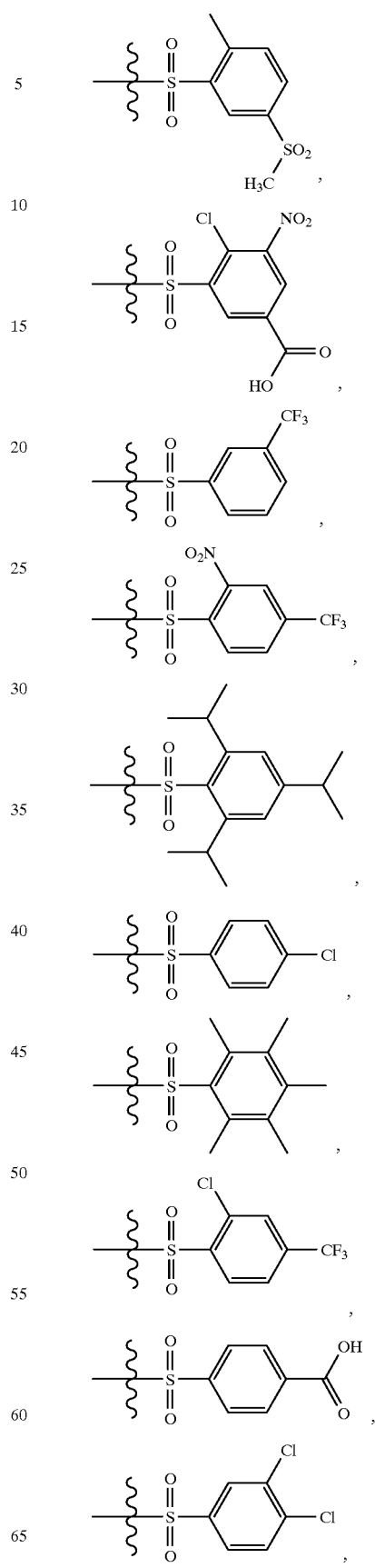

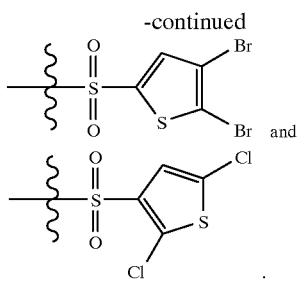
49. The compound according to claim 1 of the formula
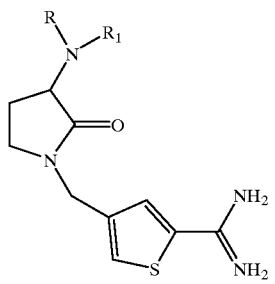
wherein R is hydrogen, methyl, aralkyl, heteroaralkyl, HO₂CCH₂—, HOC(O)CH₂—, H₂NC(O)CH₂—, (aralkyl)HNC(O)CH₂— or (heteroaralkyl)HNC(O)CH₂—; and R₁ is selected from the group of formulae
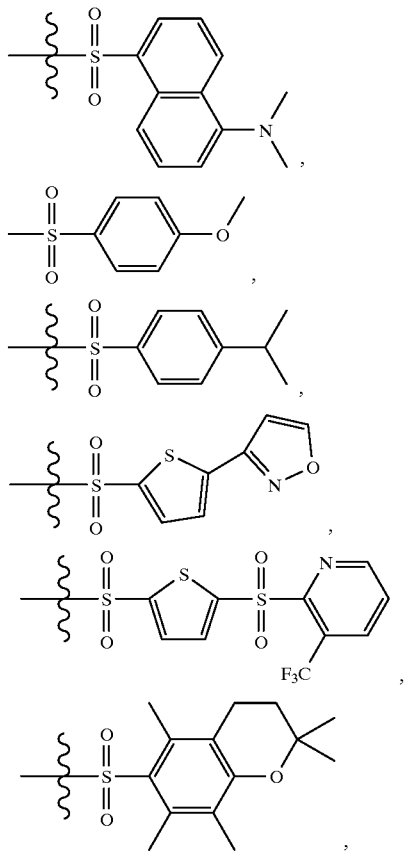
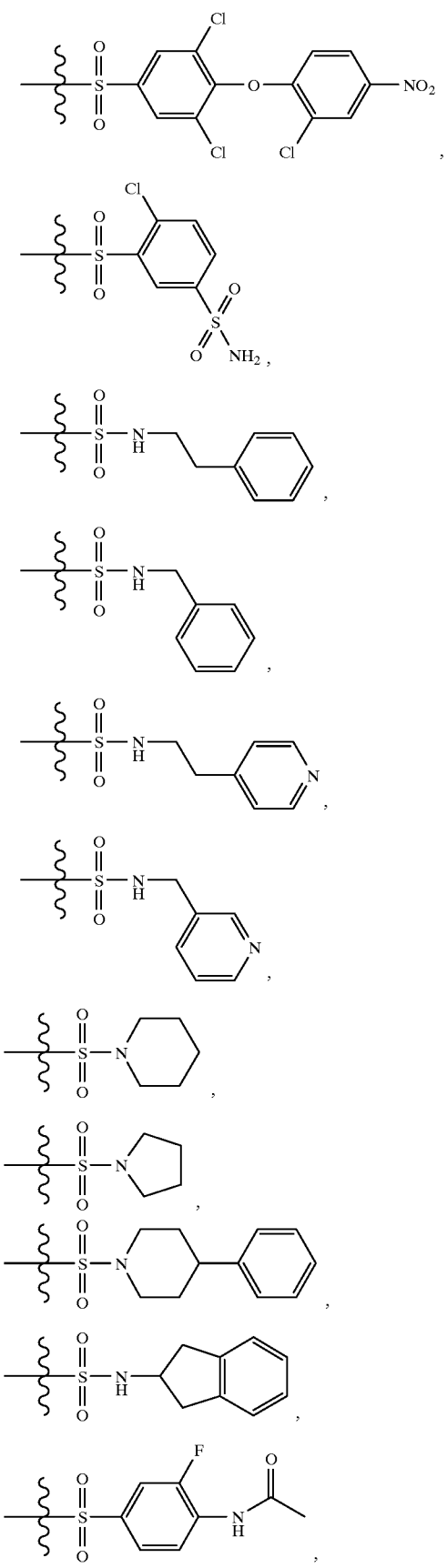

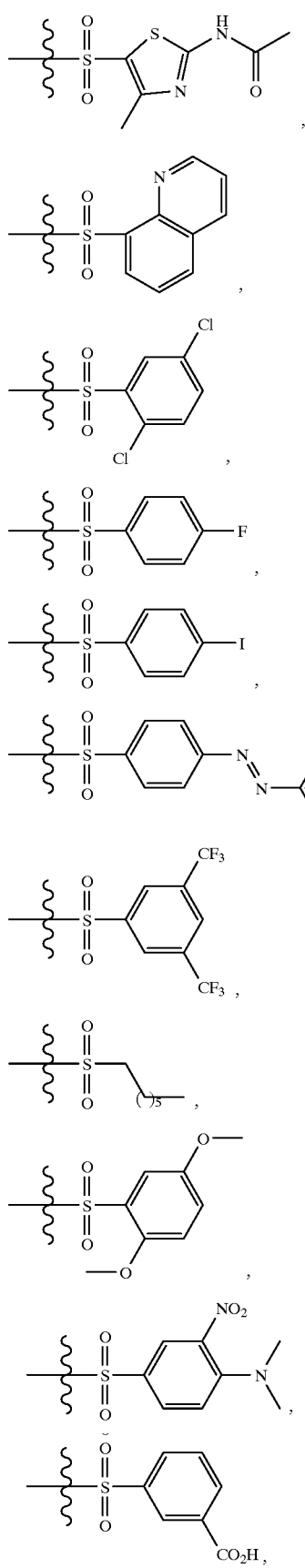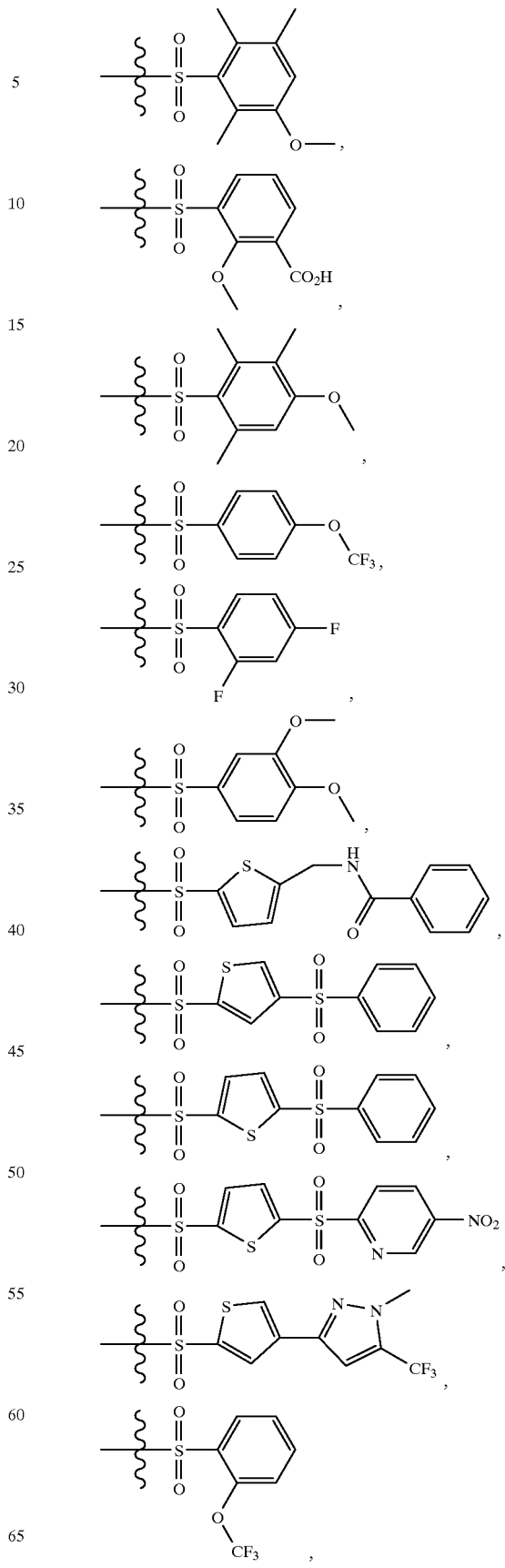

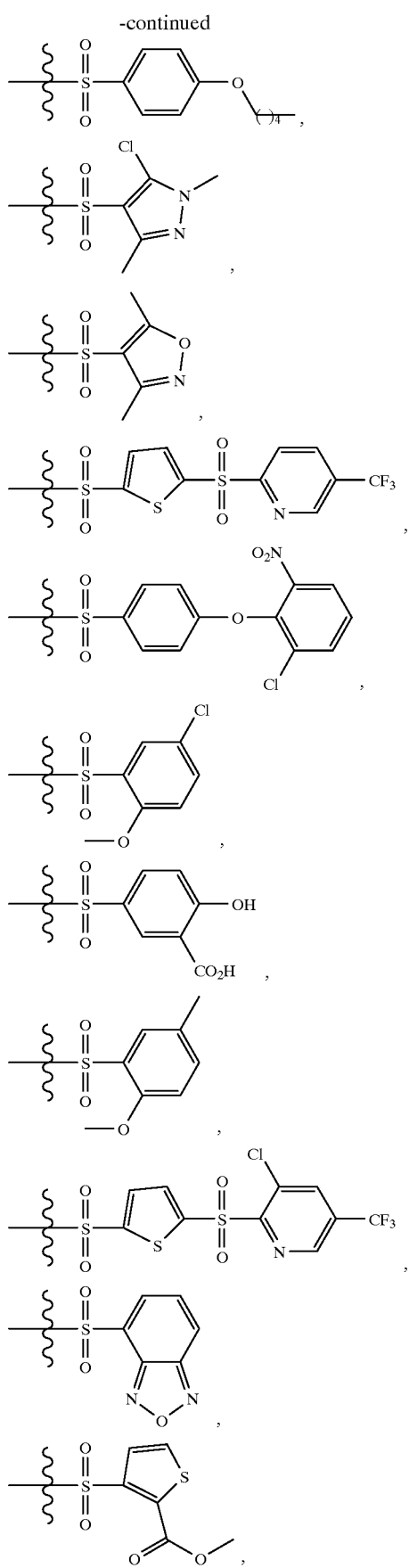
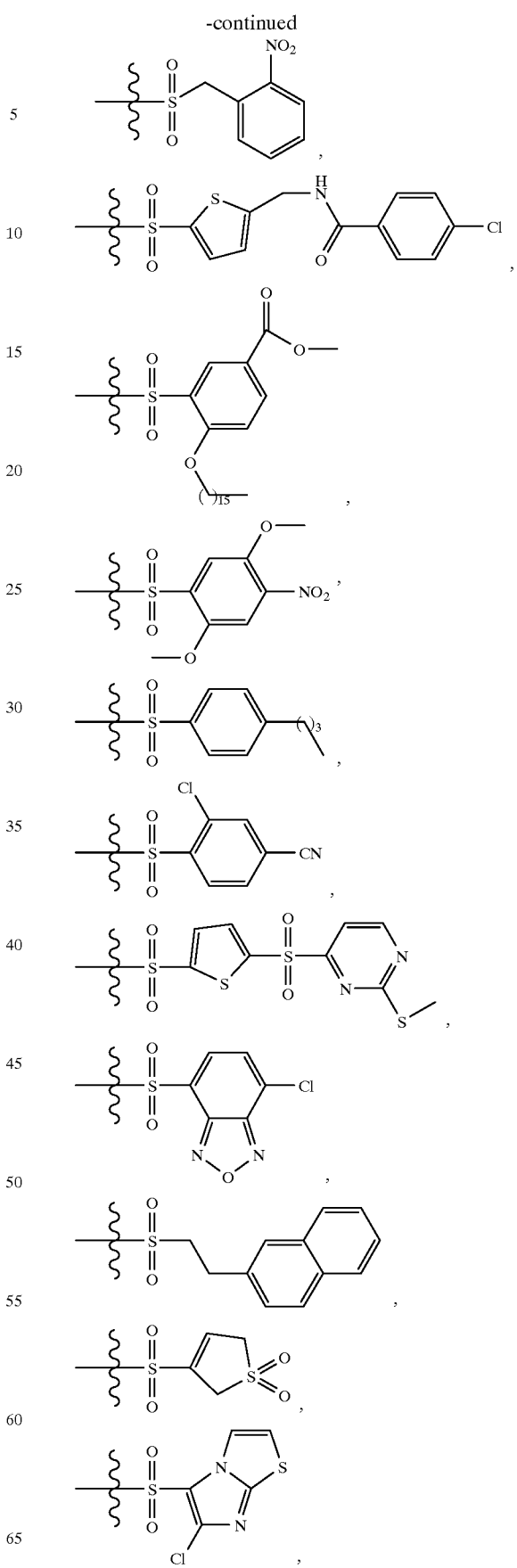

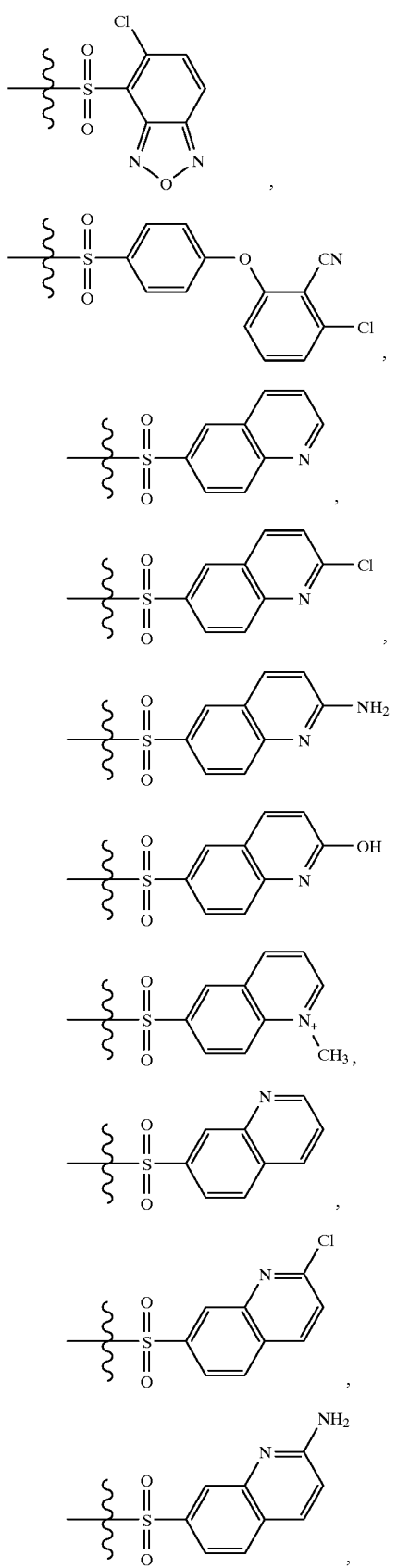
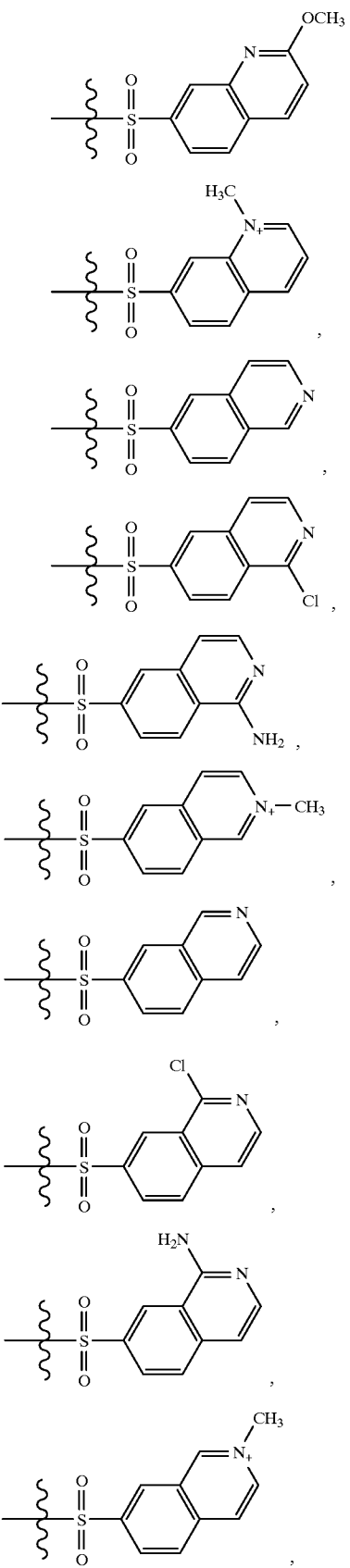

203
-continued
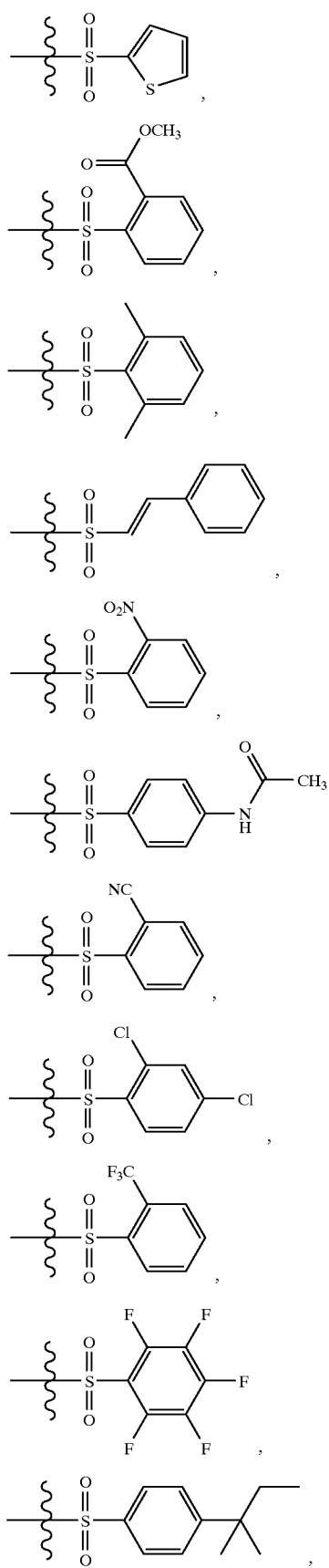
204
-continued
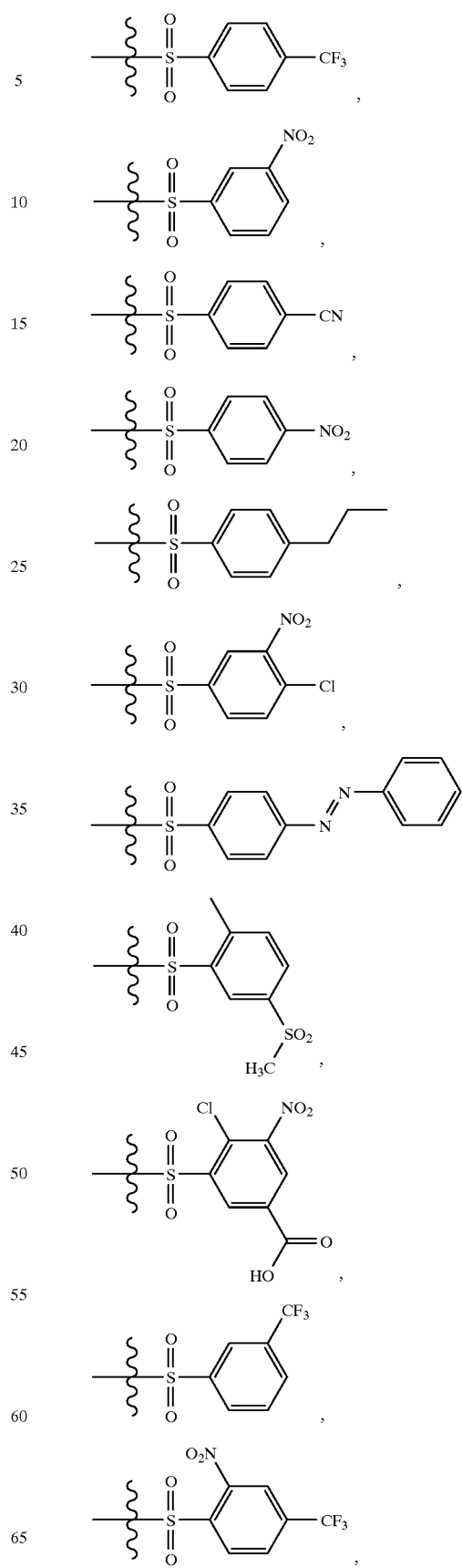

-continued

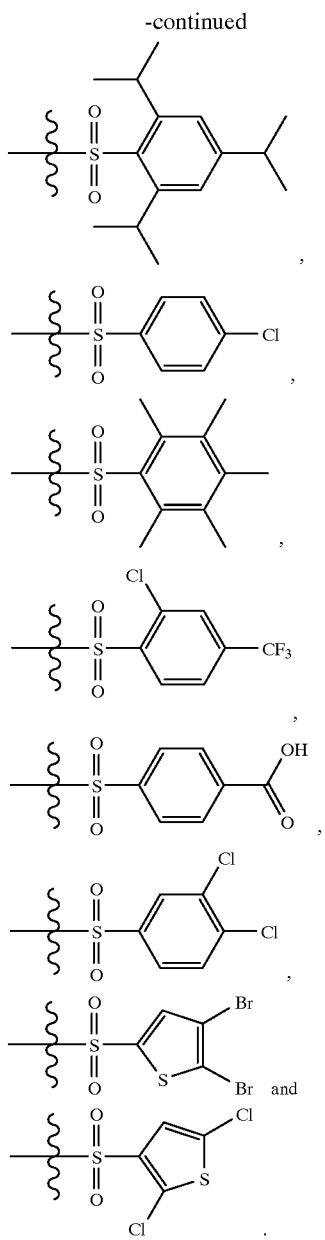

50. A pharmaceutical composition comprising a therapeutically effective amount of the compound according to claim 1 and a pharmaceutically acceptable carrier.

51. A method for treating a patient suffering from a physiological disorder capable of being modulated by inhibiting an activity of Factor Xa by administering a therapeutically effective amount of the compound according to claim 1.

52. The method according to claim 51 wherein the physiological disorder is venous vasculature, arterial vasculature, abnormal thrombus formation, acute myocardial infarction, unstable angina, thromboembolism, acute vessel closure associated with thrombolytic therapy, percutaneous transluminal coronary angioplasty, transient ischemic attacks, stroke, intermittent claudication or bypass grafting of the coronary or peripheral arteries, vessel luminal narrowing, maintenance of vascular access patency in long-term hemodialysis patients, pathologic thrombus formation occurring in the veins of the lower extremities following abdominal, knee and hip surgery, a risk of pulmonary thromboembolism, or disseminated systemic intravascular coagulopathy occurring in vascular systems during septic shock, certain viral infections or cancer.

53. A compound of the formula II

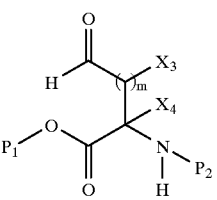

(II)

wherein $X_3$ is hydrogen, hydroxy, optionally substituted alkyl, optionally substituted aryl, optionally substituted heteroaryl, optionally substituted aralkyl or optionally substituted heteroaralkyl;

$X_4$ is hydrogen, optionally substituted alkyl, optionally substituted aralkyl, or hydroxyalkyl;

and m is 0, 1, 2 or 3, $P_1$ is alkyl, aralkyl or aryl, and $P_2$ is (alkyl, aralkyl or aryl)carbamate;

provided that when $X_3$ and $X_4$ are hydrogen, and $P_2$ is benzylcarbamate, then $P_1$ is other than t-butyl.

54. A compound of the formula

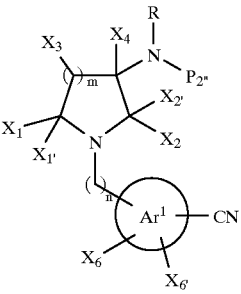

is phenyl or monocyclic heteroaryl;

$P_{2''}$ is (alkyl, aralkyl, or aryl)carbamate or $R_1$

R is hydrogen, optionally substituted alkyl, optionally substituted aralkyl, optionally substituted heteroaralkyl or hydroxyalkyl;

$R_1$ is hydrogen, $R_3S(O)_p$— or $R_3R_4N(O)_p$—;

$R_3$ is optionally substituted alkyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl or optionally substituted heteroaralkenyl, or R and $R_3$ taken together form a 5 to 7 membered ring; and $R_4$ is optionally substituted alkyl, optionally substituted cycloalkyl or optionally substituted aryl, optionally substituted heteroaryl, optionally substituted aralkyl or optionally substituted heteroaralkyl, or $R_3$ and $R_4$ taken together with the nitrogen to which $R_3$ and $R_4$ are attached form an optionally substituted 4 to 7 membered heterocyclyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$— or lower acyl;

$R_9$ is hydrogen, optionally substituted lower alkyl, lower acyl or $R_{10}(O)CCH_2$—;

$X_1$ and $X_{1'}$ are independently selected from hydrogen, optionally substituted alkyl, optionally substituted aryl, optionally substituted aralkyl, optionally substituted heteroaryl, optionally substituted heteroaralkyl or hydroxyalkyl, or $X_1$ and $X_{1'}$ taken together form oxo;

$X_2$ and $X_{2'}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1'}$ taken together form a 4 to 7 membered ring;

$X_4$ is hydrogen, optionally substituted alkyl, optionally substituted aralkyl, or hydroxyalkyl;

$X_6$ and $X_{6'}$ are independently hydrogen, $R_7R_8N$—, $R_9O$—, $R_7R_8NCO$—, $R_7R_8NSO_2$—, $R_9CO$—, halo, cyano or nitro;

m is 0, 1, 2 or 3; or n is 1, 2 or 3.

55. A compound of the formula X

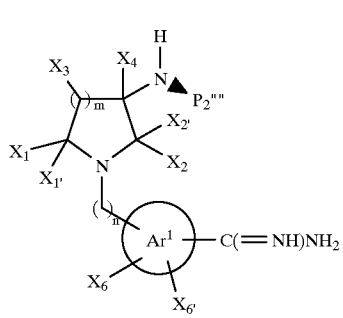

(X)

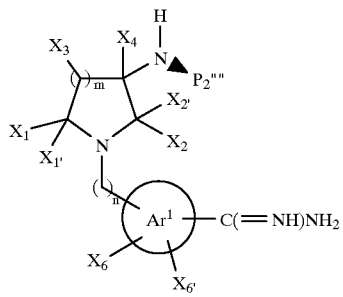

(X)

is phenyl or monocyclic heteroaryl; $P_{2''''}$ hydrogen or (alkyl, aralkyl or aryl)carbamate;

$X_1$ and $X_{1'}$ are independently selected from hydrogen, optionally substituted alkyl, optionally substituted aryl, optionally substituted aralkyl, optionally substituted heteroaryl, optionally substituted heteroaralkyl or hydroxyalkyl, or $X_1$ and $X_{1'}$ taken together form oxo;

$X_2$ and $X_{2'}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1'}$ taken together form a 4 to 7 membered ring;

$X_4$ is hydrogen, optionally substituted alkyl, optionally substituted aralkyl, or hydroxyalkyl;

X6 and $X_{6'}$ are independently hydrogen, $R_7R_8N$—, $R_9O$—, $R_7R_8NCO$—, $R_7R_8NSO_2$—, $R_9CO$—, halo, cyano or nitro;

$R_6$ is hydrogen, optionally substituted lower alkyl or optionally substituted aralkyl or optionally substituted heteroaralkyl;

$R_7$ and $R_8$ are independently hydrogen or optionally substituted lower alkyl, or one of $R_7$ and $R_8$ is hydrogen and the other of $R_7$ and $R_8$ is $R_{10}(O)CCH_2$— or lower acyl;

$R_9$ is hydrogen, optionally substituted lower alkyl, lower acyl or $R_{10}(O)CCH_2$—;

$R_{10}$ is hydrogen, optionally substituted lower alkyl, alkoxy or hydroxy;

m is 0, 1, 2 or 3; and n is 1, 2 or 3.

56. A compound of the formula XII

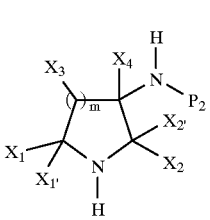

(XII)

wherein $X_1$ and $X_{1'}$ are independently selected from hydrogen, optionally substituted alkyl, optionally substituted aryl, optionally substituted aralkyl, optionally substituted heteroaryl, optionally substituted heteroaralkyl or hydroxyalkyl, or $X_1$ and $X_{1'}$ taken together form oxo;

$X_2$ and $X_{2'}$ are hydrogen, or taken together form oxo;

$X_3$ is hydrogen, hydroxy, optionally substituted alkyl, optionally substituted aryl, optionally substituted heteroaryl, optionally substituted aralkyl or optionally substituted heteroaralkyl, or $X_3$ and one of $X_1$ and $X_{1'}$ taken together form a 4 to 7 membered ring;

$X_4$ is hydrogen, optionally substituted alkyl, optionally substituted aralkyl, or hydroxyalkyl;

$X_6$ and $X_{6'}$ are independently hydrogen, $R_7R_8N$—, $R_9O$—, $R_7R_8NCO$—, $R_7R_8NSO_2$—, $R_9CO$—, halo, cyano or nitro;

$R_7$ and $R_8$ are independently hydrogen or optionally substituted lower alkyl, or one of $R_7$ and $R_8$ is hydrogen and the other of $R_7$ and $R_8$ is $R_{10}O(O)CCH_2$— or lower acyl;

$R_9$ is hydrogen, optionally substituted lower alkyl, lower acyl or $R_{10}(O)CCH_2$—, $R_{10}$ is hydrogen, optionally substituted lower alkyl, alkoxy or hydroxy;

$P_2$ is (alkyl, aralkyl or aryl)carbamate; and m is 0, 1, 2 or 3.

57. A method for inhibiting an activity of Factor Xa comprising combining a compound according to claim 1 with a composition containing Factor Xa.

* * * * *